US006403302B1

(12) United States Patent
Dervan et al.

(10) Patent No.: US 6,403,302 B1
(45) Date of Patent: Jun. 11, 2002

(54) METHODS AND COMPOSITIONS FOR TRIPLE HELIX FORMATION

(75) Inventors: Peter B. Dervan; Peter A. Beal, both of Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 08/168,920

(22) Filed: Dec. 16, 1993

Related U.S. Application Data

(63) Continuation of application No. 07/946,976, filed on Sep. 17, 1992, now abandoned.

(51) Int. Cl.[7] .............................. C12Q 1/68; C07H 21/00
(52) U.S. Cl. .......................... 435/6; 436/501; 536/22.1; 536/23.1; 536/25.3
(58) Field of Search ........................... 435/6, 91.1, 810; 436/501, 811; 536/22.1, 23.1, 25.3; 935/78, 88

(56) References Cited

U.S. PATENT DOCUMENTS

| | | | |
|---|---|---|---|
| 4,358,535 A | 11/1982 | Falkow et al. | 435/5 |
| 4,563,417 A | 1/1986 | Albarella et al. | 435/6 |
| 4,599,303 A | 7/1986 | Yabusaki et al. | 435/6 |
| 4,665,184 A | 5/1987 | Dervan et al. | 546/109 |
| 4,711,955 A | 12/1987 | Ward et al. | 536/29 |
| 4,795,700 A | 1/1989 | Dervan et al. | 435/5 |
| 4,828,979 A | 5/1989 | Klevan et al. | 435/6 |
| 4,835,263 A | 5/1989 | Nguyen et al. | 536/27 |
| 4,837,312 A | 6/1989 | Dervan et al. | 536/27 |
| 5,175,266 A | 12/1992 | Varma et al. | 536/22 |
| 5,176,996 A | 1/1993 | Hogan et al. | 435/6 |

FOREIGN PATENT DOCUMENTS

| | | |
|---|---|---|
| EP | 117777 | 9/1984 |
| EP | 169787 | 1/1986 |
| EP | 214908 | 3/1987 |
| EP | 0375408 | 6/1990 |
| WO | 8804301 | 12/1987 |
| WO | 9221690 | 12/1992 |

OTHER PUBLICATIONS

Marck et al. (1978) Nucleic Acids Res., vol. 5, No. 3, pp. 1018–1028.*
LeDoan et al. (1987) Nucleic Acids Res., vol. 15, No. 19, pp. 7749–7760.*
New England Biolabs Catalog (New England Biolabs, Beverly, MA, USA, 1986), pp. 53 and 60–62.*
Strobel, S.A., et al., "Site–Specific Cleavage of Human Chromosome 4 Mediated by Triple–Helix Formation", *Science* 254:1639–1642, 1991 (Dec. 13).
Strobel, S.A., et al., "Single–site enzymatic cleavage of yeast genomic DNA mediated by triple helix formation", *Nature* 350:172–174, 1991 (Mar. 14).
Beal, P.A., et al., "Second Structural Motif for Recognition of DNA by Oligonucleotide–Directed Triple–Helix Formation", *Science* 251:1360–1363. 1991 (Mar. 15).
Horne, D.A., et al., "Effects of an abasic site on triple helix formation characterized by affinity cleaving", *Nucleic Acids Research* 19:4863–4965, 1991 (later than Aug. 9).

(List continued on next page.)

Primary Examiner—Ardin H. Marschel
(74) Attorney, Agent, or Firm—Richard F. Trecartin; Todd A. Lorenz; Flehr Hohbach Test Albritton & Herbert LLP

(57) ABSTRACT

Improved oligonucleotides and processes for their use for specific recognition of a target sequence in double-stranded nucleic acid through the formation of an alternate strand triple-helix. The triple-helix forming oligonucleotides bind in a parallel and antiparallel orientation, respectively, to target sequences on alternate strands of the double helical nucleic acid. The oligonucleotides are useful as diagnostic or therapeutic agents and can incorporate an appropriate moiety in one or more nucleotides in the triple-helix forming oligonucleotide.

30 Claims, 52 Drawing Sheets

OTHER PUBLICATIONS

Griffin, L.C., et al., "Recognition of Thymine–Adenine Base Pairs by Guanine in a Pyrimidine Triple Helix Motif", *Science* 345:967–971, 1989.

Strobel, S.A., et al., "Double–Strand Cleavage of Genomic DNA at a Single Site by Triple–Helix Formation", *J. Am. Chem. Soc.* 110:7927–7929, 1988.

Luebke, K.H., et al., "Nonenzymatic Ligation of Oligodeoxyribonucleotides on a Duplex DNA Template by Triple–Helix Formation," *J. Am. Chem. Soc.* 111:8733–8735, 1989.

Strobel, S.A., et al., "Cooperative Site Specific Binding of Oligonucleotides to Duplex DNA", *J. Am. Chem. Soc.* 111:7286–7287, 1989.

Povsic, T.J., et al., "Triple Helix Formation by Oligonucleotides on DNA Extended to the Physiological pH Range", *J. Am. Chem. Soc.* 111:3059–3061, 1989.

Strobel, S.A., eta l., "Site–Specific Cleavage of a Yeast Chromosome by Oligonucleotide–Directed Triple–Helix Formation", *Science* 249:73–75, 1990.

Horne, D.A., et al., "Recognition of Mixed–Sequence Duplex DNA by Alternate–Strand Triple–Helix Formation", *J. Am. Chem. Soc.* 1990, 112:2435–2437, 1990.

Maher, L.J., III., et al., "Inhibition of DNA Binding Proteins by Oligonucleotide–Directed Triple Helix Formation", *Science* 245:725–730, 1989.

Taylor, J.S., et al., "DNA Affinity Cleaving—Sequence Specific Cleavage of DNA by Distamycin–Edta.Fe(II) and Edta–Distamycin.Fe(II)", *Tetrahedron* 40:457–465, 1984.

Moser, H.E., et al., "Sequence–Specific Cleavage of Double Helical DNA by Triple Helix Formation", *Science* 238:645–650, 1987.

Schultz, P.C., et al., "Sequence–specific double–strand cleavage of DNA by pentaN–methylpyrrolecarboxamide–EDTA.Fe(II)", *PNAS* 80:6834–6837, 1983.

Dreyer, G.B., et al., "Sequence–specific cleavage of single–stranded DNA:Oligodeoxynucleotide–EDTA.Fe(II)", *PNAS* 82:968–972, 1985.

Van Dyke, M.M., et al., "Echinomycin Binding Sites on DNA", *Science* 225:1122–1122–1127, 1984.

Hertzberg, R.P., et al., "Cleavage of DNA with Methidiumpropyl–EDTA–Iron (II): Reaction Conditions and Product Analyses", *Biochemistry* 23:3934–3945, 1984.

Hertzberg, R.P., et al., "Cleavage of Double Helical DNA by (Methidiumpropyl–EDTA)iron(II)", *J. Am. Chem. Soc.* 104:313–315, 1982.

LeDoan, T., et al., "Sequence–specific recognition, photo-crosslinking and cleavage of the DNA double helix by an oligo–[α]–thymidylate covalently linked to an azidoproflavine derivative", *Nucleic Acids Research* 15:7749–7760, 1987.

Praseuth, D, et al., "Sequence–specific binding and photo-crosslinking of α and β oligodeoxynucleotides to the major groove of DNA via triple–helix formation", *PNAS* 85:1439–1353, 1988.

Francois, J–C., et al., "Sequence–targeted Cleavage of Single– and Double–Stranded DNA by Oligothymidylates Covalently Linked to 1,10–Phenathroline", *J. Biol. Chem.* 264:5891–5898, 1989.

Francois, J–C., et al., "Inhibition of Restriction Endonuclease Cleavage via Triple Helix Formation by Homopyrimidine Oligonucleotides", *Biochemistry* 28:9617–9619, 1989.

Sun, J–S., et al., "Sequence–specific intercalating agents: Intercalation at specific sequences on duplex DNA via major groove recognition by oligonucleotides–intercalator conjugates", *PNAS* 86:9198–9202, 1989.

Zerial, A., et al., "Selective inhibition of the cytopathic effect of type A influenza viruses by oligodeoxynucleotides covalently linked to an intercalating agent", *Nucleic Acids Research* 15:9909–9919, 1987.

Cazenave, C., et al., "Rate of degradation of [α]—and [β]–oligodeoxynucleotides in *Xenopus oocytes*. Implications for anti–messenger strategies", *Nucleic Acids Research* 15:10507–10521, 1987.

Durland, R.H., et al., "Binding of Triple Helix Forming Oligonucleotides to Sites in Gene Promoters", *Biochemistry* 30:9246–9255, 1991.

Cooney, M., et al., "Site–Specific Oligonucleotide Binding Represses Transcription of the Human c–myc Gene in Vitro", *Science* 241:456–459, 1988.

Williams, N.G., et al., "Dimers, Trimers, and Tetramers of Cytosine with Guanine", *J. Am. Chem.Soc.* 111:7105–7209, 1989.

Letai, A.G., et al., "Specificity in Formation of Triple–Stranded Nucleic Acid Helical Complexes: Studies in Formation of Triple–Stranded Nucleic Acid Helical Complexes: Studies with Agarose–Linked Polyribonucleotide Affinity Columns", *Biochemistry* 27:9108–9112, 1988.

Broitman, S.L., et al., "Formation of the triple–stranded polynucleotide helix, poly(A.A.U)", *PNAS* 84:5120–5124, 1987.

Lipsett, M.N., "Complex Formation between Polycytidylic Acid and Guanine Oligonucleotides", *J. Biol. Chem.* 239:1256–1260, 1984.

Llyamchev, V.I., et al., "A stable complex between homopyrimidine oligomers and the homologous regions of duplex DNA", *Nucleic Acids Research* 16:2165–2176, 1988.

Rajagopal, P., et al., "Triple–strand formation in the homopurine:homopyrimidine DNA oligonucleotides d(G–A)$_4$ and d(T–C)$_4$", *Nature* 339:637–640, 1989.

Kohwi, Y., et al., "Magnesium ion–dependent triple–helix structure formed by homopurine–homopyridine sequences in supercoiled plasmid DNA", *PNAS* 85:3781–3785, 1988.

Marck, C., et al., "Poly(dG).poly(dC) at neutral and alkaline pH: the formation of triple stranded poly(dG).poly(dG-).poly(dC)", *Nucleic Acids Research* 5:1017–1028, 1978.

Hanvey, J.C., et al., "Site–specific inhibition of EcoRI restriction/modification enzymes by a DNA triple helix", *Nucleic Acids Research* 18:157–161, 1989.

Torrence, P.F., et al., "Triple–Helical Polynucleotides. Mixed Triplexes of the Poly(uridylic acid).Poly adenylic acid).Poly(uridylic acid) Class", *Biochemistry* 15:724–734, 1976.

Perlgut, L.E., et al., "Formation of triple–stranded bovine DNA in vitro", *Nature* 254:86–87, 1975.

Chu, B.C.F., et al., "Nonenzymatic sequence–specific cleavage of single–stranded DNA", *PNAS* 83:963–967, 1985.

Moffat, A.S., "Triplex DNA Finally Comes of Age", *Science* 252:1374–1365, 1991.

Häner, R., et al., "Single–Strand DNA Triple–Helix Formation", *Biochemistry* 29:9761–9765, 1990.

Cooney, M., et al., "Site–Specific Oligonucleotides Binding Represses Transcription of the Human c–myc Gene in Vitro", *Science* 241:456–459, 1988.

Durland, R.H., et al., "Binding of Triple Helix Forming Oligonucleotides to Sites in Gene Promoters", *Biochemistry* 30:9246–9255, 1991.

Koh, J.S., et al., "Design of a Nonnatural Deoxyribonucleoside for Recognition of GC Base Pairs by Oligonucleotide–Directed Triple Helix Formation", *J. Am. Chem. Soc.* 114:1470–1478, 1992.

Maher, L.J., et al., "Analysis of Promoter–Specific Repression by Triple–Helical DNA Complexes in a Eukaryotic Cell–Free Transcription System", *Biochemistry* 31:70–81, 1992.

Beal, P.A., et al., "Recognition of Double Helical DNA by Alternate Strand Triple Helix Formation", *J. Am. Chem. Soc.* 114:4976–4982, 1992.

Kiessling, L.L., et al., "Flanking Sequence Effects within the Pyrimidine Triple–Helix Motif Characterized by Affinity Cleaving", *Biochemistry* 31:2829–2834, 1992.

Griffin, L.C., et al., "Recognition of All Four Base Pairs of Duplex DNA by Triple Helix Formation. Design of Pyrimidine Specific Bases", California Institute of Technology, Division of Chemistry and Chemical Engineering, Pasadena, CA, 1991.

Koh, J. S., "Design of novel bases for recognition of GC base pairs by oligonucleotide–directed triple helix formation" PhD thesis, California Institute of Technology, Pasadena, California, published Oct. 31, 1991.

Griffin, L. C., "Oligonucleotide–directed cleavage of single– and double–stranded DNA by double and triple helix formation", PhD thesis, California Institute of Technology, Pasadena, California, published Sep. 13, 1990.

Morgan, A.R. et al. (1968) *J. Mol. Biol. 37*:63–80, "Specificity of Three–stranded Complex Formation between Double–stranded DNA and Single–stranded RNA containing Repeating Nucleotide Sequences".

De Clercq, E. et al. (1975) *J. Biol. Chem.* 250:2521–2531, "Biological, Biochemical, and Physsiocochemical Evidence for the Existence of Polyadenylic–Polyyridylic–Polyinosinic Acid Triplex".

Lipsett, M.N. (1964) *J. Biol. Chem. 239*:1256–1260, "Complex Formation between Polycytidylic Acid and Guanine Oligonucleotides".

* cited by examiner

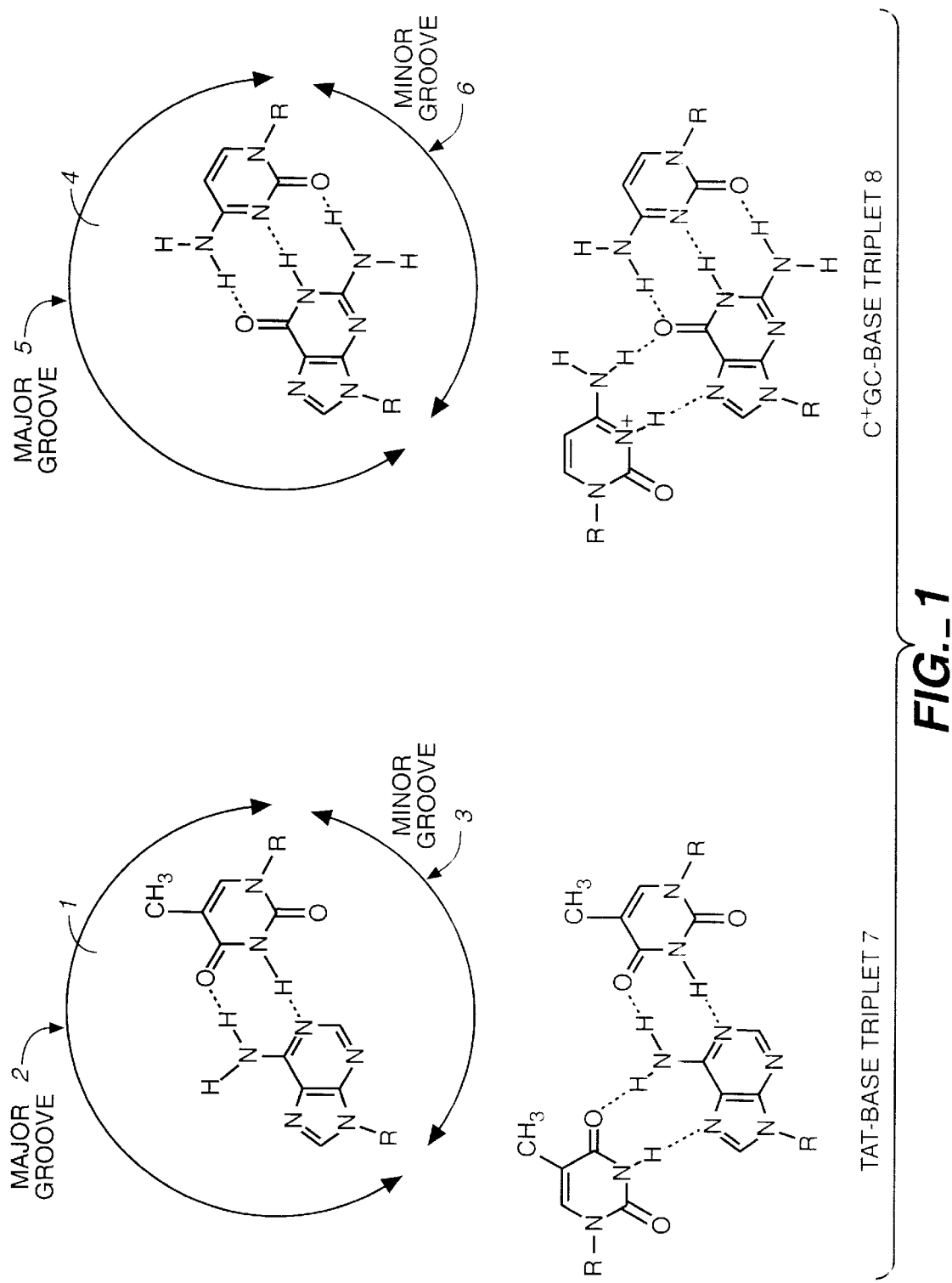
FIG._1

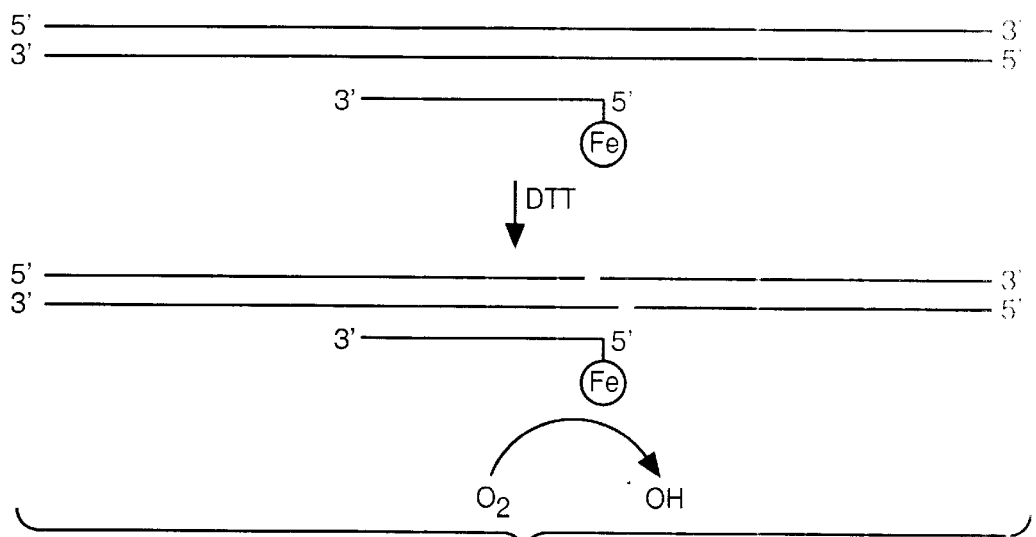
FIG._2
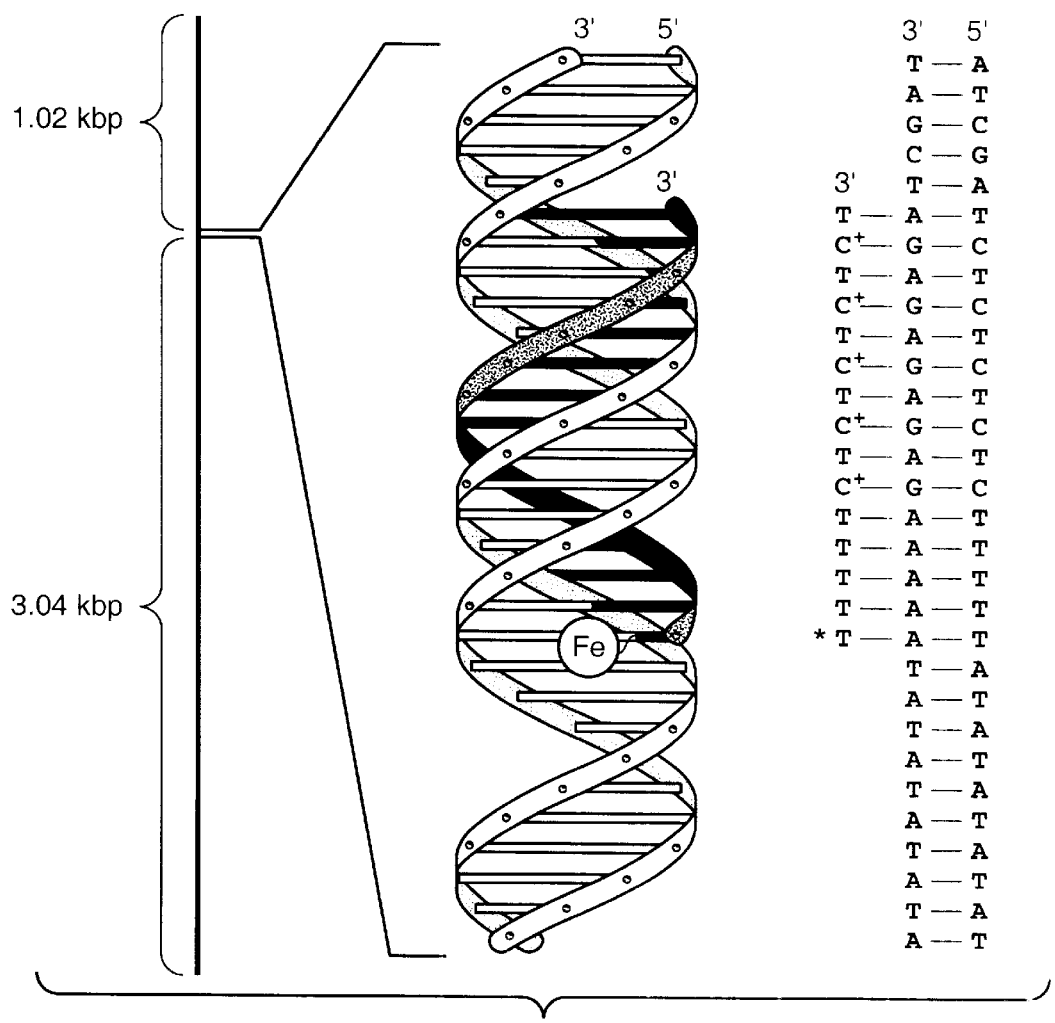
FIG._7

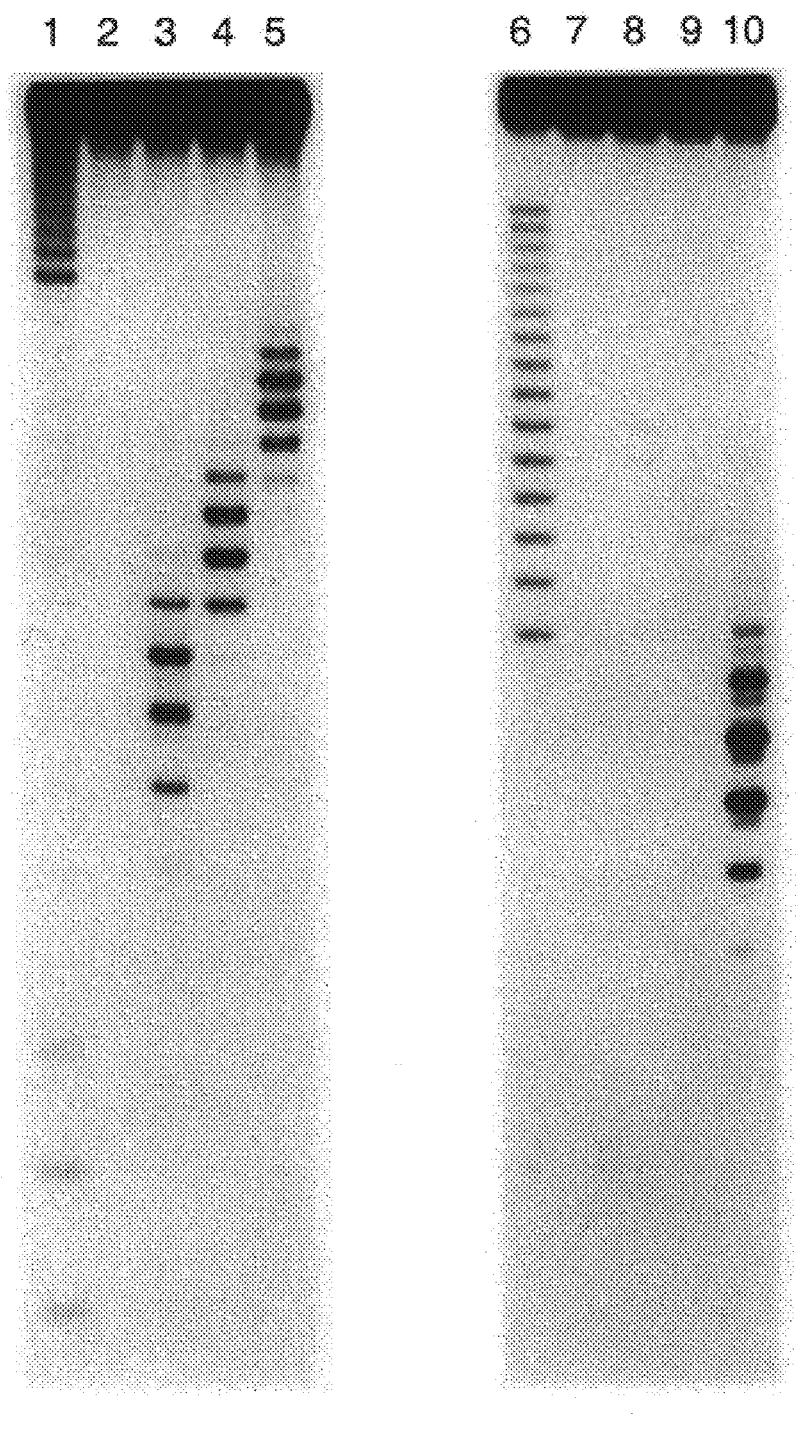
FIG._3A

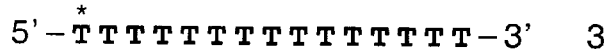
DNA-EDTA 1
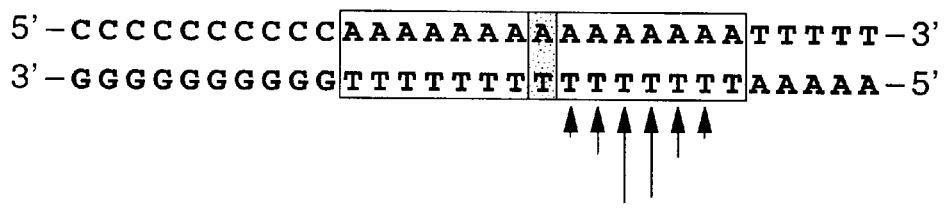
DNA-EDTA 2
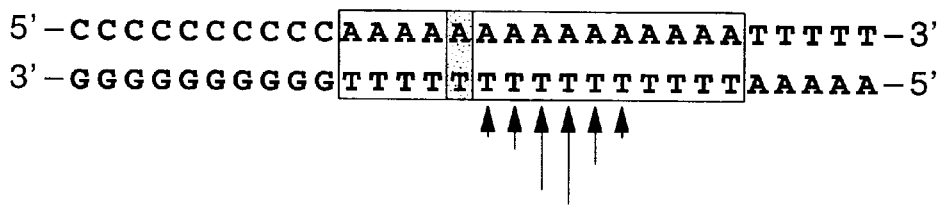
DNA-EDTA 3
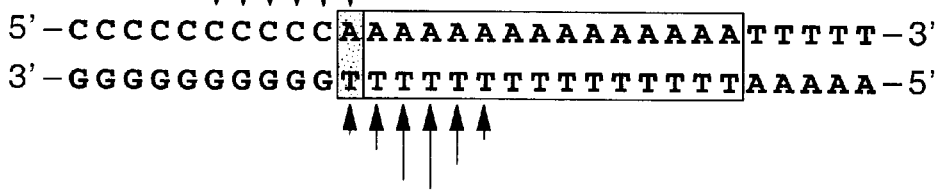
FIG._3B

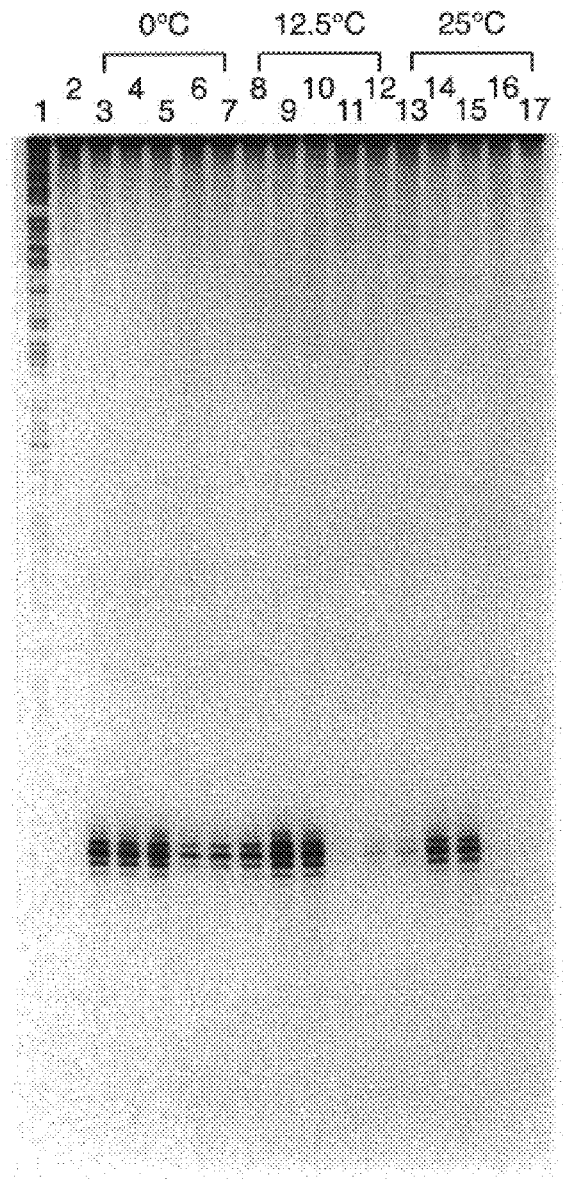
FIG._4A
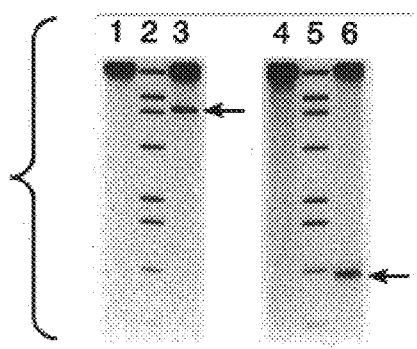
FIG._6

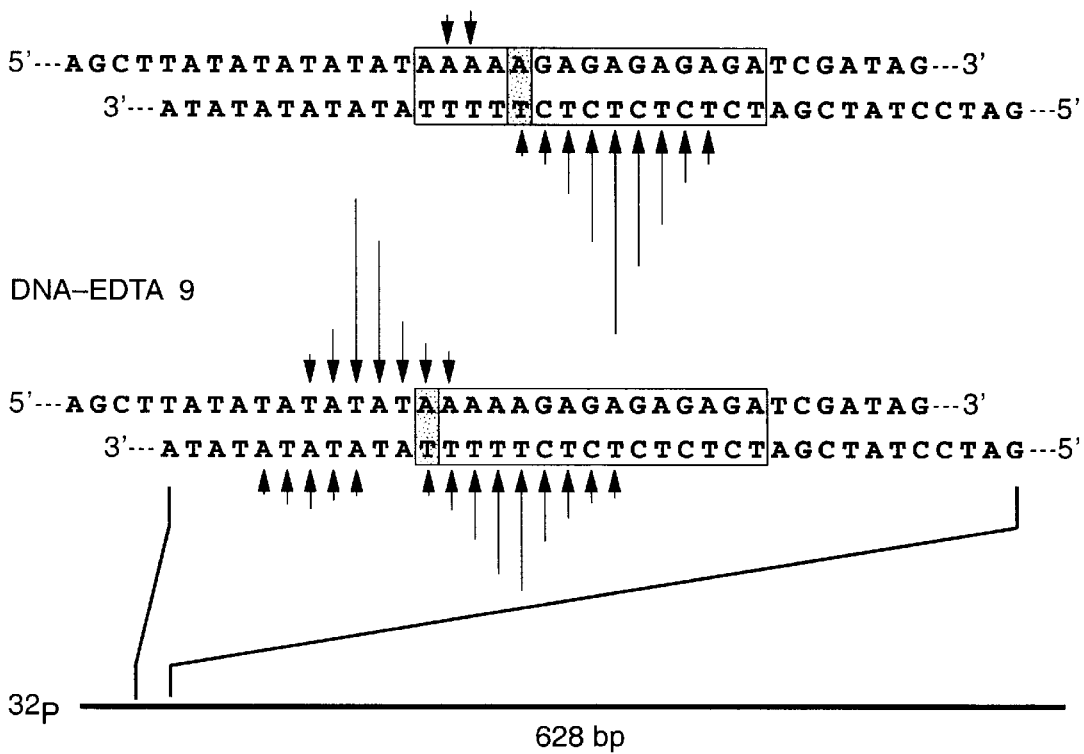
FIG._4B

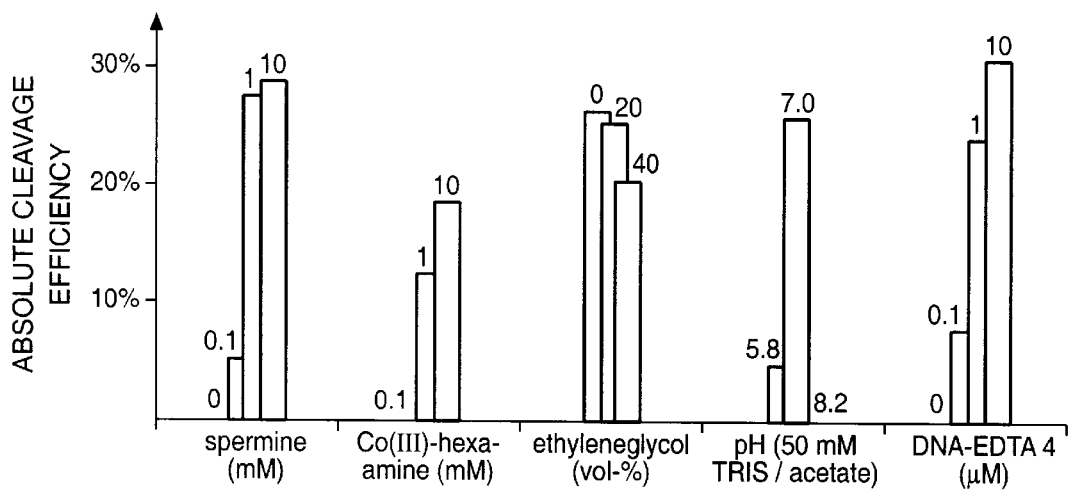
FIG._5A
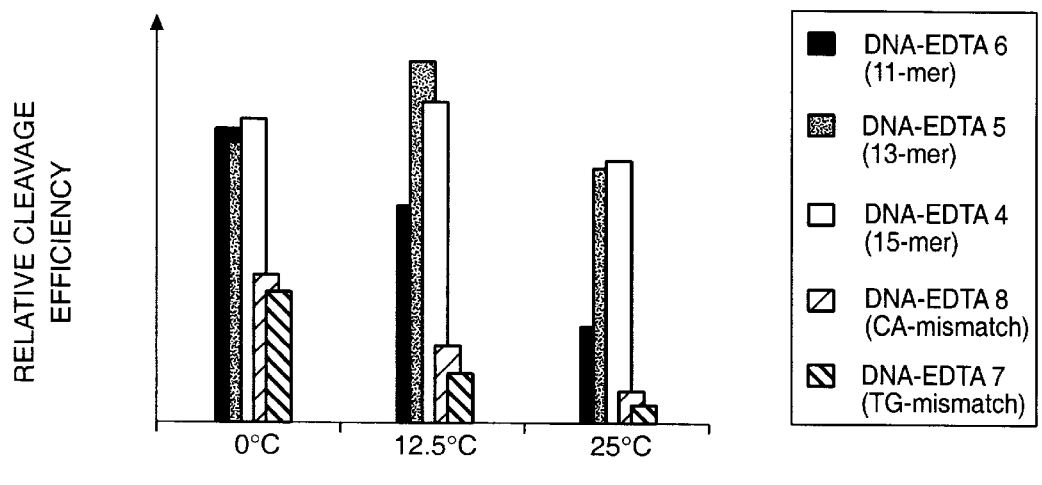
FIG._5B

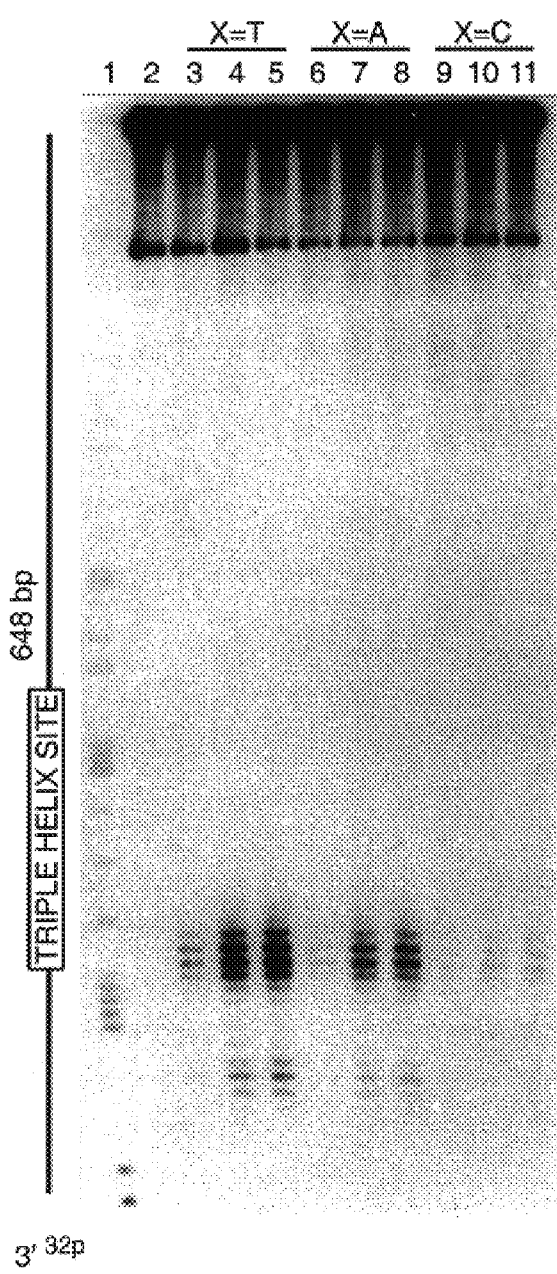
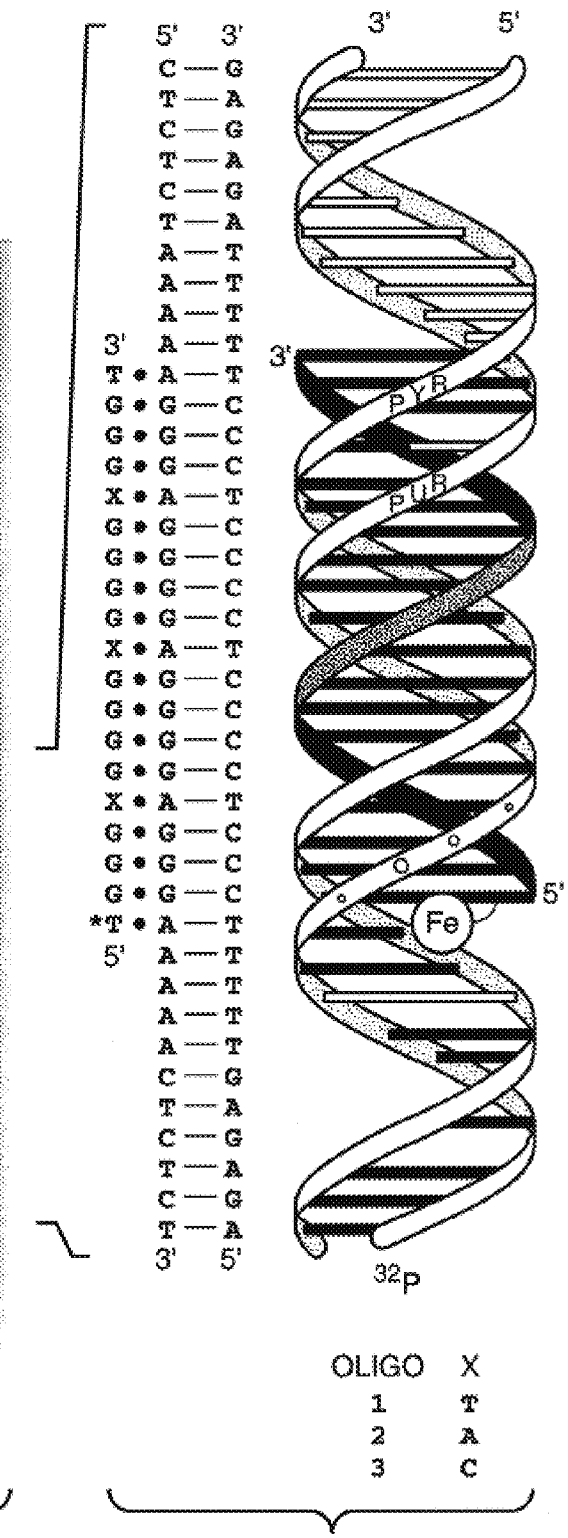
FIG._8A  FIG._8B

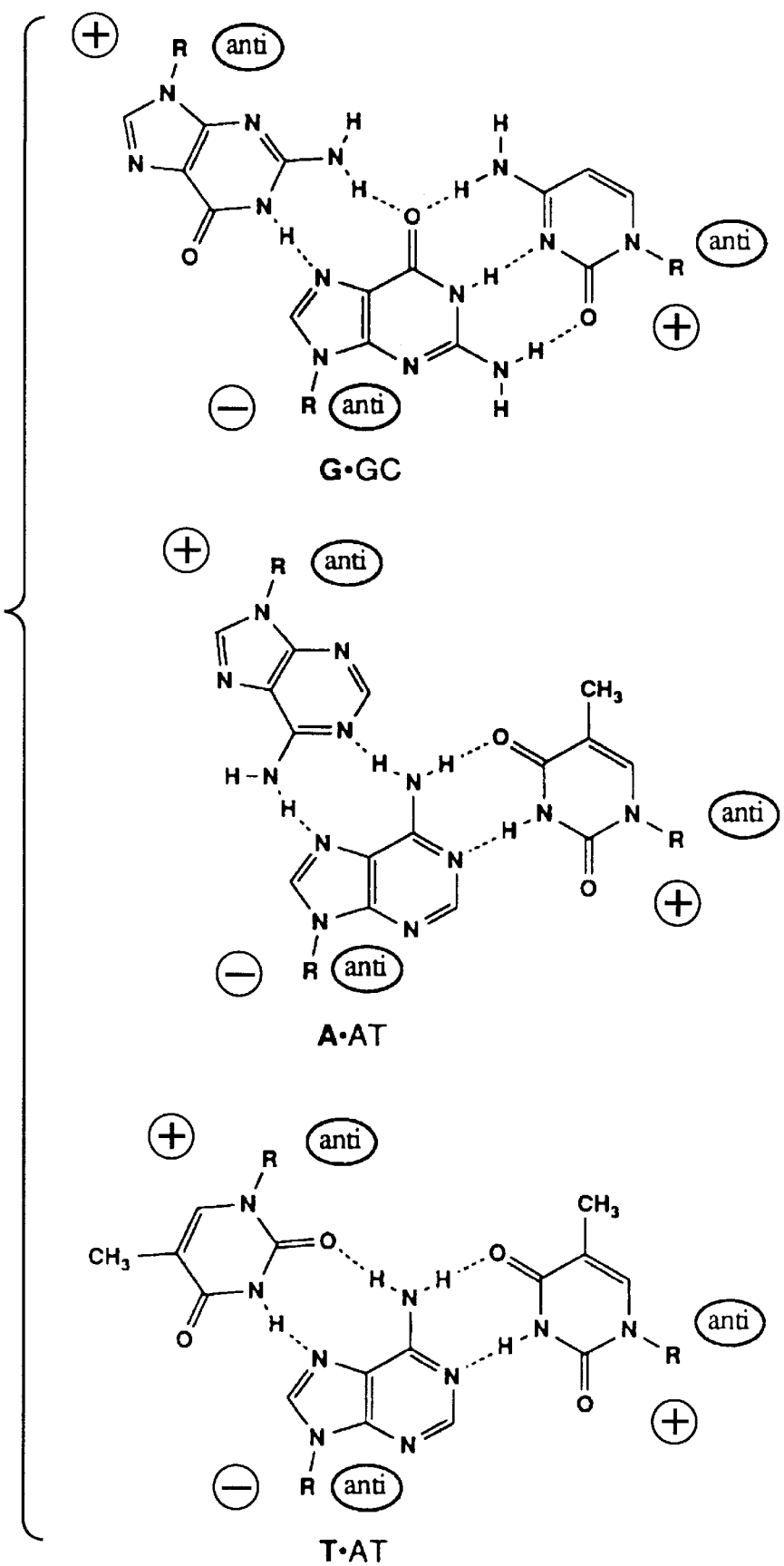
FIG._9A

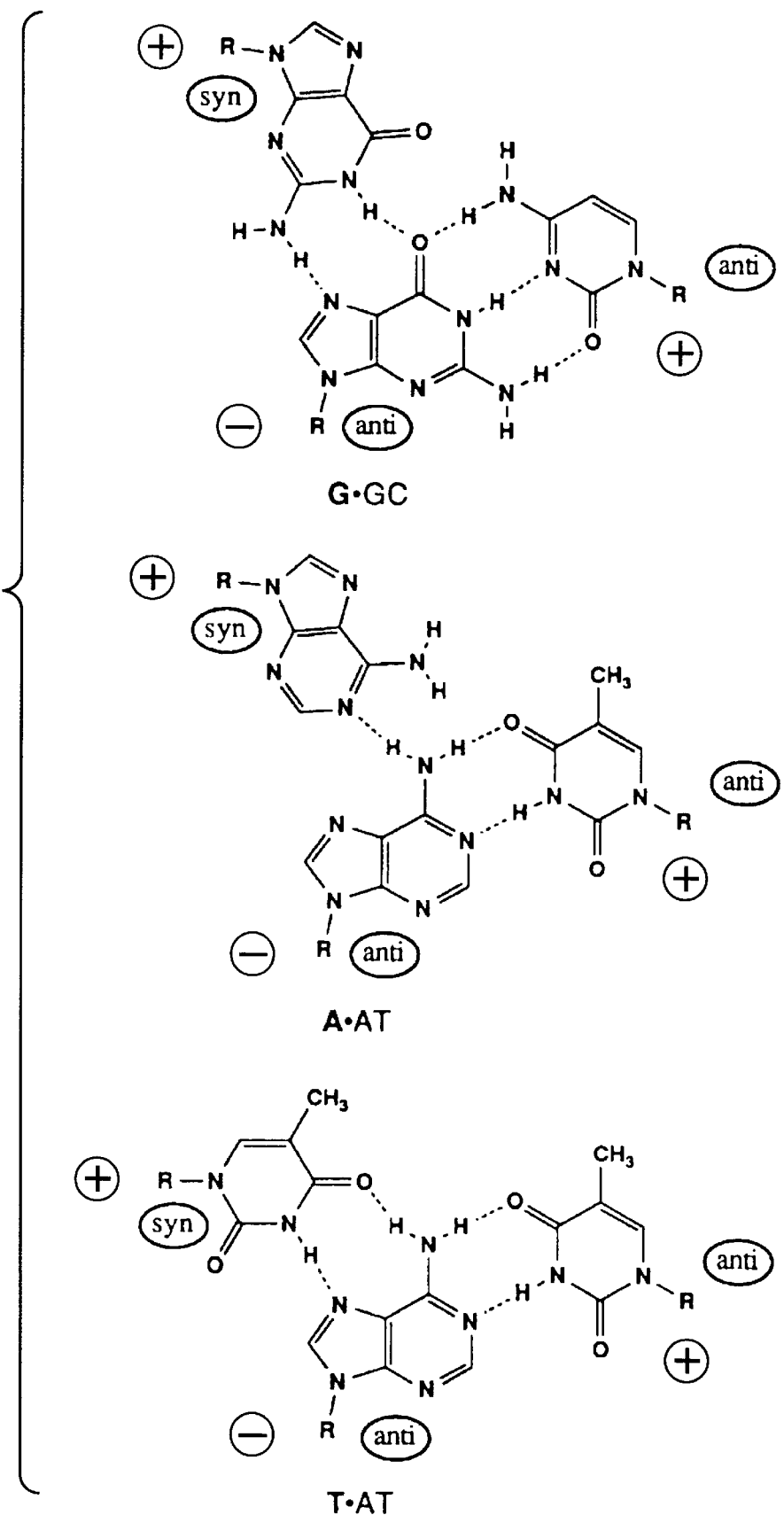
FIG._9B

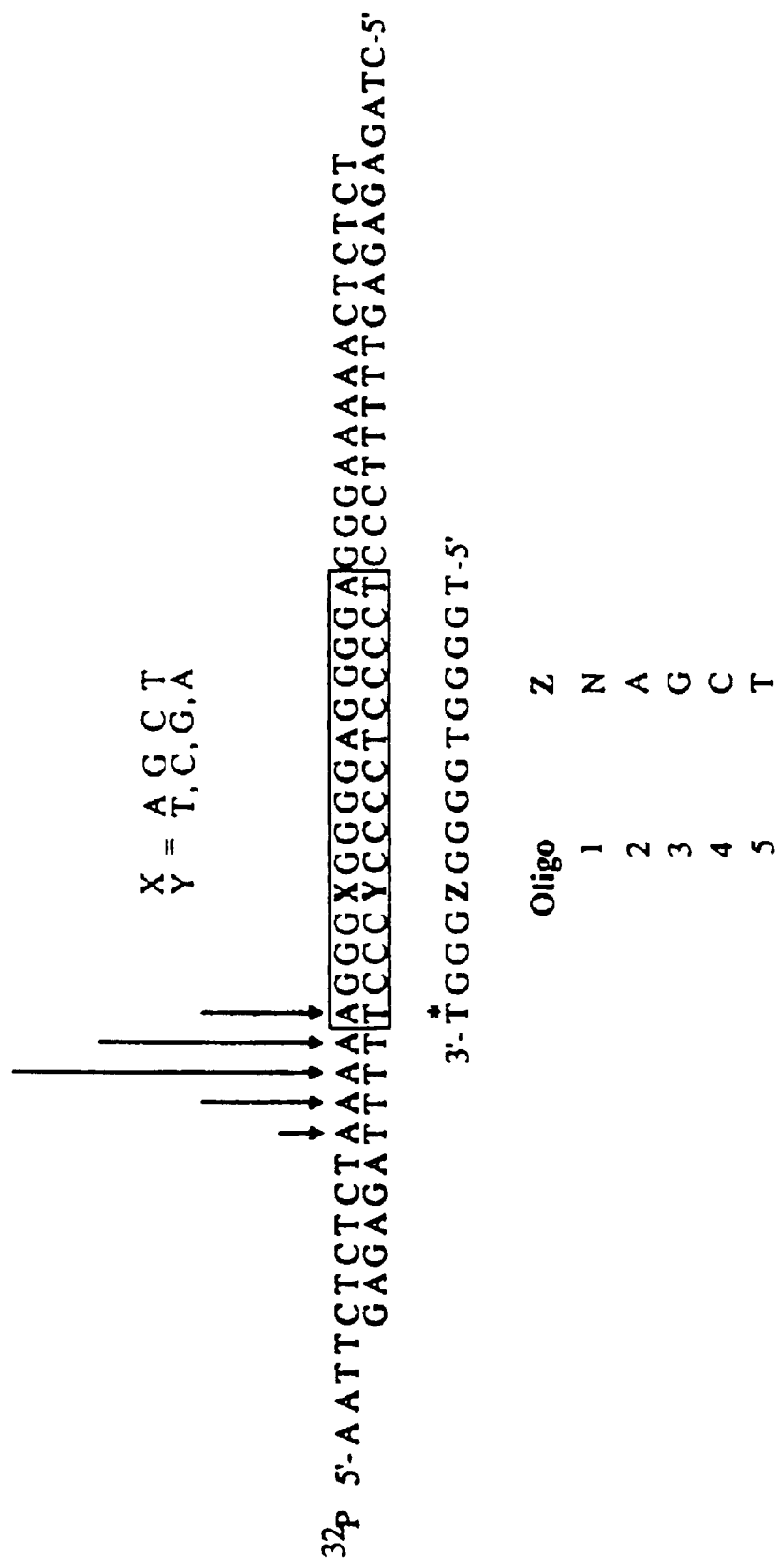
FIG._11

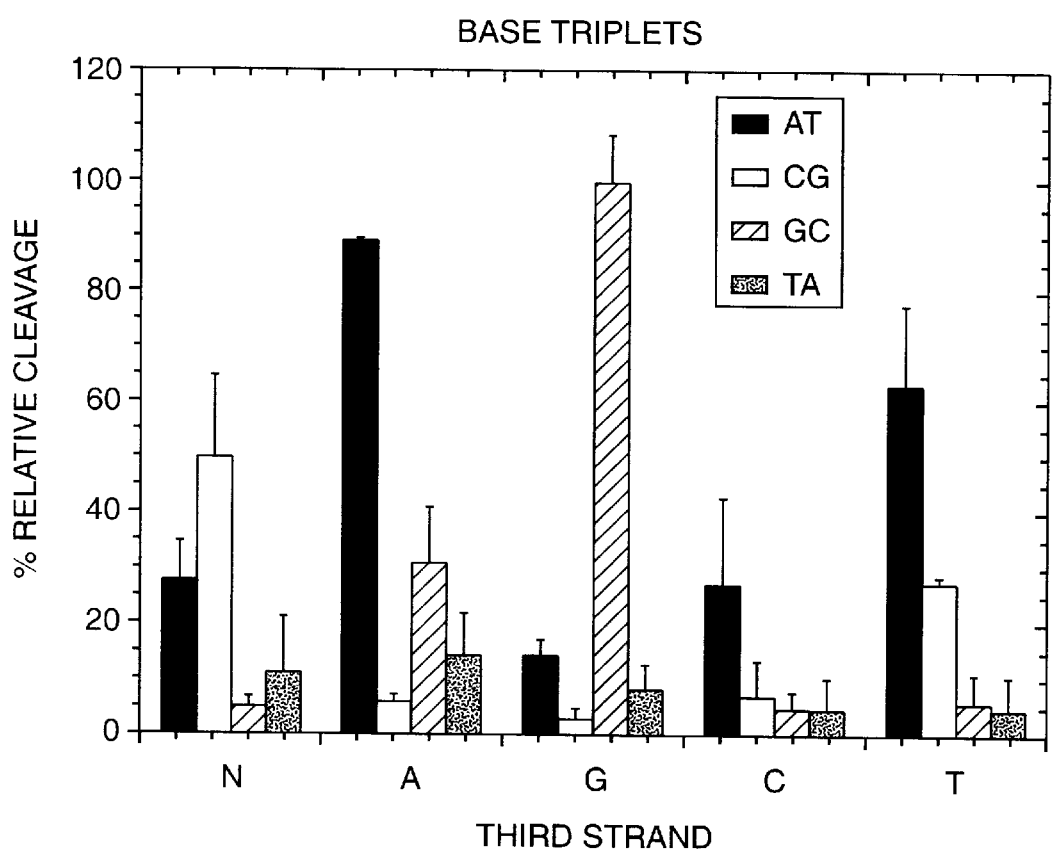
FIG._12

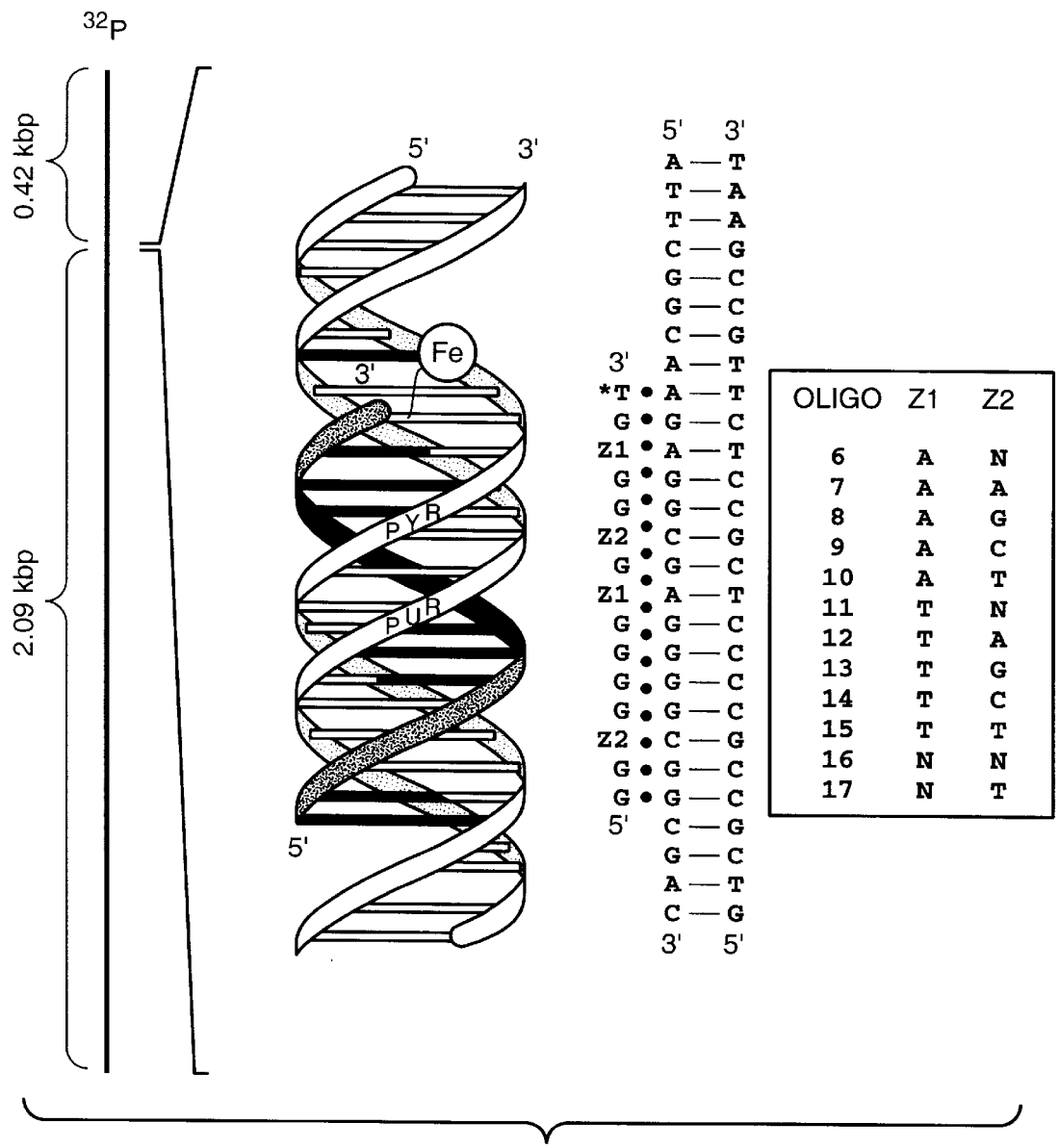
FIG._13

FIG._14
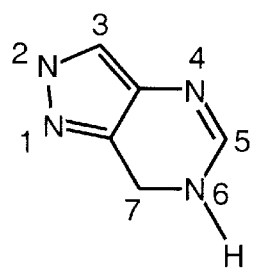
FIG._16A
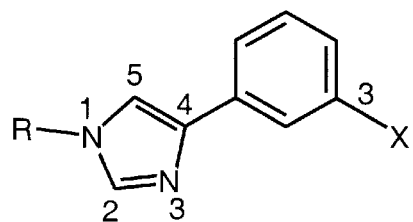
FIG._16B
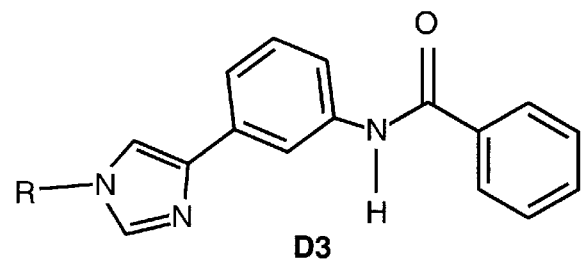

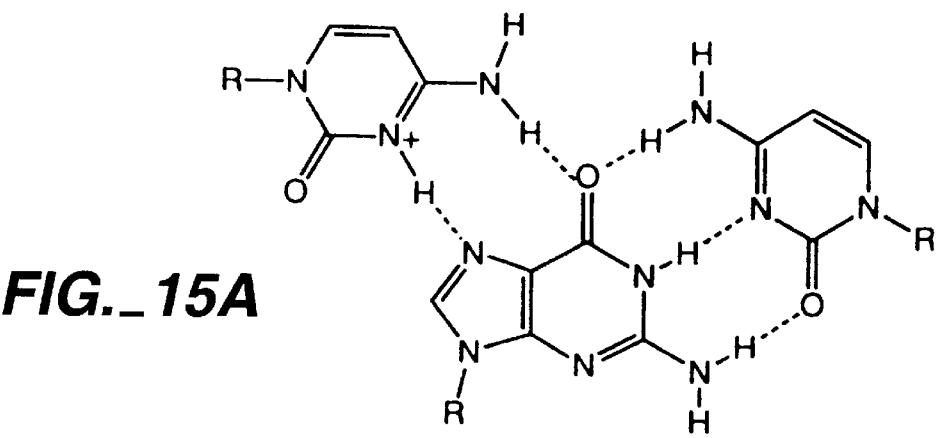
FIG._15A
C+GC
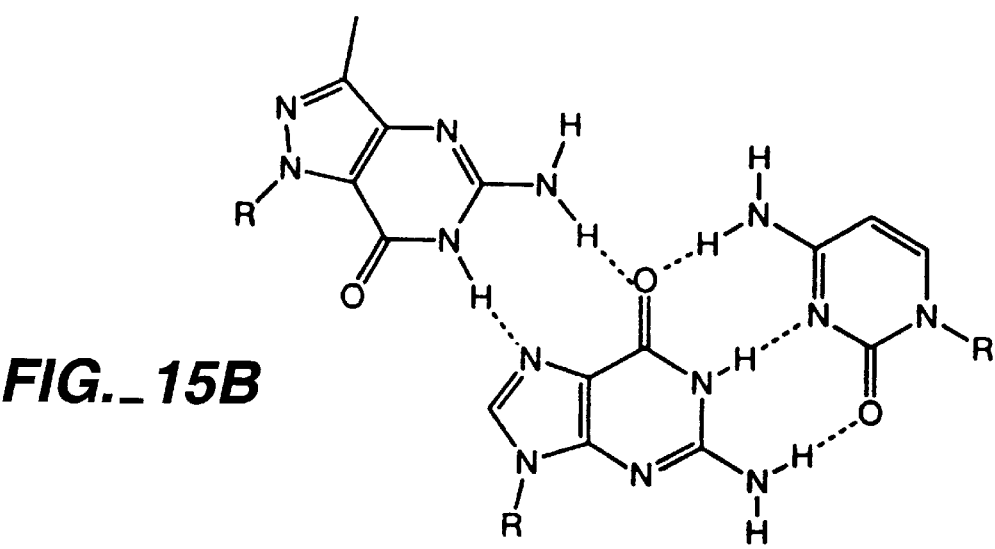
FIG._15B
P1·GC
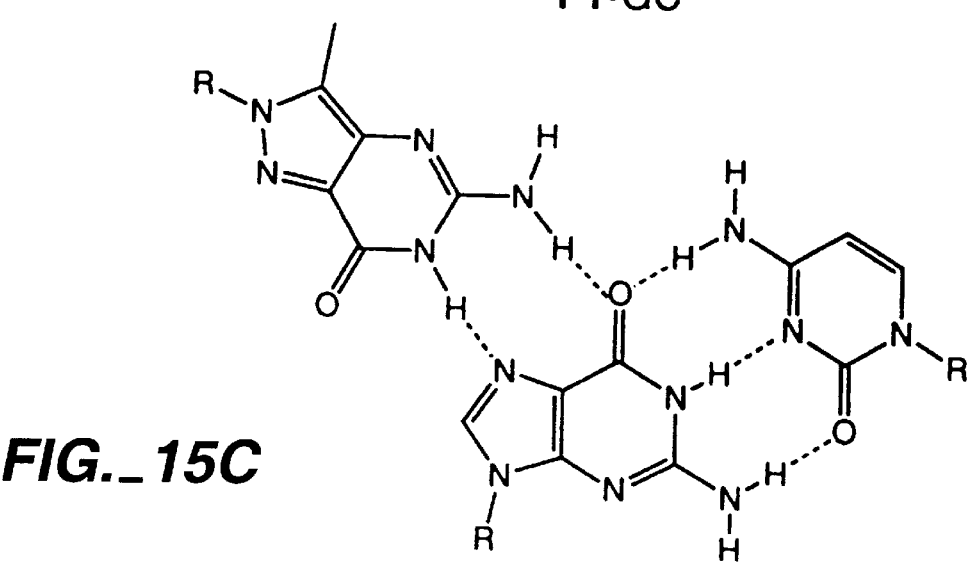
FIG._15C
P2·GC

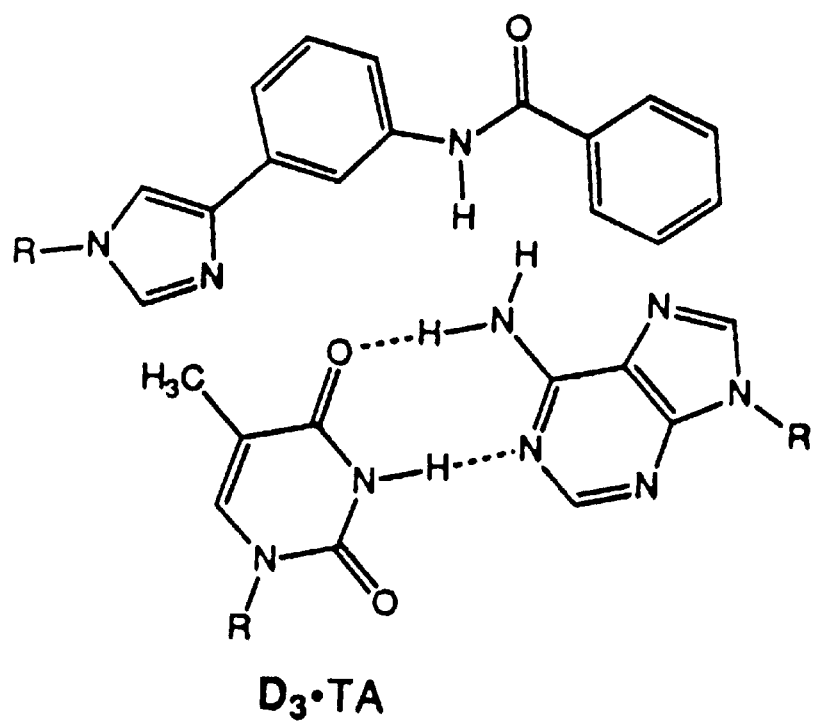
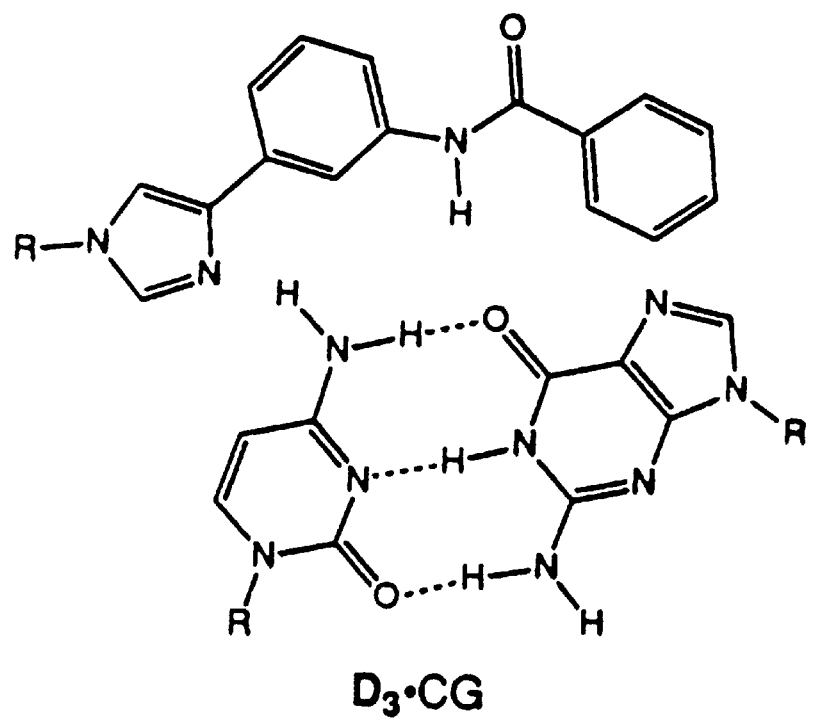
FIG._17

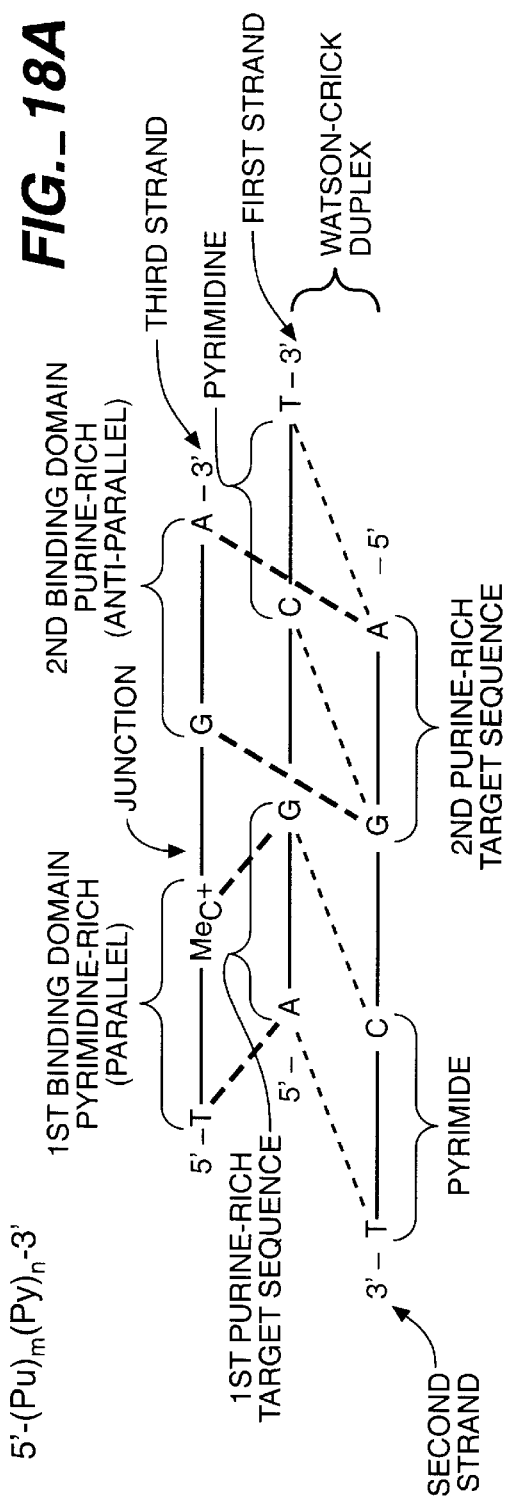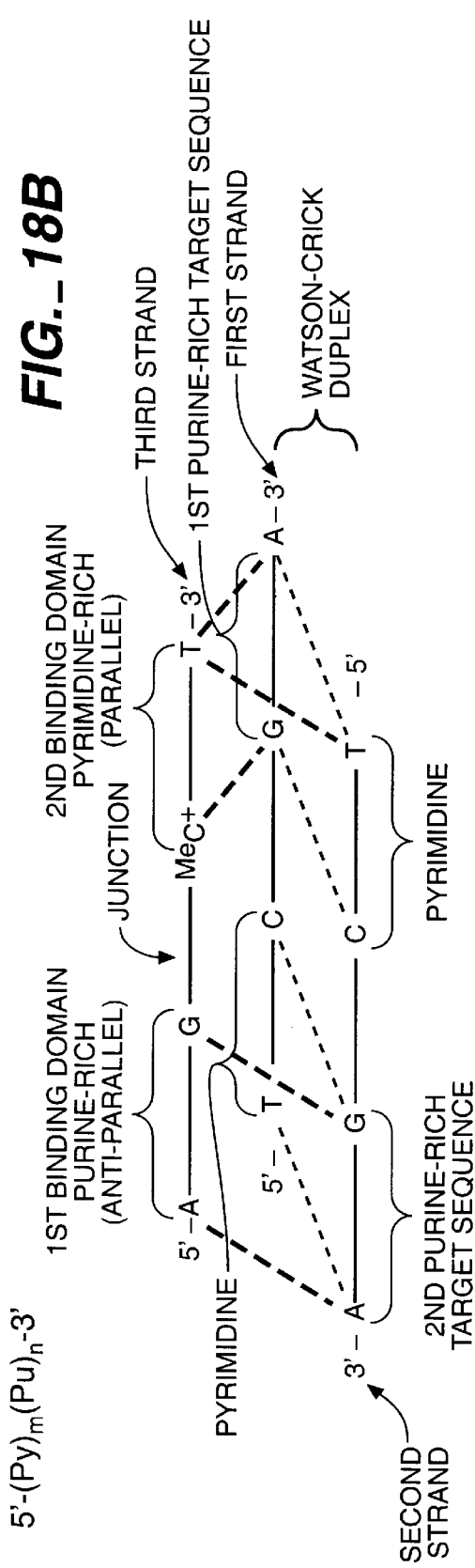

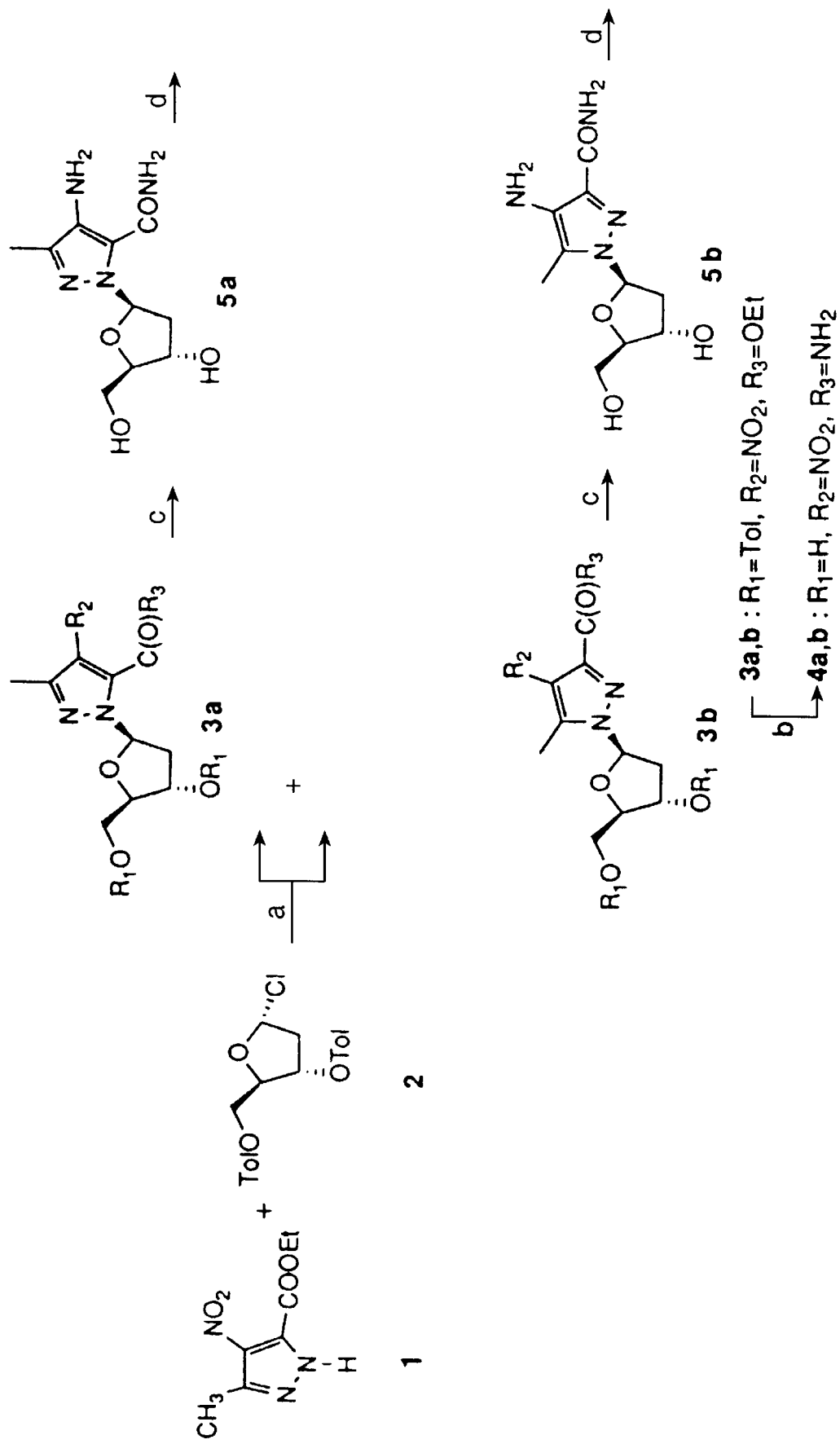
FIG._19A

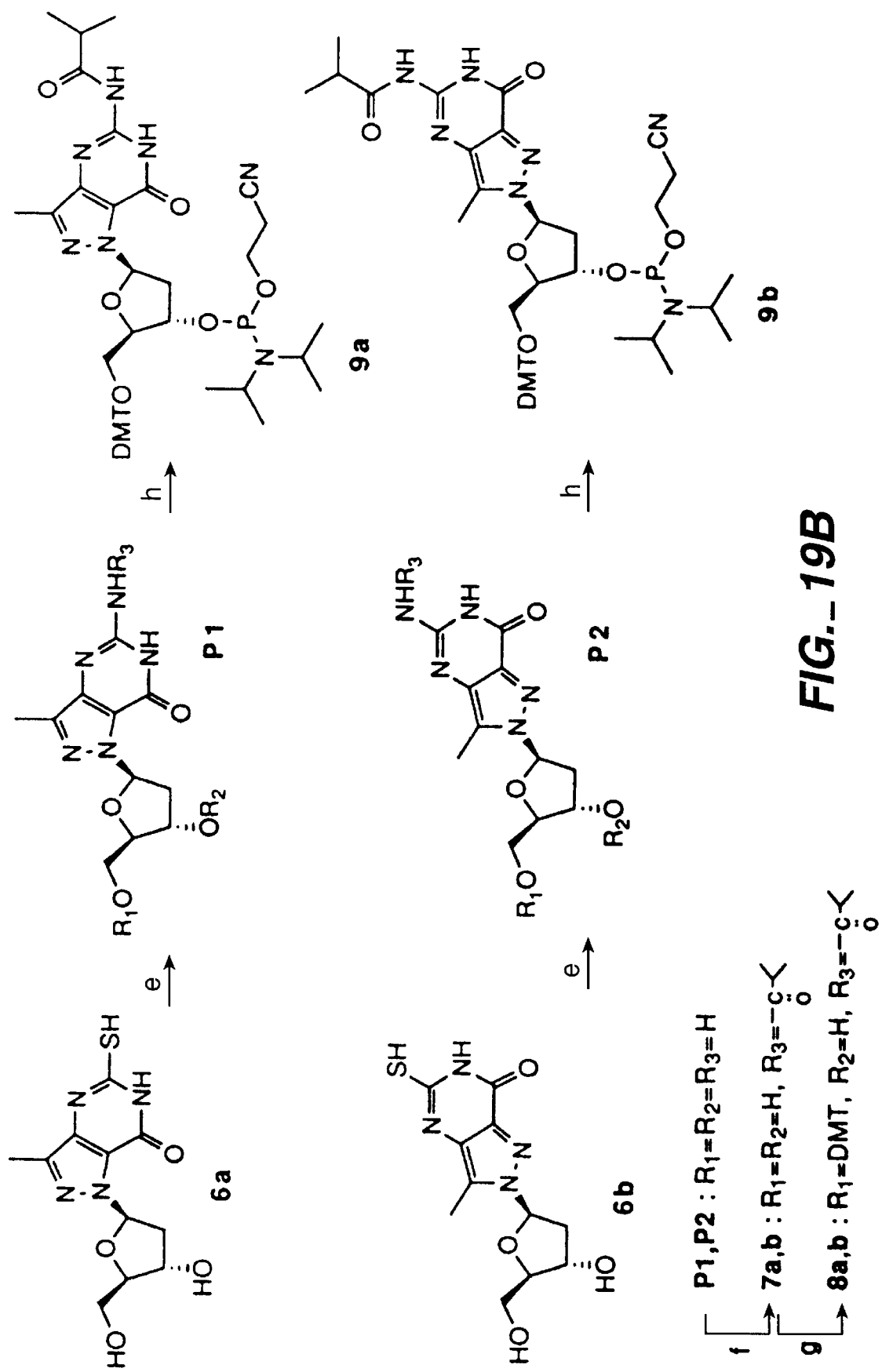
FIG._19B

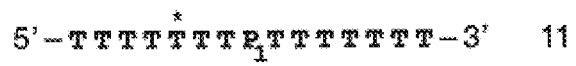
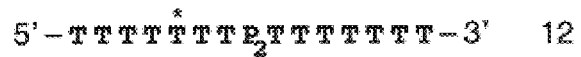
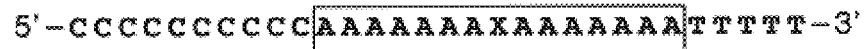
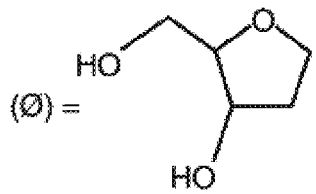
FIG._20A
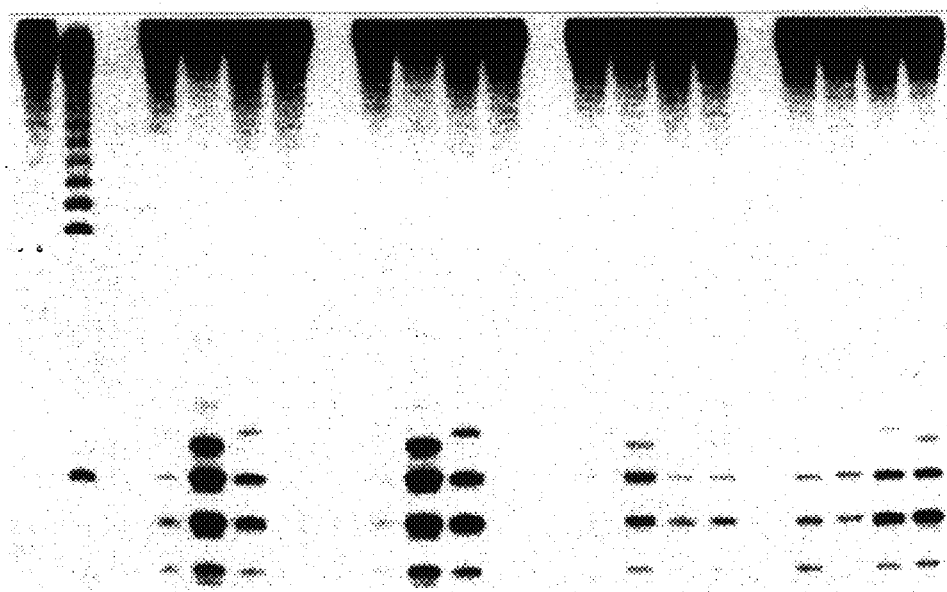
FIG._20B

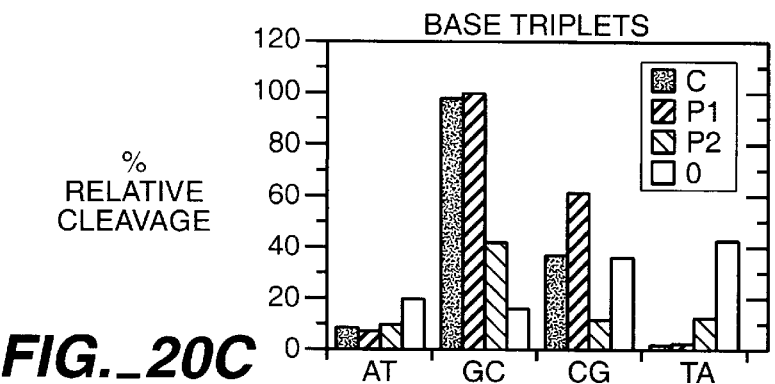
FIG._20C
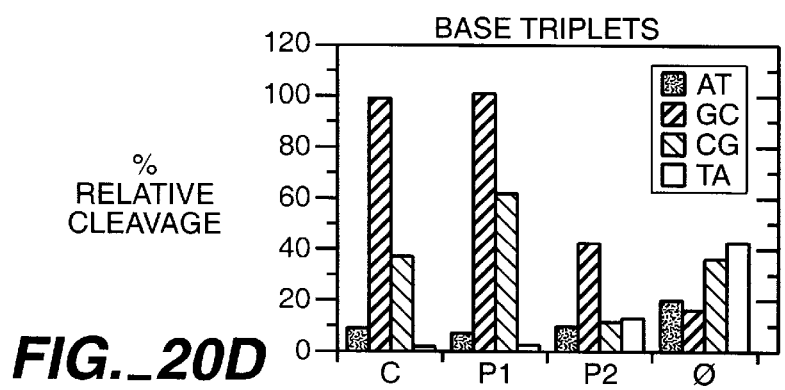
FIG._20D
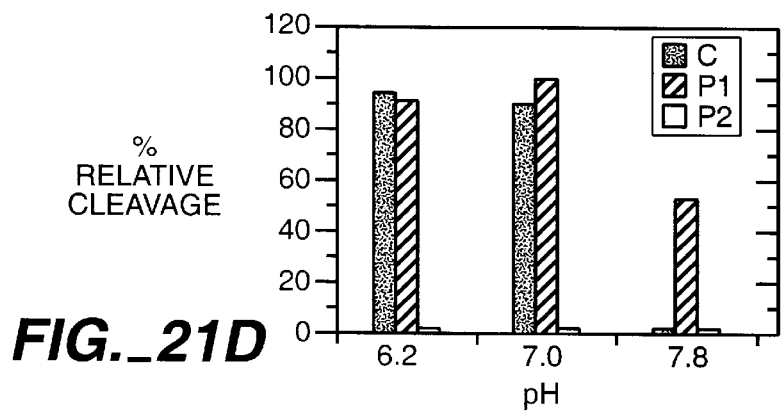
FIG._21D
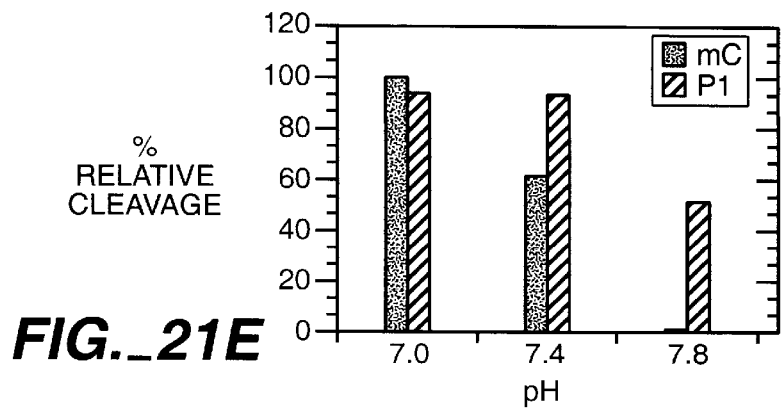
FIG._21E

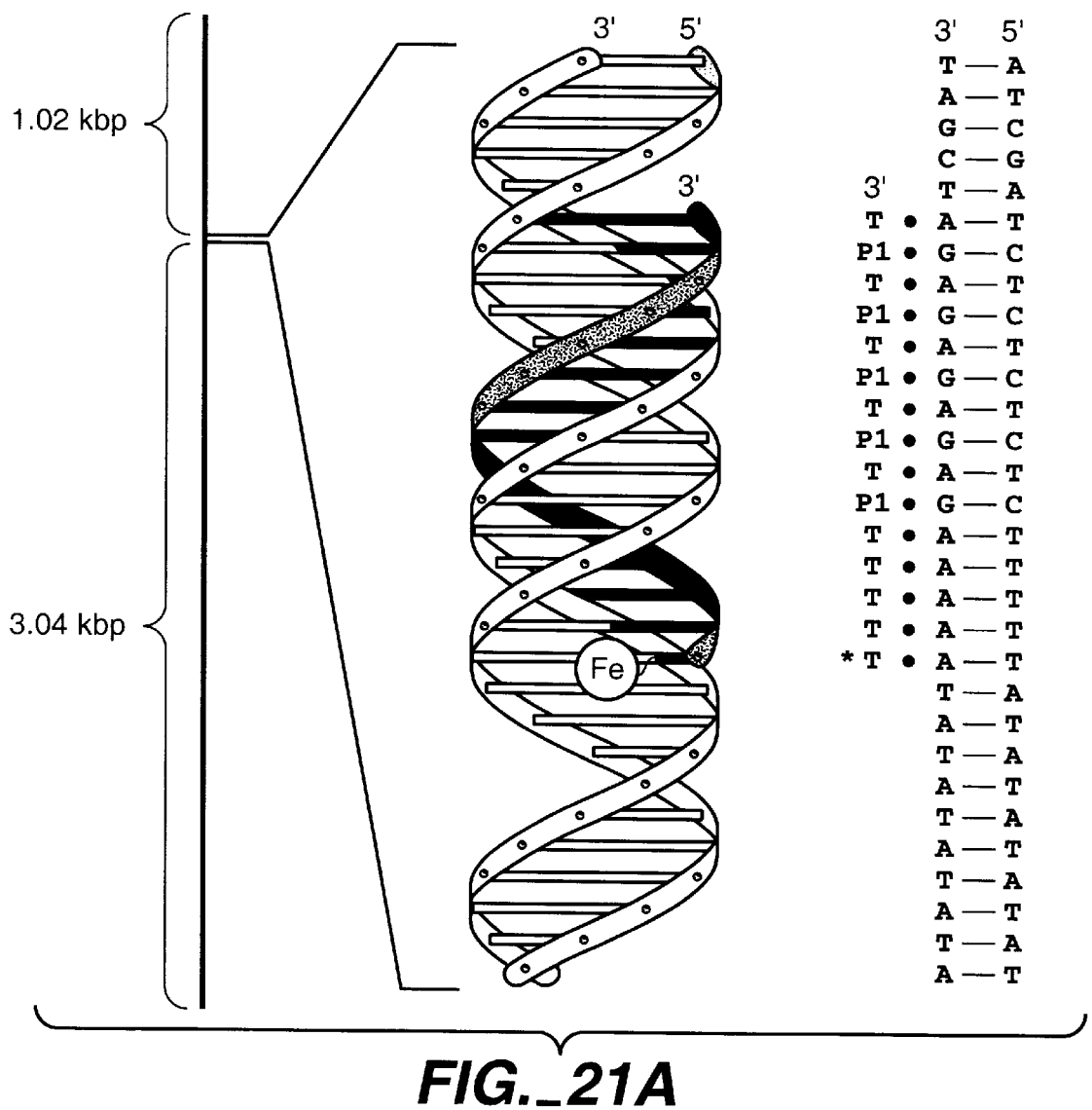
FIG._21A

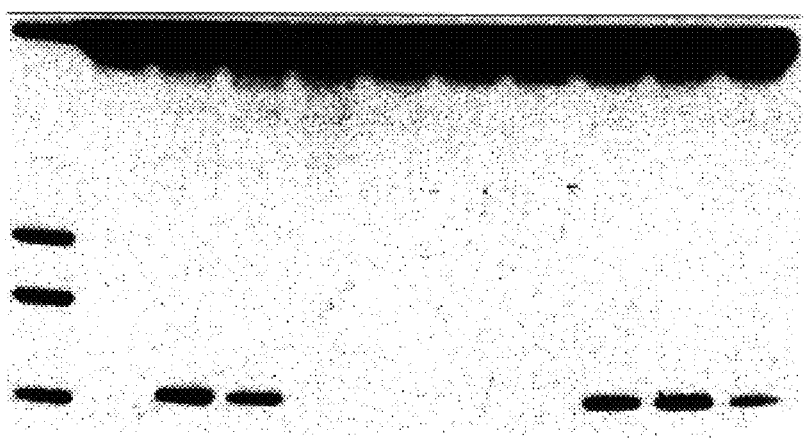
FIG._21B
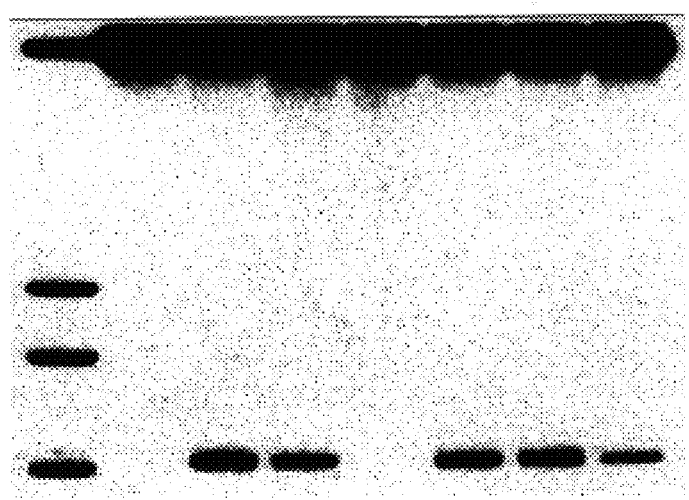
FIG._21C

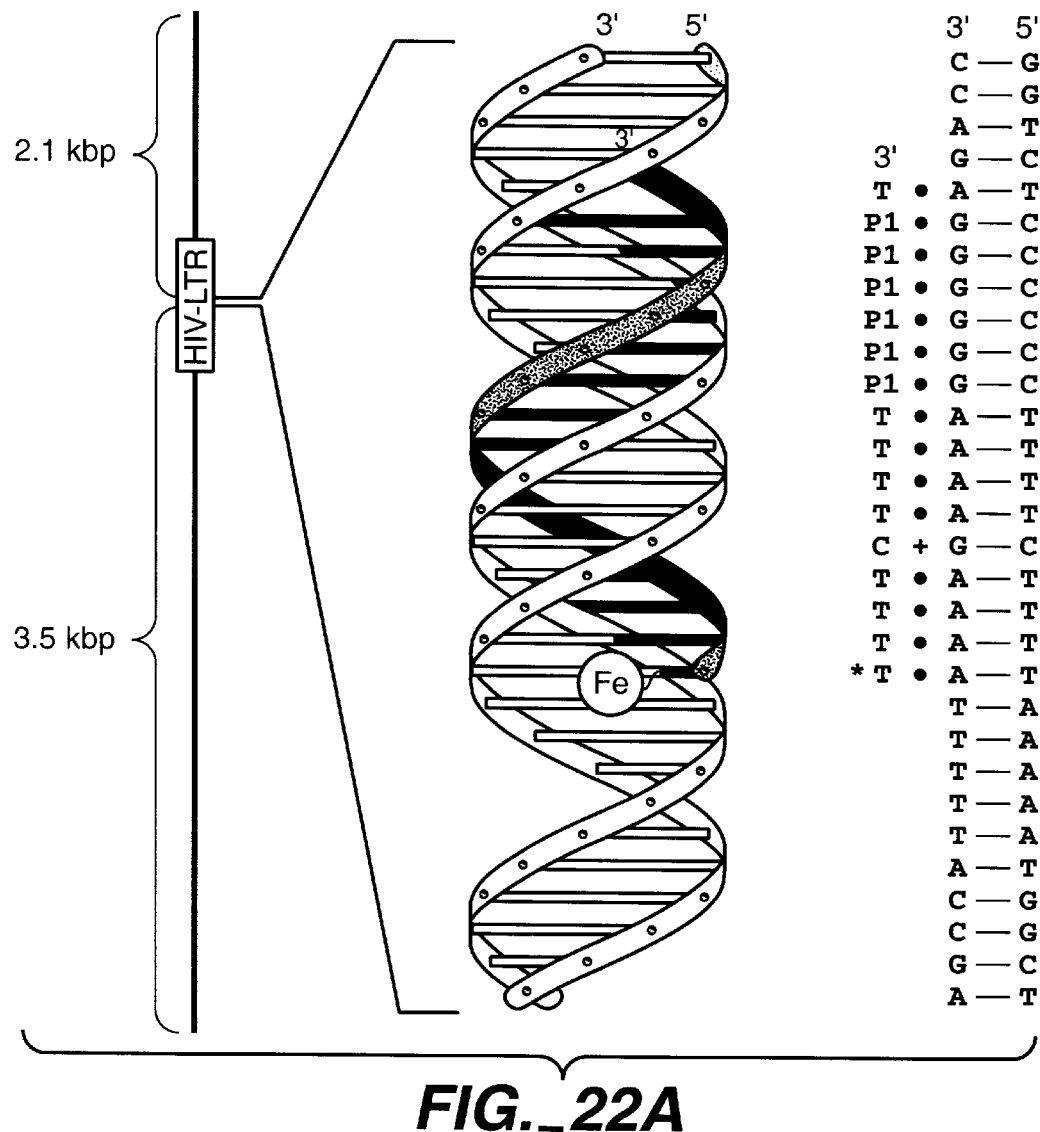
FIG._22A

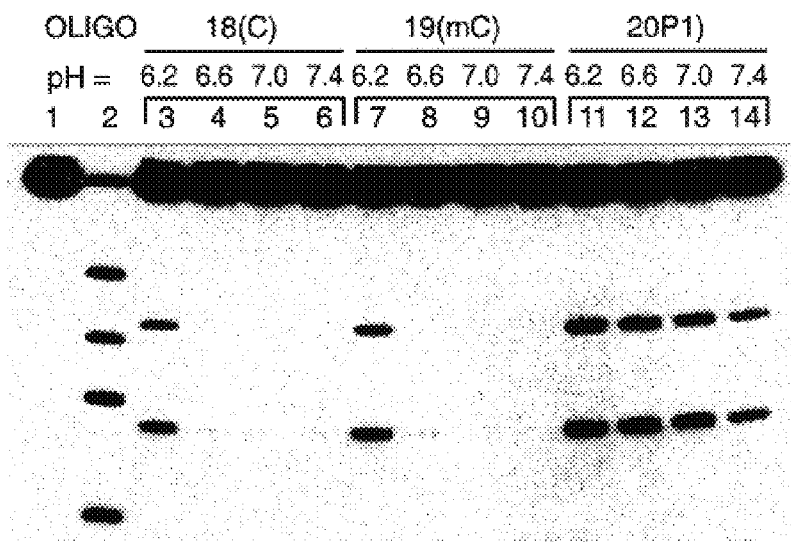
FIG._22B
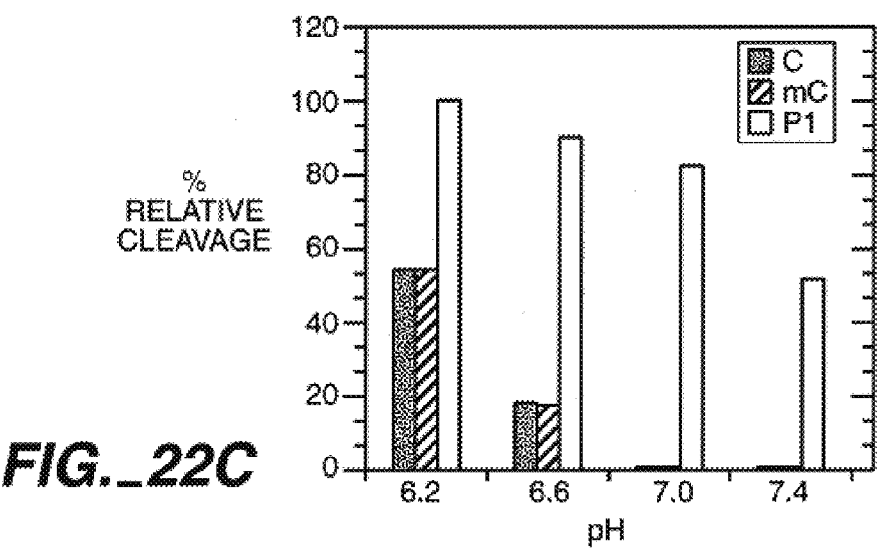
FIG._22C
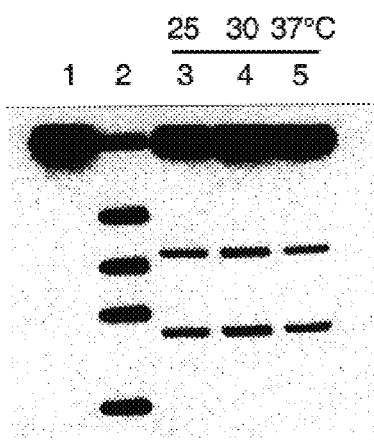
FIG._22D

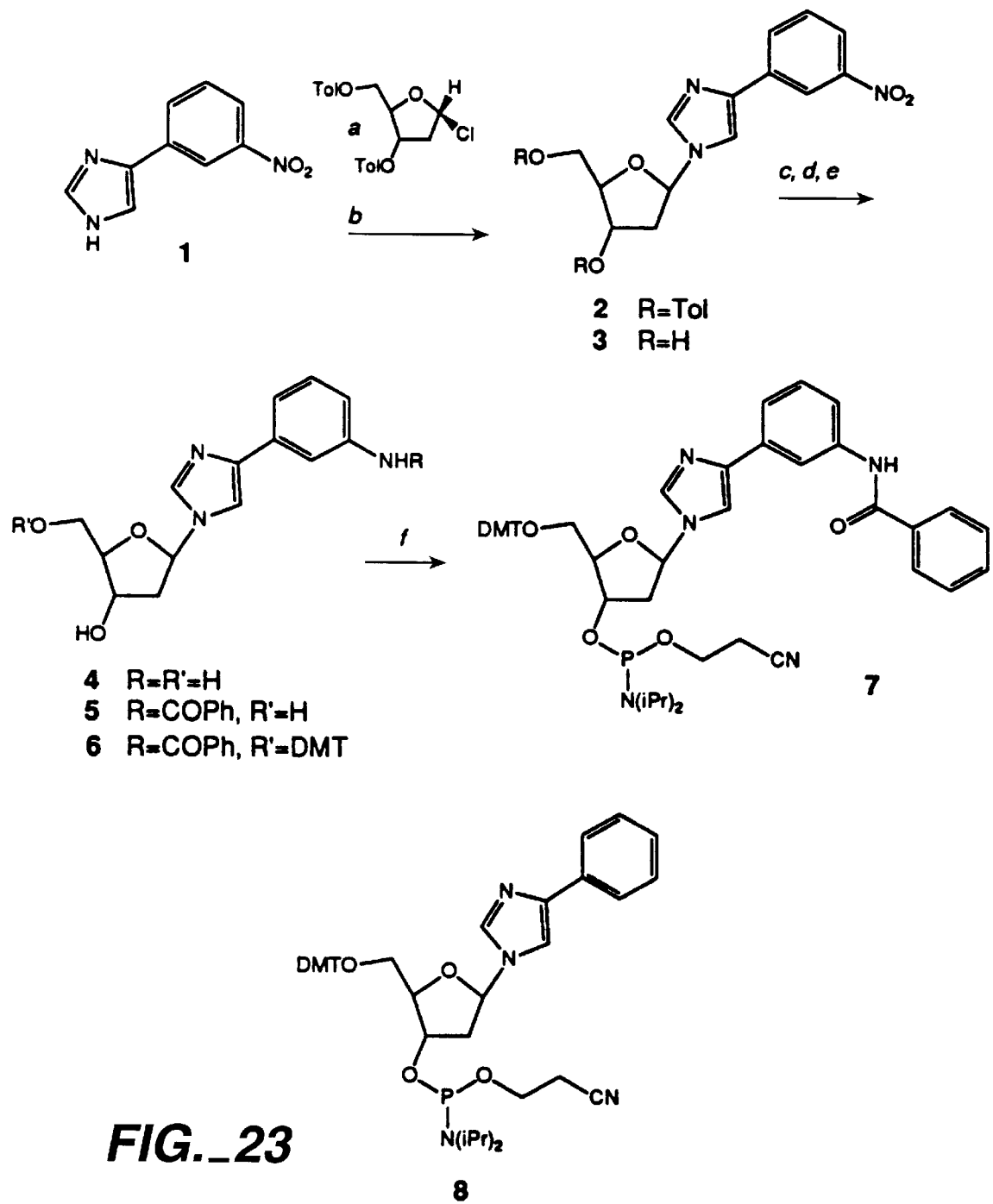
FIG._23

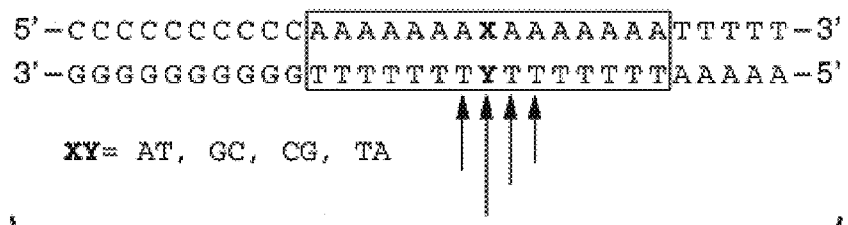
FIG._24A
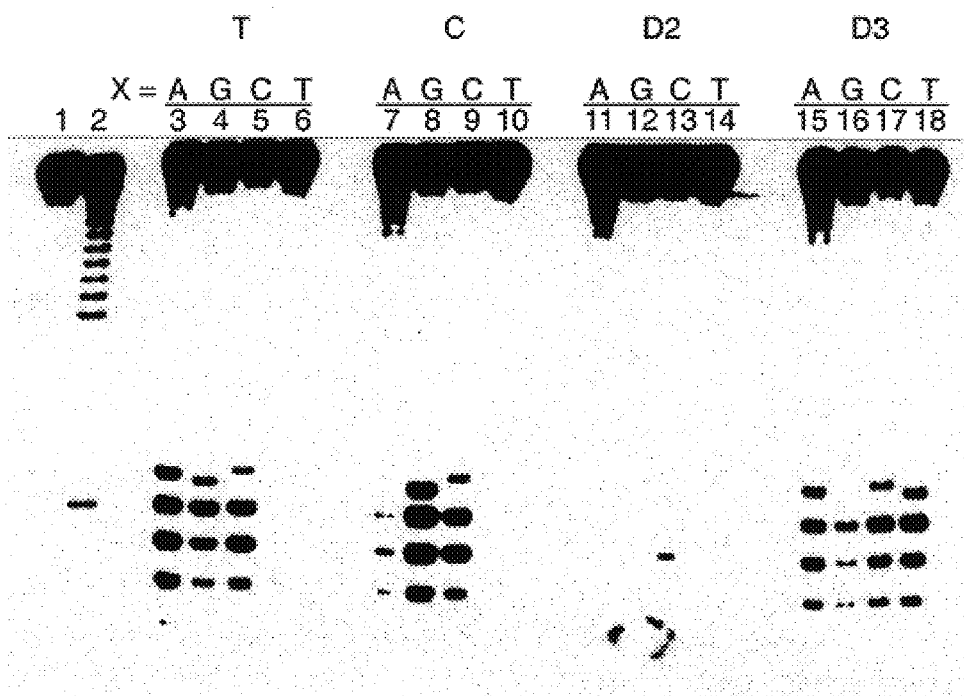
FIG._24B

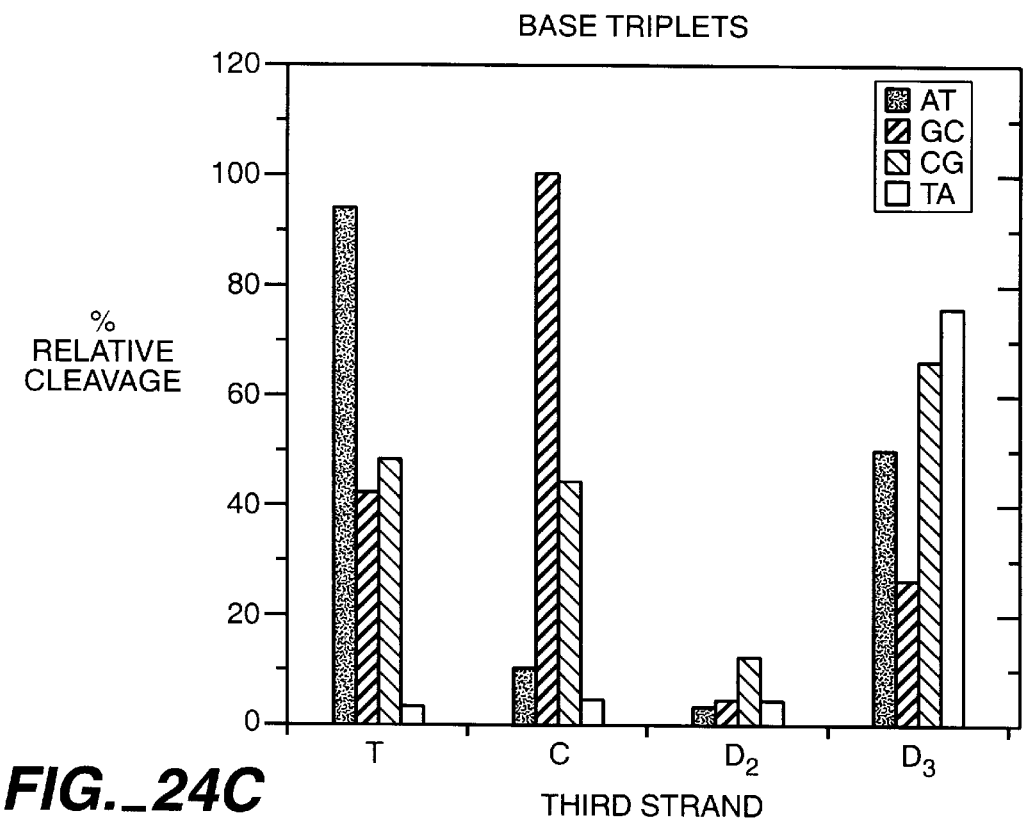
FIG._24C
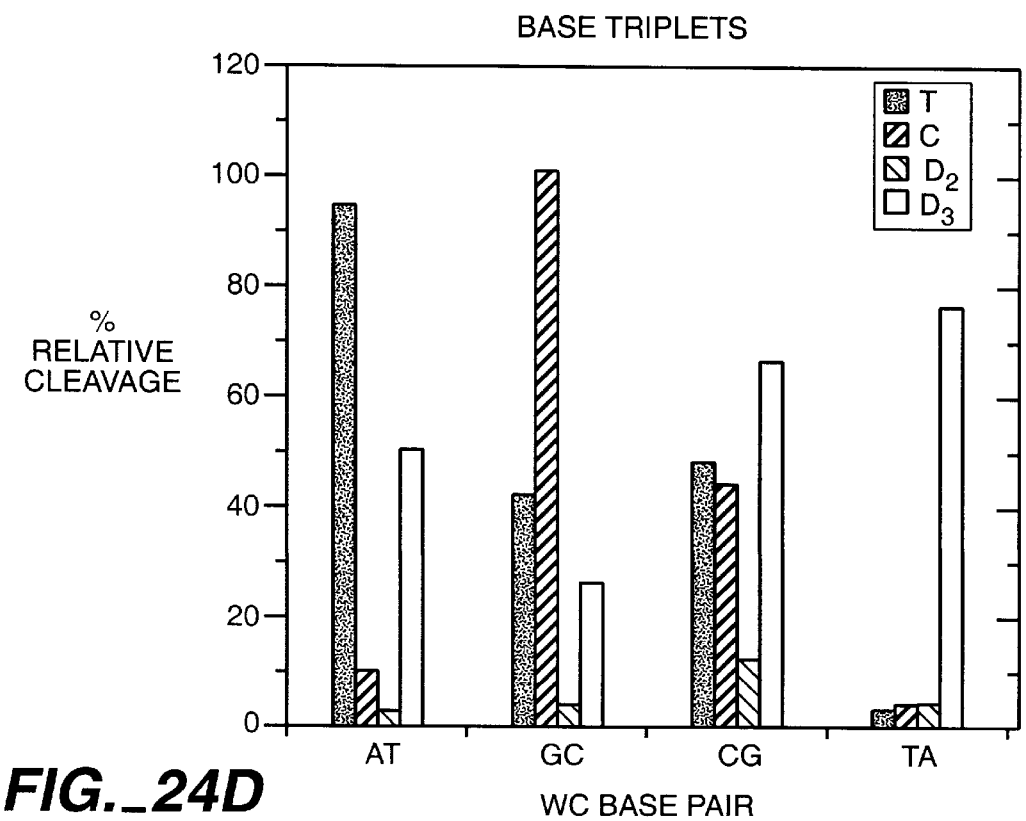
FIG._24D

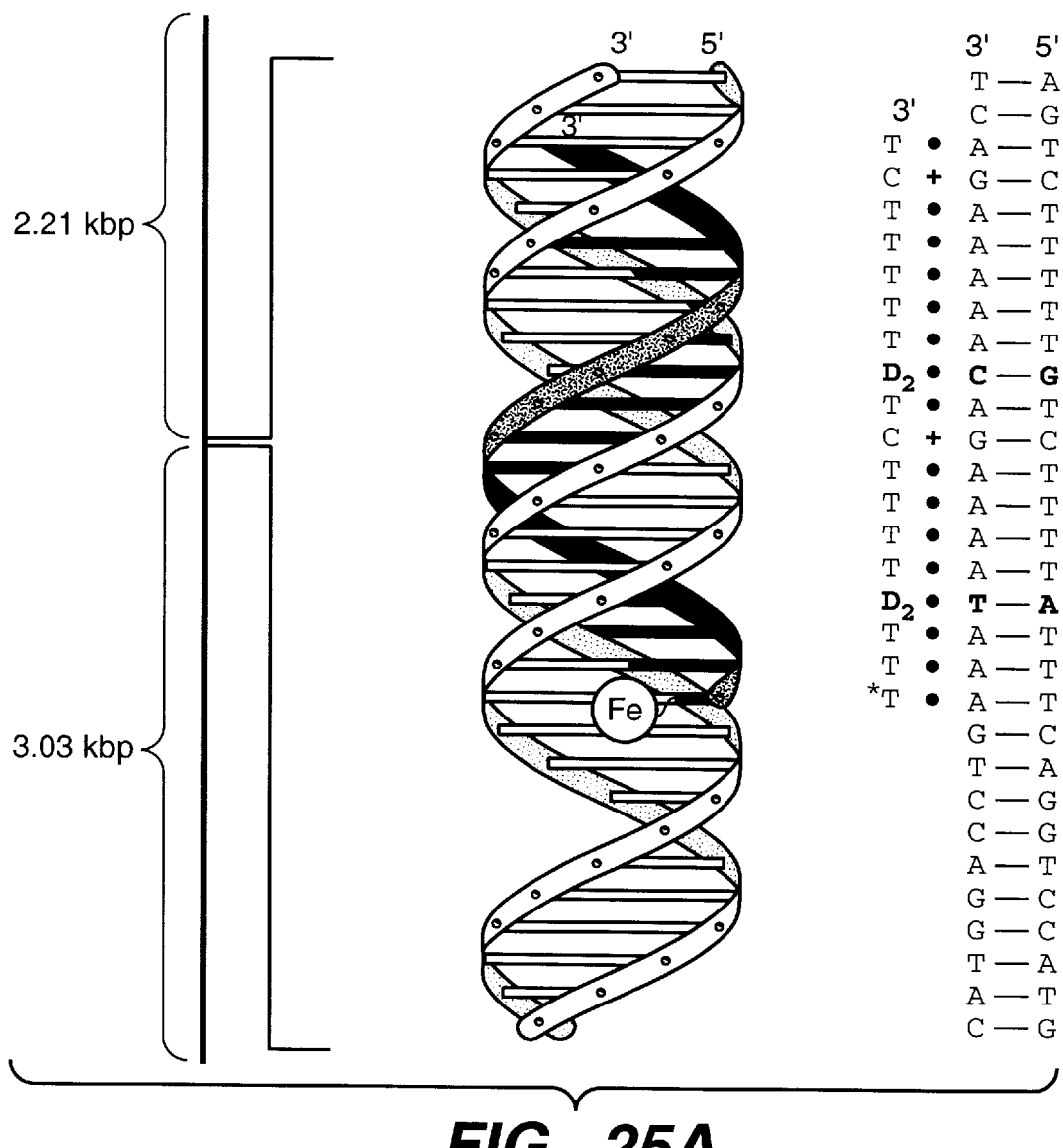
FIG._25A

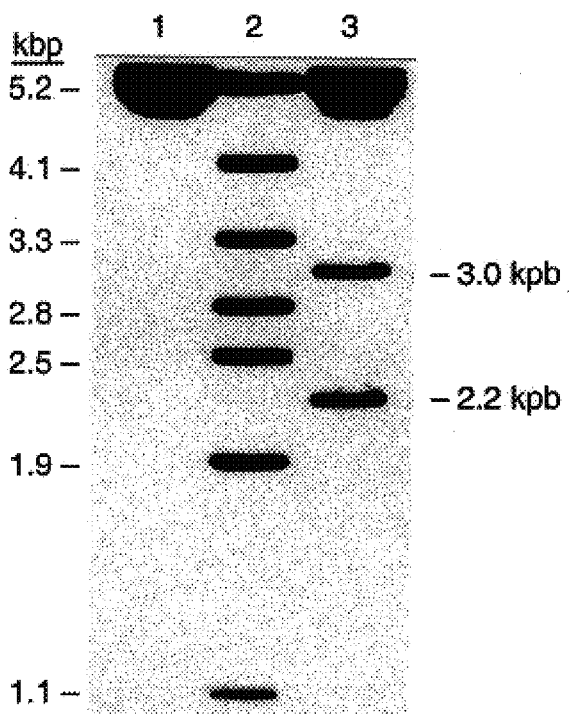
FIG._25B
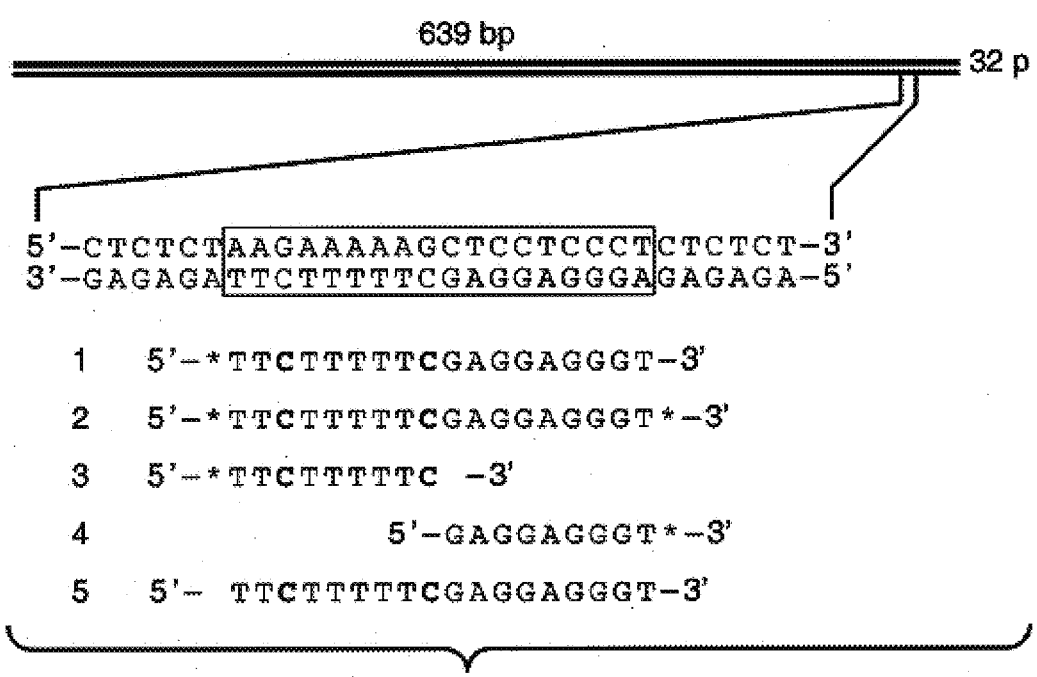
FIG._26

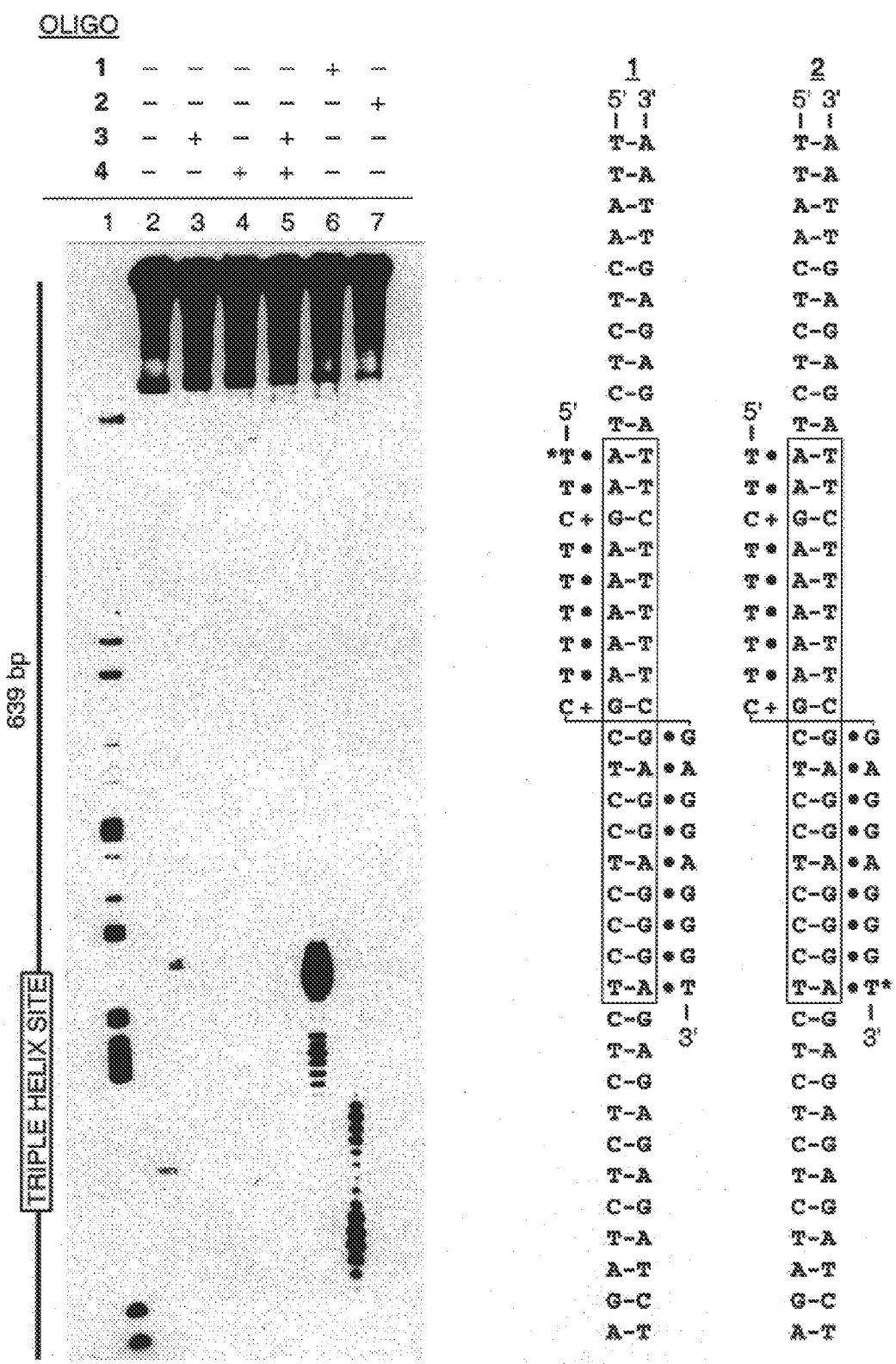
FIG._27

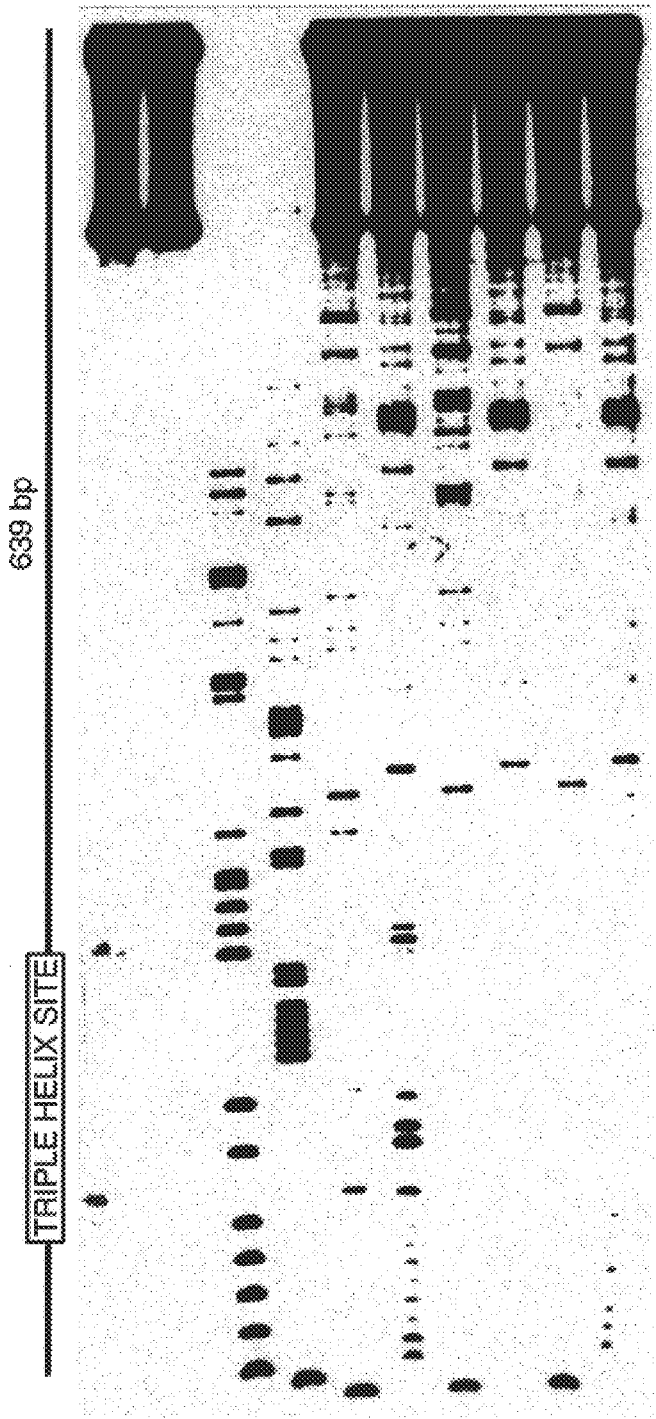
FIG._28

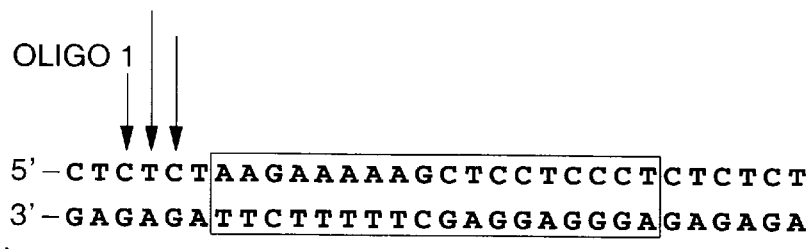
FIG._30A
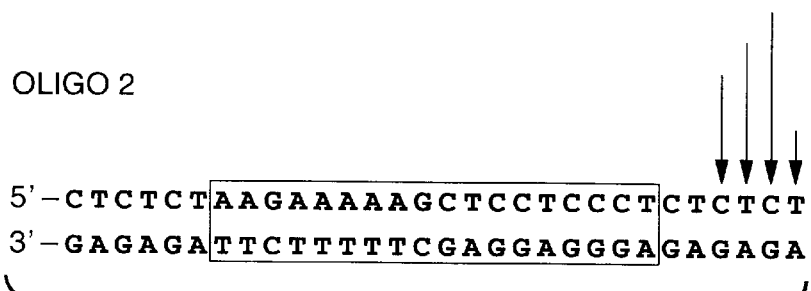
FIG._30B
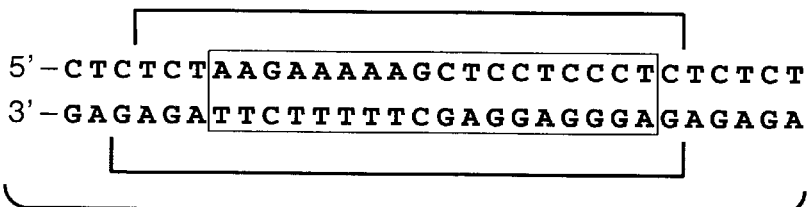
FIG._30C
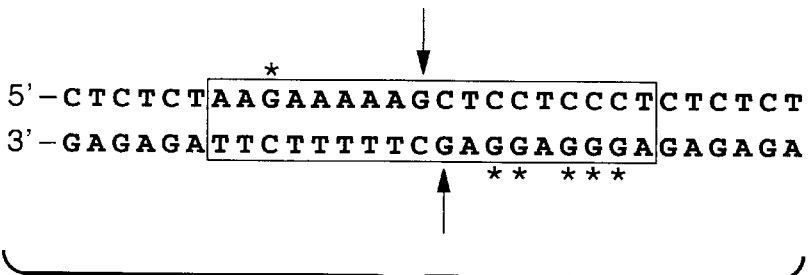
FIG._30D

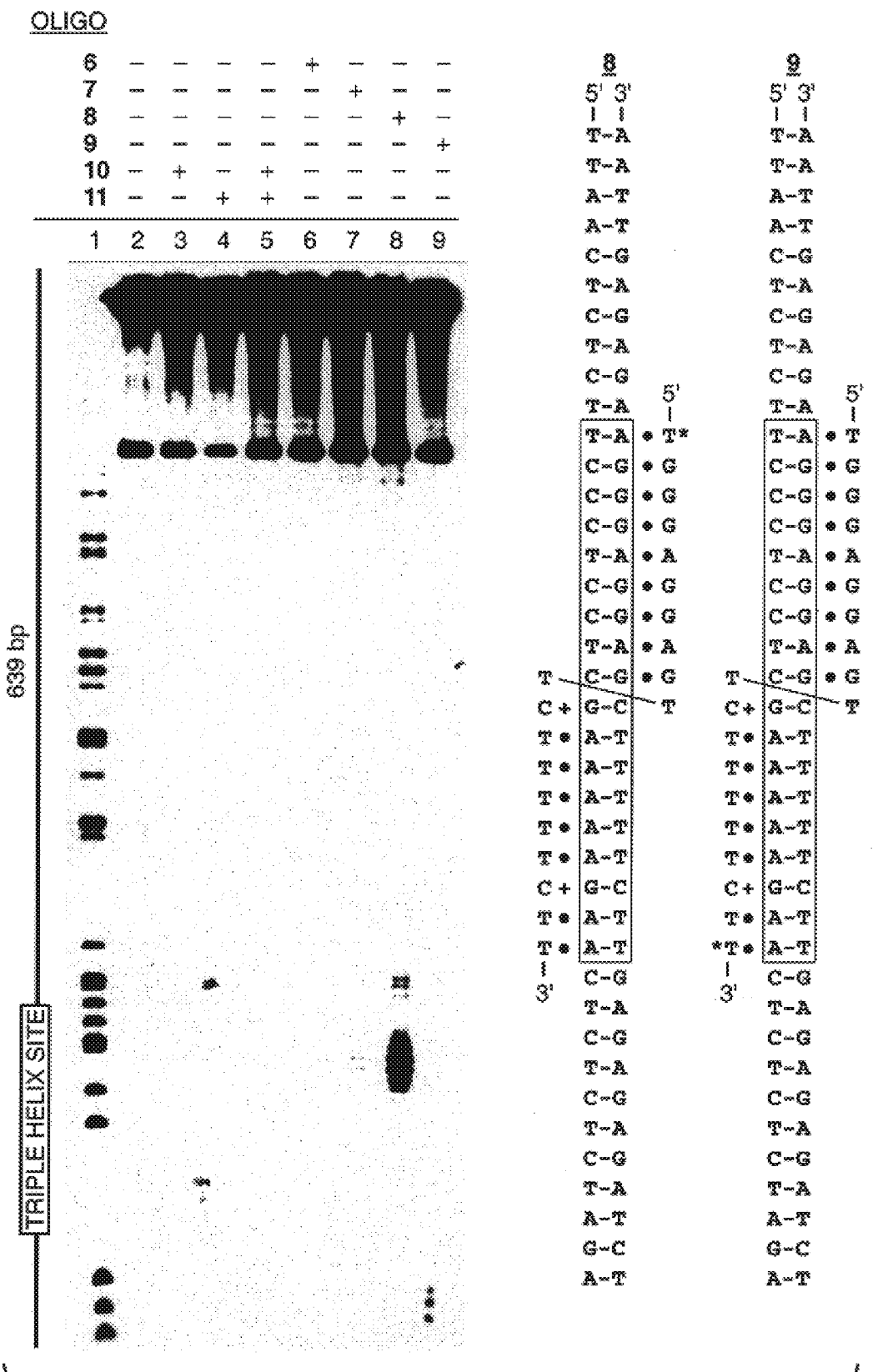
FIG._32

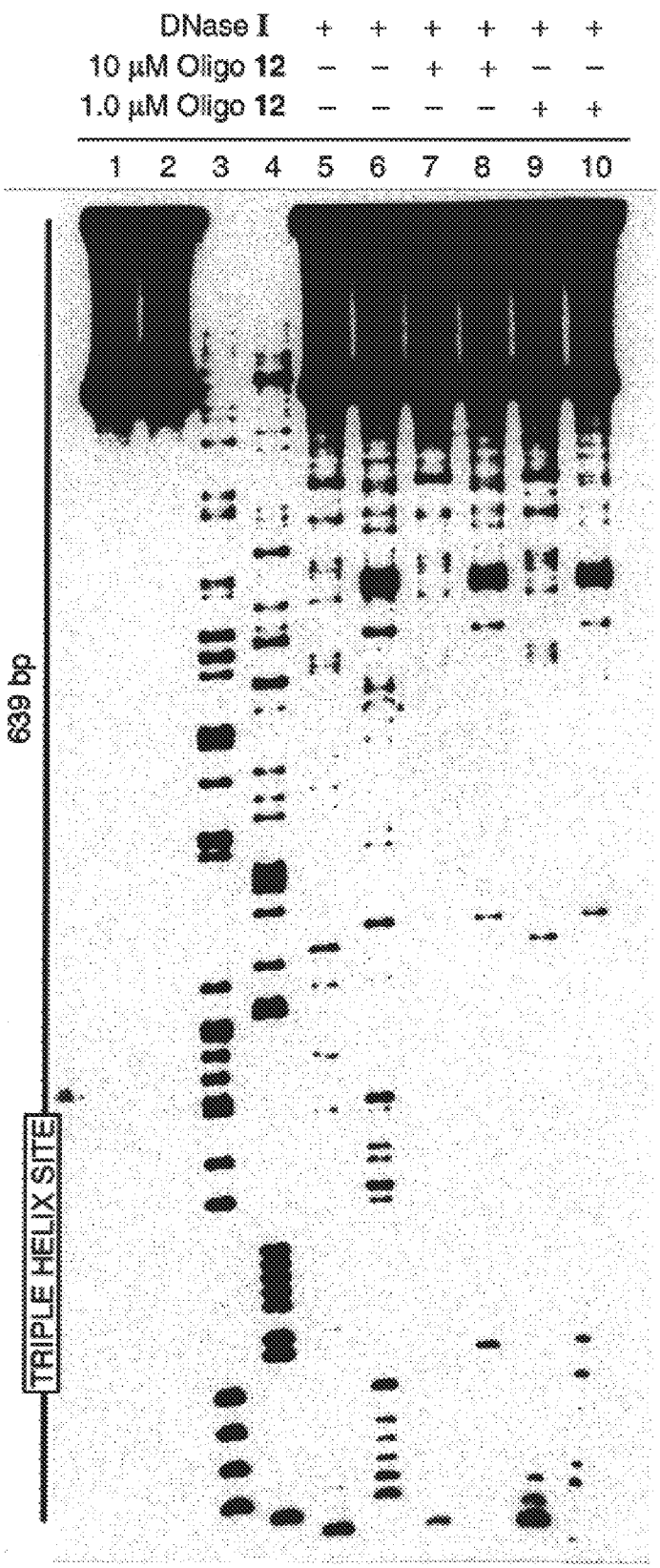
FIG._33

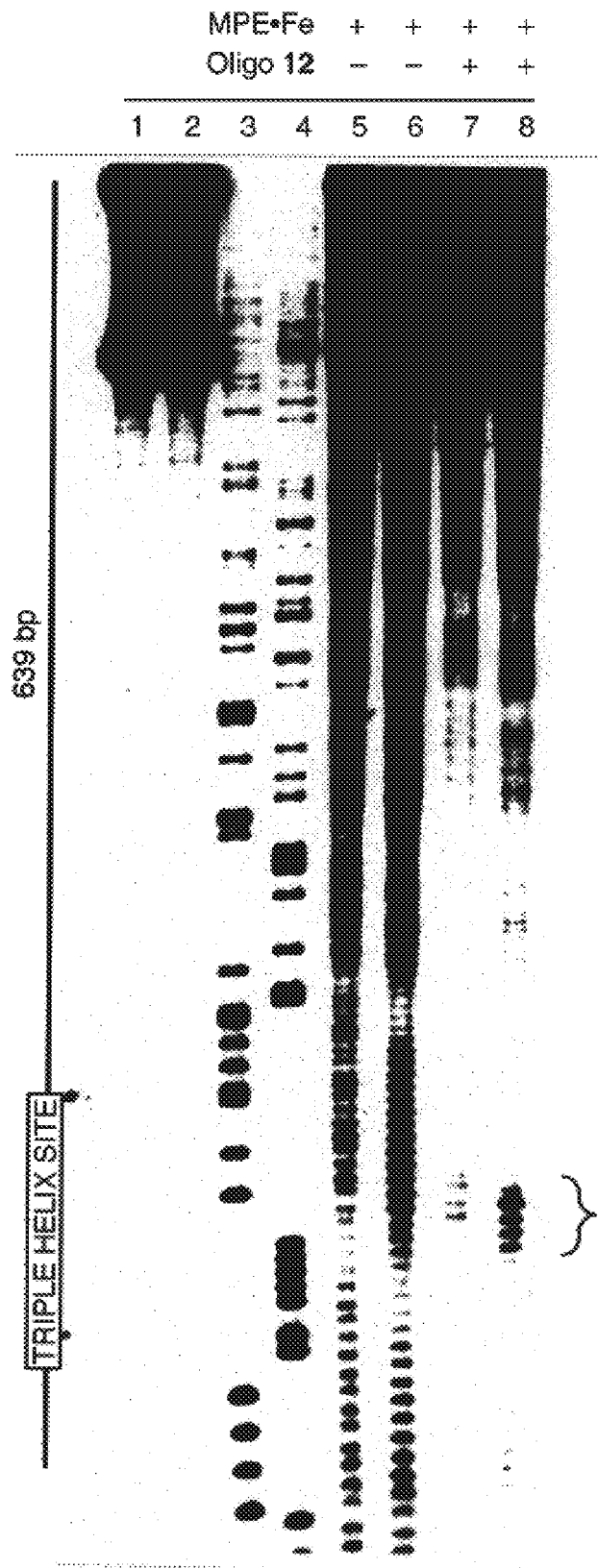
FIG._34

OLIGO 8

```
5'-CTCTCT TCCCTCCTCGAAAAAGAA CTCTCT
3'-GAGAGA AGGGAGGAGCTTTTTCTT GAGAGA
```

FIG._35A

OLIGO 9

```
5'-CTCTCT TCCCTCCTCGAAAAAGAA CTCTCT
3'-GAGAGA AGGGAGGAGCTTTTTCTT GAGAGA
```

FIG._35B

OLIGO 12 (DNase I)

```
5'-CTCTCT TCCCTCCTCGAAAAAGAA CTCTCT
3'-GAGAGA AGGGAGGAGCTTTTTCTT GAGAGA
```

FIG._35C

OLIGO 12 (MPE•Fe)

```
5'-CTCTCT TCCCTCCTCGAAAAAGAA CTCTCT
3'-GAGAGA AGGGAGGAGCTTTTTCTT GAGAGA
```

FIG._35D

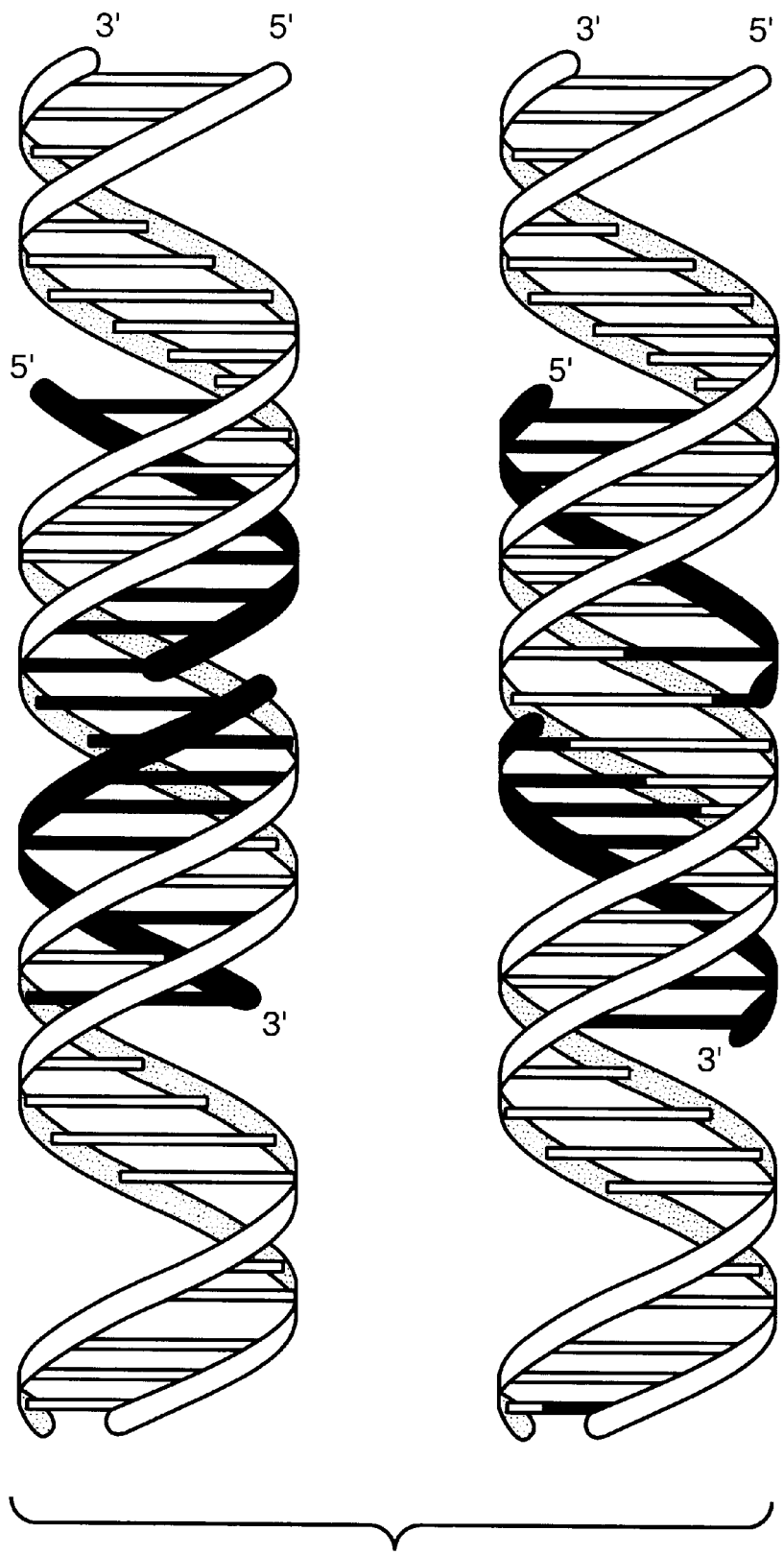
*FIG._36*

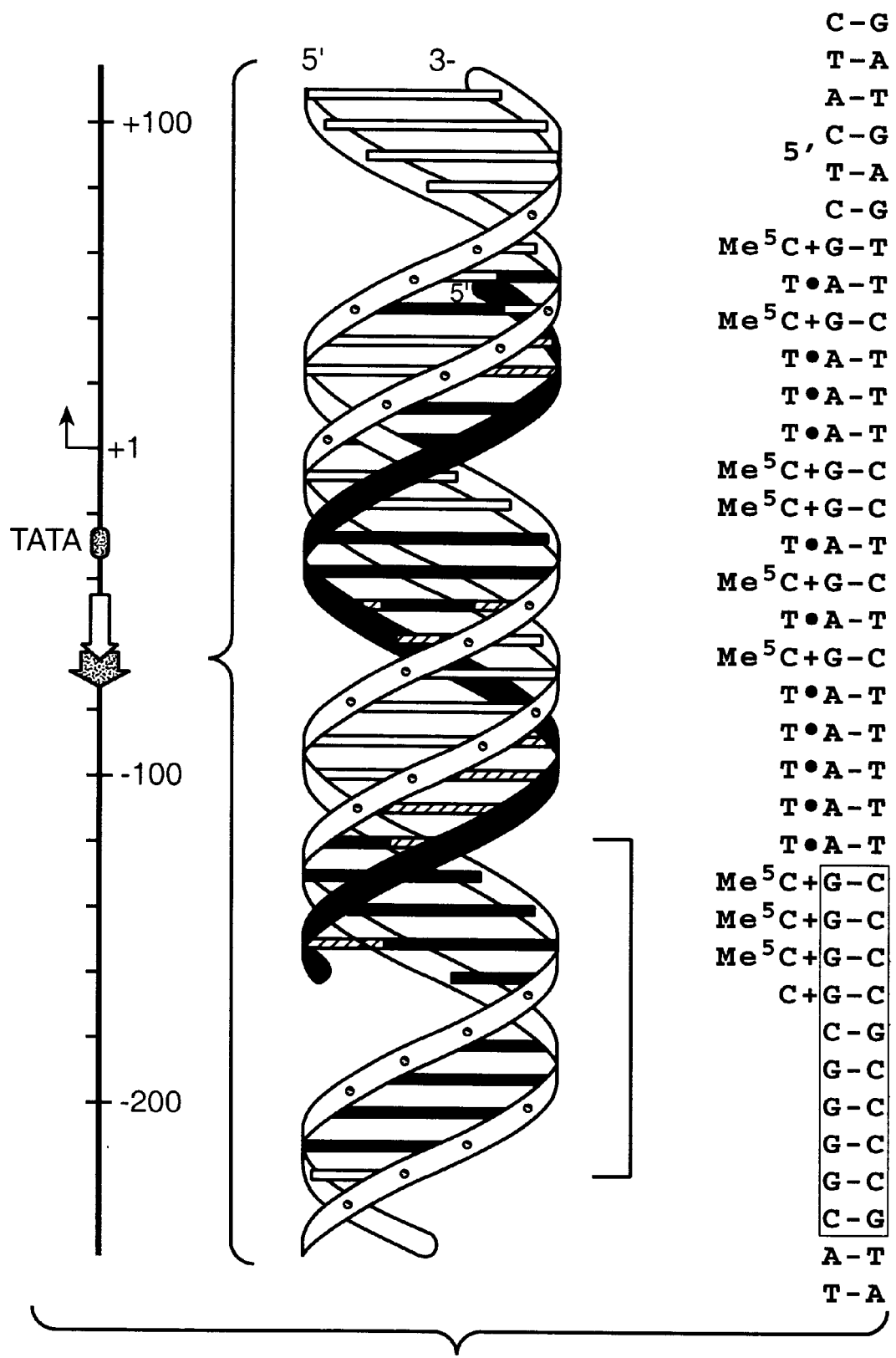
FIG._37A

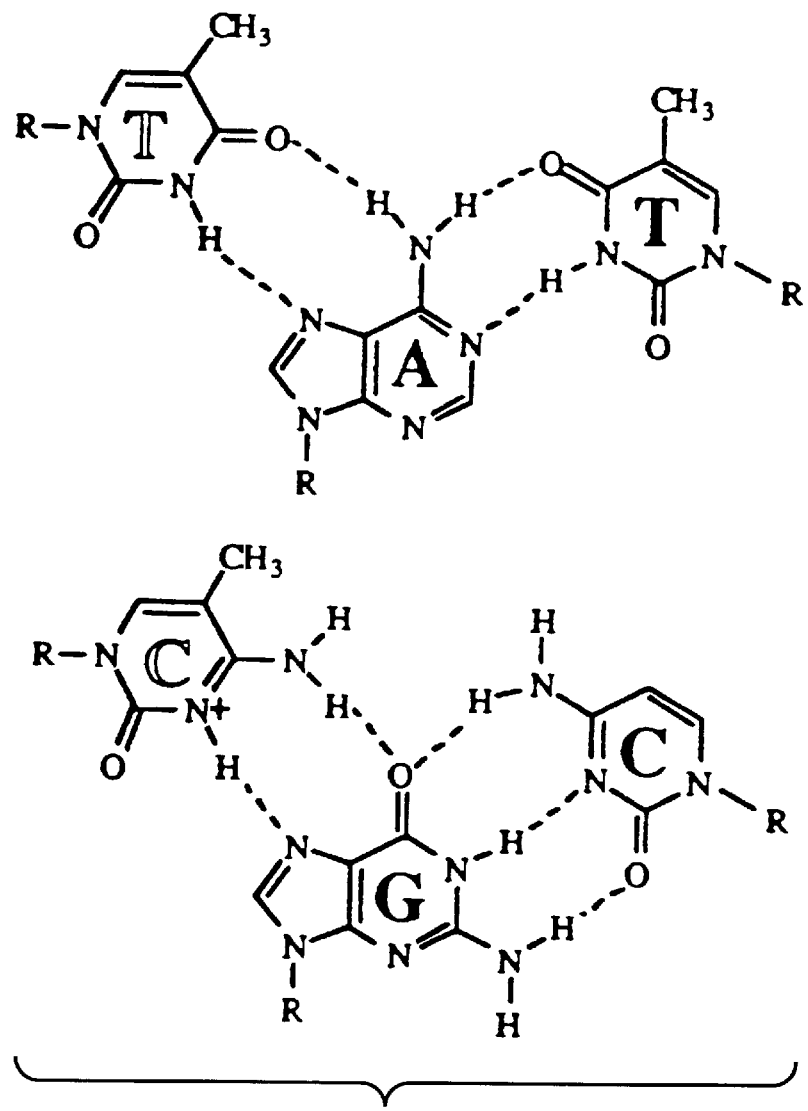
FIG._37B
```
     m  m        m m   m   m             m m m
1    C  T  C  T  T T C C T C T C T T T T C C C C
     m  m         m m    m    m
2    C  T  C  T  T T C C T C T C T T T T C
     m m m m    m     m          m  m m
3    T T C C C T C T T C T T T T C T C C T C
```
FIG._37C

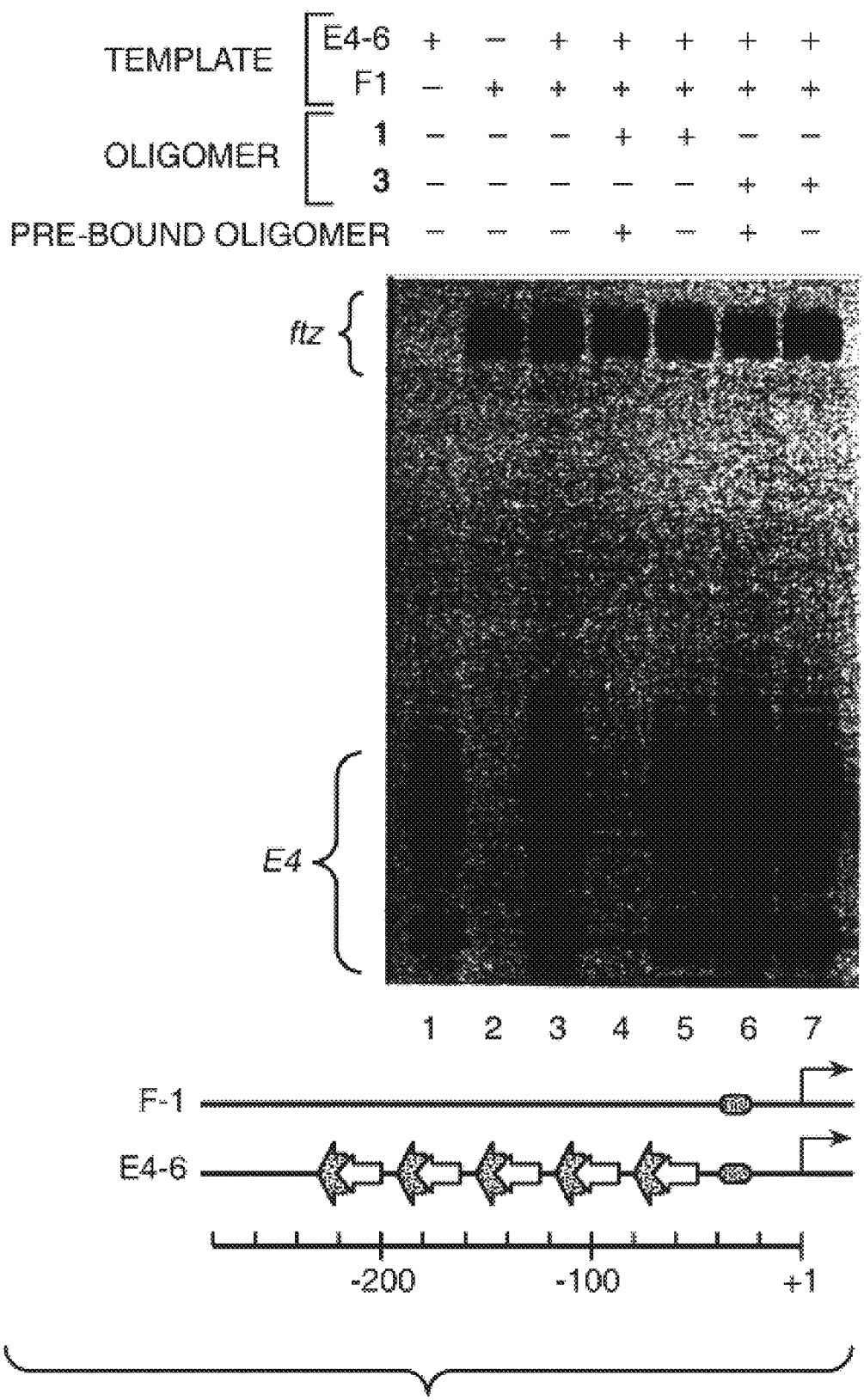
FIG._38

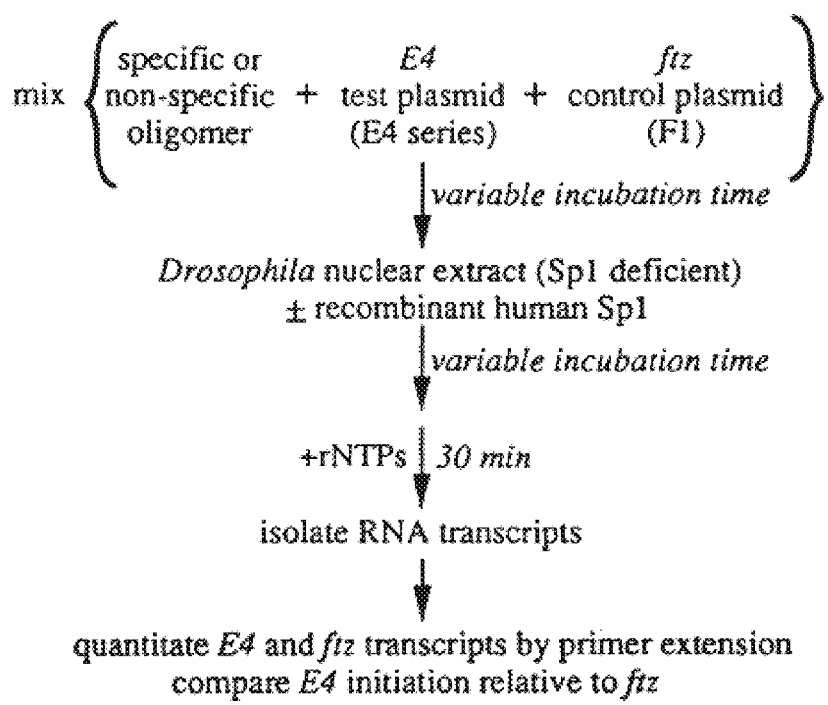
FIG._39
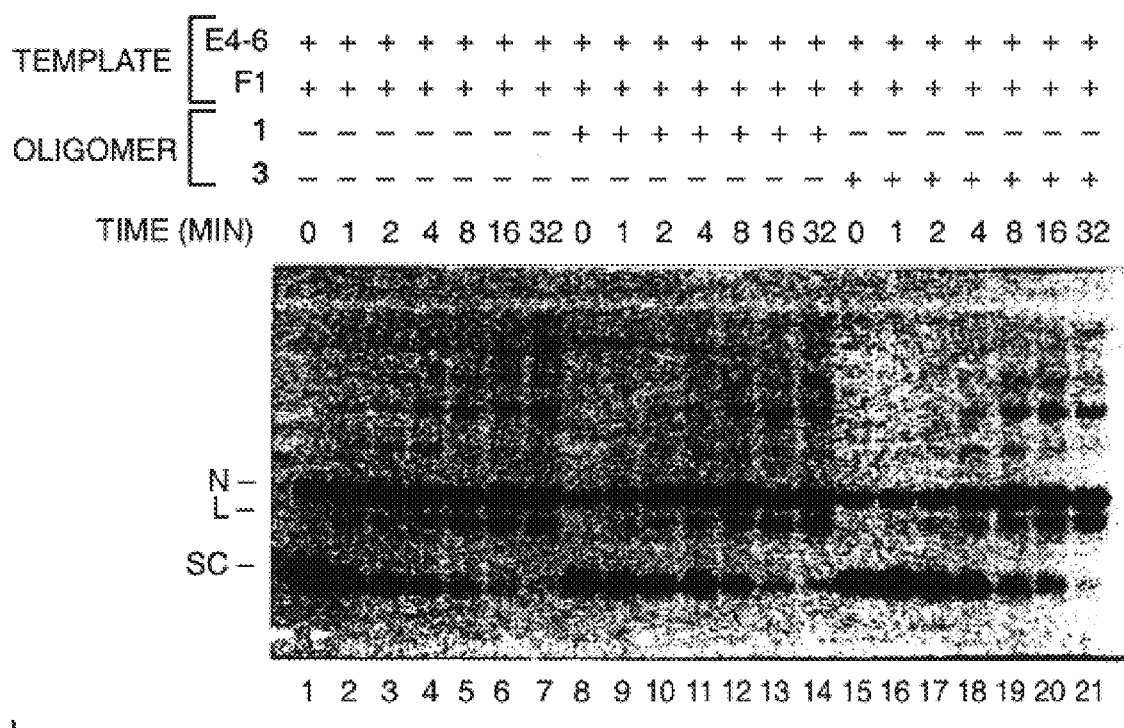
FIG._40

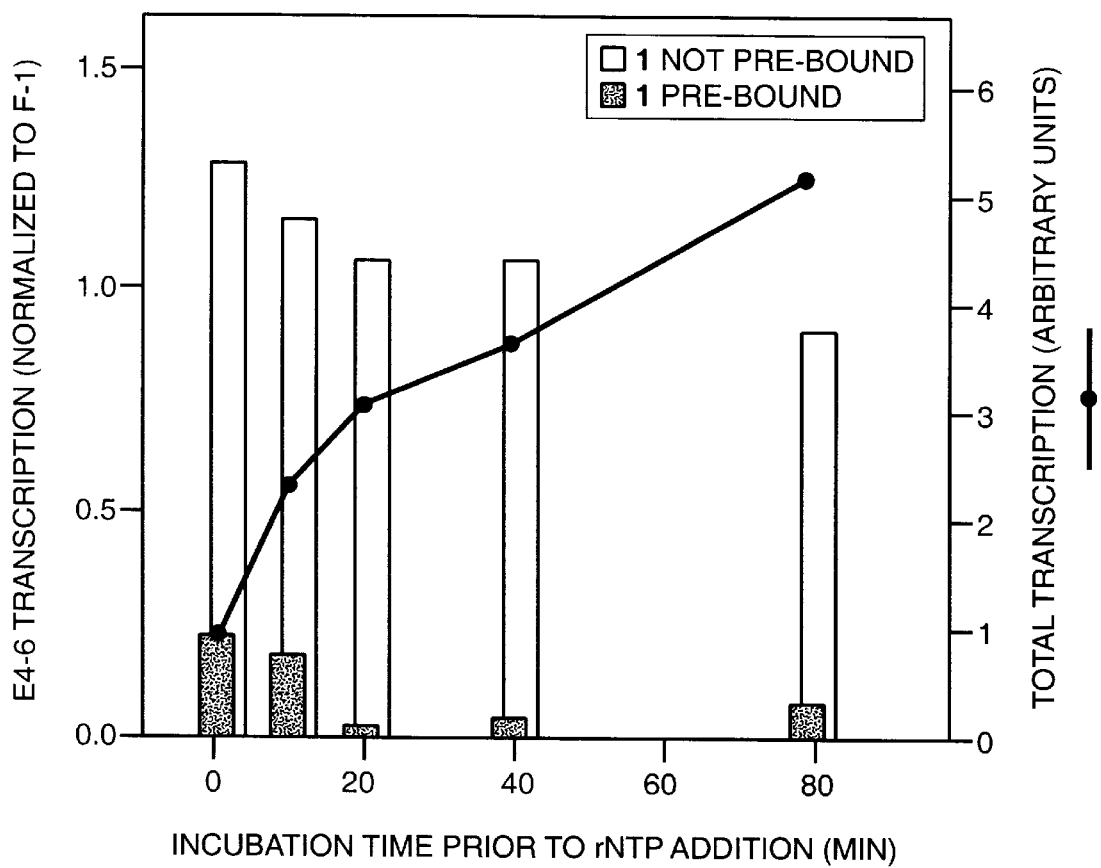
FIG._41

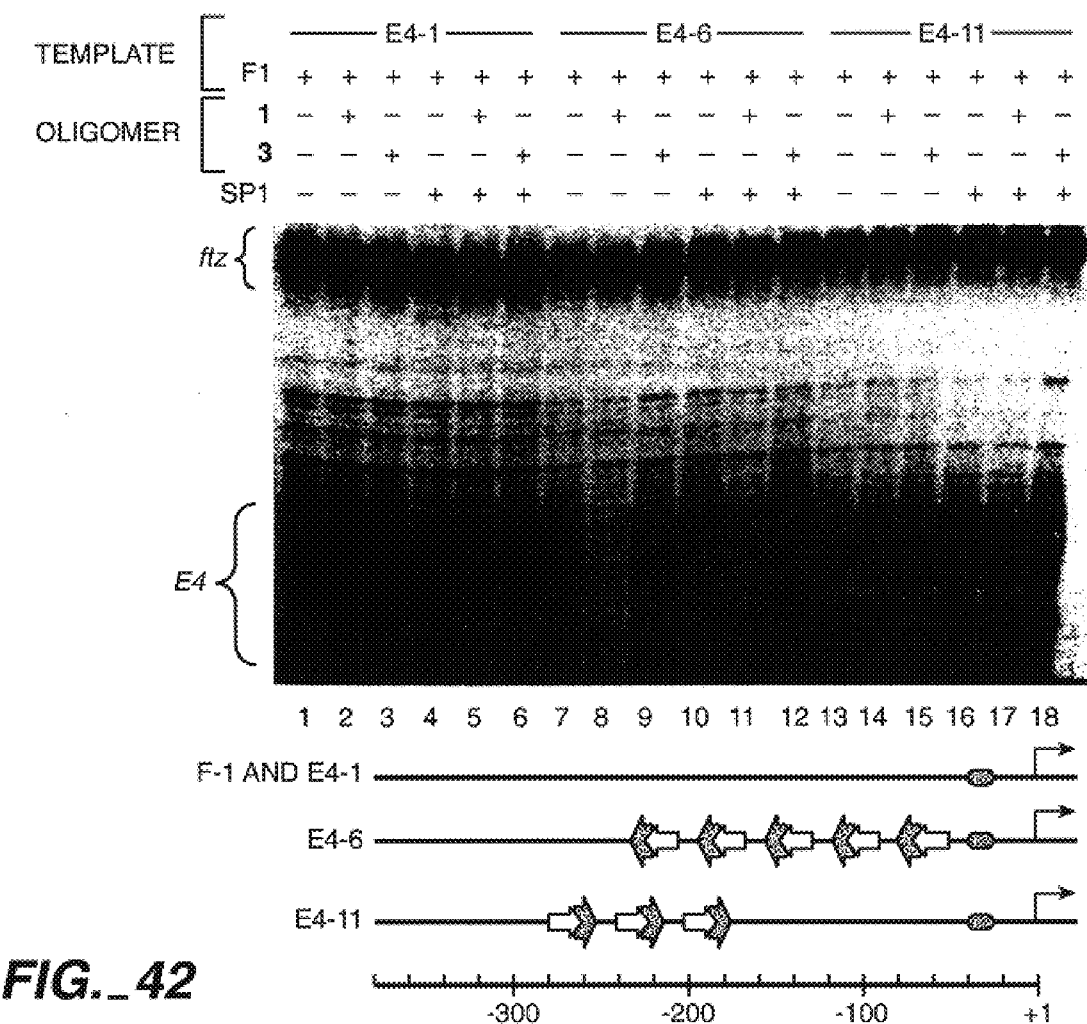
FIG._42

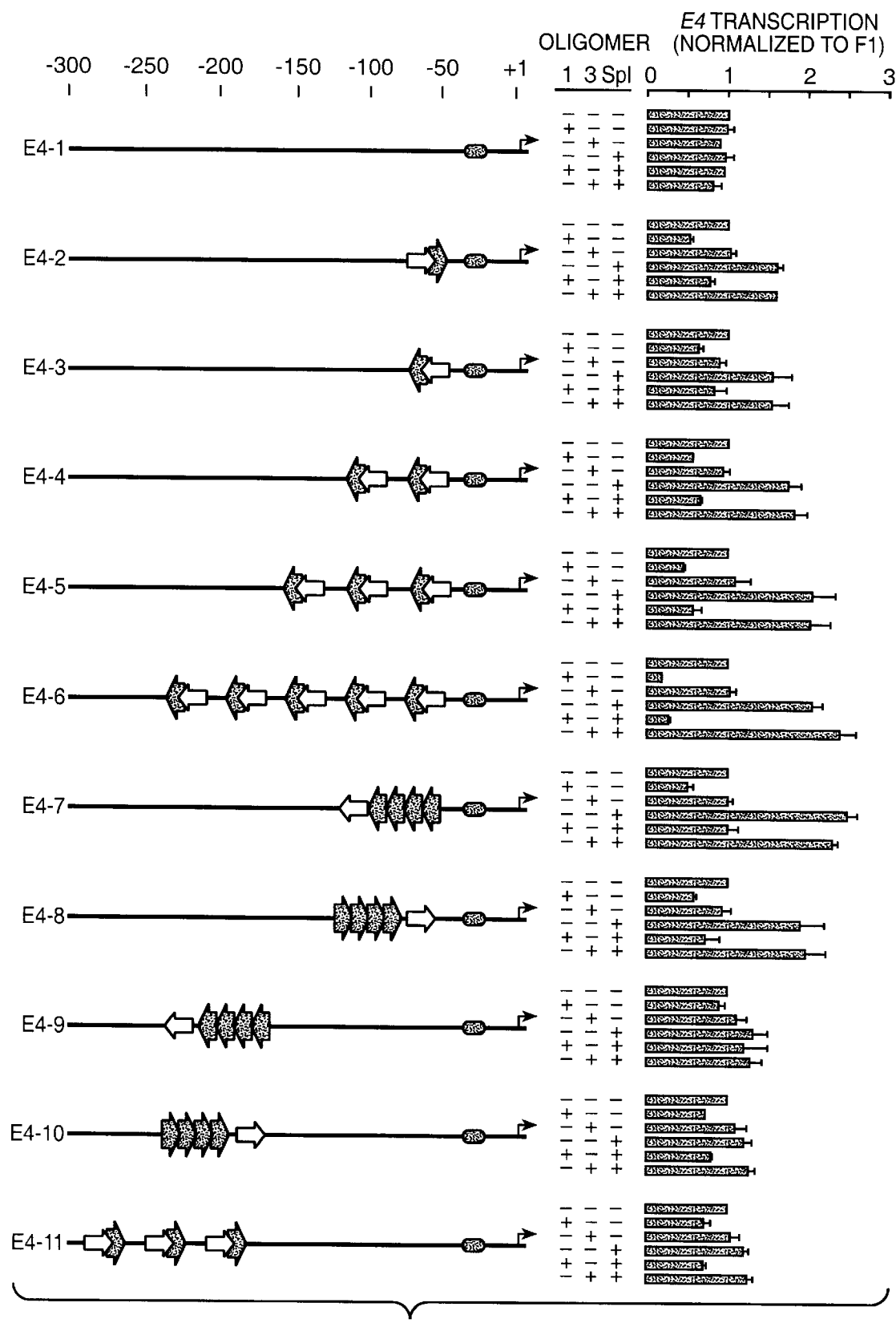
FIG._43A

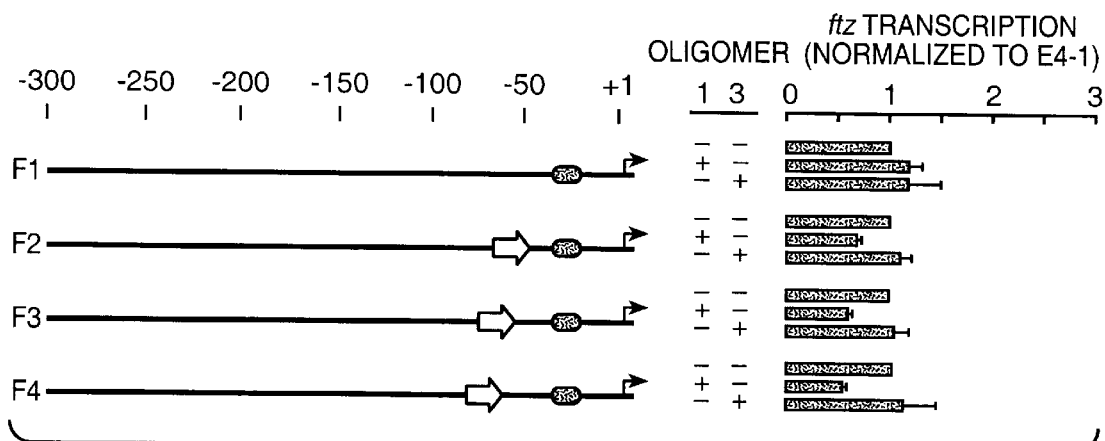
FIG._43B
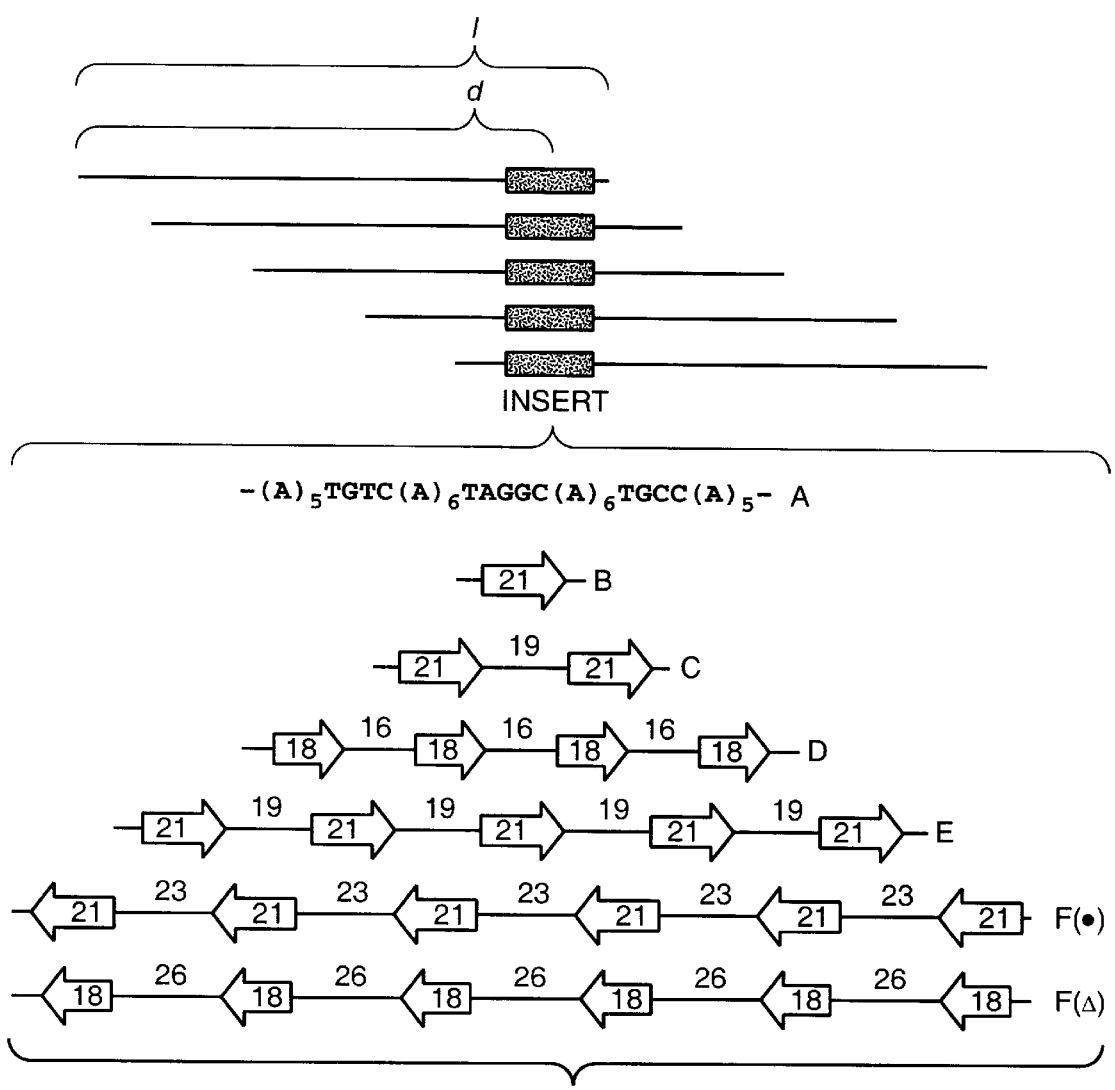
FIG._44A

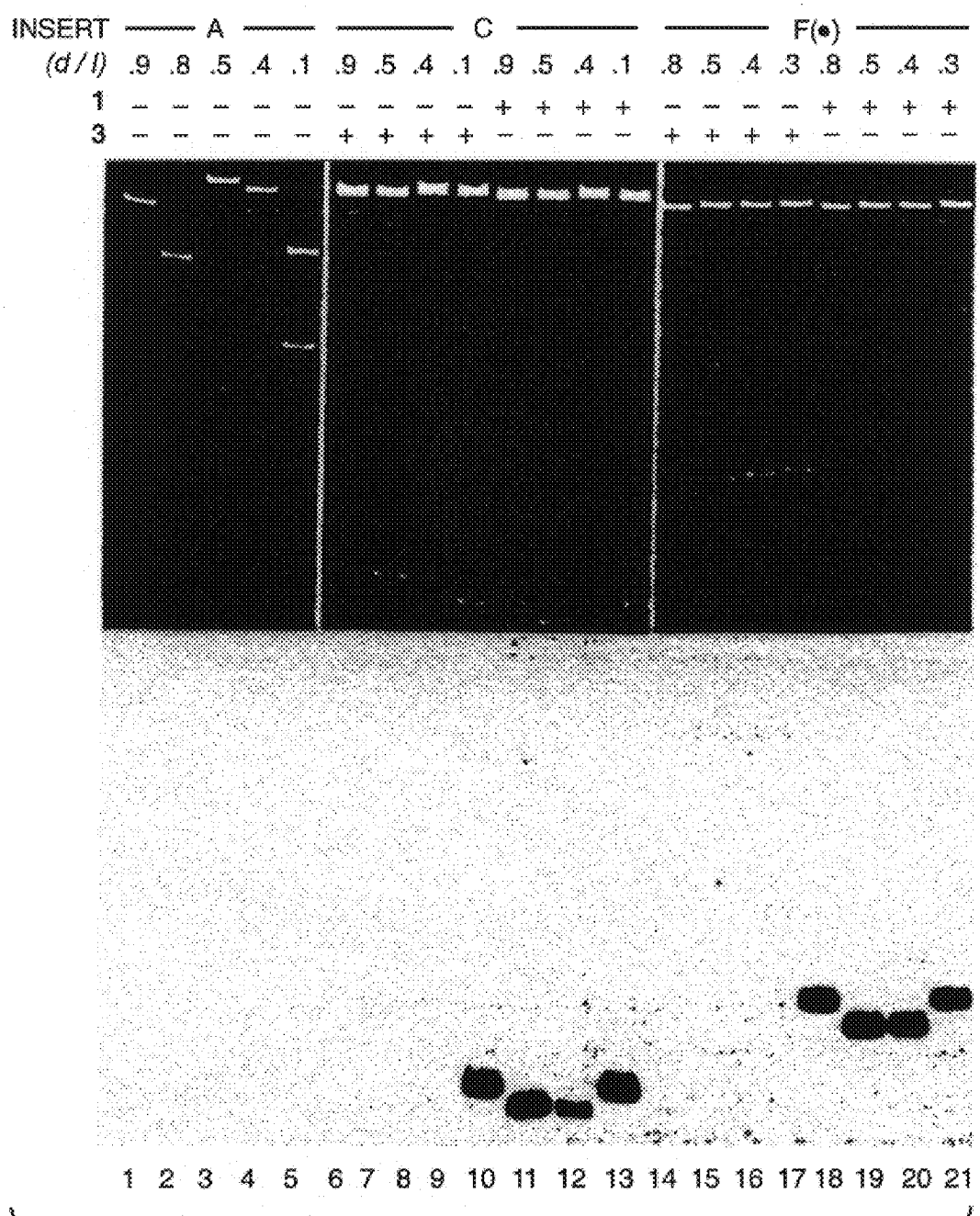
FIG._44B

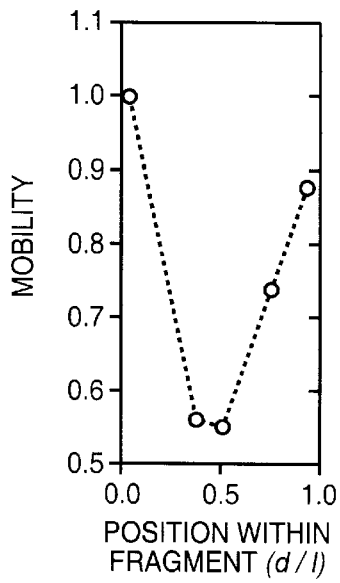
FIG._44C
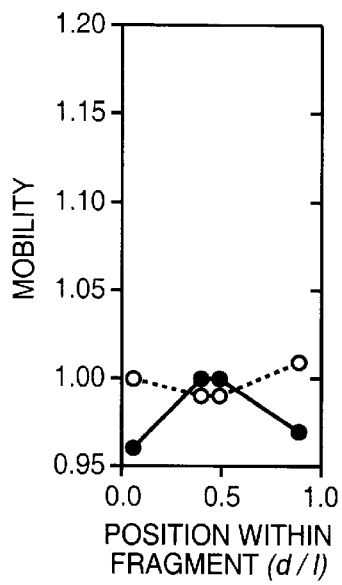
FIG._44D
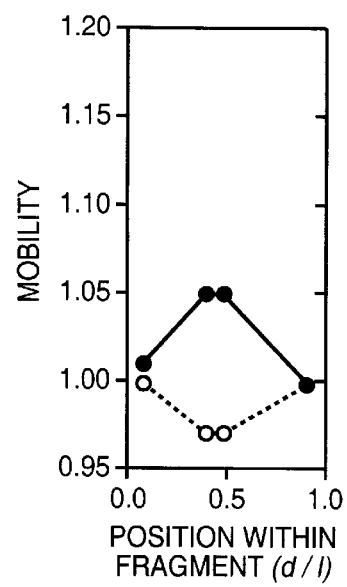
FIG._44E
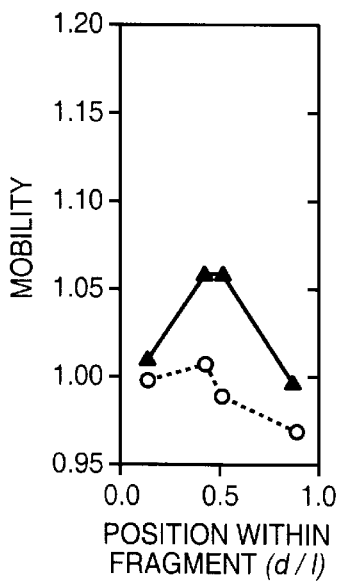
FIG._44F
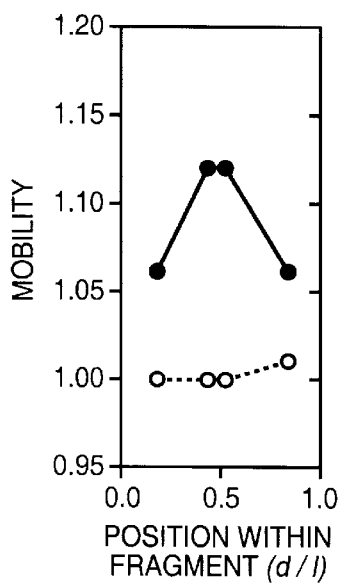
FIG._44G
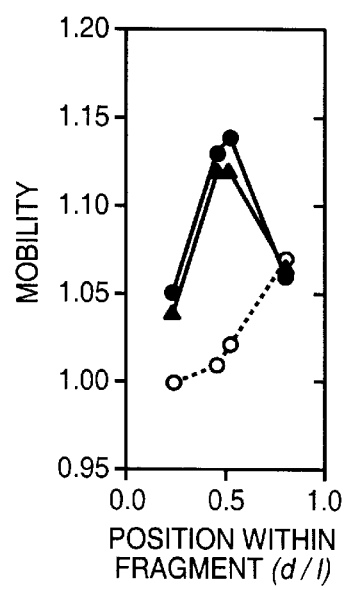
FIG._44H
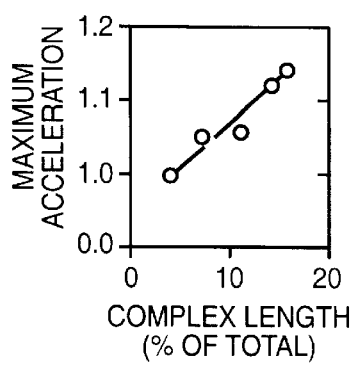
FIG._44I

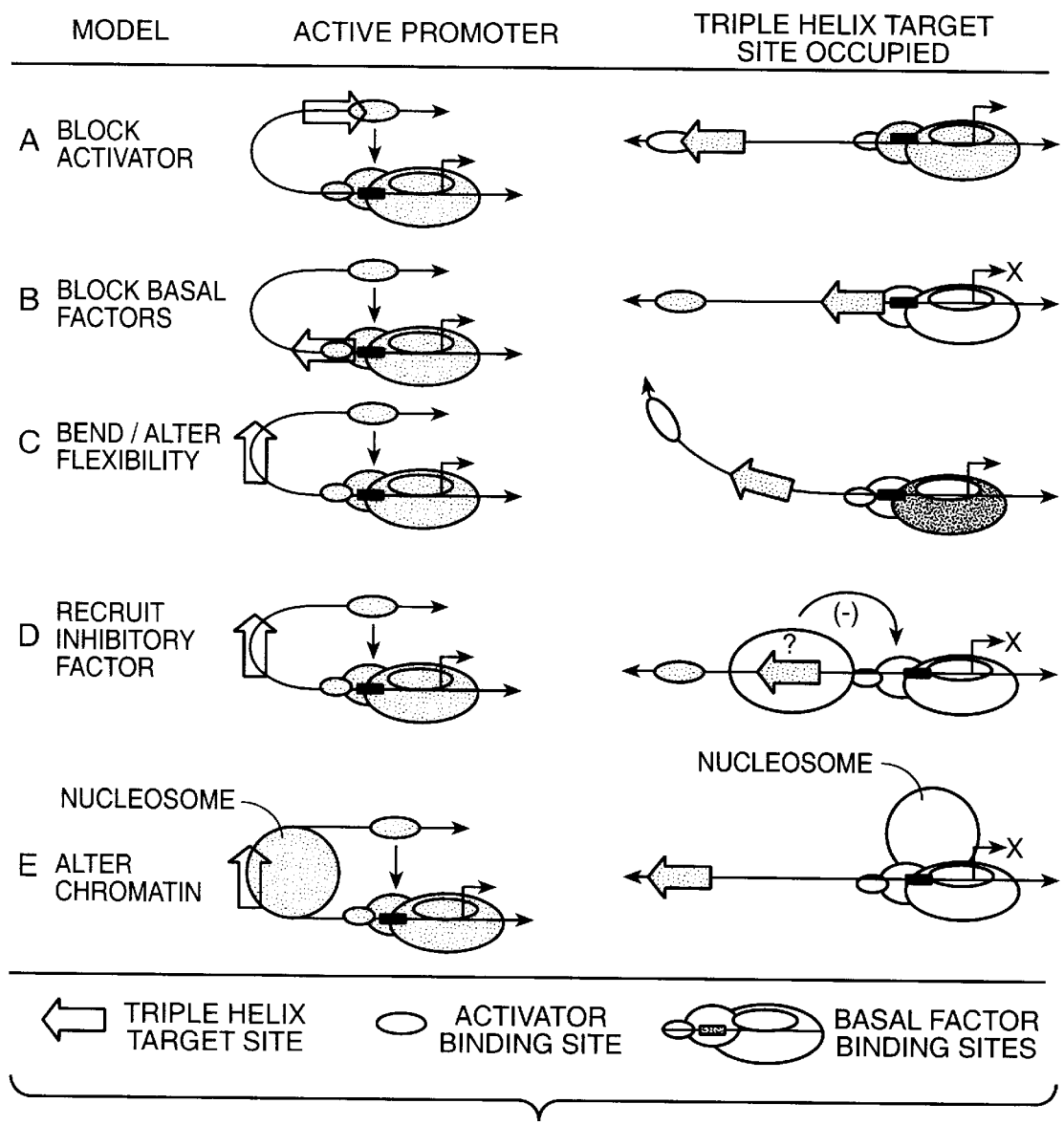
FIG._45

SEQUENCE LISTING

```
<160> NUMBER OF SEQ ID NOS: 128

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic

<400> SEQUENCE: 1
aaaaagagag agaga                                                        15

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 2
agggagggga ggggaggga                                                    19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (1)
<223> OTHER INFORMATION: T at position 1 = thymidine-EDTA.

<400> SEQUENCE: 3
tggghggggh gggghgggt                                                    19

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic

<400> SEQUENCE: 4
aattctctct aaaaggag gggaggggag ggaaaaactc tct                           43
```

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (19)
<223> OTHER INFORMATION: the n at position 19 can by any nucleic acid.

<400> SEQUENCE: 5
aattctctct aaaaagggng gggaggggag ggaaaaactc tct          43

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 6
aattcggcaa gaggcgaggg gcggcgact                          29

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 7
ctagagtcgc ctgcccctcg cctcttgccg                         30

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (15)
<223> OTHER INFORMATION: T at position 15 = thymidine-EDTA.
<221> NAME/KEY: misc_feature
<222> LOCATION: (11)
<223> OTHER INFORMATION: N at position 11 = A, T, G, C, D2, or D3.  D as
      defined on page34  of the specification.

<400> SEQUENCE: 8
tggggtgggg ngggt                                         15

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (19)
<223> OTHER INFORMATION: the n at position 19 can be any nucleic acid.

<400> SEQUENCE: 9
aattctctct aaaaagggng gggaggggag ggaaaaactc tct          43

<210> SEQ ID NO 10
<211> LENGTH: 43
<212> TYPE: DNA
<213> ORGANISM: Artificial Sequence
<220> FEATURE:

```
<223> OTHER INFORMATION: Description of Artificial Sequence: Synthetic
<221> NAME/KEY: misc_feature
<222> LOCATION: (29)
<223> OTHER INFORMATION: the n at position 29 can be any nucleic acid.

<400> SEQUENCE: 10
ctagagagag tttttccctc ccctccccnc cctttttaga gag                   43

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic

<400> SEQUENCE: 11
agaggcgagg ggcgg                                                  15

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic

<400> SEQUENCE: 12
ccgcccctcg cctct                                                  15

<210> SEQ ID NO 13
<211> LENGTH: 15
<212> TYPE: DNA
<213> ORGANISM: Artificial Sequence
<220> FEATURE:
<221> NAME/KEY: misc_difference
<222> LOCATION: (3)..(15)
<223> OTHER INFORMATION: N at 3,10 = D2, D3, A,G,C or T.  N at 8,13 =
      A,T, or D2, D3.  D2 and D3 as defined on page 34 of the
      specification.
<223> OTHER INFORMATION: Description of Artificial Sequence: Synthetic

<400> SEQUENCE: 13 ggngggggngn ggngt                                                 15

<210> SEQ ID NO 14
<211> LENGTH: 4
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (3)
<223> OTHER INFORMATION: N at position 3 = P1 as defined on page 33 of
      the specification.

<400> SEQUENCE: 14 ttnt                                                               4

<210> SEQ ID NO 15
<211> LENGTH: 4
<212> TYPE: DNA
<213> ORGANISM: Artificial Sequence
<220> FEATURE:
<221> NAME/KEY: misc_feature
<222> LOCATION: (3)
<223> OTHER INFORMATION: N at position 3 = P2 as defined on page 33 of
      the specification.
<223> OTHER INFORMATION: Description of Artificial Sequence: Synthetic

<400> SEQUENCE: 15
``` ttny                                                                    4

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (1)
<223> OTHER INFORMATION: T at position 1 = thymidine-EDTA.
<221> NAME/KEY: misc_feature
<222> LOCATION: (6)
<223> OTHER INFORMATION: N at positions 6, 8, 10, 12, and 14 = P1 as
      defined on page 33 of the specification.

<400> SEQUENCE: 16
tttttntntn tntnt                                                       15

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (1)
<223> OTHER INFORMATION: T at position 1 = thymidine-EDTA.
<221> NAME/KEY: misc_feature
<222> LOCATION: (10)..(15)
<223> OTHER INFORMATION: The N at positions 10-15 = P1 as defined on
      page 33 of the specification.

<400> SEQUENCE: 17
ttttcttttn nnnnnt                                                      16

<210> SEQ ID NO 18
<211> LENGTH: 13
<212> TYPE: DNA
<213> ORGANISM: Artificial Sequence
<220> FEATURE:
<223> OTHER INFORMATION: Description of Artificial Sequence: Synthetic

<400> SEQUENCE: 18
aaaaagagag aga                                                         13

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic

<400> SEQUENCE: 19 aaagaaaag ggggga                                                       16

<210> SEQ ID NO 20
<211> LENGTH: 4
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (3)
<223> OTHER INFORMATION: N at position 3 = D3 as defined on page 34 of
      the specification.

<400> SEQUENCE: 20 ttnt                                                                    4

<210> SEQ ID NO 21
<211> LENGTH: 4
<212> TYPE: DNA
<213> ORGANISM: Artificial Sequence
<220> FEATURE:
<221> NAME/KEY: misc_feature
<222> LOCATION: (3)
<223> OTHER INFORMATION: The N at position 3 = D2 as defined on page 34
      of the specification.
<223> OTHER INFORMATION: Description of Artificial Sequence: Synthetic

<400> SEQUENCE: 21 ttnt                                                                    4

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (23)
<223> OTHER INFORMATION: the n at position 23 can be any nucleic acid.
<221> NAME/KEY: misc_feature
<222> LOCATION: (8)
<223> OTHER INFORMATION: the n at position 8 can be any nucleic acid.

<400> SEQUENCE: 22
aaaaaaanaa aaaaattttt ttnttttttt                                       30

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 23
aaataaaaga caaaaaga                                                    18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (1)
<223> OTHER INFORMATION: T at position 1 = thymidine-EDTA.
<221> NAME/KEY: misc_feature
<222> LOCATION: (4)
<223> OTHER INFORMATION: d at position 4, and 11 = D2 as defined on
      page 34 of the specification.

<400> SEQUENCE: 24
tttdttttct dttttcct                                                    18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 25
aagaaaaagc tcctccct                                                    18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 26
tccctcctcg aaaaagaa                                          18

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Synthetic

<400> SEQUENCE: 27
gatctgagaa aggagagaaa aagggcggg gcatgcattg                   40

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic

<400> SEQUENCE: 28
actctttcct ctcttttcc ccgccccgta cgtaacctag                   40

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 29
ctagtgggcg gagttagggg cgggatactc                             30

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 30
acccgcctca atccccgccc tatgag                                 26

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 31
gagaaaggag agaaaaggg g                                       21

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic

<400> SEQUENCE: 32
ctctttcctc tcttttcccc cgatc                                              25

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 33
cgagaaagga gagaaaaagg ggtacg                                             26

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 34
tcgagctctt tcctctcttt ttccccatgc                                         30

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 35
gatcccaatt gagaaaggag agaaaaagtt aaga                                    34

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 36
ggttaactct ttcctctctt tttcaattct ctag                                    34

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 37
aacaccactc gacacggc                                                      18

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 38
gtagccatat cggatgtgta t                                                  21

<210> SEQ ID NO 39

```
<211> LENGTH: 15
<212> TYPE: DNA
<213> ORGANISM: Artificial Sequence
<220> FEATURE:
<223> OTHER INFORMATION: Description of Artificial Sequence: Synthetic

<400> SEQUENCE: 39
tttttttttt ttttt                                                15

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 40
cccccccccc aaaaaaaaaa aaaattttt                                 29

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 41
aaaaattttt ttttttttg ggggggggg                                  29

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: Synthetic

<400> SEQUENCE: 42
tttttctctc tctct                                                15

<210> SEQ ID NO 43
<211> LENGTH: 13
<212> TYPE: DNA
<213> ORGANISM: Artificial Sequence
<220> FEATURE:
<223> OTHER INFORMATION: Description of Artificial Sequence: Synthetic

<400> SEQUENCE: 43
tttttctctc tct                                                  13

<210> SEQ ID NO 44
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 44
tttttctctc t                                                    11

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: Synthetic

<400> SEQUENCE: 45
```

```
tttttctctt tctct                                              15

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence: Synthetic

<400> SEQUENCE: 46
tttttctctc cctct                                              15

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Synthetic

<400> SEQUENCE: 47
agcttatata tatataaaag agagagagat cgatag                       36

<210> SEQ ID NO 48
<211> LENGTH: 36
<212> TYPE: DNA
<213> ORGANISM: Artificial Sequence
<220> FEATURE:
<223> OTHER INFORMATION: Description of Artificial Sequence: Synthetic

<400> SEQUENCE: 48
gatcctatcg atctctctct cttttatata tatata                       36

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 49
atcgatctct ctctcttttt atatatatat                              30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 50
atatatatat aaaaagagag agagatcgat                              30

<210> SEQ ID NO 51
<211> LENGTH: 17
<212> TYPE: DNA
<213> ORGANISM: Artificial Sequence
<220> FEATURE:
<223> OTHER INFORMATION: Description of Artificial Sequence: Synthetic

<400> SEQUENCE: 51
tttttctctc tctctct                                            17

<210> SEQ ID NO 52
<211> LENGTH: 39
<212> TYPE: DNA
```

```
<213> ORGANISM: Artificial Sequence
<220> FEATURE:
<223> OTHER INFORMATION: Description of Artificial Sequence: Synthetic

<400> SEQUENCE: 52
agagagtttt tccctcccct ccctccctt tttagagag                                    39

<210> SEQ ID NO 53
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 53
ctctctaaaa agggaggga ggggagggaa aaactctct                                    39

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 54
tggghggggh gggghgggt                                                         19

<210> SEQ ID NO 55
<211> LENGTH: 45
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (21)
<223> OTHER INFORMATION: the n at position 21 can be any nucleic acid.

<400> SEQUENCE: 55
aattctctct ctaaaaaggg nggggagggg agggaaaaac tctct                            45

<210> SEQ ID NO 56
<211> LENGTH: 43
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (29)
<223> OTHER INFORMATION: the n at position 29 can be any nucleic acid.

<400> SEQUENCE: 56
ctagagagag ttttccctc cctcccnc ccttttaga gag                                 43

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (11)
<223> OTHER INFORMATION: the n at position 11 can be any nucliec acid.

<400> SEQUENCE: 57
tggggtgggg ngggt                                                             15

<210> SEQ ID NO 58
```

```
<211> LENGTH: 28
<212> TYPE: DNA
<213> ORGANISM: Artificial Sequence
<220> FEATURE:
<223> OTHER INFORMATION: Description of Artificial Sequence: Synthetic

<400> SEQUENCE: 58
gtcgcccgcc cctcgcctct tgccgaat                                    28

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 59
attcggcaag aggcgagggg cggcgac                                     27

<210> SEQ ID NO 60
<211> LENGTH: 15
<212> TYPE: DNA
<213> ORGANISM: Artificial Sequence
<220> FEATURE:
<221> NAME/KEY: misc_feature
<222> LOCATION: (3)..(4)
<223> OTHER INFORMATION: N at positions 3, 10 = A,G,C,T or
      deoxneubularene. N at positions 8, 13 = A,T, or deoxneubularene.
<223> OTHER INFORMATION: Description of Artificial Sequence: Synthetic

<400> SEQUENCE: 60 ggngggngn ggngt                                                   15

<210> SEQ ID NO 61
<211> LENGTH: 4
<212> TYPE: DNA
<213> ORGANISM: Artificial Sequence
<220> FEATURE:
<223> OTHER INFORMATION: Description of Artificial Sequence: Synthetic

<400> SEQUENCE: 61 tcga                                                              4

<210> SEQ ID NO 62
<211> LENGTH: 4
<212> TYPE: DNA
<213> ORGANISM: Artificial Sequence
<220> FEATURE:
<223> OTHER INFORMATION: Description of Artificial Sequence: Synthetic

<400> SEQUENCE: 62 agct                                                              4

<210> SEQ ID NO 63
<211> LENGTH: 4
<212> TYPE: DNA
<213> ORGANISM: Artificial Sequence
<220> FEATURE:
<223> OTHER INFORMATION: Description of Artificial Sequence: Synthetic

<400> SEQUENCE: 63 agct                                                              4

<210> SEQ ID NO 64
<211> LENGTH: 15
<212> TYPE: DNA
<213> ORGANISM: Artificial Sequence
```

```
<220> FEATURE:
<223> OTHER INFORMATION: Description of Artificial Sequence: Synthetic

<400> SEQUENCE: 64
tttttttctt ttttt                                                     15

<210> SEQ ID NO 65
<211> LENGTH: 15
<212> TYPE: DNA
<213> ORGANISM: Artificial Sequence
<220> FEATURE:
<221> NAME/KEY: misc_feature
<222> LOCATION: (8)
<223> OTHER INFORMATION: N = p1 as defined on page 33.
<223> OTHER INFORMATION: Description of Artificial Sequence: Synthetic

<400> SEQUENCE: 65
tttttttntt ttttt                                                     15

<210> SEQ ID NO 66
<211> LENGTH: 15
<212> TYPE: DNA
<213> ORGANISM: Artificial Sequence
<220> FEATURE:
<221> NAME/KEY: misc_feature
<222> LOCATION: (8)
<223> OTHER INFORMATION: N = p2 as defined on page 33 of the
      specification.
<223> OTHER INFORMATION: Description of Artificial Sequence: Synthetic

<400> SEQUENCE: 66
tttttttntt ttttt                                                     15

<210> SEQ ID NO 67
<211> LENGTH: 15
<212> TYPE: DNA
<213> ORGANISM: Artificial Sequence
<220> FEATURE:
<221> NAME/KEY: misc_feature
<222> LOCATION: (8)
<223> OTHER INFORMATION: N= a basic residue.
<223> OTHER INFORMATION: Description of Artificial Sequence: Synthetic

<400> SEQUENCE: 67
tttttttntt ttttt                                                     15

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (27)
<223> OTHER INFORMATION: n at position 27 can be any nucleic acid.

<400> SEQUENCE: 68
cccccccccc aaaaaaanaa aaaattttt                                      30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (13)
<223> OTHER INFORMATION: the n at position 13 can be any nucleic acid.
```

<400> SEQUENCE: 69
aaaaattttt ttnttttttt gggggggggg                                30

<210> SEQ ID NO 70
<211> LENGTH: 15
<212> TYPE: DNA
<213> ORGANISM: Artificial Sequence
<220> FEATURE:
<221> NAME/KEY: misc_feature
<222> LOCATION: (1)
<223> OTHER INFORMATION: T at position 1 = thymidine-EDTA.
<223> OTHER INFORMATION: Description of Artificial Sequence: Synthetic

<400> SEQUENCE: 70
tttttctctc tctct                                                15

<210> SEQ ID NO 71
<211> LENGTH: 15
<212> TYPE: DNA
<213> ORGANISM: Artificial Sequence
<220> FEATURE:
<221> NAME/KEY: misc_feature
<222> LOCATION: (1)
<223> OTHER INFORMATION: T at position 1 = thymidine-EDTA.
<221> NAME/KEY: misc_feature
<222> LOCATION: (6)
<223> OTHER INFORMATION: C at position 6, 8, 10, 12,
      14 = 5-methylcytosine.
<223> OTHER INFORMATION: Description of Artificial Sequence: Synthetic

<400> SEQUENCE: 71
tttttctctc tctct                                                15

<210> SEQ ID NO 72
<211> LENGTH: 15
<212> TYPE: DNA
<213> ORGANISM: Artificial Sequence
<220> FEATURE:
<221> NAME/KEY: misc_feature
<222> LOCATION: (1)
<223> OTHER INFORMATION: T at position 1 = thymidine-EDTA.
<221> NAME/KEY: misc_feature
<222> LOCATION: (6)
<223> OTHER INFORMATION: N at positions 6, 8, 10, 12, 14 =p1 as defined
      on page 33 of the specification.
<223> OTHER INFORMATION: Description of Artificial Sequence: Synthetic

<400> SEQUENCE: 72
tttttntntn tntnt                                                15

<210> SEQ ID NO 73
<211> LENGTH: 16
<212> TYPE: DNA
<213> ORGANISM: Artificial Sequence
<220> FEATURE:
<221> NAME/KEY: misc_feature
<222> LOCATION: (1)
<223> OTHER INFORMATION: T at position 1 = thymidine-EDTA.
<221> NAME/KEY: misc_feature
<222> LOCATION: (6)
<223> OTHER INFORMATION: N at positions 6, 8, 10, 12, and 14 = P2 as
      defined on page 33 of the specification.
<223> OTHER INFORMATION: Description of Artificial Sequence: Synthetic

<400> SEQUENCE: 73 tttttttntnt ntntnt                                              16

<210> SEQ ID NO 74
<211> LENGTH: 30

```
<212> TYPE: DNA
<213> ORGANISM: Artificial Sequence
<220> FEATURE:
<223> OTHER INFORMATION: Description of Artificial Sequence: Synthetic

<400> SEQUENCE: 74
atcgatctct ctctcttttt atatatatat                                30

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 75
tagctagaga gagagaaaaa tatatatata                                30

<210> SEQ ID NO 76
<211> LENGTH: 15
<212> TYPE: DNA
<213> ORGANISM: Artificial Sequence
<220> FEATURE:
<221> NAME/KEY: misc_feature
<222> LOCATION: (6)
<223> OTHER INFORMATION: N at positions 6, 8, 10, 12, and 14 = p1 as
      defined on page 33 of the specification.
<223> OTHER INFORMATION: Description of Artificial Sequence: Synthetic

<400> SEQUENCE: 76
tttttntntn tntnt                                                15

<210> SEQ ID NO 77
<211> LENGTH: 15
<212> TYPE: DNA
<213> ORGANISM: Artificial Sequence
<220> FEATURE:
<221> NAME/KEY: misc_feature
<222> LOCATION: (1)
<223> OTHER INFORMATION: T at position 1 = thymidine-EDTA.
<223> OTHER INFORMATION: Description of Artificial Sequence: Synthetic

<400> SEQUENCE: 77
ttttcttttc ccct                                                 15

<210> SEQ ID NO 78
<211> LENGTH: 15
<212> TYPE: DNA
<213> ORGANISM: Artificial Sequence
<220> FEATURE:
<221> NAME/KEY: misc_feature
<222> LOCATION: (1)
<223> OTHER INFORMATION: T at position 1 = thymidine-EDTA
<221> NAME/KEY: misc_feature
<222> LOCATION: (10)..(15)
<223> OTHER INFORMATION: C = 5-methylcytosine
<223> OTHER INFORMATION: Description of Artificial Sequence: Synthetic

<400> SEQUENCE: 78
ttttcttttc ccct                                                 15

<210> SEQ ID NO 79
<211> LENGTH: 16
<212> TYPE: DNA
<213> ORGANISM: Artificial Sequence
<220> FEATURE:
<221> NAME/KEY: misc_feature
<222> LOCATION: (1)
<223> OTHER INFORMATION: T at position 1 = thymidine-EDTA.
```

```
<221> NAME/KEY: misc_feature
<222> LOCATION: (10)..(15)
<223> OTHER INFORMATION: N = p1 as defined on page 33 of the
      specification.
<223> OTHER INFORMATION: Description of Artificial Sequence: Synthetic

<400> SEQUENCE: 79
ttttcttttn nnnnnt                                                     16

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 80
ggtctccccc cttttctttt aaaaatggct                                      30

<210> SEQ ID NO 81
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 81
agccattttt aaagaaagg ggggagacc                                        29

<210> SEQ ID NO 82
<211> LENGTH: 15
<212> TYPE: DNA
<213> ORGANISM: Artificial Sequence
<220> FEATURE:
<221> NAME/KEY: misc_feature
<222> LOCATION: (5)
<223> OTHER INFORMATION: T at position 5 = thymidine-EDTA.
<223> OTHER INFORMATION: Description of Artificial Sequence: Synthetic

<400> SEQUENCE: 82 ttttttttt ttttt                                                       15

<210> SEQ ID NO 83
<211> LENGTH: 15
<212> TYPE: DNA
<213> ORGANISM: Artificial Sequence
<220> FEATURE:
<221> NAME/KEY: misc_feature
<222> LOCATION: (5)
<223> OTHER INFORMATION: T at position 5 = thymidine-EDTA.
<223> OTHER INFORMATION: Description of Artificial Sequence: Synthetic

<400> SEQUENCE: 83
tttttttctt ttttt                                                      15

<210> SEQ ID NO 84
<211> LENGTH: 15
<212> TYPE: DNA
<213> ORGANISM: Artificial Sequence
<220> FEATURE:
<221> NAME/KEY: misc_feature
<222> LOCATION: (5)
<223> OTHER INFORMATION: T at position 5 = thymidine-EDTA.
<221> NAME/KEY: misc_feature
<222> LOCATION: (8)
<223> OTHER INFORMATION: N at position 8 = d2 as defined on page 34 of
      the specification.
<223> OTHER INFORMATION: Description of Artificial Sequence: Synthetic
```

```
<400> SEQUENCE: 84
tttttttntt tttt                                                15

<210> SEQ ID NO 85
<211> LENGTH: 15
<212> TYPE: DNA
<213> ORGANISM: Artificial Sequence
<220> FEATURE:
<221> NAME/KEY: misc_feature
<222> LOCATION: (5)
<223> OTHER INFORMATION: T at position 5 = thymidine-EDTA.
<221> NAME/KEY: misc_feature
<222> LOCATION: (8)
<223> OTHER INFORMATION: N at position 8 = d3 as defined on page 34 of
      the specification.
<223> OTHER INFORMATION: Description of Artificial Sequence: Synthetic

<400> SEQUENCE: 85
tttttttntt tttt                                                15

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (27)
<223> OTHER INFORMATION: the n at position 27 can be any nucleic acid.

<400> SEQUENCE: 86
cccccccccc aaaaaaanaa aaaaattttt                               30

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (13)
<223> OTHER INFORMATION: the n at position 13 can be any nucleic acid.

<400> SEQUENCE: 87
aaaaattttt ttnttttttt gggggggggg                               30

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 88 agtcttttg tctttattt caggtccatg                                 30

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 89
catggacctg aaataaaaga caaaaagact                               30

<210> SEQ ID NO 90
```

```
<211> LENGTH: 17
<212> TYPE: DNA
<213> ORGANISM: Artificial Sequence
<220> FEATURE:
<221> NAME/KEY: misc_feature
<222> LOCATION: (1)
<223> OTHER INFORMATION: T at position 1 = thymidine-EDTA.
<221> NAME/KEY: misc_feature
<222> LOCATION: (3)
<223> OTHER INFORMATION: N at position 3, and 10 = d2 as defined on
      page 34 of the specification.
<223> OTHER INFORMATION: Description of Artificial Sequence: Synthetic

<400> SEQUENCE: 90
ttnttttctn tttttct                                                    17

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 91
ctctctaaga aaagctcct ccctctctct                                       30

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 92
gagagaaggg aggagctttt tcttagagag                                      30

<210> SEQ ID NO 93
<211> LENGTH: 18
<212> TYPE: DNA
<213> ORGANISM: Artificial Sequence
<220> FEATURE:
<221> NAME/KEY: misc_feature
<222> LOCATION: (1)
<223> OTHER INFORMATION: T at position 1 = thymidine-EDTA.
<221> NAME/KEY: misc_feature
<222> LOCATION: (3)
<223> OTHER INFORMATION: C at position 3 and 9 = 5-methldeoxycytidine.
<223> OTHER INFORMATION: Description of Artificial Sequence: Synthetic

<400> SEQUENCE: 93 ttcttttcg aggagggt                                                    18

<210> SEQ ID NO 94
<211> LENGTH: 18
<212> TYPE: DNA
<213> ORGANISM: Artificial Sequence
<220> FEATURE:
<221> NAME/KEY: misc_feature
<222> LOCATION: (18)
<223> OTHER INFORMATION: T at position 18 = thymidine-EDTA.
<221> NAME/KEY: misc_difference
<222> LOCATION: (3)
<223> OTHER INFORMATION: C at positions 3, and
      9 = 5-methyldeoxycytidine.
<223> OTHER INFORMATION: Description of Artificial Sequence: Synthetic

<400> SEQUENCE: 94
ttctttttcg aggagggt                                                   18
```

```
<210> SEQ ID NO 95
<211> LENGTH: 9
<212> TYPE: DNA
<213> ORGANISM: Artificial Sequence
<220> FEATURE:
<221> NAME/KEY: misc_feature
<222> LOCATION: (1)
<223> OTHER INFORMATION: T at position 1 = thymidine-EDTA.
<221> NAME/KEY: misc_feature
<222> LOCATION: (3)
<223> OTHER INFORMATION: C at positions 3, and
      9 = 5-methyldeoxycytidine.
<223> OTHER INFORMATION: Description of Artificial Sequence: Synthetic

<400> SEQUENCE: 95 ttcttttc                                                                    9

<210> SEQ ID NO 96
<211> LENGTH: 9
<212> TYPE: DNA
<213> ORGANISM: Artificial Sequence
<220> FEATURE:
<221> NAME/KEY: misc_feature
<222> LOCATION: (9)
<223> OTHER INFORMATION: T at position 9 = thymidine-EDTA.
<223> OTHER INFORMATION: Description of Artificial Sequence: Synthetic

<400> SEQUENCE: 96 gaggagggt                                                                   9

<210> SEQ ID NO 97
<211> LENGTH: 18
<212> TYPE: DNA
<213> ORGANISM: Artificial Sequence
<220> FEATURE:
<221> NAME/KEY: misc_feature
<222> LOCATION: (3)
<223> OTHER INFORMATION: C at positions 3, and
      9 = 5-methyldeoxycytidine.
<223> OTHER INFORMATION: Description of Artificial Sequence: Synthetic

<400> SEQUENCE: 97
ttctttttcg aggagggt                                                        18

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 98
ttctttttcg cgaggagggt                                                      20

<210> SEQ ID NO 99
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 99
ttaactctct aagaaaaagc tcctccctct ctctctaga                                 39

<210> SEQ ID NO 100
<211> LENGTH: 39
<212> TYPE: DNA
<213> ORGANISM: Artificial Sequence
<220> FEATURE:
```

<223> OTHER INFORMATION: Description of Artificial Sequence: Synthetic

<400> SEQUENCE: 100
tctagagaga gagggaggag cttttttctta gagagttaa          39

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 101 ttcttttttcg cgaggagggt          20

<210> SEQ ID NO 102
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 102
ttaactctct aagaaaaagc tcctccctct ctctctaga          39

<210> SEQ ID NO 103
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 103
tctagagaga gagggaggag cttttttctta gagagttaa          39

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 104
ctctctaaga aaaagctcct ccctctctct          30

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 105
agagagaggg aggagctttt tcttagagag          30

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 106
ctctcttccc tcctcgaaaa agaactctct          30

<210> SEQ ID NO 107
<211> LENGTH: 32
<212> TYPE: DNA
<213> ORGANISM: Artificial Sequence
<220> FEATURE:
<223> OTHER INFORMATION: Description of Artificial Sequence: Synthetic

<400> SEQUENCE: 107
agagagttct ttttctcgag gagggaagag ag         32

<210> SEQ ID NO 108
<211> LENGTH: 18
<212> TYPE: DNA
<213> ORGANISM: Artificial Sequence
<220> FEATURE:
<221> NAME/KEY: misc_feature
<222> LOCATION: (1)
<223> OTHER INFORMATION: T is position 1 = thymidine-EDTA.
<221> NAME/KEY: misc_feature
<222> LOCATION: (10)
<223> OTHER INFORMATION: C at positions 10, and 16 =
    5-methyldeoxycytidine.
<223> OTHER INFORMATION: Description of Artificial Sequence: Synthetic

<400> SEQUENCE: 108
tgggaggagc tttttctt         18

<210> SEQ ID NO 109
<211> LENGTH: 19
<212> TYPE: DNA
<213> ORGANISM: Artificial Sequence
<220> FEATURE:
<221> NAME/KEY: misc_feature
<222> LOCATION: (1)
<223> OTHER INFORMATION: T at position 1 = thymidine-EDTA.
<221> NAME/KEY: misc_feature
<222> LOCATION: (11)
<223> OTHER INFORMATION: C at positions 11, and 17 =
    5-methyldeoxycytidine.
<223> OTHER INFORMATION: Description of Artificial Sequence: Synthetic

<400> SEQUENCE: 109
tgggaggagt cttttctt         19

<210> SEQ ID NO 110
<211> LENGTH: 20
<212> TYPE: DNA
<213> ORGANISM: Artificial Sequence
<220> FEATURE:
<221> NAME/KEY: misc_feature
<222> LOCATION: (1)
<223> OTHER INFORMATION: T at position 1 = thymidine-EDTA
<221> NAME/KEY: misc_feature
<222> LOCATION: (12)
<223> OTHER INFORMATION: C at positions 12, and 18 =
    5-methyldeoxycytidine.
<223> OTHER INFORMATION: Description of Artificial Sequence: Synthetic

<400> SEQUENCE: 110
tgggaggagt tcttttctt         20

<210> SEQ ID NO 111
<211> LENGTH: 20
<212> TYPE: DNA
<213> ORGANISM: Artificial Sequence
<220> FEATURE:
<221> NAME/KEY: misc_feature
<222> LOCATION: (20)
<223> OTHER INFORMATION: T at position 20 = thymidine-EDTA.
<221> NAME/KEY: misc_feature
<222> LOCATION: (12)

```
<223> OTHER INFORMATION: C at positions 12, and 18 = 5-methylcytosine.
<223> OTHER INFORMATION: Description of Artificial Sequence: Synthetic

<400> SEQUENCE: 111
tgggaggagt tcttttcctt                                                   20

<210> SEQ ID NO 112
<211> LENGTH: 9
<212> TYPE: DNA
<213> ORGANISM: Artificial Sequence
<220> FEATURE:
<221> NAME/KEY: misc_feature
<222> LOCATION: (1)
<223> OTHER INFORMATION: T at position 1 = thymidine-EDTA.
<223> OTHER INFORMATION: Description of Artificial Sequence: Synthetic

<400> SEQUENCE: 112 tgggaggag                                                                9

<210> SEQ ID NO 113
<211> LENGTH: 9
<212> TYPE: DNA
<213> ORGANISM: Artificial Sequence
<220> FEATURE:
<221> NAME/KEY: misc_feature
<222> LOCATION: (9)
<223> OTHER INFORMATION: T at position 9 = thymidine-EDTA.
<221> NAME/KEY: misc_feature
<222> LOCATION: (1)
<223> OTHER INFORMATION: C at positions 1, and 7 =  5-methylcytosine.
<223> OTHER INFORMATION: Description of Artificial Sequence: Synthetic

<400> SEQUENCE: 113 cttttctt                                                                 9

<210> SEQ ID NO 114
<211> LENGTH: 20
<212> TYPE: DNA
<213> ORGANISM: Artificial Sequence
<220> FEATURE:
<221> NAME/KEY: misc_feature
<222> LOCATION: (12)
<223> OTHER INFORMATION: C at positions 12, and 18 = 5-methylcytosine.
<223> OTHER INFORMATION: Description of Artificial Sequence: Synthetic

<400> SEQUENCE: 114
tgggaggagt tcttttctt                                                    20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 115
tgggaggagt tgttttgtt                                                    20

<210> SEQ ID NO 116
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 116
ttaactctct tccctcctcg aaaaagaact ctctctaga                              39
```

```
<210> SEQ ID NO 117
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 117
tctagagaga gttcttttc gaggagggaa gagagttaa                        39

<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 118
tgggaggagt cttttctt                                              19

<210> SEQ ID NO 119
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 119
ttaactctct ccctcctcg aaaagaact ctctctaga                         39

<210> SEQ ID NO 120
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 120
tctagagaga gttcttttc gaggagggaa gagagttaa                        39

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 121
ctctcttccc tcctcgaaaa agaactctct                                 30

<210> SEQ ID NO 122
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 122
agagagttct ttttcgagga gggaagagag                                 30

<210> SEQ ID NO 123
<211> LENGTH: 21
<212> TYPE: DNA
<213> ORGANISM: Artificial Sequence
<220> FEATURE:
<221> NAME/KEY: misc_feature
```

```
<222> LOCATION: (1)
<223> OTHER INFORMATION: C at positions 1, 3, 7, 8, 10, 12, 18, 19, and
      20 = 5-methylcytosine.
<223> OTHER INFORMATION: Description of Artificial Sequence: Synthetic

<400> SEQUENCE: 123
ctctttcctc tcttttccc c                                            21

<210> SEQ ID NO 124
<211> LENGTH: 35
<212> TYPE: DNA
<213> ORGANISM: Artificial Sequence
<220> FEATURE:
<223> OTHER INFORMATION: Description of Artificial Sequence: Synthetic

<400> SEQUENCE: 124
ctactcgaga aggagagaa aaagggggcgg ggcat                             35

<210> SEQ ID NO 125
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 125
atgccccgcc cctttttctc tcctttctcg agta                             34

<210> SEQ ID NO 126
<211> LENGTH: 21
<212> TYPE: DNA
<213> ORGANISM: Artificial Sequence
<220> FEATURE:
<221> NAME/KEY: misc_feature
<222> LOCATION: (1)
<223> OTHER INFORMATION: C at positions 1, 3, 7, 8, 10, 12, 18, 19, 20,
      and 21 =
<223> OTHER INFORMATION: Description of Artificial Sequence: Synthetic

<400> SEQUENCE: 126
ctctttcctc tcttttccc c                                            21

<210> SEQ ID NO 127
<211> LENGTH: 18
<212> TYPE: DNA
<213> ORGANISM: Artificial Sequence
<220> FEATURE:
<221> NAME/KEY: misc_feature
<222> LOCATION: (1)
<223> OTHER INFORMATION: C at positions 1, 3, 7, 8, 10, and 12 =
<223> OTHER INFORMATION: Description of Artificial Sequence: Synthetic

<400> SEQUENCE: 127
ctctttcctc tcttttc                                                18

<210> SEQ ID NO 128
<211> LENGTH: 21
<212> TYPE: DNA
<213> ORGANISM: Artificial Sequence
<220> FEATURE:
<221> NAME/KEY: misc_feature
<222> LOCATION: (3)
```

-continued

```
<223> OTHER INFORMATION: C at positions 3, 4, 5, 6, 8, 11, 16, 18, and
      19 = 5-methyldeoxycytidine.
<223> OTHER INFORMATION: Description of Artificial Sequence: Synthetic

<400> SEQUENCE: 128
ttcccctctt cttttctcct c                                              21
```

METHODS AND COMPOSITIONS FOR TRIPLE HELIX FORMATION

This is a continuation, of application Ser. No. 07/946,976 filed Sep. 17, 1992, now abandoned.

The U.S. Government has certain rights in this invention pursuant to Grant No. N00014-88-K-0441 awarded by the Department of the Navy and Grant No. GM 35724-13.

BACKGROUND OF THE INVENTION

The sequence-specific cleavage of double-helical deoxyribonucleic acid (hereafter "DNA") by naturally occurring restriction endonucleases is essential for many techniques in molecular biology, including gene isolation, DNA sequence determination, chromosome analysis, gene isolation and recombinant DNA manipulations. Other applications include the use of such endonucleases as diagnostic reagents to detect aberrant DNA sequences.

The usefulness of DNA cleavage by these naturally recurring restriction enzymes is limited. The binding site sizes of naturally occurring restriction enzymes are typically in the range of four to eight base pairs, and hence their sequence specificities may be inadequate for mapping genomes ($10^5$–$10^7$ base pairs) over very large distances. For unique recognition of DNA in the $10^5$–$10^7$ base pair range, sequence specificities at the 8–15 base pair level must be obtained. In addition, there are a limited number of known restriction endonucleases. Thus, they cannot be used to specifically recognize a particular piece of DNA (or RNA) unless that piece of DNA contains the specific nucleic acid sequences recognized by particular endonuclease. With the advent of pulsed field gel electrophoresis, separation of large (up to at least one million base pair) pieces of DNA is now possible. The design and synthesis of molecules that are capable of recognizing a specific sequence in double-stranded nucleic acids not otherwise detectable by natural restriction enzymes is clearly desirable as valuable tools for further research, diagnostics, and therapeutic.

Synthetic sequence-specific binding moieties for double-helical DNA that have been studied are typically coupled analogs of natural products (Dervan, P. D., *Science* 232:464 (1986)), transition metal complexes (Barton, J. K., *Science* 233:727 (1986)), and peptide fragments derived from DNA binding proteins (Sluka, J. et al., *Science*, in press). Additionally, methidiumpropyl-EDTA (hereafter "MPE"), which contains the metal chelator ethylenediaminetetraacetic acid ("EDTA") attached to the DNA intercalator methidium, has been shown to cleave double-helical DNA efficiently in a reaction dependent on ferrous iron (Fe(II)) and dioxygen ($O^2$) This mechanism is thought to occur by binding in the minor groove of the right-handed DNA helix. Addition of reducing agents such as dithiothreitol (hereafter "DTT") increases the efficiency of DNA cleavage, as reported by Hertzberg and Dervan, *J. Am. Chem. Soc.* 104:313–315 (1982); and Hertzberg and Dervan, *Biochemistry* 23:3934 (1984). MPE-Fe(II) cleaves DNA in a relatively non-sequence specific manner, and with significantly lower sequence specificity than the enzyme DNAseI, and therefore is useful in experiments to identify binding locations of small molecules such as antibiotics, other drugs, and proteins on DNA, Hertzberg and Dervan, Biochemistry, supra.

The most sequence-specific molecules characterized so far, with regard to the natural product analog approach is bis(EDTA-distamycin) fumaramide which binds in the minor grove and cleaves at sites containing nine contiguous A.T base-pairs (Youngquist and Dervan, *J. Am. Chem. Soc.* 107:5528 (1985)). A synthetic peptide containing 32 residues from the DNA binding domain of Hin protein with EDTA at the amino-terminus binds and cleaves at the 13 bp Hin site (Bruist, et al., *Science* 235:777 (1987); Sluka, et al., supra). Another known DNA cleaving function involves the attachment of a DNA-cleaving moiety such as a ethylenediaminetetraacetic acid-iron complex (hereafter "EDTA-Fe(II)"), to a DNA binding molecule which cleaves the DNA backbone by oxidation of the deoxyribose with a short-lived diffusible hydroxyl radical (Hertzberg and Dervan, Biochemistry, supra). The fact that the hydroxyl radical is a relatively non-specific cleaving species is useful when studying recognition, because the cleavage specificity is due to the binding moiety alone, not some combination of cleavage specificity superimposed on binding specificity.

Despite this progress, the current understanding of molecular recognition of DNA is still sufficiently primitive that the elucidation of chemical principles involved in creating specificity in sequence recognition at the $\geq 15$ base pair level has been slow in development in comparison to the interest in the field for mapping large genomes.

Recognition of single-stranded nucleic acids by nucleic acid-hybridization probes consisting of sequences of DNA or RNA are well known in the art. Typically, to construct a DNA hybridization probe, selected target DNA is obtained as a single-strand and copies of a portion of the strand are synthesized in the laboratory and labeled using radioactive isotopes, fluorescing molecules, photolytic dyes or enzymes that react with a substrate to produce a color change. When exposed to complementary strands of target DNA, the labeled DNA probe binds to (hybridizes) its complementary single-stranded DNA sequence. The label on the probe is then detected and the DNA of interest is thus located. Probes may similarly be used to target RNA sequences. DNA probes are currently well known in the art for locating and selecting genes of known sequence, and in the diagnosis and chemotherapy of genetic disorders and diseases.

Oligonucleotides (polynucleotides containing between 10 and 50 bases) equipped with a DNA cleaving moiety have been described which produce sequence-specific cleavage of single-stranded DNA. Examples of such moieties include oligonucleotide-EDTA-Fe hybridization probes ("DNA-EDTA") which cleaves the complementary single strand sequence (Dreyer and Dervan, *Proc. Natl. Acad. Sci. USA* 82:968 (1985); Chu and Orgel, *Proc. Natl. Acad. Sci. USA* 82:963 (1985)). Such probes are disclosed in U.S. Pat. No. 4,795,700.

In addition to double- and single-stranded configurations, it is also well known in the art that triplexes of nucleic acids naturally exist (Howard, et al., *Biochem. Biophys. Res. Commun.* 17:93 (1964)). Poly(U) and poly(A) were found to form a stable 2:1 complex in the presence of $MgCl_2$. After this, several triple-stranded structures were discovered (Michelson, et al., *Prog. Nucl. Acid Res. Mol. Biol.* 6:83 (1967); Felsenfeld and Miles, *Annu. Rev. Biochem.* 36:407 (1967)). Poly(C) forms a triple-stranded complex at pH 6.2 with guanineoligoribonucleotides. One of the pyrimidine strands is apparently in the protonated form (Howard, et al., supra). In principle, isomorphous base triplets (T-A-T and C-G-C$^+$) can be formed between any homopyrimidine-homopurine duplex and a corresponding homopyrimidine strand (Miller and Sobell, *Proc. Natl. Acad. Sci. USA* 55:1201 (1966); Morgan and Wells, *J. Mol. Biol.* 37:63 (1968); Lee, et al., *Nucl. Acids Res.* 6:3073 (1979)). The DNA-duplex poly(dTdC)-poly(dG-dA) associates with poly (U-C) or poly(dTdC) below pH 6 in the presence of $MgCl_2$ to afford a triple-stranded complex. Several investigators have proposed an anti-parallel orientation of the two polypyrimidine strands based on an anti conformation of the bases, ibid. X-ray defraction patterns of triple-stranded fibers (poly(A)-2poly(U) and poly(dA)-2poly-(dT)) supports this hypothesis (Arnott and Bond, *Nature New Biology* 244:99 1973); Arnott and Selsing, *J. Mol. Biol.* 85:509 (1974); and Arnott, et al., *Nucl. Acids Res.* 3:2459 (1976)), and suggested an A'-RNA-like conformation of the two Watson-Crick base paired strands with the third strand in the same conformation, bound parallel to the homopurine strand of the duplex by Hoogsteen-hydrogen bonds (Hoogsteen, *Acta Cry St.* 12:822 (1959)). The twelve-fold helix with dislocation of the axis by almost three angstroms, the C3'-endo sugar puckering and small base-tilts result in a large and deep major groove that is capable of accommodating the third strand (Saenger, *Principles Of Nucleic Acid Structure*, edited by C. R. Cantor, Springer-Verlag, New York, Inc. (1984)).

Although triple-stranded structures of polynucleotides were discovered decades ago, the biological significance has remained obscure. Such triplexes were proposed to be involved in processes such as regulation of gene expression, maintenance of folded chromosome conformations, chromosome condensation during mitosis, and induction of local conformational changes in B-DNA (Morgan, *Trends Biochem. Sci.* 4:N244 (1979); Hopkins, *Comments Mol. Cell Biophys.* 2:133 (1984); Minton, *J. Path.* 2:135 (1985)).

The above-described methods for sequence-specific DNA recognition and cleavage have been limited to single-stranded DNA hybridization probes, to natural or synthetic restriction endonucleases, and to those molecules which recognize sequences of DNA directly such as antibiotics, and DNA intercalators such as methidium.

SUMMARY OF THE INVENTION

Based upon the above described limitations in the recognition of specific sequences in nucleic acids, it an object herein to provide compositions and methods to detect target sequences within large double-helical nucleic acids without the need to denature such double-helical molecules.

In accordance with these and other objects, the present invention includes improved triple-helices, synthetic oligonucleotides and methods using such oligonucleotides to form triple-helices.

The invention provides improved triple-helices and oligonucleotides wherein one of the strands of the double helical nucleic acid contains a first purine-rich target sequence and a pyrimidine-rich sequence. The target sequence comprises the first purine-rich target sequence and a second purine-rich target sequence on the other strand of the double-helical DNA which is base-paired with the pyrimidine-rich sequence. The oligonucleotide used to form this alternate strand triple-helix comprises two binding domains. The first domain comprises a pyrimidine-rich portion which binds to the first purine-rich target sequence in a parallel orientation. The second binding domain comprises a purine-rich portion which binds to the second purine-rich target sequence in an antiparallel orientation. The general rules for parallel and antiparallel orientation and uses of non-natural nucleotides are applicable for each of the binding domains used in the triple-helix forming oligonucleotide. The two binding domains in the oligonucleotide have the same 5' to 3' orientation such that one end of the oligonucleotide comprises a 5' nucleotide and the other end comprises a 3' nucleotide. When the pyrmidine-rich sequence in one strand is adjacent and 5' to the first purine-rich sequence, a linking domain between the first and second binding domains of the oligonucleotide facilitates triple-helix formation.

The triple-helix forming oligonucleotide and the triple-helix containing it can optionally contain a nucleotide to which at least one moiety is attached. Such a moiety can be a detection moiety so as to permit detection of alternate strand triple-helix formation, a cleaving moiety capable of cleaving the double-helical nucleic acid to localize the site of triple-helix formation or a therapeutic agent wherein triple-helix formation targets the action of the therapeutic agent.

In addition, the invention includes processes for forming the above triple-helices wherein an oligonucleotide capable of forming an alternate strand triple-helix is contacted with a large double-helical nucleic acid to form the alternate strand triple-helix.

The accompanying drawings, which are incorporated in and constitute a part of the specification, illustrate some of the embodiments of the invention and, together with the description, serve to explain the principles of the invention.

BRIEF DESCRIPTION OF THE DRAWINGS

FIG. 1 depicts the bonding of two Watson-Crick base pairs, and also the bonding of isomorphous base triplets of TAT and C+GC.

FIG. 2 is a schematic representation of the cleavage of double-helical DNA by a triple- helix-forming DNA-EDTA-Fe oligonucleotide, and the generation of a localized hydroxyl radical.

FIG. 3A is an autoradiogram showing the cleavage products of a double-stranded DNA containing $(dA-dT)_{15}$ after exposure to oligonucleotide DNA-EDTA probes 1–3 as analyzed by Maxam-Gilbert sequencing methods.

FIG. 3B (SEQ ID NOS: 39–41) shows the nucleotide sequence of oligonucleotide DNA-EDTA probes 1–3. This Figure also presents histograms of the DNA cleavage patterns derived by densitometry of the autoradiogram of FIG. 3A (lanes 3–5 and 8–10).

FIG. 4A is an autoradiogram showing the cleavage products of a 628 bp EcoRI/BgII restriction fragment of plasmid pDMAG10 after exposure to oligonucleotide DNA-EDTA probes 4–9, as analyzed by Maxam-Gilbert sequencing methods.

FIG. 4B (SEQ ID NOS: 41–48) shows the nucleotide sequence of oligonucleotide DNA-EDTA probes 4–9. This figure also represents histograms of the DNA cleavage patterns derived by densitometry of the autoradiogram of FIG. 4A from the cleavage of the restriction fragment with oligonucleotide DNA-EDTA probes 4 and 9.

FIG. 5A is a bar graph presenting the absolute cleavage efficiencies obtained with oligonucleotide DNA-EDTA probe 4 under various conditions.

FIG. 5B is a bar graph presenting relative cleavage efficiencies obtained with oligonucleotide DNA-EDTA probes 4–8 at three temperatures.

FIG. 6 is an autoradiogram showing the cleavage products of plasmid pDMAG10 after exposure to oligonucleotide DNA-EDTA probe 9 under various conditions, as analyzed on a nondenaturing agarose gel.

FIG. 7 (SEQ ID NOS: 49–51) (left) is a resolution cleavage pattern from FIG. 6, a simplified schematic model depicting a triple-helix complex with the Hoogsteen bound oligonucleotide DNA-EDTA probe 9 at one unique site within the 4.06 kb of plasmid DNA. The pyrimidine-rich oligonucleotide probe is bound in a parallel orientation to the purine-rich target sequence on one of the strands of the double-helical nucleic acid.

FIG. 8A is an autoradiogram of a sequencing gel showing the dependence of cleavage efficiency on the sequence composition of purine-rich oligonucleotides capable of forming triple-helices with an antiparallel orientation to a purine-rich target sequence. The site of triple-helix formation is shown on the left (SEQ ID NOS: 52–54). FIG. 8B shows the actual sequence of the double-helical DNA and oligonucleotide within and flanking the triple-helix site. As can be seen, the triple-helix forming oligonucleotide is oriented in the antiparallel orientation to the purine-rich target sequence in the double-helical DNA. A ribbon model showing the local triple-helical complex with the oligonucleotide in antiparallel orientation is shown immediately to the right of the triple-helix sequence.

FIG. 9A depicts models for G•GC, A•AT and T•AT triplets within a triple-helix motif where the third strand oligonucleotide is antiparallel to the purine W-C strand and the bases are in the anti-conformation. FIG. 9B depicts models for G•GC, A•AT and T•AT triplets where the third strand is antiparallel to the purine W-C strand and the bases are in the syn conformation. The plus and minus signs indicate relative polarities of the phosphatedeoxyribose backbones in FIGS. 9A and 9B.

FIG. 11 (SEQ ID NOS: 55–57) depicts the sequences of oligodeoxy-nucleotide-EDTA 1–5 wherein T* indicates the position of thymidine-EDTA. The oligodeoxynucleotides differ at one base position indicated in bold type to the four common natural DNA bases (A, G, C, T) and to 2'-deoxynebularine (N). Also shown are the sequences of the target double-helical DNA. The box indicates the double stranded sequence bound by oligodeoxynucleotide-EDTA•Fe(II) 1–5. The Watson-Crick base pair (AT, GC, CG, or TA) opposite the variant base in the oligodeoxynucleotide are in bold type. The height of the arrows represent the relative cleavage efficiencies at the indicated bases as determined by quantitative analysis using storage phosphor autoradiography.

FIG. 12 is a histogram depicting relative cleavage intensities (normalized) for the twenty base triplets. The values were obtained by phosphorimager quantitative analysis and represent the mean +/– standard deviation of two determinations.

FIG. 13 (SEQ ID NOS: 58–60) is a ribbon model and sequence of the triple-helix complex between a single site in the pULHIV EcoO1091-SspI restriction fragment and oligodeoxynucleotide-EDTA 6–17. The purine oligodeoxynucleotide with EDTA•Fe(II) at the 3' termini is located near the center of the major groove of the double-helical DNA antiparallel to the purine strand. The target site is located 0.42 kbp from the $^{32}$p radiolabeled end of the restriction fragment.

FIG. 14 depicts the structure of a pyrazolopyrimidine base used to form a P nucleotide.

FIG. 15A depicts the base triplet C+GC.

FIGS. 15B and 15C depict the base triplets P1·GC and P2·GC, respectively. For the pyrimidine Motif, the third strand is in the major groove of the Watson-Crick duplex parallel to the purine W-C strand and anti-parallel to the pyrimidine W-C strand.

FIGS. 16A and 16B depict bases for D nucleotides. FIG. 16A depicts the base 4-phenylimidazole. In FIG. 16B, the C3 of the phenyl ring is substituted with a 3-benzamido group. Nucleotides containing this base are referred to as D3 nucleotides.

FIG. 17 depicts 2-conventional models of base triplets D3·TA and D3·CG.

FIGS. 18A and 18B (SEQ ID NOS: 61–63) depict alternate strand triple-helix formation. In FIG. 18A, one of the strands of the double-helical nucleic acid contains a purine-rich sequence which is 5' and adjacent to a pyrimidine-rich sequence. In FIG. 18B, one of the strands of the double-helical nucleic acid contains a pyrimidine-rich sequence which is 5' and adjacent to a purine-rich sequence.

FIGS. 19A–19B depict the protocol for syntheses of the DMT-protected phosphoramidites of P1 and P2: (a) NaH, $CH_3CN$; (b) $NH_3$, MeOH, 120° C.; (c) 10% Pd/C, $H_2$, $EtOH/H_2O$; (d) PhNCS, pyridine, reflux; (e) $NH_4OH$; $H_2O_2$; $NH_3$, 120° C.; (f) TMS-Cl; isobutyric anhydride, pyridine; (g) DMTCl, pyridine; (h) N,N-diisopropylethylamine, β-cyanoethyl N,N-diisopropylchlorophosphor-amidite, $CH_2Cl_2$.

FIGS. 20A–D depict (SEQ ID NOS: 64–69) the relative affinities of bases P1 and P2 for forming Watson-Crick base pairs within a pyrimidine MOTIF. (A, top) Sequence of oligodeoxyribonucleotides-EDTA (10–13) where T* is the position of thymidine-EDTA. The oligonucleotides differ at one base position, indicated in bold type. (Bottom) The box indicates the double-stranded sequence bound by oligonucleotides-EDTA•Fe (10–13). The Watson-Crick base pair (AT, GC, TA or CG) opposite the variant base in the oligonucleotide is also in bold type. (B) Autoradiogram of the 20% denaturing polyacrylamide gel. The cleavage reactions were carried out by combining a mixture of oligodeoxyribonucleotide-EDTA (2 μM), spermine (1 mM)), and Fe(II) (25 μM) with the $^{32}$P-end-labeled 30-mer duplex in a solution of Tris-acetate (50 mM, pH 7.4), NaCl (100 mM), calf thymus DNA (100 μM bp), and 40% ethanol and incubating at for 1 h. Cleaving reactions were initiated by the addition of dithiothreitol (DTT; 3.3 mM) and allowed to proceed for 6 h at 37° C. The reactions were stopped by freezing and lyophilization. The cleavage products were analyzed by gel electrophoresis. Key: (Lanes 1–18) 5'-end-labeled 30-mer duplex $(A_4T_7YT_7G_{10})$ (Lane 1) intact 5'-labeled 30-bp DNA standard obtained after treatment according to the cleavage reaction in the absence of oligonucleotide-EDTA. (Lane 2) products of Maxam-Gilbert G+A sequence reaction. (Lanes 3–18) DNA-cleavage products produced by oligonucleotides-EDTA•Fe (10,11); 10 (lanes 3–6), 11 (lanes 7–10), 12 (lanes 11–14), 13 (lanes 15-18). XY=AT (lanes 3, 7, 11, 15); XY=GC (lanes 4, 8, 12, 16); XY=CG (lanes 5, 9, 13, 17); XY=TA (lanes 6, 10, 14, 18). (C) Bar graph representing the relative cleavage efficiencies (±10%) from densitometric analysis of (B). Sixteen base triplets were examined for binding specificity compatible with the pyrimidine triple-helix motif by the experiment described in (B).

FIGS. 21A–E depict (SEQ ID NOS: 70–76) the results obtained for triple-helix formation using P1 containing oligonucleotides 14–17. (A) (Top) oligodeoxyribonucleotides 14–17 containing cytosine (C), 5-methylcytosine (mC), thymine (T), P1, P2, and thymidine-EDTA (T*). (Bottom) Ribbon model of triple helical complex between oligonucleotide-EDTA 16 and a 15 base pair purine site in plasmid DNA (4.06 kbp). (B, C) Double-strand cleavage of plasmid DNA analyzed on a 0.9% agarose gel. Plasmid pDMAG10 was linearized with StyI and labeled with ($\alpha$-$^{32}$P)TTP, producing a 4.06-kbp restriction fragment. The $^{32}$P-end-labeled DNA was dissolved in buffer containing NaCl, Tris-acetate, and spermine and was mixed with oligonucleotides 15–18 previously equilibrated for 30 min with 1.5 equiv of Fe(II). After incubation at 25° C. for 30 min, the reactions were initiated by the addition of DTT (final concentration. 25 mM DTT). The cleavage reactions were allowed to proceed for 6 h at 25° C. The reactions were stopped b precipitation with ethanol and the cleavage products were analyzed by gel electrophoresis. Key (B) (Lane 1) DNA size markers (bp) obtained by digestion of StyI linear pDMAG10 with EcoRI (1060), BamHI (998), Asp700 (1460), and PstI (1814). (Lane 2) Control containing lanes 5, 8 and 11 are at pH 7.8. (C) (Lane 1) DNA size markers as above. (Lane 2) Control containing no oligonucleotide-EDTA•Fe$^{II}$. (Lanes 3–5) 15, (lanes 6–8) 16. Lanes 3 and 6 are at pH 7.0; lanes 4 and 7 are at pH 7.4; lanes 5 and 8 are at pH 7.8. (D) Bar graph representing the relative cleavage efficiencies (±10%) from the densitometric analysis of (B) and (C).

FIGS. 22A–D depict (SEQ ID NOS: 77–81) the results obtained for triple-helix formation using P1 containing nucleotides 18–20. (A) (Top) oligodeoxyribonucleotides 18–20 containing cytosine (C), 5-methylcytosine (mC), thymine (T), P1, and thymidine-EDTA (T*). (Bottom) Ribbon model of triple-helical complex between oligonucleotides-EDTA 20 and a 16 base pair purine site in plasmid DNA (4.95 kbp). (B) Autoradiogram of double-strand cleavage of pHIV-CAT DNA (4.95 kbp) analyzed on a 0.9% agarose gel. the reactions were carried out by combining a mixture of oligonucleotide-EDTA 18–20 (2 $\mu$M), spermine (1 mM), and Fe(II) (2 $\mu$M) with the $^{32}$P-labeled linearized plasmid in a solution of Tri-acetate (25 mM), NaCl (100 mM), and calf thymus DNA [100 $\mu$M (bp)] and incubating for 1 h at the reaction temperature. Cleavage reactions were initiated by the addition of ascorbate (1 mM) and allowed to proceed for 10 h at 30° C. The reactions were stopped by precipitation with ethanol and the cleavage products were analyzed by agarose gel electrophoresis. Key: (Lanes 1–8) pHIV-CAT linearized with BamHI and 3'-end labeled at both ends. (Lane 1) Control containing no oligonucleotide-EDTA•Fe$^{II}$. (Lane 2) DNA size markers obtained by digestion of BamHI linearized pHIV-CAT with HindIII and XohI 5.6 (undigested), 4.6, 3.3, 2.3, and 0.96 kbp. (Lanes 3–6) DNA cleavage products produced by 18; (lanes 7–10) DNA cleavage products produced by 19; (lanes 11–14) DNA cleavage products produced by 20. Lanes 3, 7 and 11 are at pH 6.2; lanes 4, 8 and 12 are at pH 6.6; lanes 5, 9, and 13 are at pH 7.0; lanes 6, 10, and 14 are at pH 7.4. (C) Bar graph representing the relative cleavage efficiencies (±10%) from the densitometric analysis of (B). (D) Autoradiogram of double-strand cleavage of pHIV-CAT DNA (5.6 kbp) analyzed on a 0.9% agarose gel. The reactions were carried out by combining a mixture of oligonucleotide-EDTA 20 (2 $\mu$M) spermine (1 mM), ad Fe(II) (2 $\mu$M) with the $^{32}$P-labeled linearized plasmid in a solution of Tris-acetate (25 mM pH 7.0), NaCl (100 mM), calf thymus DNA [100 $\mu$M (bp)] and incubating for 1 h at the reaction temperature. Cleavage reactions were initiated by the addition of ascorbate (1 mM) and allowed to proceed for 10 h at the reaction temperature. The reactions were stopped by precipitation with ethanol and the cleavage products were analyzed by agarose gel electrophoresis. Key: (Lanes 1–5) pHIV-CAT linearized with BamHI and 3'-end labeled at both ends. (Lane 1) Control containing no oligonucleotide-EDTA•Fe$^{II}$. (Lane 3) DNA cleavage products produced by 20 at 25° C.; (lane 4) DNA cleavage products produced by 20 at 30° C.; (lane 5) DNA cleavage products produced by 20 at 37° C.

FIG. 23 depicts the scheme for the synthesis of the $\beta$-cyanoethyl phosphoramidites of D3. (a) 1.1 eq. NaH, CH$_3$CN, rt., 63%; (b) 1% NaOH, MeOH, rt., 99%; (c) H$_2$, Pd/C, MeOH, rt., 99%; (d) 5 eg. TMSCl, pyridine, 0° C., followed by 5 eq. PhCOCl, 0° C. to rt., then H$_2$O, 0° C. to rt., 92%; (e) 1.4 eq. DMTCl, pyridine, 4° C., 88%; (f) 1.5 eq. 2-cyanoethyl-N,N-diisopropylchloro-phosphoramidite, 3 eq. diisopropylethylamine, CH$_2$Cl$_2$, rt., 98%.

FIG. 24A (SEQ ID NOS: 82–87) (top) show the sequences of oligonucleotide-EDTA 9–12 where T* is the position of the thymidine-EDTA. The oligonucleotides differ at one base position indicated in bold type. The box in the lower portion indicates the double stranded sequence bound by oligonucleotide-EDTA-Fe(II) 9–12. The Watson-Crick base pair (AT, GC, CG, or TA) opposite the variant base in the oligonucleotide is also in bold type.

FIG. 24B shows an autoradiogram of the 20 percent denaturing polyacrylamide gel. The cleavage reactions were carried out by combining a mixture of oligonucleotide-EDTA (2 $\mu$M), spermine (1 mM), and Fe(II) (25 $\mu$M) with the $^{32}$P labeled 30-mer duplex [~0.5 mM (bp)] in a solution of tris-acetate, pH 7.4(25 mM), NaCl (50 mM), calf thymus DNA [100 $\mu$M (bp)], and 40% ethanol and incubated at 35° C. for 1 hr. Cleavage reactions were initiated by addition of DTT (3 mM) and allowed to proceed for 6 hours at 35° C. The reactions were stopped by freezing and lyophilization and the cleavage products were analyzed by gel electrophoresis. (Lanes 1–22) Duplexes containing 5' end-labeled d(A$_5$T$_7$YT$_7$G$_{10}$). (Lane 1) Control showing intact 5' labeled 30 bp DNA standard obtained after treatment according to the cleavage reactions in the absence of oligonucleotide-EDTA. (Lane 2) Products of G+A chemical sequencing reaction. (Lanes 3–22) DNA cleavage products produced by oligonucleotide-EDTA•Fe(II) (9–12); 9 (Lanes 3–6); 10 (lanes 7–10); 11 (lanes 11–14); 12 (lanes 15–18). XY=AT (Lanes 3, 7, 11, 15); XY=GC (lanes 4, 8, 12, 16); XY=CG (lanes 5, 9, 13, 17); XY=TA (lanes 6, 10, 14, 18).

FIGS. 24C and 24D are a bar graphs presenting the relative cleavage data from densitometric analysis of FIG. 24B. Sixteen base triplets were examined in each graph for binding specificity compatible with the pyrimidine triple helix motif. The data are reproducible within ±10% of reported values.

FIG. 25A (SEQ ID NOS: 88–90) depicts a ribbon model of the triple helix complex between the bound oligonucleotide-EDTA•Fe(II) 13 and a single site containing all four base pairs within the 5.24 kb plasmid DNA.

FIG. 25B is an autoradiogram of double strand cleavage of SV40 length analyzed on a 1 percent agarose gel. The cleavage reactions were carried out by combining a mixture of oligonucleotide-EDTA 13(8 mM), spermine (1 mM), and Fe(II) (25 mM) with the $^{32}$P labeled linearized plasmid [100 mM (bp)] in a solution of tris-acetate, pH 7.0 (50 mM), NaCl (50 mM), and calf thymus DNA [100 mM (bp)] and incubated 1 hour at 37° C. (51). Cleavage reactions were initiated by addition of DTT (3 mM) and allowed to proceed for 4 hours at 37° C. The reactions were stopped by precipitation with ethanol and the cleavage products were analyzed by gel electrophoresis (120 V, BPB to the bottom of the gel). (Lanes 1–3) SV40 linearized with BclI and labeled at both 3' ends with $^{32}$P. (Lane 1) Control containing no oligonucleotide-EDTA•Fe(II). (Lane 2) DNA size markers obtained by digestion of BclI linearized SV40 with AccI, HaeII, and BglI 5243 (undigested DNA), 4101, 3305, 2778, 2465, 1938, 1142. (Lane 3) DNA cleavage products produced by oligonucleotide-EDTA•Fe(II) 13.

FIG. 26 (SEQ ID NOS: 91–97) depicts the duplex target site present on the 639 bp Hind III/Ssp I restriction fragment from plasmid pPBCRI containing two nine-mer purine tracts on alternate strands joined at a 5'-PuPy-3' junction. The double stranded region bound in the triple helix is boxed. The sequences of oligonucleotide-EDTA's 1–5 are shown, where T* indicates the position of thymidine-EDTA and bold type C indicates 5-methyldeoxycytidine.

FIG. 27 (SEQ ID NOS: 98–103) left is an autoradiogram of an 8% denaturing polyacrylamide gel used to separate affinity cleavage products. The cleavage reactions were carried out by combining a mixture of oligonucleotide-EDTA (200 mM) and Fe(NH$_4$)$_2$(SO$_4$)$_2$·6H$_2$O (500 mM) with the 3'end $^{32}$P labelled Hind III/Ssp I restriction fragment from plasmid pPBCRI [~15,000 cpm] in a solution of tris acetate, pH=7.0 (50 mM), spermine (1 mM), NaCl (10 mM), and calf thymus DNA (0.1 mM bp), and then incubating for one hour at 37° C. Concentrations listed are final concentrations. The reactions were initiated by the addition of dithiothreitol (DTT) (4 mM) and allowed to proceed for 18 hours at 37° C. The DNA was precipitated with ethanol and the cleavage products were analyzed by gel electrophoresis. (Lane 1) Products of an adenine-specific sequencing reaction.[15] (Lane 2) Intact 3' labelled fragment obtained after incubation under the conditions of the cleavage reactions in the absence of oligonucleotide-EDTA•Fe(II). (Lanes 3–7) DNA cleavage products produced by oligonucleotide-EDTA•Fe(II) 1–4; 3 (lane 3); 4 (lane 4) 3+4(200 mM each) (lane 5); 1 (lane 6); 2 (lane 7). FIG. 27 right shows the sequences of triple helical complexes formed between oligonucleotides 1 and 2 and the 5'-(Pu)$_9$(Py)$_9$-3' target site.

FIG. 28 is an autoradiogram of an 8% denaturing polyacrylamide gel used to separate DNase I footprinting products. The cleavage reactions were carried out by incubating oligonucleotide 5 with the 3' end or 5' end $^{32}$P labelled Hind III/Ssp I restriction fragment from plasmid pPBCRI [~20,000 cpm] in a solution of trisHCl, pH=7.0 (40 mM), spermine (1.5 mM), NaCl (5 mM), MgCl$_2$ (10 mM), CaCl$_2$ (10 mM) for two hours at 24° C. The reactions were initiated by the addition of nonspecific single stranded oligonucleotide (1 µM) and DNase I (0.25 units/µL) and allowed to proceed for 10 minutes at 24° C. The reactions were stopped by *the addition of calf thymus DNA (0.1 µM bp) and EDTA (50 mM). Concentrations listed are final concentrations. The DNA was precipitated with ethanol and the cleavage products were analyzed by gel electrophoresis. Odd numbered lanes contain 5' end labelled fragment, even numbered lanes contain 3' end labelled fragment. (Lanes 1 and 2) Intact labelled fragment in the absence of oligonucleotide 5 and DNase I. (Lanes 3 and 4) Products of adenine-specific sequencing reactions (Iverson, B. L., et al., *Nucleic Acids Res*. (1987) 15, 7823). (Lanes 5 and 6.) DNase I cleavage products in the absence of oligonucleotide 5. (Lanes 7 and 8.) DNase I cleavage products in the presence of 10 µM oligonucleotide 5. (Lanes 9 and 10.) DNase I cleavage products in the presence of 1 µM oligonucleotide 5.

FIGS. 30A–D depict (SEQ ID NOS: 104–105) the cleavage pattern generated by oligonucleotide 1. The box indicates the double stranded sequence bound. Positions of the arrows show the sites of cleavage and heights indicate extent of cleavage at that site. FIG. 30B depicts the cleavage pattern generated by oligonucleotide 2. FIG. 30C is a DNase I footprint generated by oligonucleotide 5. Bases within the brackets are protected from cleavage by DNase I. FIG. 30D depicts Dimethylsulfate (DMS) reactivity within the target site bound by oligonucleotide 5. Asterisks (*) indicate bases within the binding site protected from methylation by DMS. Arrows indicate bases within the binding site which remain reactive to DMS upon binding.

FIG. 32 (SEQ ID NOS: 115–120) (left) is an autoradiogram of an 8% denaturing polyacrylamide gel used to separate affinity cleavage products. The cleavage reactions were carried out by combining a mixture of oligonucleotide-EDTA (200 mM) and Fe(NH$_4$)$_2$(SO$_4$)$_2$·6H$_2$O (500 mM) with the 5' end $^{32}$P labeled Hind III/Ssp I restriction fragment from plasmid pPBCRII [~15,000 cpm] in a solution of tris acetate, pH=7.0 (50 mM), spermine (1 mM), NaCl (10 mM), and calf thymus DNA (0.1 mM bp) and then incubating for one hour at 37° C. The reactions were initiated by the addition of dithiothreitol (DTT) (4 mM) and allowed to proceed for 18 hours at 37° C. Concentrations listed are final concentrations. The DNA was precipitated with ethanol and the cleavage products were analyzed by gel electrophoresis. (Lane 1) Products of an adenine-specific sequencing reaction (Iverson, B. L., et al., *Nucleic Acids Res*. (1987) 15, 7823). (Lane 2) Intact 5' labelled fragment obtained after incubation under the conditions of the cleavage reactions in the absence of oligonucleotide-EDTA•Fe(II). (Lanes 3–9) DNA cleavage products produced by oligonucleotide-EDTA•Fe(II) 6–11; 10 (lane 3); 11 (lane 4) 10+11 (200 mM each) (lane 5); 6 (lane 6); 7 (lane 7); 8 (lane 8); 9 (lane 9).

FIG. 32 (right) shows the sequences of triple helical complexes formed between oligonucleotides 8 and 9 and the 5'-(Py)$_9$(Pu)$_9$-3' target site.

FIG. 33 is an autoradiogram of an 8% denaturing polyacrylamide gel used to separate DNase I footprinting products. The cleavage reactions were carried out by incubating oligonucleotide 12 with the 3' end or 5' end $^{32}$P labelled Hind III/Ssp I restriction fragment from plasmid pPBCRII [~20,000 cpm] in a solution of trisHCl, pH=7.0 (40 mM), spermine (1.5 mM), NaCl (5 mM), MgCl$_2$ (10 mM), CaCl$_2$ (10 mM) for two hours at 24° C. The reactions were initiated by the addition of nonspecific single stranded oligonucleotide (1 µM) and DNase I (0.25 units/µL) and allowed to proceed for 10 minutes at 24° C. The reactions were stopped by the addition of calf thymus DNA (0.1 µM bp) and EDTA (50 mM). Concentrations listed are final concentrations. The DNA was precipitated with ethanol and the cleavage products were analyzed by gel electrophoresis. Odd numbered lanes contain 5' end labelled fragment, even numbered lanes contain 3' end labelled fragment. (Lanes 1 and 2) Intact labelled fragment in the absence of oligonucleotide 12 and DNase I. (Lanes 3 and 4) Products of adenine-specific sequencing reactions.[15] (Lanes 5 and 6) DNase I cleavage products in the absence of oligonucleotide 12. (Lanes 7 and 8) DNase I cleavage products in the presence of 10 µM oligonucleotide 12. (Lanes 9 and 10) DNase I cleavage products in the presence of 1 µM oligonucleotide 12.

FIG. 34 is an autoradiogram of an 8% denaturing polyacrylamide gel used to separate MPE•Fe footprinting products. The cleavage reactions were carried out by incubating oligonucleotide 12 with the 3' end or 5' end $^{32}$P labelled Hind III/Ssp I restriction fragment from plasmid pPBCRII [~20,000 cpm] in a solution of trisHCl, pH=7.0 (40 mM), spermine (1.5 mM), NaCl (5 mM), MgCl$_2$ (10 mM), CaClz (10 mM) for two hours at 24° C. The reactions were initiated by the addition of MPE•Fe (5 µM) and DTT (4 mM) and allowed to proceed for five minutes at 24° C. Concentrations listed are final concentrations. The reactions were stopped by precipitation with ethanol and the cleavage products were analyzed by gel electrophoresis. Odd numbered lanes contain 5' end labelled fragment, even numbered lanes contain 3' end labelled fragment. (Lanes 1 and 2) Intact labelled fragment in the absence of oligonucleotide 12 and MPE•Fe. (Lanes 3 and 4) Products of adenine-specific sequencing reactions.[15] (Lanes 5 and 6) MPE•Fe cleavage products in the absence of oligonucleotide 12. (Lanes 7 and 8) MPE•Fe cleavage products in the presence of 10 µM oligonucleotide 12. Bracket indicates bases in the binding site hyperreactive to MPE•Fe.

FIGS. 35A–D depict (SEQ ID NOS: 121–122) the cleavage pattern generated by oligonucleotide 8. The box indicates the double stranded sequence bound. Positions of the arrows show the sites of cleavage and heights indicate extent of cleavage at that site. FIG. 35B depicts the cleavage pattern generated by oligonucleotide 9. FIG. 35C is a DNase I footprint generated by oligonucleotide 12. Bases within the brackets are protected from cleavage by DNase I. (D) MPE•Fe(II) reactivity within the target site bound by oligonucleotide 12. Arrows indicate positions of increased cleavage upon binding. Arrow heights indicate extent of cleavage at that site.

FIG. 36 (left) is a ribbon model depicting nine-mer oligonucleotides binding to adjacent triple helix binding sites for the sequence 5'-(Pu)$_9$(Py)$_9$-3'. The 3' end of one binding site appears to overlap with the 5' end of the adjacent site in the major groove. FIG. 36 (right) is a ribbon model depicting nine mer oligonucleotides binding to adjacent triple helix binding sites for the sequence 5'-(Py)$_9$(Pu)$_9$-3'. No binding site overlap is apparent in the major groove.

FIGS. 37A–C are (SEQ ID NOS: 123–128) a schematic representation of a triple-helical complex involving oligonucleotide 1 and template E4-2. An adenovirus EV4 promoter containing a TATA element and initiator has been modified by insertion of a 21 bp homopurine element (open arrow) overlapping a single Sp1 transcription factor binding site (filled arrow, left; bracketed base pairs, center; boxed sequence, right). Arrow orientation indicates 5' to 3' pelarity of the purine-rich strands of the homopurine and Sp1 elements. (−) indicates Watson-Crick base pairing (right), whereas (·) and (+) indicate Hoogsteen hydrogen bonding between adenine and thymine, or guanine and protonated 5-methylcytosine, respectively, as shown in FIG. 37B. FIG. 37C shows the nucleotide sequence of synthetic oligodeoxyribonucleotides used in this study. Oligomers 1 and 2 bind specifically to the homopurine element. Oligomer 3 is a control compound with the same base composition as 1, but with a random base sequence.

FIG. 38 depicts the protocol for in vitro transcription experiments. Oligonucleotides and templates (both test plasmid and internal control plasmid) were added, with or without a prebinding incubation, to Drosophila nuclear extract in the presence or absence of recombinant human Sp1-516C. Transcription reactions were incubated 30 min after initiation by addition of ribonucleoside triphosphates. RNA transcripts were subsequently isolated and quantitated as described under Experimental Procerdures.

FIG. 39 is a autoradiogram of reverse transcripts obtained after transcription of templates E4-6 and F1 at pH 7.0 in the presence or absence of oligomer 1 or 3, resolved by denaturing polyacrylamide gel electrophoresis. Homopurine elements (21 bp) are indicated by open arrows. Sp1 binding sites are indicated by filled arrows. In both cases, arrow direction indicates the 5' to 3' polarity of the purine-rich strand.

FIG. 40 depicts the time course of template fate. At various times after initiation of in vitro transcription of templates E4-6 and F1 (pH 7.0) in the presence or absence of oligomer 1 or 3, template DNA was purified and resolved by agarose gel electrophoresis. The DNA was denatured, blotted to nylon membrane, and hybridized with radiolabeled probe speefic for the E4-6 template (bottom strand of synthetic 40-mer duplex; see Experimental Procedures) according to standard procedures (Sambrook et al., 1989). Mobilities of supercoiled (SC), nicked open circular (N), and linear (L) plasmid DNA forms are indicated at left.

FIG. 41 depicts the time course of triple-helix-mediated repression. Transcription reactions with oligomer 1 either prebound (dark shading) or not prehound (light shading) to template E4-6 were assembled in the absence of ribonucleoside triphosphates. At various times after assembly (x-axis), 30-min transcription reactions (pH 7.5) were initiated by addition of ribonucleoside triphosphates. Bar heights (y-axis, left) reflect EV transcription, normalized to the internal F1 control template, and scaled relative to a value of 1.0 defined for each time roint as the level of transcription from template E4-6 in the presence of control oligomer 3. The effect of incubation time prior to ribonucleoside triphosphate addition on total transcription during the 30-min reaction (°) is also indicated (y-axis, right).

FIG. 42 depicts repression by triple-helical DNA complexes. In FIG. 42A transcription initiation from E4-series templates was assayed at pH 7.0 by transcription of templates in the presence or absence of SpI-516C after a prebinding step in the presence or absence of oligonucleotide 1 or 3. Homopurine elements (21 bp) are indicated by open arrows. Spi binding sites are indicated by filled arrows. In both cases, arrow direction indicates the 5, to 3' polarity of the purine-rich strand. Bars at right indicate E4 transcription, normalized to the internal control template and scaled relative to a value of I 0.0 for E4 transcription in the absence of both added oligonucleotide and Spi as described under Experimental Procedures. Error bars display standard error of the mean (SEM) derived from 2–5 independent replications. FIG. 42B depicts transcription initiation from series templates using E4-I as internal control.

FIGS. 43A and B are an autoradiogram of reverse transcripts obtained after transcription of templates E4-1, E4-6, and E4-1 I (with template F1 as internal control) at pH 7.0 in the presence or absence of oligomer 1 or 3, and in the presence or absence of Sp1-516C. Homopurine elements (21 bp) are indicated by open arrows. Sp1 binding sites are indicated by filled arrows. In both eases, arrow direction indicates the 5' to 3' polarity of the purine-rich strand. See FIG. 6 for scale.

FIGS. 44B–I depict permutation-dependent triple-helix-induced DNA mobility shifts. FIG. 44A is a schematic diagram of permuted DNA restriction fragments carrying an insert that is either know to be inherently bent (insert A) or whose bending/stiffening character is unknown [inserts BE, F(°), and F(~)]. Values of d (the distance from the insert center to the left restriction fragment terminus) and l (the restriction fragment length) were used to define the value (d/l) specifying the insert position within the permutation series. FIG. 44B is an ethidium bromide stained agarose gel (above) and autoradiogram (below) displaying permutation-dependent deceleration for bent control insert A (lanes 1–5; relevant fragment corresronds to highest mobility band in each lane) and permutation-dependent acceleration for triple-helical complexes involving inserts C and F(°) and radiolabeled oligomers 1 and 3 (lanes 6–13 and 14–21, respectively). FIGS. 44C–44I show quantitation of permutation-dependent DNA mobilities for the inserts tested in these experiments. Mobilities were assigned using the method described under Experimental Procedures. Panels 44C–44H correspond to inserts A–F, where the mobilities of permuted fragments carrying these inserts in the presence of oligomers 1 (°), 2 (~), or 3 (0) are indicated. No oligomer was present in the case of panel 44C. Panel 44I depicts the relationship between the total triple-helical character of the restriction fragment (% of restriction fragment length) and maximal mobility acceleration.

FIG. 45 depicts five models suggesting possible mechanisms for repression of eukaryotic transcription initiation by triple helical DNA complexes.

DETAILED DESCRIPTION OF THE INVENTION

Figure 10:
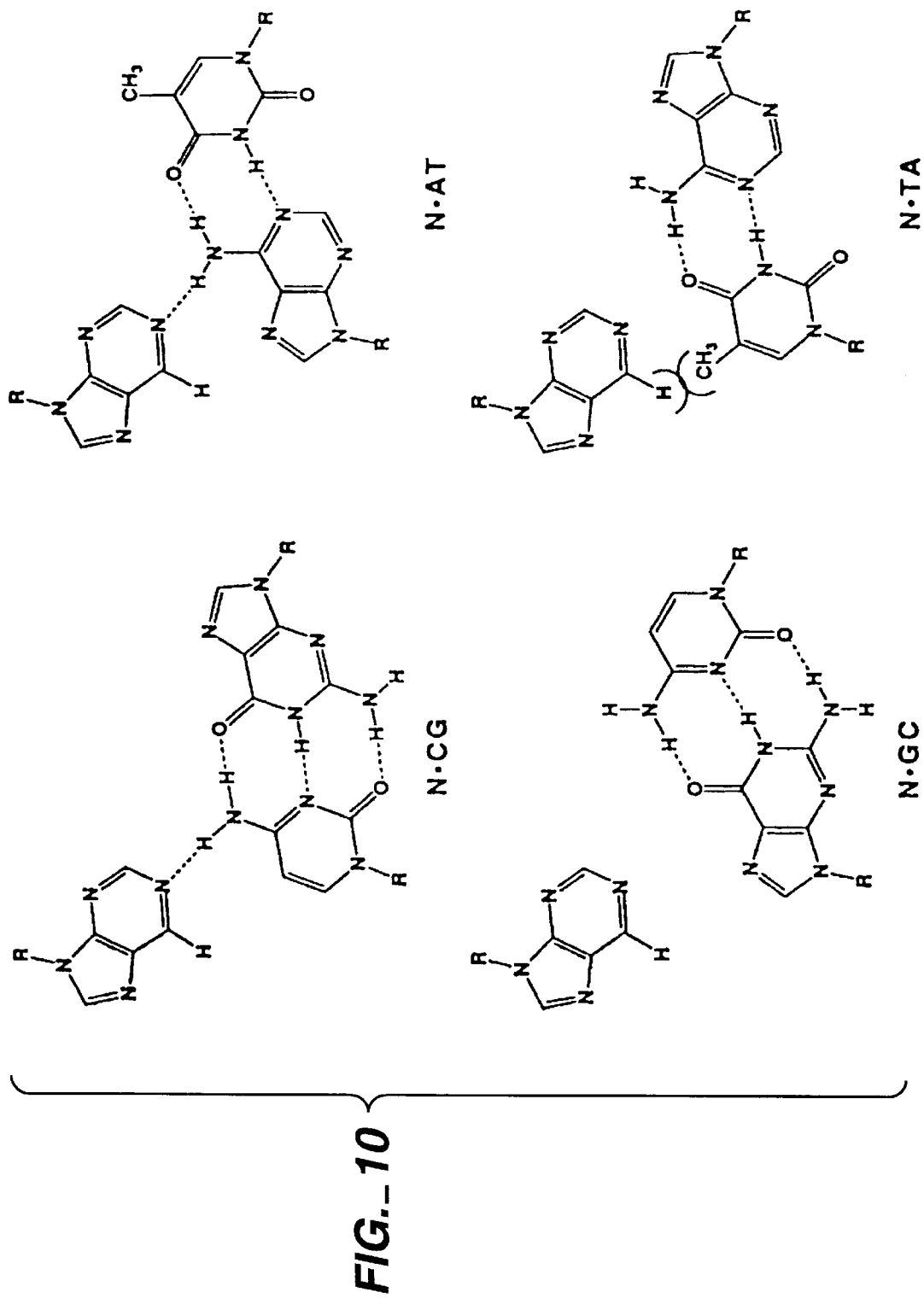
FIG. 10 depicts the models for base triplets N•AT, N•CG, N•GC, and N•TA formed between 2'-deoxynebularine and the Watson-Crick duplex within the pur•pur•pyr triple-helix motif. All bases are depicted with anti glycosidic bonds and the phosphate-deoxyribose backbone of the third strand was positioned as to be compatible with the purine triple-helix motif.

As used herein, a "triple-helix" is defined as a double-helical nucleic acid with an oligonucleotide bound to a target sequence within the double-helical nucleic acid. The double-helical nucleic acid can be any double-stranded nucleic acid including double-stranded DNA, double-stranded RNA and mixed duplexes between DNA and RNA. Such double-helical nucleic acids preferably have a length greater than 500 bp, more preferably greater than 1 kb and most preferably greater than about 5 kb. In many applications, the double-helical nucleic acid comprises genomic DNA from procaryotic or eucaryotic sources. When such genomic DNA is used it can comprise fragmented DNA, DNA digested with restriction endonucleases, or DNA cleaved according to the methods of the invention or as described by Strobel and Dervan, Nature 350:172–174 (1991), and Strobel, et al., Science 254:1639–1642 (1991). While such portions of genomic DNA are useful in practicing the invention, an important aspect of the invention is the formation of triple-helices with chromosomal DNA either in situ or in vivo. When genomic DNA is utilized, the oligonucleotides used to form triple-helices are particularly useful to detect the presence or absence of specific sequences within the genomic DNA for diagnostic and therapeutic purposes. Further, such genomic triple-helices can be used in conjunction with the protocols of Strobel and Dervan, and Strobel, et al., supra, for limited enzymatic cleavage of genomic DNA.

For example, numerous genetic diseases have been identified wherein a gene has been modified by way of substitution, insertion or deletion of one or more nucleotides to cause an inheritable recessive or dominant genotype. In addition, a number of polymorphisms, including restriction fragment length polymorphisms and other unique sequences, have been found to be associated with as yet unidentified inheritable gene defects such as associated with autoimmune diseases and the like. Appropriate oligonucleotides can be used in the methods of the invention to detect such diagnostic sequences in genomic DNA (or in some cases in double-stranded cDNA derived from an appropriate tissue) as a means to diagnose the presence of one or more defective alleles for a particular disease, provided such diagnostic sequences are amenable to triple-helix formation.

In addition, the triple-helices of the invention have an enormous potential for the treatment of various disease states. For example, oligonucleotides can be selected which specifically bind to pathogenic double-stranded DNA including specific sequences required by pathogenic bacteria or viruses for replication or virulence. Alternatively, the oligonucleotide can be chosen to target a unique sequence of the pathogen which is not found in the genome of the pathogen's host. Such an oligonucleotide further includes a therapeutic agent which selectively kills the pathogen or a cell containing it based upon the selective specificity of the oligonucleotide for the pathogenic DNA.

Another important potential therapeutic application of triple-helix technology involves controlling gene expression by selective triple-helix formation within expresion regulation sequences of a target gene. For example, triple-helix forming oligonucleotides can be used for cancer treatment by way of triple-helix suppression of specific oncogenes including those of endogenous or viral origin. When so used, one or more oncogenes identified with a particular tumor type are used as targets for triple-helix formation. Specific oligonucleotides designed for triple-helix formation to suppress the expression of hyper-expressed oncogenes are designed to repress expression. Alternatively, when an activated oncogene contains unique sequences associated with such activation, oligonucleotides specific for the unique sequence and which contain a therapeutic agent can be used. Such therapeutic oligonucleotides are capable of selectively forming a triple-helix with such sequences in those cancerous cells containing the activated oncogene thereby preferentially killing or repressing the cancer causing cell type.

As used herein, a "target sequence" within a double-helical nucleic acid comprises a sequence preferably greater than 10 nucleotides in length but preferably less than 20 nucleotides within the double-helical nucleic acid. The target sequence is most preferably between 11 to 18 bases. The target sequence, in one aspect of the invention, is defined by the nucleotide sequence on one of the strands of the double-helical nucleic acid. In another aspect, the target sequence is defined by two or more purine-rich sequences which are located on alternate strands of the double-helical nucleic acid. The nucleotide content of the target sequence is used in conjunction with the rules of triple-helix formation herein to determine which nucleotides should be included in a triple-helix forming oligonucleotide. In this regard, the nucleotides in the target sequence and nucleotides in the triple-helix forming oligonucleotide are disclosed as being directly involved in the interaction which causes triple-helix formation. However, it is to be understood that the invention is not limited to those triple-helices wherein the proposed binding interaction actually exists but rather includes any triple-helix and oligonucleotide used to form such a triple-helix according to the disclosure herein. In the preferred embodiments herein, the target sequence is defined by one or more purine-rich sequence on one or more strands of the double-helical nucleic acid containing strand.

As used herein, a "purine-rich sequence" is defined as a contiguous sequence wherein greater than 50% of the nucleotides contain a purine base. However, it is preferred that the purine-rich sequence contain greater than 60% purine nucleotides, more preferably greater than 75% purine nucleotides, next most preferably greater than 90% purine nucleotides. When such a purine-rich sequence contains greater than approximately 90% purine nucleotides, it is sometimes referred to as a purine sequence or a substantially homopurine sequence. Consistent with the definition of purine-rich sequence, a "pyrmidine-rich" sequence is a continguous sequence wherein greater than 50% of the nucleotides contain a pyrmidine base. As with purine-rich sequence, the pyrmidine-rich sequence preferably contains greater than 60%, and more preferably greater than 75%, the next most preferably greater than 90%. When a pyrmidine-rich sequence contains greater than approximately 90% pyrmidine, nucleotides are sometimes referred to as a pyrimidine sequence or a substantially homopyrmidine sequence.

The oligonucleotides used in triple-helix formation are generally of substantially the same length as the target sequence in the double-helical nucleic acid and have a sequence which permits binding of the oligonucleotide to the double-helical nucleic acid in either a parallel or anti-parallel orientation as compared to the target sequence. In a parallel orientation, the oligonucleotide is oriented such that its 5' end is positioned at the 5' end of the target sequence and its 3' end is positioned at the 3' end of the target sequence. When oriented in an antiparallel orientation the 5' end of the oligonucleotide is positioned at the 3' end of the target sequence and the 3' end of the oligonucleotide is positioned at the 5' end of the target sequence. It is to be understood, of course, that reference to the 5' end and 3' end of the target sequence is not to be construed as the physical end of the double-helical nucleic acid but rather refers to the 5' to 3' sequence orientation in the strand containing one or more purine-rich sequences forming the target sequence.

When the target sequence is a purine-rich sequence, parallel binding of the oligonucleotide occurs when the oligonucleotide is a pyrimidine-rich oligonucleotide. Anti-parallel binding, however, occurs when a purine-rich oligonucleotide is used. As indicated hereinafter, the specific rules for parallel and antiparallel binding define a particular nucleotide contained within an oligonucleotide when the nucleotide at the "complementary position" in the target sequence is a specified nucleotide. This term means that when the oligonucleotide is positioned in a parallel or antiparallel orientation at a target sequence that there is a correspondence in the position of the various nucleotides in the oligonucleotide with the nucleotides contained in the target sequence. While it is believed that the oligonucleotide binding is within the major groove of a double-helical nucleic acid such as DNA and that the rules defining sequence binding have a physical basis with regard to the triplets proposed for triple-helix formation, the use of such language is not to be construed as a limitation on the mechanism of triple-helix formation. Further, to the extent the rules disclosed herein refer to nucleotides found in DNA, such rules are equally applicable to double-helical nucleic acid containing RNA except that the nucleotides which form triplets with TA can be used to form triplets with UA.

Parallel Binding to Purine-Rich Target Sequences

As indicated, parallel binding of an oligonucleotide to a purine-rich target sequence occurs when the oligonucleotide comprises a pyrimidine-rich oligonucleotide. In general, the following rules apply to the formation of triplets within the triple-helix.

1. Naturally Occurring Nucleotides

The pyrimidine-rich oligonucleotide contains a T when the nucleotide at the complementary position in the purine-rich target sequence is A. Further, the pyrimidine-rich oligonucleotide contains a C when the nucleotide at the complementary position in the purine-rich target sequence is G.

Naturally occurring nucleotides include not only those found naturally in nucleic acids but also analogs thereof which do not change the underlying structure of the base ring but which enhance the formation of a triple-helix. Thus, for example, 5-methylcytosine can be used rather than cytosine to recognize GC base pairs. Accordingly, the naturally occurring nucleotides referred to above and elsewhere herein include those containing naturally occurring bases, e.g., A, T, G, and C and those wherein additions or substitutions have been made to naturally occurring purine or pyrimidine bases.

FIG. 1 shows typical binding of base pairs and triplets as referred to herein for parallel binding to a purine-rich target sequence according to the foregoing rules. Structure 1 of FIG. 1 shows a standard representation of Watson-Crick base pairing of nucleotide bases A (adenine) and T (thymine). Major groove 2 and minor groove 3 are shown where they would appear in an A-helical structure; B-helical structures (not shown) are also encompassed within the scope of this invention. Structure 4 of FIG. 1 shows Watson-Crick base pairing of G (guanine) and C (cytosine). Major groove 5 and minor groove 6 are indicated. Structure 7 of FIG. 1 shows isomorphous base triplets of TAT wherein the additional pyrimidine strand is bound by Hoogsteen-hydrogen bonds in the major groove to the complementary purine strand shown in Watson-Crick duplex 1. Structure 8 of FIG. 1 shows isomorphous base triplets of C+GC. The additional pyrimidine is bound as described above.

2. Non-Natural Nucleotides

In addition to naturally occurring nucleotides, a number of non-natural nucleotides can be used in the oligonucleotides used to form triple-helices.

a. P Nucleotides

Pyrimidine-rich oligonucleotides containing predominately T and C nucleotides and which recognize, respectively, A and G nucleotides in a target sequence can be modified by substituting the C in the pyrimidine-rich nucleotide with a P nucleotide.

As used herein, a "P nucleotide" is a nucleotide containing a pyrazolopyrimidine base or an analog thereof. The structure of a pyrazolopyrimidine is shown in FIG. 14. When linked to ribose at N1, it is referred to as a P1 nucleoside. When attached to ribose through N2, it is referred to as P2 nucleoside. In the preferred embodiments, the P nucleoside is further substituted at C5 so as to contain a hydrogen donor moiety. A preferred moiety is a primary amino group, however, secondary amines may also be used as well as other moieties such as OH. In addition, other modifications may be made to the base structure such as the formation of a ketone group at C7.

FIG. 15 depicts a P1 and P2 nucleotide which has formed a base triplet with a GC base pair. Of the two P nucleotides presented, P1 with the structure shown in FIG. 15B is preferred.

An important advantage of using a P nucleotide and in particular a P1 nucleotide is that triple-helix formation occurs at a higher pH as compared to the use of a pyrimidine-rich oligonucleotide utilizing a C nucleotide to recognize a GC base pair. See FIG. 15A. As indicated in the examples, oligonucleotides containing P1 residues have been shown to bind a single 15 base pair site containing 5 GC base pairs at pH 7.8 and a single 16 base pair site containing 6 contiguous GC base pairs at pH 7.4. Thus, oligonucleotides utilizing such P nucleotides are capable of forming triple-helices more readily at physiological pH as compared to those containing C or 5-methylcytosine.

b. Oligonucleotides Containing D Nucleotides

As indicated, an oligonucleotide containing T to recognize A in an AT base pair and C or a P nucleotide to recognize G in a GC base pair can be used to form a triple-helix wherein the oligonucleotide is oriented in a parallel orientation with the purine-rich target sequence. When T and C are present in a target sequence, a D nucleotide can be used in the corresponding position in the oligonucleotide used to form the triple-helix.

As used herein, a "D nucleotide" is a nucleotide which contains a 4-phenylimidazole base. The structure of such a base is set forth in FIG. 16A. In the preferred embodiments, the base is further substituted at C3 in the phenyl ring. When X in FIG. 16A is H, the nucleotide is referred to as a D2 nucleotide. When 3-benzamido is substituted at the C3 position, the nucleotide is referred to as a D3 nucleotide. The structure of the base in the D3 nucleotide is shown in FIG. 16b and the base pair interactions with TA and GC base pairs is shown in FIG. 17. The D3 nucleotide was designed to be capable of forming two hydrogen bonds across both strands of the Watson-Crick CG base pair: one between the imidazole N3 and the $NH_2$ of cytosine; the second between the amido group on D3 and the ketone oxygen of guanidine. In the case of D2, this nucleotide was designed to produce one hydrogen bond between the imidazole N3 and the amino group of cytosine. However, as indicated in the examples, the benzamido group appears to be largely responsible for the specific interaction stabilizing the triple-helix formation. D3 is therefore the preferred nucleotide for recognizing T and C nucleotides. Other substituents at X can be used, however, although diminished affinity and specifiity is observed. Such substiuents include acetamide, cyclohexanecarboxamide and 1-naphthamide.

Antiparallel Binding to Purine-Rich Target Sequences

As indicated, antiparallel binding of an oligonucleotide to a purine-rich target sequence occurs when the oligonucleotide comprises a purine-rich oligonucleotide. In general, the following rules apply to formation of triplets in such a triple-helix.

The purine-rich oligonucleotide contains a G when the nucleotide at the complementary position in the purine-rich target sequence is G. Such an oligonucleotide also contains an A when the nucleotide in the complementary position in the purine-rich target sequence is A.

In addition to the foregoing rules, it has been determined that an N nucleotide containing the base nebularine, or its analogs (e.g., 2'-deoxynebularine), is capable of binding to the pyrimidine nucleotide C in a purine-rich target sequence. This binding occurs when the nebularine is incorporated into an oligonucleotide designed for antiparallel binding to the purine-rich, but C-containing target sequence. When nebularine is used, it can be the sole nucleotide used to pair with a C nucleotide in the target sequence. However, since T is also capable of pairing with a C nucleotide in the purine-rich target sequence, albeit in a less energetically favorable manner, the oligonucleotide can contain N nucleotides alone or N nucleotides in combination with the pyrimidine nucleotide T.

When one or more N nucleotides are used, the following rules apply. The purine-rich oligonucleotide contains a G when the nucleotide at the complementary position of purine-rich target sequence is G. In addition, the purine-rich oligonucleotide contains an A or a T when the nucleotide at the complementary position in the purine-rich target sequence is A. However, the total T content of the triple-helix forming oligonucleotide is preferably less than 40% of the oligonucleotide sequence and most preferably less than 25%. When greater amounts of T nucleotides are used in an oligonucleotide, the antiparallel orientation of the oligonucleotide to the purine-rich target strand becomes less favorable and as a consequence, a shift to a parallel orientation can occur. Thus, an oligonucleotide containing 20 nucleotides designed for antiparallel orientation to a purine-rich target sequence of 20 nucleotides preferably contains no more than 5 to 8 T nucleotides to maintain the antiparallel orientation.

Recognition of Double-Helical Nucleic Acid by Alternate Strand Triple-Helix Formation The foregoing rules relating to triple-helix formation wherein an oligonucleotide is bound in a parallel or anti-parallel orientation to a purine-rich target sequence can be combined to further expand the scope of target sequence recognition. In this approach, oligonucleotides capable of triple-helix formation can be rationally designed which are capable of forming a triple-helix with a double-helical nucleic acid wherein one strand contains a pyrimidine-rich sequence adjacent to or in close proximity with a purine-rich sequence. The oligonucleotide is designed so that it has at least first and second binding domains. The first binding domain comprises a pyrimidine-rich portion which is capable of forming a triple-helix with a first purine-rich target sequence in a double-helical nucleic acid in a parallel orientation. The second binding domain in the oligonucleotide comprises a purine-rich portion which is capable of forming a triple-helix in an anti-parallel orientation with a second purine-rich target sequence located on the alternate or second strand of the double-helical nucleic acid. The stabilities and structures of these alternate strand triple-helices, however, depend upon whether the bindings site sequence is 5'-(purine-rich)$_m$(pyrimidine-rich)$_n$-3' or 5'-(pyrimidine-rich)$_m$(purine-rich)$_n$-3'.

Referring now to FIGS. 18A and 18b, two types of double-helical DNA are shown together with the third strand which forms the triple-helix. FIG. 18A shows a purine-rich sequence 5' and adjacent to a pyrimidine-rich sequence whereas FIG. 18B shows a pyrimidine-rich sequence which is 5' and adjacent to a purine-rich sequence. The normal base pairing as between the first and second strands of the double-helical DNA is also shown.

The oligonucleotide used to form the triple-helices as shown in FIG. 18 is also depicted as a third strand. As can be seen, this third strand is a 5' to 3' oligonucleotide which contains pyrimidine-rich and purine-rich sequences each of which correspond to a binding domain in the oligonucleotide. The first and second purine-rich target sequences, which are bound by the binding domains in the oligonucleotide, are also shown in FIGS. 18A and 18B. In this regard, the binding domain containing a pyrimidine-rich sequence is in a parallel orientation to the corresponding purine-rich target sequence in the double-helical DNA. Further, the purine-rich binding domain in the third strand is in an anti-parallel orientation as compared to the second purine-rich sequence located on the second strand of the double-helical nucleic acid. Although the third strand comprises a 5' to 3' oligonucleotide, this shift from parallel to anti-parallel orientation occurs because the binding interaction between the third strand and the double-helical nucleic acid shifts between alternate strands.

A particular advantage of alternate strand recognition of double-helical nucleic acid lies in the fact that triple-helices can be formed when all four base pairs are present on a single strand. Thus, an oligonucleotide capable of forming an alternate strand triple-helix and having a known sequence can be used to target a predetermined sequence or to determine a sequence either directly or indirectly upon alternate strand triple-helix formation. For example, in FIGS. 18A and 18B, all four different nucleotides are present on each of the first and second strands. When an alternate strand triple-helix is formed, the nucleotides in the purine-rich target sequence can be deduced based upon the known triplet formation for the pyrimidine-rich and purine-rich binding sequences which bind in a parallel or anti-parallel orientation, respectively. Since the other nucleotide in the base pair of the nucleic acid is known, the formation of the triplet provides an indirect indication of the base pair in the alternate strand.

While alternate strand triple-helix formation may be useful to detect all four different nucleotides in a single strand, the oligonucleotides to form such triple-helices can utilize any of the aforementioned non-naturally occurring nucleotides. For example, an oligonucleotide containing a first binding domain comprising a pyrimidine-rich sequence can form a triple-helix with a first purine-rich sequence containing A and G. However, if the first purine-rich target sequence also contains one or more T or C nucleotides, an appropriate D nucleotide can be incorporated into the first binding domain of the oligonucleotide. In addition, a P nucleotide can be used in place of C or 5 methylcytosine. Similar modifications can be made to a second binding domain in an oligonucleotide comprising a purine-rich domain which binds in an anti-parallel orientation to a second target sequence. If, for example, a purine-rich target sequence contains one or more C nucleotides, an N nucleotide can be utilized in the second purine-rich binding domain of the oligonucleotide.

As indicated in the examples, when a purine-rich sequence is 5' and adjacent to a pyrimidine sequence, an oligonucleotide can be rationally designed based upon the known triplet formation rules. However, when a pyrimidine-rich sequence is 5' and adjacent to a purine-rich sequence, the junction between the first and second binding domains in the oligonucleotide requires the presence of a linking domain to accommodate the shift in binding as between the first and second strand. The linking domain in such cases comprises a linking moiety equivalent to about two nucleotides. Such linking moieties may be naturally occurring nucleotides such as T or non-naturally occurring nucleotides including ribo and deoxyribo groups which do not contain a base moiety.

Production of Triple-Helix Forming Oligonucleotides

The oligonucleotides used in the invention to form triple-helices can be made synthetically by well-known synthetic techniques to contain a structure corresponding to the naturally occurring polyribonucleic or polydeoxyribonucleic acids. Alternatively, the phosphoribose backbone of such oligonucleotides can be modified such that the thus formed oligonucleotide has greater chemical and/or biological stability. Biological stability of the oligonucleotide is desirable when the oligonucleotides are used in vivo for diagnostic or therapeutic uses. Such modified oligonucleotides are synthesized with a structure which is stable under physiological conditions which include enhanced resistance to nuclease degradation. Further, when used in vivo, such nucleotides preferably have a minimal length which permits targeted triple-helix formation so as to facilitate the transport of the oligonucleotide across the membranes of the cytoplasm and nucleus.

In specific embodiments of this invention, a moiety is included in the triple-helix forming oligonucleotide. Moieties such as a label, a therapeutic agent, or a cleavage moiety are incorporated along the length of any such oligonucleotide so as to provide precisely the detection, treatment or cleavage desired by the practitioner. Also, more than one moiety may be included in the oligonucleotide. Previously known and familiar synthesis protocols can be employed, in some cases using currently available automated technology, wherein such moieties can be incorporated into the triple-helix forming oligonucleotide.

A nucleic acid-cleaving moiety can be attached to a nucleoside base during synthesis of a novel nucleoside and the so-modified nucleoside then incorporated into a selected oligonucleotide using standard procedures.

This oligonucleotide containing the cleavage moiety recognizes the corresponding target sequence of a double-helical nucleic acid. For example, a metal chelator for cleaving a specific double-helical nucleic acid sequence is tethered to a triple-helix forming oligonucleotide. FIG. 2 depicts oligonucleotide-directed cleavage of double-helical DNA by a triple-helix forming oligonucleotide DNA-EDTA-Fe probe. One thymidine has been replaced by thymidine with the iron chelator EDTA covalently attached at C-5. Reduction of dioxygen generates a localized hydroxyl radical at this point. Alternatively, the metal chelator may be attached to a selected nucleotide located within a given oligonucleotide sequence. In the presence of dioxygen ($O_2$), an appropriate metal ion, and a reducing agent, the DNA-chelator probe yields a strand break at the target complementary DNA sequence, cleaving one or both strands at that site.

Oligonucleotides equipped with a DNA cleaving moiety have been described which produce sequence-specific cleavage of single-stranded DNA. See, e.g., U.S. Pat. No. 4,795,700. Examples of such moieties include oligonucleotide-EDTA-Fe probes (DNA-EDTA) which cleave a complementary single strand sequence (Dreyer and Dervan,

*Proc. Natl. Acad. Sci. USA* 82:968 (1965); and Chu and Orgel, *Proc. Natl. Acad. Sci. USA* 82:963 (1965)). One example of a DNA-EDTA probe is a novel nucleoside, 5'-DMT-T*-triethylester derived from deoxyuridine to which is attached the metal chelator EDTA as described in detail in U.S. Pat. No. 4,795,700. Such probes are also described in Dreyer and Dervan, *Proc. Natl. Acad. Sci. USA*, supra. These references disclose an EDTA-nucleoside composition incorporated into a 19-nucleotide base pair sequence of DNA complementary to a 19 bp sequence in a 167 bp restriction fragment of DNA from the plasmid pBR322. This DNA-EDTA probe was then used in the presence of the metal ion Fe(II), atmospheric dioxygen, and the reducing agent dithiothreitol (DTT) to afford specific cleavage at its complementary 9 bp complement in single-stranded plasmid DNA.

Chelators or other cleavage moieties, as well as marker labels and therapeutic agents may also be incorporated into the triple-helix forming oligonucleotide of the present invention at various positions for which the chemistry for attachment at such positions is known, provided that such attachment is accomplished so as not to disrupt the hydrogen-base pair bonding between the DNA or RNA sequences during triple-helix formation.

The triple-helix forming oligonucleotide may be labeled in various well known ways for detection and diagnostic applications. For example, with radioactive metals such as $^{99}$Tc following the procedures of Elmalch, D. R., et al., *Proc. Natl. Acad. Sci. USA* 81:918 (1984) and EDTA or with fluorescent elements such as the lanthanides Tb+$^3$ or Eu+$^3$. Leung, et al., *Biochem. Biophys. Res. Comm.* 75:15 (1977). If a chelator is desired to be used in a cleavage moiety, other metal chelators may be used in place of EDTA such as polyamines or other chelators capable of binding Fe(II-III) or Cu(I-II). Other polyamino carboxylic metal chelators may be utilized in place of EDTA such as 1,2-diaminocyclohexane tetraacetic acid, diethylenetriamine pentaacetic acid, ethylenediamine di-(-O-hydroxyphenol-acetic acid), and hydroxyethylene diamine triacetic acid. A metal chelator may be attached to the nucleotide probe during synthesis via a hydrocarbon-amide linkage which may consist of several carbon atoms. The specificity of the probe for the reaction site is prescribed by the nucleotide sequence within which the metal chelator or other cleavage moiety is attached. The moiety can be incorporated into polydeoxyribonucleotides or polyribonucleotides of any desired length and sequenced using routine phosphoramidite or phosphotriester procedures.

One convenient synthesis of DNA-EDTA probes involves the incorporation of a modified thymidine into an oligonucleotide by chemical methods. This approach allows for automated synthesis and affords control over the precise location of the EDTA moiety at any thymidine position in the oligonucleotide strand, Felsenfeld, et al., supra.

In an embodiment of this invention, bifunctional DNA-EDTA probes are used for recognition and cleavage of a double-stranded nucleic acid. These probes allow triple-helix formation at a discrete location to be mapped on large DNA using gel electrophoresis. An important part of the present invention involves the development of preferred assay conditions for measuring formation and cleavage of the triple-helix. This will be discussed in more detail in Example 2 below. However, the preferred general conditions for the cleavage reactions are as follows: approximately 100 nM in bp radio labeled restriction fragment (approximately 10,000 cpm), 25 nM tris/acetate, pH 7.0, 1 nM spermine, (MY), 100 nM NaCl, 100 umolar in vp sonicated, deproteinized cath-thimus DNA, 20 volume-percent ethyleneglycol, 1 probe, 25 umolar Fe(II) and 2 nM DTT. The cleavage reactions were run for approximately 16 hours at 0–25° C. These conditions may be varied without departing from the scope of this invention.

As described in the examples below, the affinity cleaving method utilizing DNA, EDTA and known in the art allows the effect of reaction conditions, probe length, and single base mismatches on triple-helix formation to be analyzed on high resolution sequencing gels. Precise methods for quantitation and measurement and determination of the presence and orientation of triple-helices is set out in more detail in the Examples below.

As will be seen in the Examples, the directional orientation of the third strand as well as the identity of the grooves in right-handed DNA-helix occupied by the bound DNA-EDTA probe can be analyzed by high resolution gel electrophoresis (FIG. 2). Additionally, the location of triple-helices within large pieces of DNA can be mapped by double-strand breaks analyzed by nondenaturing agarose gel electrophoresis.

Synthesis and the preparation of necessary and desired component parts of the probes of the present invention, and their assembly is believed to be within the duties and tasks performed by those with ordinary skill in the art and, as such, are capable of being performed without undue experimentation.

The oligonucleotide probes of the present invention are not limited to the production of sequence-specific cleavage of double-stranded DNA by triple-helix formation, but may also be utilized as diagnostic agents when a radioisotope labeled, fluorescing, or otherwise detectable metal ion is attached to the probe. The probes of the present invention may also be used as target-specific therapeutics with the attachment of an "artificial" or natural gene repressor or other effective agent to the oligonucleotide.

The following is presented by way of example, and not to be construed as a limitation to the scope of the appended claims.

EXAMPLE 1

Determination of Parallel Orientation and Groove Location of Hoogsteen Strand Binding Watson-Crick DNA Nine homopyrimidine DNA probes, 11–15 nucleotides in length, described in more detail below, each containing a single thymidine with EDTA covalently attached at C-5 (labeled T*), were synthesized for binding and cleavage studies with two different duplexed target DNA's.

Generally, unless specifically controverted below, the following definitions apply: DMT refers to 4,4-dimethoxytrityl; DTT refers to dithiothreitol; DNA-EDTA 1–9, the probes examined below, refers to oligodeoxyribonucleotides with an EDTA-modified thymidine at positions 1, 5, or 8; Spermine indicates spermine-4-HCl (Aldrich, 98× pure) which was dissolved in water and then pH adjusted with NaOH to 7.4; TBE-buffer includes 0.89 nM TRIS (meaning TRIS(hydroxymethyl)aminomethane), 0.89 mM Boric acid, and 1 mM EDTA-disodium salt; Fe(II) refers to Fe(NH$_4$)$_2$(SO$_4$)$_2$-6H$_2$O. Aqueous solutions of DTT and Fe(II) were freshly prepared before use.

A double-stranded DNA was examined that contains (dA-dT)$_{13}$ as a target sequence which could, in principle, bind a d(T)$_{13}$ oligonucleotide in parallel or antiparallel orientation. A 30-base pair duplex of DNA containing (dAdT)$_{13}$ with all purines on one strand was labeled separately at the 5' end of each strand. This was allowed to incubate with d(T)$_{13}$-EDTA probes 1 to 3 (shown in FIG. 3B) with the thymidine-EDTA located at oligonucleotide positions 8, 5, and 1, from the 3'-end, respectively. The $^{32}$P-labeled DNA was dissolved in buffer containing calf-thymus DNA, NaCl, TRIS, spermine and ethylene glycol and was mixed with the DNA-EDTA-FeII) probes, previously equilibrated with Fe(II) for 1 minute. After incubation at 0° C. for 10 minutes, the reactions were initiated by addition of an aqueous solution of DTT, such that the final concentrations were 10 mM TRIS/HCl (pH 7.4), 1 mM spermine, 100 mM NaCl, 40 vol—ethylene glycol, 100 µM (bp) of calf thymus DNA, 0.67 µM DNA-EDTA probe, 25 µM Fe(II) and 1 mM DTT. The pH values are not corrected for temperature or different ethylene glycol percentage and are given for the ten-fold concentrated buffer solution at 25° C. The cleavage reactions were allowed to proceed for 15 hours at 0° C. and then stopped by freezing and lyophilization. The resulting cleavage products were separated by electrophoresis on a denaturing 20 percent polyacrylamide gel and visualized by autoradiography (FIG. 3A).

FIG. 3A shows an autoradiogram of the 20 percent Maxam-Gilbert sequencing gel. Lanes 1 to 5 contain 5'-End-labeled d(A$_5$T$_{15}$G$_{10}$); lanes 6 to 10 contain 5'-End-labeled d(C$_{10}$A$_{15}$T$_5$). The Maxam-Gilbert G+A sequencing reactions used for lanes 1 and 6 are disclosed in Maniatis Ct *Molecular Cloning, A Laboratory Manual*, Cold Spring Harbor Laboratory (1982), and Maxam and Gilbert, *Methods Enzymol.* 65:499 (1987). Controls in lanes 2 and 7 showing the two 5'-labeled 30-bp DNA standards were obtained by treatment according to the cleavage reactions in the absence of oligonucleotide DNA-EDTA-Fe probes. Lanes 3 to 5 and 8 to 10 are the DNA cleavage products in the presence of oligonucleotide DNA-EDTA-Fe probes 1 to 3, approximately 0.5 µM (bp) 5µ-$^{32}$P-labeled DNA, (approximately 10,000 cpm), 10 mM TRIS/HCl, pH 7.4, 1 mM spermine, 100 mM NaCl, 100 µM (bp) sonicated, deproteinized calf thymus DNA, 40 percent by volume ethylene glycol, 0.67 µM oligonucleotide probe, 25 yM Fe(II) and 1 mM DTT; incubated for 15 hours at 0° C. Lanes 3 and 8 contain oligonucleotide DNA-EDTA-Fe 1, lanes 4 and 9 contain DNA-EDTA-Fe 2, lanes 5 and 10 are oligonucleotide DNA-EDTA-Fe 3.

On the d(T)$_{15}$ strand of the Watson-Crick duplex, one major cleavage site is observed for each oligonucleotide DNA-EDTA probe 1–3 with the maximum cleavage site shifted to the 5'-side of T*. The location of the cleavage patterns on Watson-Crick DNA produced by the oligonucleotide probes 1–3 with respect to the position of T* reveal the orientation of the DNA-EDTA probe on the duplex DNA (FIG. 3B).

FIG. 3B shows the oligonucleotide (T)$_{15}$-EDTA probes 1–3, where T* is the position of the thymidine-EDTA. Also shown are histograms of the DNA cleavage patterns for these probes, derived by densitometry of the autoradiogram shown in FIG. 3A (lanes 3–5 and 8–10). The heights of the arrows represent the relative cleavage intensities at the indicated bases. Arrows are shown if the cleavage intensity at a particular nucleotide was greater than 5% when compared to that of the nucleotide cleaved the most efficiently. The box in each histogram indicates the double-stranded sequence which is bound by the oligonucleotide DNA-EDTA-Fe(II) probes 1–3. The Watson-Crick base-pair to which T* is Hoogsteen hydrogen bonded in the triple-strand helix is shaded.

As seen from the orientations, the pyrimidine-rich EDTA oligonucleotide binds parallel to the purine-rich and anti-parallel to the pyrimidine-rich strands of the Watson-Crick double-helical DNA. These observations rule out strand displacement (D-loop) as the mode of binding. The asymmetry of the cleavage patterns on opposite strands of DNA reveals the identity of the groove in right handed DNA occupied by the oligonucleotide DNA-EDTA-Fe probes. An asymmetric cleavage pattern with maximal cleavage shifted to the 5' or 3' side on opposite strands corresponds to the diffusible hydroxyl radical being generated in the major or minor groove, respectively. The cleavage patterns shown in FIG. 3B reveal that the oligonucleotide DNA-EDTA-Fe(II) probe is located in the major groove of the Watson-Crick DNA.

Pyrimidine-rich oligonucleotide probes 1 and 2 which bear the EDTA at an internal base position cleave exclusively the pyrimidine-rich strand of the DNA containing the target sequence. A model of the triple-helix between these pyrimidine-rich oligonucleotide EDTA-Fe(II) probes and the double-helical DNA (not shown) reveals that the purine-rich Watson-Crick strand in the triple-helix is protected from the hydroxyl radical by the sugar-phosphate backbones of the Hoogsteen-paired strand. In effect there are now three grooves in the triple-helix and EDTA-Fe is exposed to only one groove (FIG. 1). The nucleotides 3 to 4 bases on the 5'-side of T* in the right-handed triple-helix are proximal to the EDTA-Fe(II) and are therefore expected to be cleaved most efficiently. oligonucleotide DNA-EDTA-Fe(II) 3, which carries the cleaving moiety at the 5'-end, should form a triplex with no flanking nucleotides on the 5'-side of T*. A pyrimidine-rich oligonucleotide probe with the cleaving function at the 5'-end should generate cleavage on both strands. Indeed, the oligonucleotide d(T)$_{15}$-EDTA-Fe(II) 3, carrying the EDTA at the 5' end, cleaves both strands of the target duplex DNA (FIG. 3B).

EXAMPLE 2

Specific Cleavage of a DNA Restriction Fragment and Determination of Assay Conditions This example illustrates two important aspects of the present invention. In the first part, it is shown that an unsymmetrical mixed oligonucleotide probe can precisely recognize a purine-rich target sequence within double-helical DNA having a length 50-fold greater than the oligonucleotide probe. In this example, restriction fragments with mixed bases are used which vary in length, have single mismatches with the known target, and vary in the positions of the EDTA (FIG. 4B).

In the second part preferred assay conditions are determined, as well as the effect of varying those conditions with probes oligonucleotide of 11–15 bp in length.

Specific Cleavage of a DNA Restriction Fragment

Cleavage by triple-helix formation with oligonucleotide DNA-EDTA-Fe(II) probes 4–9 was examined on a restriction fragment 628 base pairs in length that contained the sequence d(AAAAAGAGAGAGAGA) (SEQ ID NO: 1). This sequence was obtained from plasmid pDMAG10 which was a gift from D. Mendel, who constructed it by inserting the d(AAAAAGAGAGAGAGA) containing duplex in the large BamHI-HindIII restriction fragment of pBR322 (Mendel and Dervan, *Proc. Natl. Acad. Sci. USA* 84:910 (1987)). A single site labeled 628 bp EcoRI-BglI restriction fragment containing the purine-rich target sequence was obtained by linearizing pDMAG10 with EcoRI, labeling with $^{32}$P (Van Dyke and Dervan, *Science* 225:1122 (1984)), and cleaving with BglI. This sequence represents a mixed purine-rich target which is located 47 nucleotides from the 3'-(and 5')$^{32}$P-label of the DNA fragment. The concentration of the single stranded oligodeoxynucleotides were determined using the following epsilon values (260 mm) for each base: 15400(A), 11700(G), 7300(C) and 8800(T).

FIG. 4A shows an autoradiogram of the 8 percent Maxam-Gilbert high-resolution polyacrylamide sequencing gel run on oligonucleotide probes 4–9. The EcoRI/BglI restriction fragment of plasmid pDMAG10 is labeled at the 3' end with $^{32}$P The Maxam-Gilbert GNA sequencing reactions described in the previous example were used here for lane 20. In general, the cleavage reactions were carried out as follows: a mixture of oligonucleotide DNA-EDTA probe (1 μM) and Fe(II) (25 μM) was combined with the $^{32}$P-labeled restriction fragment (approximately 100 μM (bp)) in a solution of calf-thymus DNA (100 μM (bp)), NaCl (100 mM), TRIS/acetate, pH 7.4 (25 mM TRIS), spermine (1 mM) and ethyleneglycol (20 vol-%) and incubated for 10 minutes at 0° C. Cleavage reactions were initiated by addition of 2 mM DTT, proceeded 16 hours at 0° C. to 25° C., and stopped by precipitation with ethanol. The reaction products were analyzed on a high resolution polyacrylamide gel. For each lane the parameters differing from these general conditions are given below. (lane 21): Control, minus oligonucleotide DNA-EDTA; (lanes 22, 27 and 32): 1 μM oligonucleotide DNA-EDTA 6; (lanes 23, 28 and 33): 1 μM oligonucleotide DNA-EDTA 5; (lanes 24, 29 and 34): 1 μM oligonucleotide DNA-EDTA 4; (lanes 25, 30 and 35): 1 μM oligonucleotide DNA-EDTA 7 (Hoogsteen-type TG-mismatch); (lanes 26, 31 and 36): 1 μM oligonucleotide DNA-EDTA 8 (Hoogsteen-type CA-mismatch). The reactions were run for 16 hours at 0° C. (lanes 22 to 26), 12.5° C. (lanes 27 to 31) and 25° C. (lanes 21 and 32 to 36) respectively. Electrophoresis on a 5 percent polyacrylamide gel separated the radiolabeled 628 bp fragment from other digest products.

FIG. 4B shows the sequence of oligonucleotide DNA-EDTA probes 4–9 where T* is the position of the thymidine-EDTA. Histograms shown in this figure of the DNA-cleavage patterns were determined by densitometry of the autoradiogram from the cleavage of the 628 bp restriction fragment with oligonucleotide DNA-EDTA probes 4 and 9.

On the 3' end-labeled DNA-strand, carrying the pyrimidine-rich sequence, DNA-EDTA-Fe(II) 4 and 9 both produce sequence specific cleavage patterns shifted to the 5' side of the T* position (FIG. 4B) consistent with major groove binding. The efficiency of the sequence specific cleavage of the DNA restriction fragment by oligonucleotide DNA-EDTA-Fe(II) 4 is dependent on spermine and/or Co(NH$_3$)$_6$$^{+3}$-concentrations, ethylene glycol, pH and probe concentration (FIG. 5A).

The cleavage efficiency of oligonucleotide probes 4–6 which differ in length (15, 13 and 11 nucleotides) and oligonucleotide probes 7 and 8 which differ in sequence (each contain one Hoogsteen base mismatch in the triple-helix complex) were examined under identical conditions at different temperatures. Identical cleavage patterns are observed for the oligonucleotide DNA-EDTA-Fe(II) probes 4–8. At 0° C., oligonucleotide probes 4–6 which differ in length but have in common T* at position 5 each produce a cleavage pattern of the same intensity. At 25° C. oligonucleotide probe 6 which is 11 nucleotides in length cleaves the target DNA 3 times less efficiently than oligonucleotide probes 5 or 4 which are 13 and 15 nucleotides in length, respectively. Oligonucleotide DNA-EDTA probes 7 and 8 which contain a single base mismatch at position 10 and 11 generate cleavage patterns of reduced intensity and is temperature sensitive. Compared to oligonucleotide DNA-EDTA probe 4, the relative cleavage efficiency decreases for the single base mismatch probes 7 from 0.4 (at 0° C.) to 0.08 (25° C.) and 8 from 0.5 (at 0° C.) to 0.13 (25° C.) (FIG. 5B).

Optimization of Assay Conditions

In this example, the effect of added cations, organic solvents, pH, temperature, oligonucleotide probe length and sequence homology were studied. The results, detailed below, are summarized in FIG. 5.

FIG. 5A shows a bar graph presenting the absolute cleavage efficiencies obtained with oligonucleotide DNA-EDTA-Fe probe 4 under various conditions. The values were determined by cutting out the corresponding pieces of the dried gel and measuring their radioactivity by scintillation counting. The numbers given are calculated by dividing the radioactivity of the cleavage site (sum of 5 most efficiently cleaved nucleotides) with the total radioactivity obtained from the uncleaved fragment, the cleavage site and the background, which is corrected for the background that resulted from the untreated 628 bp fragment. The remaining values were assigned by correlation of absolute with relative cleavage efficiencies determined by densitometry of the autoradiogram. FIG. 5(B) shows a bar graph presenting the relative cleavage efficiencies (sum of 6 most efficiently cleaved nucleotides) obtained with oligonucleotide DNA-EDTA-Fe probes 4–8 (FIG. 4A) at three temperatures as determined by densitometry. The data is reproducible within +10% of reported values.

Importance of Added Cations

The importance of added cations for formation of triple-stranded DNA or RNA has been known since the discovery of those structures. To bind double-helical DNA, the oligonucleotide DNA-EDTA-Fe(II) probe must overcome the repulsion between two anionic chains of the Watson-Crick duplex and its own negatively charged phosphodiester backbone. One way to achieve this is to use multivalent cations (Michelson, et al., *Nucl. Acid. Res. Mol. Biol.* 6:83 (1967); and Felsenfeld and Miles, supra). The naturally occurring polyamines and their derivatives are known to stabilize double-and triple-helical structures of nucleic acids. (Blaser and Gabbay, *Biopolymers* 6:243 (1968)). We find preferred cleaving efficiencies for oligonucleotide DNA-EDTA-Fe(II) probe 4 in the presence of mM concentrations of spermine or Co(NH$_3$)$_6$ $^{+3}$. No cleavage occurs in the absence of spermine or Co(NH$_3$)$_6$$^{3+}$ which demonstrates the importance of these or similar cations for triple-helix formation (FIG. 5A). Spermine appears to be ideal for the stabilization of the triple-stranded complex with oligonucleotide DNA-EDTA-Fe(II) probes. It efficiently neutralizes the negative charges of the sugar-phosphate backbones and does not compete with the Fe(II) for the EDTA-moiety. No cleavage is observed if MgCl$_2$ or CaCl$_2$ (up to 8 mM) are substituted for spermine which could also be due to competition with Fe(II) for the metal chelator EDTA (Hertzberg and Dervan, *Biochemistry* 23:3934 (1984)).

Role of Organic Solvents

According to x-ray fiber diffraction studies, the three strands of a triple-helix occur in a A'RNA-like conformation (Arnott, *Nucl. Acids Res.* 3:2459 (1976)). A conformational transition may be necessary to allow the binding of the oligonucleotide DNA-EDTA-Fe(II) probe. It is established that a B to A conformational change takes place on lowering the relative humidity. This transformation is dependent on the ratio of (A+T) to (G+C) and can be achieved by the addition of a variety of organic solvents to the DNA aqueous solution. The increase in organic solvent concentration should favor the B to A conformational transition and suggest that triple-helices should form more readily (Saenger, *Principles of Nucleic Acid Structure*, edited by C. R. Cantor, Springer-Verlag, New York, Inc. (1984)). As a result, the cleavage due to the oligonucleotide DNA-EDTA probe should increase correspondingly. We find that the efficiency of duplex cleavage by oligonucleotide $(T)_{15}$-EDTA-Fe(II) probes 1–3 is increased by a factor of 10 upon addition of ethyleneglycol (40 percent by volume). Other organic solvents such as methanol, ethanol, dioxane or DMF give rise to similar behavior. In the presence of ethyleneglycol, oligonucleotide DNA-EDTA-Fe(II) probes provide cleavage patterns without detectable background, a result that may be due to radical scavenging by this solvent.

Curiously, the mixed T and C pyrimidine-rich oligonucleotide EDTA-Fe(II) probe 4 demonstrates different behavior. The addition of 20 vol-% ethyleneglycol is not necessary and does not increase the cleavage efficiency as found in the $(T)_{15}$ case. One explanation for this difference is that a mixed T, C oligonucleotide probe may have a higher affinity than the oligo T probe to the corresponding Watson-Crick target sequence due to the protonated cytosines required to form the Hoogsteen-hydrogen bonds in the triple-helix. The alternative explanation is that the target Watson-Crick sequences differ in conformation and one may be more A like than the other.

The pH-Dependence of Cleavage Efficiency

Mixed pyrimidine-rich oligonucleotide DNA-EDTA-Fe(II) probe 4 cleaves double-helical DNA over a relatively narrow range of pH values producing the maximum cleavage at pH 7.0 (FIG. 5A) (the pH values are not corrected for temperature or different ethyleneglycol percentage and are given for the tenfold concentrated buffer solutions at 25° C.). This behavior could be caused by two independent properties of the oligonucleotide-EDTA probes. On one hand, triplex formation requires protonation of cytosines at N-3 in the third strand to enable the Hoogsteen hydrogen bonds between oligonucleotide DNA-EDTA-Fe(II) probes and the target Watson-Crick DNA sequence. It was previously demonstrated that complexes of triple-helical nucleic acids, containing cytosines in the homopyrimidine strands, are stable in slightly acidic to neutral solutions and start to dissociate on increasing pH (Lipsett, *J. Biol. Chem.* 239:1256 (1964); Morgan and Wells, *J. Mol. Biol.* 37:63 (1969)). Therefore it seems not unreasonable that the oligonucleotide DNA-EDTA-Fe(II) probes do not bind Watson-Crick DNA in slightly basic solutions (pH≧8) and consequently do not produce cleavage under these conditions. On the other hand, studies with methidiumpropyl-EDTA-Fe indicate that the cleavage efficiency of EDTA-Fe decreases sharply below pH 7 (Hertzberg and Dervan, supra), presumably due to either partial protonation of the EDTA and the resulting loss of Fe(II) or some pH-dependence of the cleavage reaction. Based on known EDTA cleavage chemistry, it is anticipated that at slightly acidic pH-values, oligonucleotide DNA-EDTA-Fe(II) probes do not produce efficient cleavage. In data not shown, footprinting experiments confirm that the triple-helix is forming at acidic pH values.

Influence of Probe Length, Temperature, and Sequence Homology

At 1 uM concentration the oligonucleotide DNA-EDTA probe approaches the maximum cleavage efficiency on the 628 bp restriction fragment (FIG. 5A). We chose oligonucleotide DNA-EDTA probes 13 nucleotides in length for our initial studies to attain reasonable binding affinities at the double-helical target sequence (Cassani and Bollum, *Biochemistry* 8:3928 (1969); Raae and Kleppe, *Biochemistry* 17:2939 (1978)). Having determined the preferred cleavage conditions for oligonucleotide DNA-EDTA-Fe(II) probe 4, we focused on the size dependence for oligonucleotide DNA-EDTA-Fe(II) probes to form a triple-helix complex with the Watson-Crick DNA. Oligonucleotide DNA-EDTA-Fe(II) probes 5 and 6, which are 13 and 11 nucleotides in size, produce cleavage patterns of similar intensities at 0° C., indicating that homopurine-homopyrimidine sequences as short as 11 nucleotides can specifically bind the 628 bp restriction fragment. The influence of oligonucleotide length becomes more apparent if the cleavage reactions are allowed to proceed at higher temperatures. Oligonucleotide DNA-EDTA probes 4 and 5 cleave the target duplex DNA at 25° C. with approximately the same efficiency, whereas the relative intensity of the cleavage pattern produced by the shorter oligonucleotide probe 6 becomes significantly weaker (FIGS. 4A, 5B).

In order to test the importance of sequence homology for triple-helix formation and cleavage, two probes, oligonucleotide DNA-EDTA-Fe(II) probes 7 and 8, were synthesized that contained single base mismatches compared to oligonucleotide DNA-EDTA-Fe(II) 4 probe but had in common the location of T* at position 5. When bound to the double-helical target sequence, probes 7 and 8 should give rise to one mismatched base-triplet with respect to the Hoogsteen hydrogen bonding. The mismatching bases in the oligonucleotide probe strands were chosen so that the corresponding tautomeric or protonated structures of the mismatching pyrimidine base could still allow the formation of isomorphous base triplets. Compared to oligonucleotide DNA-EDTA-Fe(II) probe 4, both single mismatch probes 7 and 8 generate weaker cleavage patterns at 0° C. and the difference becomes more apparent for the cleavage patterns produced at 25° C. (FIG. 5B). Oligonucleotide probes 7 and 8 cleave the target DNA less efficiently than the corresponding homologous oligonucleotide DNA-EDTA-Fe(II) probe 4. This result indicates that a single base-mismatch in an oligonucleotide DNA-EDTA-Fe(II) probe, 15 nucleotides in length, can lower the cleavage efficiency by at least a factor of 10. Clearly, the sequence specific recognition of large double-helical DNA by oligonucleotide DNA-EDTA-Fe(II) probes is sensitive to single base mismatches indicating the importance of the correct pyrimidine-rich probe sequence for the formation of a triple-stranded complex with the target-DNA.

EXAMPLE 3

Site Specific Double-Strand Cleavage Of Plasmid DNA

The ability of oligonucleotide DNA-EDTA-Fe(II) probe 9 to cause double-strand breaks at a homopurine-homopyrimidine insert in large DNA is presented in FIG. 6A. This figure shows double-strand cleavage of plasmid DNA analyzed on a nondenaturing 0.9% agarose gel. The plasmid pDMAG10 (Mendel and Dervan, *Proc. Natl. Acad. Sci. USA* 84:910 (1987)) was digested with StyI restriction endonuclease to produce a linear DNA fragment 4.06 kb in size which contains the homopurine site $d(A_5(AG)_5)$ located 1.0 kb upstream from the restriction site. This affords heterogenous overhangs and each end could be labeled separately using either $\alpha\text{-}^{32}\text{P-ATP}$ or $\alpha\text{-}^{32}\text{P-TTP}$ according to standard procedures. Lanes 1–3 of FIG. 6A shows plasmid pDMAG10 linearized with StyI and labeled at the downstream end of the restriction site with $\alpha$-$^{32}$P-ATP. Lanes 4–6 show the same plasmid with the other end labeled with $\alpha$-$^{32}$P-TTP.

The $^{32}$P-end-labeled DNA was allowed to incubate with oligonucleotide DNA-EDTA-Fe(II) probe 9 (5 $\mu$M) for 10 minutes at 0° C. as previously described and the cleavage reaction was initiated by the addition of DTT (2 mM) and run at 0° C. for 16 hours. Cleavage conditions included $^{32}$P labeled DNA plasmid, 100 mM NaCl, 1 mM spermine, 25 mM TRIS/acetate pH 7.0, 100 $\mu$M (bp) sonicated, deproteinized calf thymus DNA, 5 $\mu$M oligonucleotide DNA-EDTA-Fe(II) probe 9, 25 $\mu$M Fe(II) and 2 mM DTT. Lanes 1 and 4 are controls containing no oligonucleotide DNA-EDTA-Fe(II) probe 9. Lanes 2 and 5 are DNA size markers obtained by digestion of StyI linearized pDMAG10 with EcoRI, PvuI, SalI (both ends labeled), and XmnI labeled with $\alpha$-$^{32}$P-TTP): 4058 (undigested DNA), 53338, 2994, 2368, 1690, 1460, 1064, and 720. Lanes 3 and 6 are oligonucleotide DNA-EDTA-Fe(II) probe 9 at 5 $\mu$M added.

Separation of the cleavage products by agarose gel electrophoresis followed by autoradiography reveals only one major cleavage site producing two DNA fragments, 3.04 and 1.02 kb in size as determined by comparison with comigrating DNA size markers (FIG. 6A, lanes 3 and 6).

FIG. 6B (left) shows the course resolution cleavage pattern from gel 6A. FIG. 6B (middle) depicts a simplified model of the triple-helix complex with the Hoogsteen bound oligonucleotide DNA-EDTA-Fe(II) probe 9 at one unique site within 4.06 kb of plasmid DNA. The high resolution cleavage pattern at that site is shown in FIG. 4B.

This example demonstrates that pyrimidine-rich probes can recognize a purine-rich target sequence in a very large piece of double-stranded DNA to form a triple-helix under physiological conditions.

EXAMPLE 4

The Orientation of a Purine-Rich Oligonucleotide Bound in the Major Groove of Double-Helical DNA is Antiparallel to the Purine-Rich Strand The target binding site chosen was a 19-bp purine-rich sequence, 5' -AG$_3$AG$_4$AG$_4$-AG$_3$A-3', within a 648-bp restriction fragment. The target sequence is identically read from 3' to 5' or 5' to 3'. Therefore, it could a priori support two putative triple-helical structures within a purine-purine-pyrimidine motif with the third strand parallel or anti-parallel to the W-C purine strand. Oligonucleotides 1 to 3 of sequence composition 5'-T*G$_3$XG$_4$XG4XG$_3$T-3' (SEQ ID NO: 2) (where X=T,A,C, respectively) were synthesized with thymidine-EDTA (T*) at each 5' end.

FIG. 8A contains an autoradiogram of an 8% polyacrylamide sequencing gel showing the dependence of cleavage efficiency on sequence composition of oligonucleotides 1 to 3, each at three different concentrations (0.1, 0.5, and 1.0 $\mu$M). The cleavage reactions were performed on the HindIII-SspI restriction fragment of plasmid pPBAG19 labeled at the 3' end with $^{32}$P The plasmid pPBAG19 was constructed by inserting the sequence d(A$_2$T$_2$ (CT)$_3$A$_5$G$_3$AG$_4$AG$_4$AG$_3$A$_5$-(CT)$_3$) (SEQ ID NO: 4) into the large EcoRI-XbaI restriction fragment of pUC19. Reactions were performed on the 3' end-labeled HindIII-SspI restriction fragment. The reactions were carried out by combining a mixture of oligonucleotide-EDTA and 2.5 equivalents of Fe(NH$_4$)$_2$(SO$_4$)$_2$•6H$_2$O with the $^{32}$P-labeled restriction fragment [~100 nM in base pairs, ~10,000 cpm] in a solution of tris acetate, pH=7.8 (50 mM), NaCl (10 $\mu$M), spermine (100 $\mu$M), and calf thymus DNA (100 $\mu$M in base pairs), which was then incubated at 24° C. for 1 hour. Cleavage reactions were initiated by the addition of dithiothreitol (DTT) (4 mM) and allowed to proceed for 12 hours at 24° C. The reactions were stopped by precipitation with ethanol, and the cleavage products were analyzed by gel electrophoresis. Lane 1 contains products of an A-specific cleavage reaction (The plasmid pPBAG19 was constructed by inserting the sequence d(A$_2$T$_2$(CT)$_3$A$_5$G$_3$AG$_4$AG$_4$AG$_3$A$_5$-(CT)$_3$) into the large EcoRI-XbaI restriction fragment of pUC19. Reactions were performed on the 3' end-labeled HindIII-SspI restriction fragment.) Lane 2 is a control showing the intact 3' end-labeled restriction fragment obtained after treatment according to the cleavage reactions in the absence of oligonucleotide-EDTA•Fe. Lanes 3 to 11 show the cleavage products produced by oligonucleotides-EDTA-Fe of general sequence T*G$^3$XG$_4$XG$_4$XG$_3$T-3'. In lanes 3 to 5, X=T, in lanes 6 to 8, X=A, and in lanes 9 to 11, X=C. The concentration of the oligonucleotide-EDTA-Fe probes 1 to 3, in lanes 3, 6 and 9 was 1 to 3 at 0.1 $\mu$M. In lanes 4, 7 and 10, the oligonucleotide probe concentration was 0.5 $\mu$M. Finally, the oligonucleotide probe concentrations in lanes 5, 8 and 11 was 1.0 $\mu$M. Cleavage efficiencies were quantitated by using storage phosphorimaging plates with a Molecular Dynamics 400S PhosphoImager.

The oligonucleotide EDTA-Fe probes cleaved the double-helical DNA at the target site but with different efficiencies. Cleavage occurred near the 3' end of the purine-rich target sequence. The cleavage maximum on each strand was shifted asymmetrically in the 5' direction. The asymmetry and location of the cleavage pattern on one end of the binding site indicate that oligonucleotides 1 to 3 were bound in the major groove anti-parallel to the W-C purine strand. This result rules out strand displacement (D-looping) as the mode of recognition. No cleavage products corresponding to a parallel orientation could be detected. A ribbon model and sequence of the local triple-helical complex between oligonucleotides-EDTA-Fe 1 to 3 and the target sequence is set forth in FIG. 7B. The circles represent backbone positions of cleavage. The size of circles represent extent of cleavage. The third strand is located near the center of the major groove of the double-helical DNA based upon the models of triplet formation in FIG. 9A. In FIG. 9A the models for G•GC, A•AT, and T•AT triplets within a triple-helix motif are shown were the third strand is anti-parallel to the purine W-C strand and bases are in the anti-conformation. FIG. 9B on the other hand shows models for G•GC, A•AT, and T•AT triplets where the third strand is anti-parallel to the purine W-C strand and the bases are in the syn conformation. In both FIGS. 9A and 9B, plus and minus indicate relative polarities of the phosphate-deoxyribose backbones.

From phosphorimager quantitative analysis of the absolute cleavage efficiencies, oligonucleotides 1 to 3 at 1.0 $\mu$M concentration appeared to bind the target sequence with relative affinities 1.0 (X=T), 0.56 (X=A), and 0.16 (X=C), respectively. Therefore, for this particular sequence and under these reaction conditions, the contribution to the stability of the triple-helix from three A•AT triplets differed from that of three T•AT triplets by less than a factor of 2. However, when C was placed opposite three AT base pairs, the binding of the oligonucleotide decreased by nearly a factor of 8. Although the binding of oligonucleotides 1 to 3 is dominated by the formation of G•GC triplets, we believe the difference in affinities for 1 to 3 may be evidence for specific hydrogen bond contributions in the T•AT and A•AT triplets (FIG. 9).

The efficiency of strand scission depended upon the concentration of multivalent cations such as spermine and $Mg^{2+}$, with maximum cleavage occurring $\geq 100$ μM concentration of spermine. Cleavage efficiencies were comparable throughout the pH range 6.6 to 7.8. The pH dependence on the recognition of G-rich sequences through pyrimidine oligonucleotide-directed triple-helix formation is well documented (Moser and Dervan, *Science* 238:645 (1987); Strobel, S. A., Moser, H. E., Dervan, P. B., *J. Am. Chem. Soc.* 110:7927 (1988); Povsic, T. J. and Dervan, P. B., ibid., 111:3059 (1989); Strobel, S. A. and Dervan, P. B., ibid. p. 7286; Luebke, K. J. and Dervan, P.B., ibid., p. 8733; Horne, D. A. and Dervan, P. B., ibid., 112:2435 (1990); Strobel, S. A. and Dervan, P. B., *Science* 249:73 (1990); Maher, L. J. III, Wold, B., Dervan, P. B., *Science* 245:725 (1989); Griffin, L. C. and Dervan, P. B., ibid., p. 967; Praseuth, D., et al., *Proc. Natl. Acad. Sci. USA* 85:1349 (1988); Francois, J. C., Saison-Behmoaras, T. C., Chasignol, M., Thuong, N. T., Helene, C., *J. Biol. Chem.* 264:5891 (1989); Lyamichev, V. I., Mirkin, S. M., Frank-Kamenetskii, M. D., Cantor, C. R., *Nucl. Acids Res.*, 16:2165 (1988); Francois, J. C., Saison-Behmoaras, T., Thuong, N. T., Helen, C., *Biochemistry* 28:9617 (1989); Sun, J. S., et al., *Proc. Natl. Acad. Sci. USA* 86:9198 (1989); Rajogopal, P. and Feigon, J., *Nature* 339:637 (1989)). The apparent requirement for protonation of cytosines in the third strand to form C+GC triplets limits the pH range (typically $\leq$ pH 7.0) within which this triple-helical structure can be formed. With oligonucleotide-EDTA probes 1 and 2, for which the target duplex is 75% guanine-rich, we observed efficient cleavage at pH 7.8. Therefore, purine-rich oligonucleotides bound double-helical DNA in a relatively pH-independent fashion.

Within the constraints of our experimental data that the third strand is anti-parallel to the purine-rich W-C strand, models of possible hydrogen-bonding patterns for A•AT, T•AT, and G•GC base triplets place the phosphate-deoxyribose backbone in different locations in the major groove depending on whether the base in the third strand is in the anti- or syn-conformation (FIG. 9). The anti-conformation would generate a structure with the phosphate-deoxyribose backbone centrally located in the major groove of the double-helix (FIG. 8A). The syn-conformation would place the backbone in a similar location in the major groove as found with the pyrimidine motif (FIG. 9B). Although reasonable hydrogen-bonding models for T•AT and G•GC triplets can be written for both the syn- or anti-conformations of the third strand, models for the A•AT triplet suggest the most reasonable structure is the anti-conformation (FIG. 9A). Hence, we tentatively favor the anti-conformation and placement of the phosphate-deoxyribose backbone near the center of the major groove located more equidistant between the W-C strands (FIG. 9A). This triple-helix structure differs from the pyrimidine-rich motif in which the phosphate-deoxyribose backbone is located proximal (and parallel) to the purine-rich W-C strand.

EXAMPLE 5

This example describes the design of heterocycles for the recognition of CG Watson-Crick base pairs within the pur.pur.pyr triple-helical motif. Model building studies suggested that the deoxyribonucleoside 2'-deoxynebularine (N) would fulfill this role (FIG. 10). It was assumed that the purine core of 2'-deoxynebularine would mediate base stacking interactions in the third strand. In addition, the heterocyclic ring system provides a hydrogen bond acceptor (Ni) which should allow the formation of one hydrogen bond to the exocyclic amino group of cytosine or adenine (FIG. 10).

The affinity cleaving method was used to analyze the binding of 2'-deoxynebularine (N) to all four possible combinations of the two Watson-Crick base pairs. It was found that within the particular DNA sequence studied N interacts preferential with CG base pairs. The new recognition element was employed to target a single site of the HIV genome containing two CG base pairs within plasmid DNA.

Deoxynebularine phosphoramidite was purchased from Glen Research. All other phosphoramidites and chemicals for DNA synthesis were obtained from Applied Biosystems Inc. Restriction endonucleases and all other enzymes were purchased from Boehringer-Mannheim, New England Biolabs or Sigma. The Sequenase DNA sequencing kit (Version 2.0) was obtained from United States Biochemical Inc. Deoxynucleoside triphosphates (100 mm solutions), calf thymus DNA and Nick™-columns were purchased from Pharmacia LKB. The radiolabeled triphosphates 5'-($\alpha$-$^{32}$P) dGTP (>3000 Ci/mmol), 5 ($\gamma^{32}$P) ATP(>5000 Ci/mmol) and 5'-($\alpha$-$^{35}$S)dATP (>1000 Ci/mmol) were obtained from Amersham. All other chemicals were of analytical or HPLC grade.

Whenever possible, standard molecular biological methods were used (Sambrook, J., Fritsch, E. F., Maniatis, T. (1989) in Molecular Cloning: A Laboratory Manual, 2nd ed., Cold Spring Harbor Laboratory Press, Cold Spring Harbor, N.Y.). Agarose gel electrophoresis was performed in 1×TAE buffer and polyacrylamide gel electrophoresis was carried out in 1×TBE buffer (Sambrook et al., ibid.). Cerenkov radioactivity was measured with a Beckman LS 2801 scintillation counter.

Oligodeoxynucleotides were synthesized on an Applied Biosystems Model 3808 DNA synthesizer using β-cyanoethyl phosphoramidite triester chemistry (Beaucage, S. L., and Caruthers, M. 1-1. (1981) Tetrahedron Lett. 22, 1859–1862; Sinha, N. D., Biernat, J., McManus, J., Koster, H. (1984) *Nucleic Acids Res.* 12:4539–4557) The nucleoside analog T* was prepared according to published procedures and was incorporated at the 3' end of oligodeoxynucleotides via the 5'-O-DMT-thymidine-EDTA-triethylester-3'-succinyl controlled pore glass (Dreyer, G. B., and Dervan, P. B. (1985) *Proc. Natl. Acad Sci. USA* 82:968–972). Unmodified oligodeoxynucleotides were deprotected under standard conditions using concentrated ammonium hydroxide. oligodeoxynucleotides containing the nucleoside analog T* were treated with 0.1 N NaOH (1.5 mL) at 55° C. for 24 hours. The DMT protected oligomers were purified by reverse phase FPLC chromatography (Pharmacia ProRPC 15 mm HR 10/10; gradient of 0–40% acetonitrile in 100 mM triethylammonium acetate (pH=7.0)). Lyophilized fractions were treated (20 min, 23° C.) with an 80% solution of acetic acid in water (500 μl) in order to remove the DMT protecting group. The oligomers were then repurified by FPLC. The concentrations of the oligodeoxynucleotides were determined by UV measurements ($A_{260}$), using the following molar extinction coefficients: 15400 (A), 11700 (G), 7300 (C), 8800 (T and T*), and 6000 (N) $cm^{-1}M^{-1}$. After lyophilization the oligodeoxynucleotides were stored dry at −78° C.

Analytical HPLC was performed with a Hewlett-Packard 1090 Liquid Chromatograph using a reverse phase VYDAC 201HS54 4.6 mm×25 cm 5 micron C18 column. The purified oligodeoxynucleotides (3 nmol) were digested simultaneously with snake venom phosphodiesterase (3 μL, 2.4 μg/μL) and calf intestine alkaline phosphatase (3 μL, 1 U/μL) in 50 mM Tris-HCl (pH 8.1), 100 mM $MgCl_2$. The reaction mixture was incubated at 37° C. for 3 h, filtered through a 0.45 μm Nylon-66 syringe filter (Rainin) and lyophilized. The sample was dissolved with 10 μL of 10 mM ammonium phosphate (pH=5.1)/8% methanol buffer, and an aliquot of the solution was injected onto the C18 reverse phase column. The products were eluted with 10 mM ammonium phosphate (pH=5.1)/8% methanol and detected at $A_{260}$. Comparison with standard solutions of A, T and N established the composition of the oligodeoxynucleotides.

Affinity Cleaving Reactions of 39mer Duplex Targets

For the preparation of the duplex targets, each single-stranded oligodeoxynucleotide (100 pM) of sequence composition 5'd($A_2T_2(CT)_3A_5G_3XG_4AG_4AG_3A_5(CT)_3$)3' (SEQ ID NO: 5) (X=A, G, C, or T) was 5' end labeled using T4 polynucleotide kinase and γ-$^{32}$P ATP according to standard procedures (Sambrook et al., supra.). The reaction mixture was twice extracted with TE buffer-saturated phenol (1.0 volume) and twice extracted with 24:1 chloroform/isoamyl alcohol (1.0 volume). The DNA was ethanol precipitated, and the radiolabeled oligodeoxynucleotides were annealed to their unlabeled complementary oligodeoxynucleotides. The resulting duplexes were purified on 15% nondenaturing polyacrylamide gels (19:1; monomer/bis). Gel bands were visualized by autoradiography and desired bands were excised from the gel, crushed and eluted with 1 mL 200 mM NaCl at 37° C. for 20 h. The eluents were passed through 0.45 μm Centrex filters and lyophilized. The residue was taken up in 100 μL distilled water and the solution was then desalted by passing it through a Nick™-column. The radio-labeled duplex-DNA was finally isolated by ethanol precipitation.

Specific DNA cleavage reactions for adenine were performed as described previously (Iverson, B. L., and Dervan, P. B. (1987) *Nucleic Acids Res.* 15:7823–7830). The affinity cleaving reactions were executed in a total volume of 80 μL by combining a mixture of oligodeoxynucleotide-EDTA (100 nM) and Fe($NH_4$)$_2$($SO_4$)$_2$·6$H_2O$ (250 nM) with the $^{32}$P-labeled duplex (~120 000 cpm) in a solution of tris-acetate (50 mM, pH=7.4 at 23° C.), NaCl (20 mM), spermine (100 μM) and calf thymus DNA (100 μM in base pairs). The oligodeoxynucleotide probe was allowed to equilibrate with the DNA duplex target at 37° C. for 4 hr. The cleavage reactions were then initiated by the addition of dithiothreitol (4 mM final concentration) and allowed to proceed at 37° C. for 14 h. The reactions were quenched by freezing (liquid $N_2$) followed by lyophilization. The residue was suspended in 10 μL formamide loading buffer (90% formamide, 10% 10×TBE buffer, 0.02% bromophenol blue, 0.02% xylene cyanol) and transferred to new tubes. The DNA suspensions were assayed for specific activity by scintillation counting and diluted to 5000 cpm/μL. The cleavage products were denatured at 90° C. for 5 min and 4 μL of each sample were separated by 20% denaturing polyacrylamide gel electrophoresis (19:1; monomer/bis). The gels were exposed to X-ray film (Amersham Hyperfilm™-MP) at –78° C. with a single intensification screen or to a storage phosphor screen.

Quantitation of Cleavage Efficiencies by Storage Phosphor Technology Autoradiography The relative cleavage efficiencies were determined by quantitation on a Molecular Dynamics 400S Phosphorimager. Gels were exposed to the storage phosphor screen (Kodak storage screen S0230 obtained from Molecular Dynamics) in the dark at 23° C. for 4 h (Johnston, R. F., et al. (1990) *Electrophoresis* 11:355–360). The data were analyzed using the ImageQuant v. 3.0 software. The radiation background of the screen was determined by performing volume integrations over four independent reference sites. All other volume integrations were based on the averaged background value obtained. Integration of the cleavage bands was performed over the five most efficiently cleaved nucleotides. Rectangles of the same size were used for each lane and the amount of radioactivity found in the respective untreated control lane was subtracted from the obtained values. The relative cleavage efficiencies were evaluated by calculating the ratio of the radioactivity of the site-specific cleavage band by the integrated volume of the entire lane. The given values represent the average over two independent experiments.

Construction of the Plasmid pULHIV

The plasmid pULHIV was obtained by cloning the oligodeoxynucleotides 5'd($A_2T_2CG_2C$-$A_2GAG_2CGAG_4CG_2CGACT$)3' (SEQ ID NO: 6) and 5'd(CTAGAGT$CGC_2GC_4TCGC_2TCT_2GC_2G$)3' (SEQ ID NO: 7) into the large EcoRI/XbaI restriction fragment of pUC19 by using T4 DNA Ligase. The ligation mixture was employed to transform Epicurianm™ Coli XL1 Blue competent cells (Stratagene). The cells were grown on Luria Bertani medium agar plates containing 100 μg/mL ampicillin, X-gal, and IPTG. Large scale plasmid isolation of appropriate clones was performed using QIAGEN purification kits (Diagen) according to the manufacturer's protocol. The sequence of the insert was subsequently confirmed by dideoxynucleotide sequencing (Sanger, F., Nicklen, S., and Coulson, A. R. (1977) *Proc. Natl. Acad. Sci. USA* 72:2251–2255) using the #1201 M13 reverse sequencing primer (New England Biolabs).

Affinity Cleaving Reactions of the pULHIV EcoO1091-SspI Restriction Fragment

The pULHIV EcoO1091-SspI restriction fragment was produced as follows. Plasmid DNA (20 μg) was linearized with EcoO1091 and then end labeled with 5'-(α-$^{32}$P)dGTP employing sequenase™ (version 2.0) as the enzyme. The reaction mixture was applied to a Nicks™-column to remove unincorporated radiolabeled nucleotide triphosphates. The labeled DNA was then ethanol precipitated and digested with SspI. The resulting 3'-$^{32}$P-end labeled fragment (2515 bp) was purified by agarose gel electrophoresis (1% Nusieve GTG Agarose, FMC). Gel bands were visualized by autoradiography, the desired band was excised from the gel and transferred to an eppendorf tube. The agarose was frozen and thawed (3×) and the resulting suspension was centrifuged (20 min, 14K). The supernatant was removed and was twice extracted with TE buffer saturated phenol (1.0 volume) and twice extracted with 24:1 chloroform/isoamyl alcohol (1.0 volume). The DNA was ethanol precipitated, dissolved in 100 μL TE buffer and then passed through a Nick™-column. Finally the DNA was ethanol precipitated and dissolved in water to a final concentration of 10000 cpm/μL.

The affinity cleaving reactions were executed in a total volume of 80 μL by combining a mixture of oligodeoxynucleotide-EDTA (2 μM) and Fe($NH_4$)$_2$($SO_4$)$_2$·6$H_2O$(5 μM) with the $^{32}$P-labeled restriction fragment (~40 000 cpm) in a solution of tris-acetate (50 mM, pH 7.4 at 23° C.), NaCl (10 mM), spermine (1 mM) and calf thymus DNA (100 μM in base pairs). The oligodeoxynucleotide probe was allowed to equilibrate with the DNA duplex target at 37° C. for 4 h. The cleavage reactions were then initiated by the addition of dithiothreitol (4 mM) and allowed to proceed at 37° C. for 12 h. The reactions were stopped by precipitation of the DNA with ethanol. The residue was resuspended in TE buffer (30 μL) and transferred to new tubes. The DNA suspensions were assayed for specific activity by scintillation counting and diluted to 5000 cpm/20 μL. An aliquot (10 μL) of glycerol gel loading buffer (30% glycerol in water, 0.25% bromophenol blue, 0.25% xylene cyanol) was added to 20 μL of each of the samples. The cleavage products were separated by 5% nondenaturing polyacrylamide gel electrophoresis (19:1 monomer/bis). The gel was dried on a slab dryer and visualized by autoradiography (Amersham Hyperfilm™-MP, −78° C., intensification screen).

Synthesis of Oligodeoxynucleotides Containing 2'-Deoxynebularine and Base Composition Analysis Oligodeoxynucleotides 1–17 were synthesized by solid phase methods using β-cyanoethyl phosphoramidite chemistry (Beaucage, S. L., amd Caruthers, M. 1–1. (1981) *Tetrahedron Lett.* 22:1859–1862; Sinha, N. D., Biernat, J., McManus, J., Koster, H. (1984) *Nucleic Acids Res.* 12:4539–4557). The 2'-deoxynebularine phosphoramidite coupled as efficiently as the A, G, C, and T phosphoramidites. The base composition of oligodeoxynucleotides 1, 6, 11, 16, and 17 containing 2'-deoxynebularine were established by HPLC analysis. For this, the oligodeoxynucleotides were treated with snake venom phosphodiesterase and calf intestine phosphatase. The nucleoside monomers obtained were separated by HPLC and identified by their HPLC retention times and UV spectra. Comparison of the integrated areas of the HPLC peaks with that of standard solutions of A, T and N confirmed the correct base composition of the oligodeoxynucleotides.

Analysis of Binding Specificity

The relative affinity of 2'-deoxynebularine for all four Watson-Crick base pairs within a pur-pur-pyr triple-helix motif was examined by affinity cleaving (Dreyer and Dervan, 1985, supra.). A series of 15 nt oligodeoxynucleotides 1–5 (FIG. 11), differing at one base position 5'd (TG$_4$TG$_4$ZG$_3$T*)3' (SEQ ID NO: 8) (Z=N, A, G, C, or T); and equipped with the DNA cleaving moiety, thymidine-EDTA•Fe(II) (T*) at a single thymidine position at the 3' end was prepared. The relative stabilities of the triple-helical structures formed upon complexation of these oligodeoxynucleotides with 39-bp DNA duplexes containing one variable base pair site 5'-$^{32}$P-A$_2$T$_2$(CT)$_3$A$_5$G$_3$XG$_4$AG$_4$AG$_3$A$_5$(CT)$_3$)3' (SEQ ID NO: 9)•5'd(CT(AG)$_4$T$_5$C$_3$T-C$_4$TC$_4$YC$_3$T$_5$(AG)$_3$)3' (DEQ ID NO: 10) (XY=AT, CG, GC, or TA) were then measured. The DNA affinity cleaving reactions were performed under conditions which allowed the difference in stability between single base triplets to be distinguished (100 nM oligodeoxynucleotide-EDTA, 100 μM spermine, 20 mM NaCl). The most efficient cleavage was observed for the combinations Z=A or T, XY=AT, and Z=G, XY=GC (results not shown). These cleavage patterns reflect the known ability of G, A, and T to form G•GC, A•AT, and T•AT base triplets, respectively (Beal, P. A., and Dervan, P. B. (1991) *Science* 251:1360–1363). Importantly, intense cleavage was also detected for a N•CG triplet (results not shown). The base triplets N•AT, C•AT, T•CG, and A•GC produced moderate cleavage. Only weak cleavage was observed for the 12 additional triplet combinations. The relative cleavage intensities were determined by quantitative storage phosphor autoradiography and are presented as histograms in FIG. 12.

Site-specific double-stranded cleavage of plasmid DNA. The plasmid pULHIV was prepared in order to determine whether 2'-deoxynebularine can be used to recognize CG base pairs within a larger fragment of double-helical DNA. For this, the purine-rich target sequence 5'd (AGAG$_2$CGAG$_4$CG$_2$)3' (SEQ ID NO: 11)•5'd (C$_2$GC$_4$TCGC$_2$TCT)3' (SEQ ID NO: 12), a sequence which occurs naturally in the HIV genome (Ratner, L., et al. (1985) *Nature* 313:277–284), was cloned into pUC19 DNA. The ability of oligodeoxynucleotides 6–17 (FIG. 13) to bind specifically to the target sequence was examined by affinity cleaving. Conditions sensitive to the stability of the base triplet at the CG sites (2 μM oligodeoxynucleotide-EDTA, 1 mM spermine, 10 mM NaCl) were used. A 2.51 kbp EcoO1091-SspI restriction fragment of pULHIV, which contains the target sequence, located 0.42 kbp from the $^{32}$P radiolabeled end (FIG. 13), was isolated. This restriction fragment was allowed to react with 5'd (G$_2$Z2G$_4$Z1GZ2G$_2$Z1GT*)3' (SEQ ID NO: 13) oligodeoxynucleotides-EDTA•Fe(II) 6–17, which differ at four variable positions (Z1=A, T or N; Z2=N, A, G, C, or T), in the presence of dithiothreitol at 37° C. (pH 7.4). The cleavage products were separated by 5% nondenaturing polyacrylamide gel electrophoresis. One major cleavage product, 0.42 kbp in size, indicated sequence specific cleavage was only observed for the oligodeoxy-nucleotides 6 (Z1=A; Z2=N), 10 (Z1=A; Z2=T), 11 (Z1=T; Z2=N), and 15 (Z1=T; Z2=T), respectively (results not shown).

EXAMPLE 6

Nucleotides for Recognition of GC Base Pairs By Triple-Helix Formation

This example describes the synthesis and specificity of triple-helix formation utilizing P nucleotides.

Synthesis of Nucleosides P1 and P2

A scheme for the five-step syntheses of nucleosides P1 and P2 is shown in FIG. 19. Ethyl 3-methyl-4-nitropyrazole-5-carboxylate (1) (Lewis, A. F.; Townsend, L. B., In *Nucleic Acid Chemistry*, Townsend & Tipson Eds; Wiley: N.Y. 1978, Vol. 1, p. 121) was condensed with 1-chloro-2-deoxy-3,5-di-O-p-toluoyl-α-D-ribofuranose (2) (Hoffer, M., *Chem. Ber.* (1960) 93, 2777) (H to give the N1 and N2 β anomers, 3a and 3b, which could be readily separated by column chromatography. The structures of isomers 3a and 3b were assigned by $^1$H NMR (NOE) and X-ray crystallographic analysis (Koh, J-S., Ph.D. Thesis, California Institute of Technology, 1990). Irradiation at the C-H1' proton enhanced the methylene proton peaks of ethyl 5-carboxylate of one isomer by 8.9% and the 5-methyl protons of the other isomer by 13.3%. These were assigned to 3a and 3b, respectively. These assignments were confirmed by X-ray crystallographic analysis of crystalline 3b. Ammonolysis of 3a in methanol afforded carboxamide 4a, which in turn was reduced (H$_2$, 10% Pd/C) to amine 5a. Treatment of 5a with phenyl isothiocyanate provided thiol 6a (Rousseau, R. J. et al., *J. Am. Chem. Soc.* (1968) 90, 2661), which was oxidized to its corresponding sulfonate. Displacement with saturated aqueous ammonium hydroxide (Yamzaki, et al., *J. Org. Chem.* (1967) 32, 3032) affords the amine, P1. Nucleoside P1 was selectively acylated on N5 by the transient protection method (*Oliconucleotide Synthesis*, Gait, M. J. Ed; IRL Press: Oxford, U.K., 1984) to afford 7a, and the 5'-hydroxy group was treated with dimethoxytrityl chloride to give the DMT-protected phosphoramidite of P1 (Id). Nucleoside P2 and the corresponding DMT-protected phosphoramidite 9b were prepared by the same methods.

Synthesis of Oligodeoxyribonucleotides Containing Nucleosides P1 and P2

Oligodeoxyribonucleotides 10–20 were synthesized using standard solid-phase β-cyanoethyl phosphoramidite chemistry (Id.). P1, P2, and the abasic phosphoramidites (Horne, D. A., et al. (1991) *Nucleic Acids Res.* 19:4963) coupled with efficiencies equal to those of A, G, C, and T phosphoramidites. Oligonucleotides 10–20, which contain T* (thymine-EDTA), were deprotected with 0.1 N NaOH (Dreyer, G. B. et al. (1985) *Proc. Natl. Acad. Sci. U.S.A* 82:968). To examine the stability of the novel bases through several machine-assisted coupling cycles and base deprotection, two short oligodeoxyribonucleotides, 5'-T-T-P1-T-3' (SEQ ID NO: 14) and 5'-T-T-P2-T-3' (SEQ ID NO: 15), were synthesized on a 10-$\mu$mol scale for $^1$H NMR and mass spectral analysis of the purified tetramer oligodeoxyribo-nucleotides, it was found that the N-isobutyroyl protecting group of P1 and P2 was completely removed to afford a free amine and the novel pyrazole base.

Base Composition Analysis of Oligodeoxyribonucleotides Containing P1 and P2

The integrity of the nonnatural nucleosides P1 and P2 after automated synthesis and deprotection steps was analyzed by enzymatic degradation. The base composition of oligodeoxyribonucleotides containing nucleosides P1 and P2 was analyzed by HPLC to ensure that the pyrazole heterocycle was not chemically altered during automated synthesis. Purified oligodeoxyribonucleotides containing P1 and P2 were treated with snake venom phosphodiesterase and calf intestine alkaline phosphatase to give the corresponding nucleoside monomers. Analysis of HPLC of the enzymatic digestion products oligonucleotide 5'-T*(T)$_4$(P$_1$T)$_5$-3' (SEQ ID NO: 16) revealed T*, P1 and T nucleosides. Similarly, oligonucleotide 5'-T*(T)$_3$C(T)$_4$(P$_1$)$_6$T-3' (SEQ ID NO: 17) afforded T and P2 nucleosides. These analyses suggest that the P1 and P2 nucleosides can be used in automated oligodeoxyribonucleotide synthesis without complications.

P1-GC and P2-GC Triplet Stabilities Characterized by Affinity Cleaving

The relative affinities of the novel bases P1 and P2 for all four Watson-Crick base pairs within a pyrimidine triple-helix motif were examined (FIG. 20A). As a control, these were compared with an abasic residue φ, which contains no base at that same position. oligodeoxyribonucleotides equipped with the DNA-cleaving moiety, thymidine-EDTA•FE$^{II}$(T*), allowed the relative stabilities of triple-helix formation between 30 base pair (bp) DNA duplexes containing one variable site d(A$_7$XA$_7$)-d-(T$_7$YA$_7$) (XY=AT, GC, TA, or CG) and a series of 15-mer oligonucleotides 10–13 differing at one base position d(T$_7$NT$_7$) (N=C, P1, P2, φ) to be determined by the affinity cleaving method. The 30-bp duplexes were labeled with $^{32}$P at the 5'-end of the Watson-Crick target strand d(T$_7$YT$_7$). The DNA-cleaving reactions with oligodeoxyribonucleotides 10–13 were performed under conditions that were sensitive to the stability of the variable base triplet in the middle of the triple-helical complex (pH 7.4, 35° C., 40% ethanol).

The most intense cleavage was observed when N=C, XY=GC and N=P1, XY=GC (FIGS. 20B and C). The binding for one of these combinations demonstrates the ability of C to form C+GC base triplets. Efficient cleavage was observed when P1 was opposite a GC base pair (P1•GC triplet), while moderate cleavage was observed with the isomer P2 (P2•GC triplet). The strong cleavage observed for the P1•GC triplet would be consistent with two hydrogen bonds formed. The weaker cleavage pattern observed for the P2•GC triplet indicates that there may be an energetically unfavorable distortion of the third-strand backbone or that the methyl group disfavors the anti conformation of P2 in the triple helix. For comparison, oligodeoxyribonucleotides containing the abasic residue φ at the variable position show weak binding with a modest preference for TA and CG base pairs.

Specific Binding of Sites Containing a (GA)$_6$ Sequence

The ability of oligonucleotides containing several P1 residues to target single sites containing the 12 base pair purine tract (GA)$_6$ was characterized by affinity cleaving. A 4.06-kbp plasmid containing the 15 base pair purine target site, 5'-AAAAAGAGAGAGAGA-3' (SEQ ID NO: 18), 1.02 kbp from the end was labeled with $^{32}$P. This DNA was allowed to react with four oligonucleotides-EDTA•Fe, 14–17, which differ at five variable positions and contain C, mC, P1, and P2 residues, respectively, (24° C., pH 6.2–7.8). Analysis of the products by gel electrophoresis revealed one major cleavage product 1.02 kbp in size. The site-specific cleavage efficiency of oligonucleotide 14 containing residues C/T decreased sharply above pH 7.0. Replacement of C with mC (oligonucleotide 15) extended the binding/cleavage reaction to pH 7.4. However, oligonucleotide 15 (mC/T) did not bind strongly at pH 7.8. Substitution of P1 for mC (oligonucleotide 16) afforded the same cleavage efficiency as C and mC at pH 7.0, but extended the pH range for binding of the target to pH 7.8 (FIGS. 21B and C). Oligodeoxyribonucleotide 17 containing five isomeric P2 residues showed no cleavage even at lower pH (FIG. 21B).

Specific Binding of Sites Containing a (G)6 Sequence

The ability of oligodeoxyribonucleotides 18–20 to bind single sites on double-helical DNA containing six *contiguous* GC base pairs was examined by affinity cleaving. Plasmid DNA, which contained the naturally occurring site from the HIV-LTR region, 5'-AAA-AGAAAAGGGGGGA-3' (SEQ ID NO: 19), located 1.7 and 3.2 kbp from the ends, was allowed to react with oligodeoxyribo-nucleotides-EDTA•Fe 18–20 (30° C., pH 6.2–7.4) which differ at six contiguous positions by substitution of C, mC, or P1, respectively. Separation of cleavage products by gel electrophoresis revealed a major cleavage site producing two DNA fragments, 1.7 and 3.2 kb in size (FIGS. 22B and C). Perhaps, charge repulsion disfavors the protonation of N3 of all cytosines and 5-methylcytosines in contiguous C+GC and mC+GC triplets. These results suggest that the pK$_a$'s of C+GC and mC+GC triplets may be sequence dependent, which may limit the utility of 5-methylcytosine for oligonucleotide-directed triple-helix formation for certain G-rich sequences. However, oligodeoxyribo-nucleotide 20 containing six contiguous P1 residues cleaved the single site in plasmid DNA up to pH 7.4 (30° C.). Moreover, oligodeoxyribonucleotide 20 at neutral pH can bind the HIV-LTR G-rich sequence at physiological temperatures (37° C.) (FIG. 22D). It is to be understood that various other modifications will be apparent to and can readily be made by those skilled in the art, given the disclosure herein, without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

EXAMPLE 7

Triple-Helix Formation Utilizing D Nucleotides

This example describes the synthesis of deoxyribonucleosides D2 and D3 and the specificity of such nucleotides in triple-helix formation when incorporated into an appropriate oligonucleotide.

Syntheses of Deoxyribonucleosides $D_2$ and D3

A scheme for the synthesis of the phosphoramidites 7–8 is depicted in FIG. 23. For the synthesis of 7 containing the base component D3, the sodium salt of 4-(3-nitro) phenylimidazole (m-Nitro-ω-bromo-acetophenone [8 g] and formamide [50 ml] were boiled for 2 hours. After cooling down the solution was poured into a boiling solution of 200 ml diluted HCl, boiled under addition of charcoal. The solution was made slightly basic by adding ammonia. The precipitate was recrystallized using benzene and water. Yield: 5.2 g.). (Bredereck, H., et al. (1953) *Chem. Ber.* 86:88–96) was condensed with 1-chloro-2-deoxy-3,5-di-O-p-toluoyl-α-D-ribofuranose (Hoffer, M. (1960) *Chem. Ber.* 93:2777) to give the imidazole N-1 β-anomer 2 as the major product in 63% yield (Kazimierczuk, Z., et al. 91984) *J. Am. Chem. Soc.* 106:6379–6382). A crystal structure of reaction product 2 confirmed the regio- and stereochemical course of this reaction. The p-toluoyl protecting groups were removed (Mashimo, K., et al. (1970) *Tetrahedron* 26:803, and the nitro group was subjected to hydrogenation to generate the aminobenzene derivative 4. The aromatic amino group was selectively acylated by the transient protection method to provide benzamide 5 (Ti, G. S., et al. (1982) *J. Am. Chem. Soc.* 104:1316). Treatment of the resulting amide with 4,4'dimethoxytrityl chloride furnished protected nucleoside 6 *Oligonucleotide Synthesis*, Gait, M. J., Ed. IC Press, Oxford (1984)), which was then activated with 2-cyanoethyl-N,N-diisopropylchlorophosphoramide to afford phosphoramidite 7 (Id. and Sinha, N. D., et al. (1984) *Nucleic Acids Res.* 12:459). The phosphoramidite 8 corresponding to the novel base component D1 was synthesized in a similar manner.

Synthesis of Oligodeoxyribonucleotides Containing D2 and D3 Heterocycles

Oligodeoxyribonucleotides 9–12 were synthesized by automated methods using β-cyanoethyl-phosphoramidite chemistry (Id.). The phosphoramidites containing the novel bases D2 and D3 coupled with efficiencies equal to those observed for A, G, C, and T phosphoramidites (>97%). Because oligodeoxyribonucleotides 9–22 contained T* (thymidine-EDTA), 0.1N sodium hydroxide was utilized in the deprotection step (Dreyer, G. B., er al. (1985) *Proc. Natl. Acad. Sci. U.S.A.* 82:968). To examine the stabilities of the novel bases under the conditions for automated synthesis and subsequent deprotection, tetramers 5'-T-T-D3-T-'3 (SEQ ID NO: 20), and 5'-T-T-D2-T-3' (SEQ ID NO: 21) were synthesized and characterized by $^1$H NMR. Neither glycosidic bond anomerization nor base modification of D2 and D3 was observed under these conditions (Griffin, L. C. Ph.D., Thesis (1990), California Institute of Technology). After the deprotection step, the benzamido group of D3 was found to be stable.

The integrity of the nonnatural nucleosides D2 and D3 after automated synthesis and deprotection was analyzed by HPLC. Purified oligodeoxyribonucleotides containing D2 and D3 were treated with snake venom phosphodiesterase and calf intestine alkaline phosphatase to afford the corresponding nucleoside monomers. Correlation of HPLC retention times and UV spectra with those of authentic samples provided a means of product identification. These results suggest that D2 and D3 can be utilized in automated oligodeoxyribonucleotide synthesis without complications.

Analysis of Binding Specificity by Affinity Cleaving

The relative affinities of the bases D2 and D3 for all four Watson-Crick base pairs within a pyrimidine triple-helix motif were examined by affinity cleaving. Oligodeoxyribonucleotides equipped with the DNA cleaving moiety, thymidine-EDTA•Fe(II) (T*), allowed the relative stabilities of triple helix formation between 30 base pair (bp) DNA duplexes containing one variable base pair site $d(A_7XA_7)$•$d(T_7YT_7)$ (SEQ ID NO: 22) (XY=AT, GC, CG, or TA) and a series of 15 nt oligomers differing at one base position $d(T_7NT_7)$ [N=T, C, D2, D3] to be determined (FIG. 24A). The 30-bp duplexes were labeled with $^{32}$P at the 5' end of the Watson-Crick target strand $d(T_7YT_7)$. The DNA affinity cleaving reactions were performed under conditions sensitive to the stability of the variable base triplet in the center of the triple helical complex (pH 7.4, 35° C., 40% ethanol). The most efficient cleavage was observed for the combinations N•XY=C•GC, T•AT, $D_2$•TA and $D_2$•CG (FIGS. 24B, 24° C.). The cleavage observed in the reactions of two of these oligonucleotides (FIG. 24B, lanes 3 and 8) indicates the known stabilities of T•AT and C+GC base triplets, respectively. With oligonucleotides possessing modified bases, efficient cleavage was observed when D3 was opposite a TA or CG base pair ($D_2$•TA and $D_2$•CG base triplets) (FIG. 24B, lanes 17 and 18). Within this motif, the D3 base shows an affinity for pyrimidine•purine base pairs over purine-pyrimidine base pairs (D3•TA~D3•CG>D3•AT>D3•GC).

The base D2 exhibits weak binding affinity for all four base pairs which is comparable to that observed for the natural base triplet mismatches (FIG. 24C).

From examination of the two-dimensional representation of base triplets containing D3, it is difficult to assign the observed selectivity to specific hydrogen bonding interactions (FIG. 24D). The differences between D2 and D3 suggest that the benzamido group is largely responsible for a specific interaction stabilizing triple helix formation. Affinity cleaving analyses of three analogs reveal that the benzamide component is essential. When the benzamide is replaced by acetamide, cyclohexane-carboxamide or 1-naphthamide, diminished affinity and specificity is observed. Modeling studies suggest D3 may lie out of the plane of the opposite Watson-Crick base pair to avoid steric clashes between the benzamide group and the purine base in a D3•TA or D3•CG triplet. The shape of pyrimidine-purine base pairs is distinct from purine-pyrimidine base pairs in the major groove. The observation that D3 prefers binding both TA and CG but not AT or GC suggests that the specificity may be due to shape selective recognition of pyrimidine-purine vs. purine-pyrimidine base pairs. It is likely that the stability of D3•TA and D3•CG triplets is due to an ensemble of favorable van der Waals interactions. Additional studies have shown that neighboring base triplets influence the stabilities of D3•TA and D3•CG triplets (Kiessling, L. L., et al. (1992) *Biochemistry* 31:2829). They are most stable when flanked by T•AT triplets and less stable when a C+GC triplet is on the 3' side (Id.). This suggests that interactions between the walls of the major groove and the benzamido group are important.

Site-specific Double Strand Cleavage of Plasmid DNA

In a formal sense, the D3•TA and D3•CG triplets constitute a degenerate code in part and, therefore, a test of oligonucleotide specificity in larger DNA is appropriate. The ability of oligonucleotide-EDTA•Fe(II) containing T, C and D3 to cause site-specific double strand breaks at a naturally occurring mixed sequence containing all four base pairs in SV40 DNA (5.2 kbp in size) was examined under physiologically relevant pH and temperature. (FIG. 25A). SV40 was digested with BglI to produce a 5.2-kbp fragment, which contained the sequence d(AAATAAAAGACAAAAAGA) (SEQ ID NO: 23) located 2.2 kbp and 3.0 kbp from the ends. The cleavage reaction between the $^{32}$P end-labeled DNA and oligonucleotide-EDTA•Fe(II) of sequence composition 5'-T*TTD$_2$TTTTCTD$_2$TTTTTCT-3' (SEQ ID NO: 24) was initiated with dithiothreitol (DTT) (pH 7.0, 37° C.). Separation of the cleavage products by agarose gel electrophoresis revealed one cleavage site producing two DNA fragments, 2.2 and 3.0 kb in size (FIG. 25B).

The novel base 4-(3-benzamido)phenylimidazole (D3) enables the selective binding of TA and CG Watson-Crick base pairs within a pyrimidine triple helix motif.

When used in combination with the natural triplets T•AT and C+GC, this allows the oligonucleotide-directed sequence specific recognition of double helical DNA sequences containing all four base pairs. Although the D3•TA and D3•CG triplets within a pyrimidine oligonucleotide formally extend triple helix specificity to all four possible base pairs of double helical DNA, limitations exist. The first limitation is that D3 does not distinguish TA and CG base pairs. A second limitation is that there are nearest neighbor interactions that influence the stabilities of D3•TA and D3•CG triplets. However, these results provide important structural insight in the design of deoxyribonucleosides with nonnatural heterocycles with specific recognition properties directed toward a more general solution to sequence-specific recognition of double helical DNA. The 4-(3-benzamido)phenylimidazole binding of pyrimidine-purine base pairs is likely an example of recognition of Watson-Crick base pairs by triple helix formation dominated by an ensemble of van der Waals interactions (shape) rather than specific hydrogen bonds.

EXAMPLE 8

Recognition of Double-Helical Nucleic Acid by Alternate Strand Triple-Helix Formation This example describes a triple-helix formation wherein the third strand contains binding domains which recognize two purine-rich sequences located on alternate strands of a double-helical nucleic acid.

Figure 31:
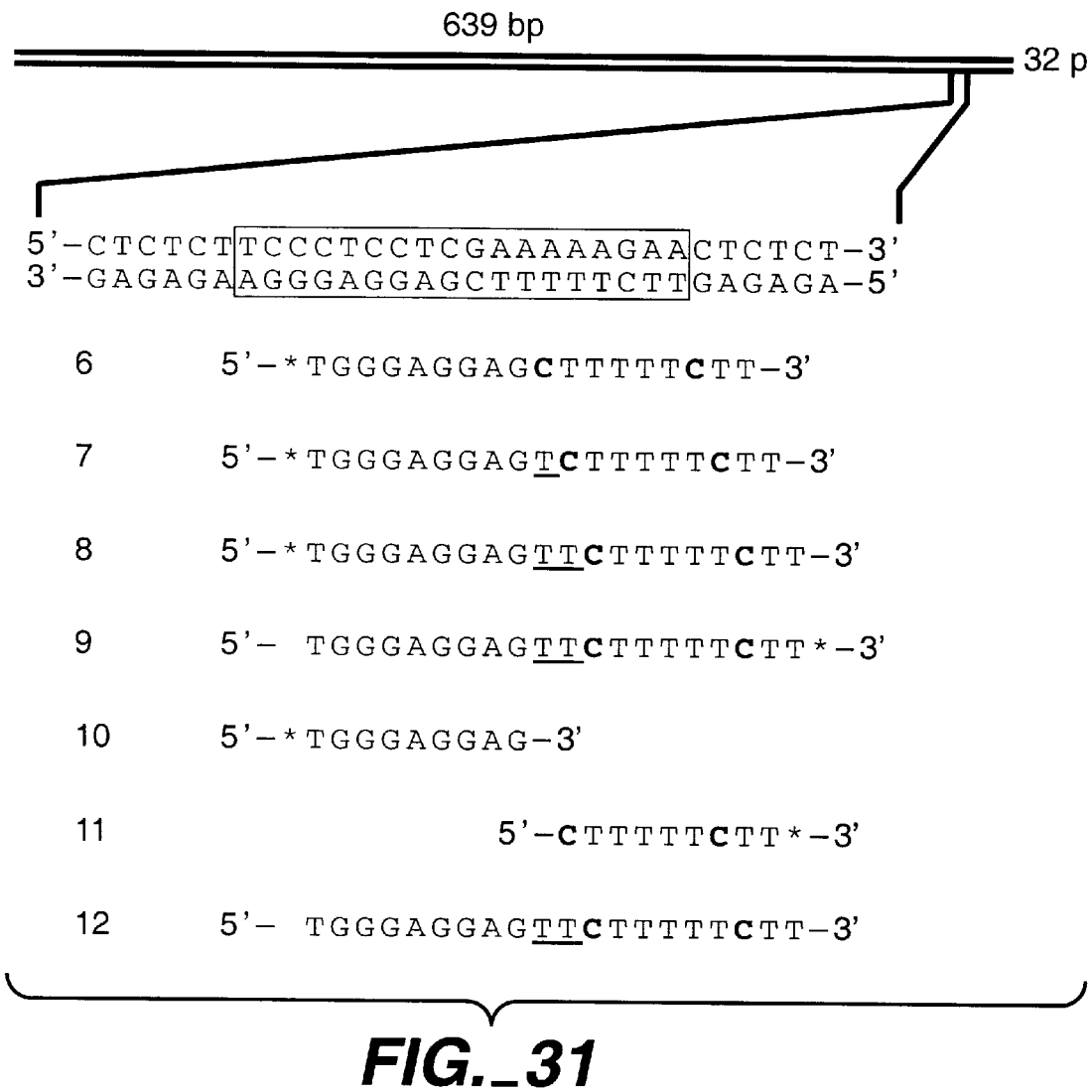
FIG. 31 (SEQ ID NOS: 106–114) depicts the duplex target site present on the 639 bp Hind III/Ssp I restriction fragment from plasmid pPBCRII containing two nine-mer purine tracts on alternate strands joined at a 5'-PyPu-3' junction. The double stranded region bound in the triple helix is boxed. The sequences of oligonucleotideEDTA's 6–12 are shown, where T* indicates the position of thymidine-EDTA, bold type C indicates 5-methyldeoxycytidine and the underlined thymidines indicate the linker domain.

The two duplex sequences shown in FIGS. 26 and 31 were prepared, each containing 18 bp binding sites composed of two adjacent nine bp half sites on alternate strands capable of being bound in a triple helical sense by either pyrimidine or purine oligonucleotides. The sequence content is identical in both binding sites, however they are opposite in polarity such that the two sequence types 5'-(Pu)$_m$(Py)$_n$-3' and 5'-(Py)$_m$(Pu)$_n$-3' can be compared. Modelling of these two sequences suggests that the adjacent triple helix binding sites are in different relative positions in space. Therefore, designing triple helix forming oligonucleotides to bind to these two sequence types will likely require different structures at the junction where the transition from one motif to the other takes place.

The 5'(Pu)$_m$(Py)$_n$-3' Sequence

The potential binding site, 5'-AAGAAAAAGCTCCTCCCT-3' (SEQ ID NO: 25), shown in FIG. 26, consists of two adjacent nine bp purine tracts on alternate strands with a 5'-GC-3' junction. Oligonucleotides 1–5 were designed to bind this sequence by the formation of a pyr-pur-pyr triple helix at the 5' half site and/or a pur•pur•pyr triple helix at the 3' half site. Oligonucleotides 1–4 were modified with thymidine-EDTA so that the affinity cleaving method could be used to monitor their binding properties (Dreyer, G. B., et al. (1985) *Proc. Natl. Acad. Sci. U.S.A.* 82:968).

Under conditions in which very little binding is detected for the nine-mer controls, 3 and 4, alone or in combination, both termini of the 18-mer oligonucleotide are bound to the duplex as indicated by cleavage generated by 5' thymidine-EDTA in 1 and 3' thymidine-EDTA in 2 (FIG. 27). In data not shown, a 16 mer oligonucleotide lacking the center two nucleotides cleaves the target equally as efficiently as 1.

DNase I footprinting was used to confirm the binding site size for 5, identical in sequence to 1 and 2, lacking thymidine-EDTA (FIG. 28). As expected from the affinity cleaving results, 5 protects both strands of the duplex from cleavage by DNase I over a region of approximately 25 base pairs centered around the proposed binding site. DNaseI footprint titrations with 5 yielded an association constant $K_a=5.7\pm1.4\times10^6$ M$^{-1}$ (pH=7.0, 1.5 mM spermine, 5 mM NaCl, 10 MM MgCl$_2$, 10 mM CaCl$_2$) corresponding to a binding free energy $\Delta4G_b=-9.2\pm0.1$ kcal/mol (Brenowitz, M., et al. (1986) *Proc. Natl. Acad. Sci. U.S.A.* 83:8462).

Figure 29:
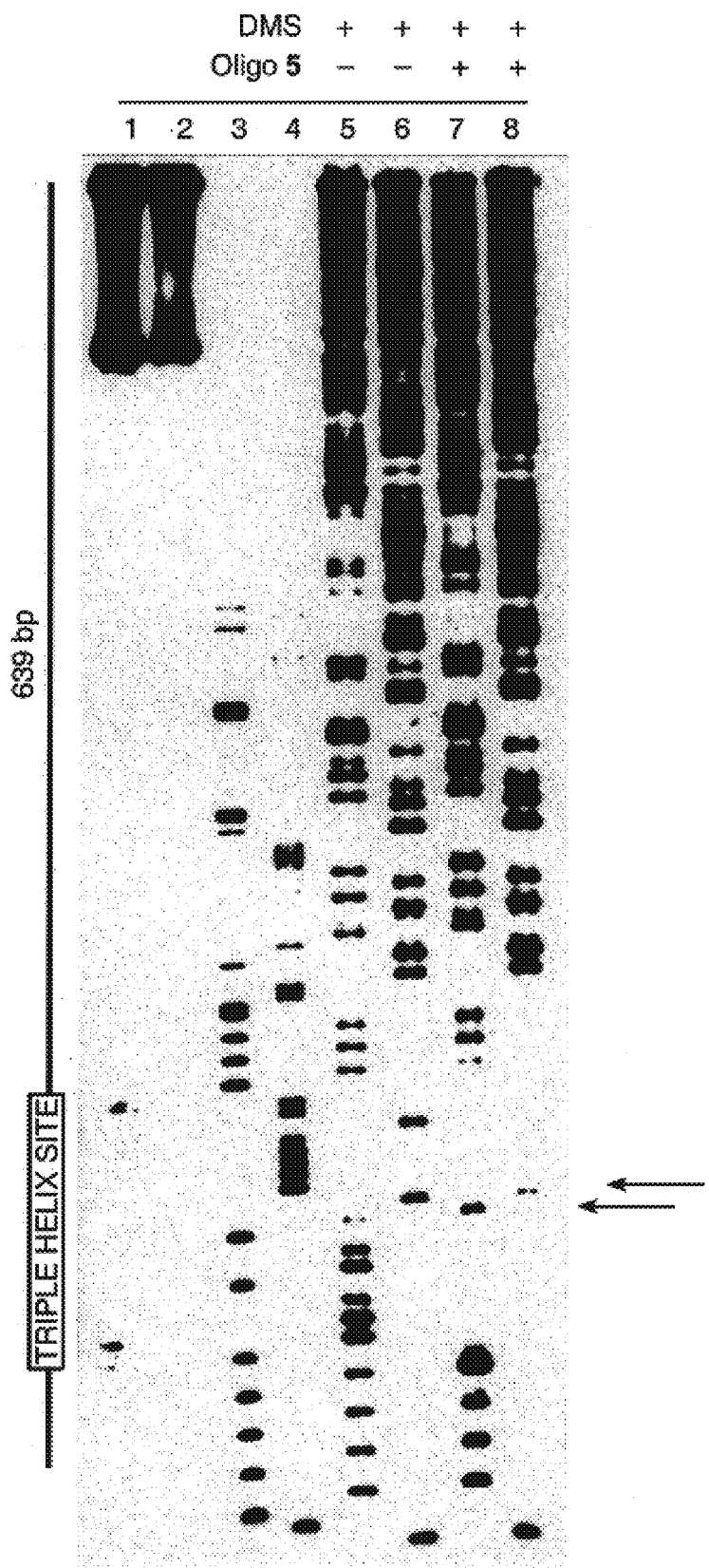
FIG. 29 is an autoradiogram of an 8% denaturing polyacrylamide gel used to separate DMS footprinting products. The reactions were carried out by incubating oligonucleotide 5 with the 3' end or 5' end $^{32}$P labelled Hind III/Ssp I restriction fragment from plasmid pPBCRI [~20,000 cpm] in a solution of trisHCl, pH=7.0 (40 mM), spermine (1.5 mM), NaCl (5 mM), MgCl$_2$ (10 mM), CaCl$_2$(10 mM) for two hours at 24° C. The reactions were initiated by the addition of dimethylsulfate (DMS) (0.2% v/v) and allowed to proceed for 90 seconds at 24° C. The reactions were stopped as described by Maxam and Gilbert (Maxam, A., et al., *Methods in Enzymology* (1980) 65, 499). The DNA was precipitated with ethanol, redissolved in 50 µL 10% aqueous piperidine and heated at 90° C. for 30 min. Concentrations listed are final concentrations. The solutions were lyophilized and the cleavage products were analyzed by gel electrophoresis. Odd numbered lanes contain 5' end labelled fragment, even numbered lanes contain 3' end labelled fragment. (Lanes 1 and 2.) Intact labelled fragment in the absence of oligonucleotide 5 and DMS. (Lanes 3 and 4.) Products of adenine-specific sequencing reactions (Iverson, B. L., et al., *Nucleic Acids Res*. (1987) 15, 7823). (Lanes 5 and 6.) Cleavage products generated in the presence of DMS in the absence of oligonucleotide 5. (Lanes 7 and 8.) Cleavage products generated in the presence of DMS and 10 µM oligonucleotide 5. Arrows indicate guanines in the binding site not protected by oligonucleotide 5.

The reactivity of dimethylsulfate (DMS) can be used to determine the accessibility of the N-7 position of guanine (Williamson, J. R., et al.(1989) *Cell* 59:871), which is involved in both the $^{Me}$C+GC and CG•G base triplets. Formation of these triplets should protect the guanines in the duplex from methylation by DMS. In the presence of 10 μM 5, all the guanines in the binding site are fully protected from methylation except the two at the junction, which are only marginally protected (FIG. 29).

The results of these experiments are summarized in FIG. 7. These data show that this duplex sequence can be targeted for alternate strand triple helix formation by linking binding domains with a 3'–5' phosphodiester. However, the two bases in the center of the third strand apparently do not stabilize the structure to a great extent and DMS footprinting indicates that the two base pairs at the junction are likely not involved in stable base triplets.

The 5'-(PY)$_m$(Pu)$_n$-3' Sequence

The target site, 5'-TCCCTCCTCGAAAAAGAA-3' (SEQ ID NO: 26), shown in FIG. 31, is identical in sequence content to that shown in FIG. 26, but opposite in polarity. Therefore, the two adjacent nine-mer purine tracts on alternate strands are joined at a 5'CG-3' junction. Oligonucleotides 6–12 were designed to bind the target by the formation of a pur•pur•pyr triple helix at the 5' half site and/or a pyr•pur•pyr triple helix at the 3' half site.

In this case, when the two nine-mers are linked by a phosphodiester, there is no significant increase in binding affinity, as evidenced by comparison of the cleavage efficiency for 6 with that for 10 plus 11. (FIG. 32, lanes 5 and 6.) However, when the oligonucleotide contains two thymidines between the purine and pyrimidine domains as in 8 and 9, both termini are bound to the duplex (FIG. 32, lanes 8 and 9). One thymidine is not sufficient, as shown by the low cleavage efficiency of 7 (FIG. 32, lane 7). oligonucleotide 12, which contains the two thymidine linker but lacks thymidine-EDTA was used for footprinting studies. In the presence of 10 μM 12, both strands of the duplex are protected from DNase I degradation in the region corresponding to the putative binding site (FIG. 33). DNaseI footprint titrations yielded an association constant $K_a=1.5\pm0.4\times10^6$ $M^{-1}$ (pH=7.0, 1.5 mM spermine, 5 mM NaCl, 10 mM $MgCl_2$, 10 mM $CaCl_2$) corresponding to a binding free energy $\Delta G_b=-8.4\pm0.2$ kcal/mol. DMS footprinting studies on this structure show that all the guanines in the binding site are protected equally from methylation (data not shown).

The footprinting reagent MPE•Fe was used to investigate the triplex formed by 12 at the 5'-$(Py)_m(Pu)_n$-31' target site (Hertzberg, R. P., et al. (1982) *J. Am. Chem. Soc.* 104:313) (FIG. 34). In addition to protection from cleavage within the binding site, a region of increased reactivity at the center of the 5'-$(Py)_m(Pu)_n$-3' site was detected. This single locus of hyperreactivity suggests a single high affinity intercalation site at the junction (Collier, D. A., et al. (1991) Nucleic Acids Res. 19:4219).

A summary of the studies for this duplex target is given in FIG. 35. These results show that targeting the 5'-$(Py)_m(Pu)_n$-3' sequence requires at least a two nucleotide linker between the two binding domains. This is in contrast to the 5'-$(Pu)_m(Py)_n$-3' sequence, for which no linker nucleotides were necessary and in fact the two nucleotides at the center likely do not form base triplets. The triplex formed at the 5'-$(Py)_m(Pu)_n$-3' site is less stable, with an association constant lower by a factor of four. Also, the MPE•Fe reactivity pattern for this structure indicates that the base pairs near the site of crossover between strands provide an unusually stable binding site for an intercalator. Interestingly, Ono et al. have proposed an ethidium bromide binding site at the center of the sequence 5'-$(Py)_8(PU)_8$-3' when bound on alternate strands by pyrimidine oligonucleotides linked at their 5' ends (Ono, A., et al. (1991) *Biochemistry* 30:9914–9921).

It is clear that the structure and stability of the alternate strand triple helix depends on whether the duplex target is 5'-$(Pu)_m(Py)_n$-3' or 5'-$(Py)_m(Pu)_n$-3'. Analysis of models of these sequences with oligonucleotides bound to adjacent binding sites may explain some of these observations. For the sequence 5'-$(Pu)_m(Py)_n$-3', the site of crossover between strands is located where adjacent binding sites overlap (FIG. 36, left). Therefore, no linker between binding domains besides a phosphodiester is necessary for a successful crossover. In fact, it is likely that the two base pairs at the junction are not specifically recognized in base triplets, allowing the third strand to maintain helical continuity as it winds along the major groove.

For the sequence 5'-$(Py)_m(Pu)_n$-3', the adjacent binding sites do not overlap (FIG. 36, right). A linker domain is necessary for successfully crossing the major groove in this fashion, with a minimum length determined here to be two nucleotide residues. Although thymidines were used for this purpose, further optimization of the linker structure may still be possible. Also, the unusual MPE•Fe reactivity at the center of this triple helix may indicate that the duplex undergoes conformational reorganization upon binding of the third strand. This might involve a local unwinding or bending at the center of this alternate strand triple helical structure, creating a site for intercalation.

EXAMPLE 9

Analysis of Promoter-Specific Repression by Triple-Helix Formation in a Eukaryotic Cell-Pretranscription System This example describes the effect of pyrimidine motif triple-helical complexes position upstream of the TIId binding site (TATA box) on transcription initiation from eurkaryotic promoters in a cell free system. Although this Example describes the use of hompyrimidine oligonucleotides binding to a purine strand in a parallel orientation, triple-helix formationto control gene expression can also be utilized wherein expression is controlled by (1) pyrimidine-rich oligonucleotides binding in an anti-parallel orientation, (2) triple-helix formation on alternate strands, and (3) oligonucleotides utilizing non-naturally occuring nucleotides such as N, D and P nucleotides as described herein.

Transcription Templates

The E4 template series is based on $pG_5E4T$, herein designated E4-1 (Lin et al. (1988) *Cell* 54:659–664). This plasmid contains adenovirus gene E4 sequences from −38 to +250 and five copies of a 19 bp synthetic GAL4 binding site placed 21 bp upstream of the E4 TATA element. This cassette was inserted between the BamHI and HindIII sites of pGEM3 (Promega, Madison, Wis.). Templates E4-2 through E4-6 were constructed by inserting one or more copies of the synthetic 40-mer duplex:

GATCTGAGAAAG-
  GAGAGAAAAAGGGGCGGGGCATGCATTG (SEQ ID NO: 27)
ACTCTTTCCTCTCTTTTTCCCCGCCCCG-
  TACGTAACCTAG (SEQ ID NO: 28)

containing a 21 bp homopurine sequence overlapping a canonical Sp1 element (Maher et al. (1989) *Science* 245:725–730) into the BamHI site 13 bp upstream from the E4 TATA element in $pG_5E4T$. Template E4-11 was constructed by insertion of a tandem trimer of the synthetic 40-mer duplex (above) into the HindIII site at position −170 in $pG_5E4T$, after filling all recessed termini with DNA polymerase Klenow fragment. Templates E4-7 and E4-8 were constructed by insertion of the synthetic 73-mer duplex:

```
CTAG {TGGGCGGAGTTAGGGGCGGGAT  ACTC}  (SEQ ID NO:29)
     {ACCCGCCTCAATCCCCGCCCTA  TGAT}₂ (SEQ ID NO:30)

GAGAAAGGAGAGAAAAAGGGG             (SEQ ID NO:31)
     CTCTTTCCTCTCTTTTTCCCCGATC         (SEQ ID NO:32)
``` containing two copies of GC boxes III and IV from the SV40 early promoter (Courey et al. (1989), *Cell* 59:827–836) and the 21 bp homopurine sequence, in either orientation into the XbAI site 19 bp upstream from the E4 TATA element in $pG_5E4T$. Templates E4-9 and E4-10 were constructed by first partially filling recessed termini of the synthetic 73-mer duplex (above) using dTTP, dCTP, and DNA polymerase Klenow fragment. The fragment was then inserted into compatible termini in pG$_5$E4T generated by a similar partial filling reaction with dATP and dGTP after HindIII cleavage.

The F template series is based on pF1, which contains *Drosophila fushi tarazu* (ftz) sequences from −42 to +570 (Dearolf et al. (1989) *Genes Dev.* 3:384–398; Laughon et al. (1984) *Nature* 310:25–31) cloned between the BamHI and SalI sites of pBluescriptII KS+ (Stratagene, La Jolla, Calif.). The construct retains the ftz TATA element, but excludes all upstream ftz transcription control sequences. Templates F2 through F4 were constructed by inserting the synthetic 26 bp duplex:

CGAGAAAGGAGAGAAAAAGGGGTACG (SEQ ID NO: 33)

TCGAGCTCTTTCCTCTCTTTTTCCCCATGC (SEQ ID NO: 34)

between the SacI site of pF1 (48 bp upstream of the ftz TATA element) and either the BamHI (17 bp upstream from TATA; F3), the SpeI (23 bp upstream from TATA; F3), or the XbaI (30 bp upstream from TATA; F4) sites of pF1 after filling recessed termini of the latter sites with DNA polymerase Klenow fragment. The homopurine triple-helix target sites of templates F2 through F4 are therefore spaced 51 bp, 59 bp, and 65 bp upstream of the ftz transcription initiation point, respectively. Template E4-6/F1 was constructed by ligating the 600 bp KpnI-SacI promoter fragment of pF1 between the KpnI and SacI sites of template E4-6. This operation places the E4 promoter from E4-6 and the ftz promoter from F1 in convergent orientation, separated by 850 bp.

Permutation Constructs

The construction of plasmid pHW122 has been described (Wu et al. (1984) *Nature* 308:509–513). Permutation constructs B-F were created by inserting one or more copies of synthetic duplexes into polylinker sites in plasmid pCY7 (Prentki et al. (1987) *Nucleic Acids Res.* 15:10060). Plasmid pCY7 contains a tandem 375 bp repeat of the initial EcoRI-BamHI segment of pBR322. Host strain HB101 was employed for subcloning in order to maximize construct stability. Permutation constructs B and C were prepared by insertion of one or two copies of the synthetic 40-mer duplex (see above) into the BglII site of pCY7. Permutation construct F was prepared by filling recessed termini of the synthetic 40-mer duplex (see above) with DNA polymerase Klenow fragment, oligomerizing the duplex by blunt end ligation, and inserting six tandem copies of the resulting 44-mer duplex into the SmaI site of pCY7. Permutation construct D was prepared by insertion of four tandem copies of the synthetic duplex:

GATCCCAATTGAGAAAG-GAGAGAAAAAGTTAAGA (SEQ ID NO: 35)
GGTTAACTCTTTCCTCTCTTTTTCAATTCTCTAG (SEQ ID NO: 36)

into the BglII site of pCY7. Permutation construct E was prepared by subcloning the 250 bp BamHI-HaeIII promoter fragment of E4-6 between the BglII and SmaI sites of pCY7.

Sp1

A polypeptide comprising the 516 carboxyl-terminal amino acids of human transcription factor Sp1 (Sp1-516C) was expressed in *Escherichia coli* strain C600 Δlon (Maher et al. (1989) supra.) by isopropyl β-D-thiogalactopyranoside induction of plasmid pSp1-516C (Kadonaga et al. (1987) *Cell* 51:1079–1090). Bacterial extracts were prepared as described (Kadonaga et al. (1987) supra.; Kadonaga et al. (1988) *Science* 242:1566–1570). Sp1-516C was further purified from crude bacterial extracts by sequence-specific DNA affinity chromatography as described (Kadonaga et al. (1986) *Proc. Natl. Acad. Sci. U.S.A.* 83:5889–5893). Purified Sp1-516C (30 ng/μL; the major band upon silver staining after sodium dodecyl sulfate-polyacrylamide gel electrophoresis) was obtained upon dialysis against either buffer $Z^e_{150}$ [25 mM HEPES(K+), pH 7.5, 20% (v/v) glycerol, 0.1% (v/v) Nonidet P-40, 10 μM ZnSO$_4$, 1 mM DTT, 150 mM KCl] or buffer $X_{50}$ [25 mM HEPES(K+), pH 7.0, 20% (v/v) glycerol, 0.1% Nonidet P-40, 10 μM ZnSO$_4$, 1 mM DTT, 50 mM KCl].

Drosophila $K_c$ Cell Nuclear Extract. The Drosophila nuclear extract was prepared from cultured $K_c$ cells as previously described (Parker et al. (1984) *Cell* 36:357–369) with the following modifications. All extraction steps were performed using buffer A [15 mM KCl, 10 mM HEPES (K+), pH 7.9, 5 mM MgCl$_2$, 0.1 mM EDTA, 1 mM DTT]. The crude nuclear pellet was first extracted with 0.25 M ammonium sulfate, and extracted proteins were subsequently precipitated by addition of 0.27 g of solid ammonium sulfate/mL of extract. Nuclear extract preparations buffered to pH values of 7.0 or 7.5 were obtained by dialysis for 4 h against buffer $Y_{100}$ [25 mM HEPES(K+), pH 7.0 or pH 7.5, 100 mM KCl, 10% (v/v) glycerol, 0.1 mM EDTA, 0.1% Nonidet P-40, 1 mM DTT], clarification by 10-min centrifugation at 10000 g, and freezing of aliquots in liquid nitrogen.

In Vitro Transcription Reactions

Template mixtures (10 μL) containing oligonucleotide (25 pmol), MgCl$_2$ (25 mM) spermidine trihydrochloride (2.5 mM), KCl (50 mM), and supercoiled E4 series and F series templates (125 ng each) were incubated 30 min at 22° C. Transcription reactions (25 L) were assembled by addition to the template mixture of buffer $Y_{100}$ (pH 7.0 or pH 7.5; 2.5 μL) purified Sp1-516C or Sp1 buffer (pH 7.0 or 7.5; 2.5 μL) and nuclear extract (buffered to pH 7.0 or 7.5; 7.5 μL). The final KCl and MgCl$_2$ concentrations in all transcription reactions were 70 and 10 mM, respectively. When the importance of oligonucleotide pre binding was studied, oligonucleotide was withheld until after addition of nuclear extract. Transcription reactions were initiated immediately, or after subsequent incubation intervals by addition of a mixture of the four ribonucleoside triphosphates (0.6 mm each). Transcription reactions were then incubated a further 30 min at 22° C.

RNA Isolation and Quantitation

Transcription reactions were terminated by addition of 125 μL stop mix [200 mM NaCl, 20 mM EDTA, 1% (w/v) sodium lauryl sarcosinate, 250 μg/mL tRNA]. This mixture was extracted with phenol, and the nucleic acids were precipitated with ethanol and dried. The resulting pellets were resuspended in 5 μl of water, to which was added Tris-HCl, pH 8.0 (10 mM), EDTA (1 mM), KCl (0.2 M), and 100 fmol of each reverse primer (radiolabeled with T4 polynucleotide kinase and [γ-$^{32}$P]ATP) in a final volume of 10 μl. The E4 reverse primer (AACACCACTCGACACGGC) (SEQ ID NO: 37) binds positions +24 to +41 of E4 RNA. The ftz reverse primer (GTAGCCATATCGGATGTGTAT) (SEQ ID NO: 38) binds positions +58 to +78 of ftz RNA. Primer binding reactions were heated to 80° C. for 5 min and were then incubated at 37° C. for 30 min. A 25-µL volume of a solution containing Tris-HCl, pH 8.3(20 mM), MgCl$_2$ (10 mM), DTT (5 mM), each of the four deoxyribonucleoside triphosphates (0.3 mM each), actinomycin D (10 µg/mL), and Moloney murine leukemia virus reverse transcriptase (Bethesda Research Laboratories; 20 units) was then added, and the reaction was incubated for 30 min at 45° C. Control experiments demonstrated that the pyrimidine oligonucleotides used for triple-helix formation in this study did not inhibit these reverse transcription reactions. Primer extension products were collected by ethanol precipitation, suspended in formamide electrophoresis loading buffer, and resolved on 6% polyacrylamide-7.5 M urea sequencing gels in 0.5×TBE buffer (Sambrook et al. (1989) *Molecular Cloning: A Laboratory Manual*, Cold Spring Harbor Laboratory Press, Cold Spring Harbor, N.Y.). Dried gels were autoradiographed using Kodak XAR-5 X-ray film. Radio active signals were subsequently quantitated by storage phosphor technology (Molecular Dynamics, Sunnyvale, Calif.). For each gel lane the signal corresponding to transcription initiation from the test promoter ($S_t$) was first normalized to the signal produced from the internal control promoter ($S_c$) to provide the ratio R=($S_t$)J ($S_c$). The corresponding transcription index is given by (R/R), where R is the value of R obtained in the absence of added oligonucleotide. Reported transcription indices are based on a minimum of two independent experiments.

Permuted DNA Fragment Mobility Analysis

Plasmid restriction fragments (200 ng) and radiolabeled oligonucleotide (1 µM) were combined in 10-µL binding reactions containing Tris-OAc, pH 6.8 (25 mM), NaCl (70 mM), MgCl$_2$ (20 mM), spermine tetrahydrochloride (0.4 mM), β-mercaptoethanol (10 mM), and bovine serum albumin (100 µg/mL). Oligonucleotide binding reactions were incubated for 30 min at 37° C. Loading dyes [50% (v/v) glycerol, 0.05% (w/v) each xylene cyanol and bromophenol blue; 2 µL] were added, and the samples were loaded onto a 5% polyacrylamide [1:29 acrylamide/N,N'-methylenebis (acrylamide)] gel that had been preequilibrated at 4° C. in 1×TAM buffer [90 mM Tris-OAc, pH 6.0, 1 mM Mg(OAc)$_2$] at 10 V/cm with buffer recirculation. Electrophoresis was performed for 16 h. The gel was then stained with ethidium bromide, photographed under ultraviolet transillumination, and autoradiographed. Fragment mobility was measured relative to the absolute mobility (distance from gel origin) of the corresponding permuted fragment with the minimum value of d/l (defined in the description of FIG. 44A) as measured in the absence of specific oligonucleotide.

Experimental Strategy

Effects of triple-helical DNA complexes on promoter function were determined by insertion of homopurine sequences and Sp1 binding sites in various configurations upstream of the TATA element in recombinant eukaryotic promoters. The structure of one such triple-helical complex is shown schematically in FIG. 37. In this example, the 21 bp homopurine sequence has been designed to overlap 4 bp of a 10 bp consensus Sp1 binding site (Maher et al. (1989) supra.) inserted upstream of the TATA element of the adenovirus E4 gene. Effects of triple-helical complexes on promoter function were measured in a soluble transcription extract prepared from cultured Drosophila cells (Parker et al. (1984) supra.). This experimental system is naturally devoid of Sp1 activity, permits facile adjustment of reaction conditions (e.g., pH), and presents no membrane barriers to oligonucleotide uptake (Courey et al. (1988) *Cell* 55:887–898). Effects on transcription from modified E4 templates were measured relative to an internal control promoter lacking both homopurine sequence inserts and Sp1 binding sites. A plasmid carrying basal promoter elements from the *fushi tarazu* (ftz) gene was used for this purpose. This experimental protocol is shown in FIG. 38. The test plasmid (based on the E4 gene) and the internal control plasmid (based on the, ftz gene) were mixed and incubated for variable times with specific or nonspecific oligonucleotides (2.5 µM concentrations of compounds 1 or 3, respectively) under conditions that favor triple-helix formation. This oligonucleotide concentration is 250-fold higher than the observed dissociation constant for the oligomer 1 complex at this homopurine sequence under similar conditions and should promote rapid and quantitative complex formation during a 30-min binding reaction (Maher et al. (1990) *Biochemistry* 29:8820–8826). The templates were then incubated with Drosophila nuclear extract in the presence or absence of added recombinant Sp1-516C protein (1 µM final oligonucleotide concentration). Ribonucleoside triphosphates were typically added immediately to initiate transcription, but were withheld for various times in some experiments, as indicated. After a 30-min incubation in the presence of ribonucleoside triphosphates, RNA transcripts were isolated and quantitated by primer extension, electrophoretic resolution of the extension products, and radiometric analysis.

Effects on Basal Transcription

FIG. 39 shows the result of an experiment specifically testing effects of triple helices on basal (Sp1-independent) transcription using template E4-6, bearing five tandem copies of the homopurine/Sp1element (FIG. 37A). In this case, transcription reactions were per-formed at pH 7.0, in the absence of added Sp1. As shown in lanes 1 and 2 of FIG. 39, primer extension products from the E4 and ftz transcripts are readily distinguishable. E4 transcripts are typically rather heterogeneous with respect to initiation site, as compared to transcripts originating from the ftz template. Interestingly, lanes 3 and 4 of FIG. 39 show that triple helices formed by the binding of oligomer 1 repressed basal transcription from template E4-6 between 5- and 10-fold in a promoter-specific manner. Transcription after template incubation in the presence of nonspecific oligomer 3 (FIG. 39, lane 6) was unaffected. Thus, an array of five triple-helical complexes upstream of the E4 TATA element substantially repressed basal transcription in the absence of Sp1.

Repression Specificity and Template Fate

Specificity of triple-helix-mediated repression was examined according to several criteria. In all experiments oligomer 1 (specific sequence) and oligomer 3 (random sequence control with the same base content as oligomer 1) were compared and oligomer 3 was found to have no effect on transcription. Therefore, repression was oligonucleotide-specific. Furthermore, promoter specificity was monitored in two ways. First, transcription quantitation in all experiments relied on normalization of the absolute level of transcription from the E4-series test promoter to the internal control signal provided by the F-series template. Second, linearized or supercoiled forms of recombinant template E4-6/F-1 (bearing convergent E4-6 and F1 promoters in cis, separated by 850 bp) were tested. These experiments gave results identical to those obtained with unlinked promoters, demonstrating that repression is specific to the E4-6 promoter even when he F1 control promoter is present on the same plasmid (data not shown). This result also indicates that triple-helix-mediated repression is not dependent on template superhelicity.

To eliminate the possibility that apparent repression was the result of a triple-helix-activated template degradation activity, E4-6 plasmid DNA was analyzed after extraction from standard transcription reactions at various times (FIG. 40). Blot analysis indicated that supercoiled templates are gradually nicked and partially linearized during the course of 30-min transcription reactions (lanes 1–7). This pattern was unaltered after template preincubation and transcription in the presence of 1 $\mu$M concentrations of either specific oligomer 1 (lanes 8–14) or control oligomer 3 (lanes 15–21). Thus, the observed 5- to 1-fold repression of transcription from template E4-6 cannot be attributed to differential template cleavage or degradation in the nuclear extract.

Requirement for Triple-Helix Preassembly

It was observed that oligonucleotide-mediated repression required template preincubation with oligonucleotide, prior to addition of nuclear extract (FIG. 3, lanes 4 and 5). This observation was investigated to determine if prolonged incubation of oligonucleotides and templates in the presence of nuclear extract would ultimately result in repression. Templates (with or without prebound triple-helical complexes) were incubated for various times with nuclear extract in the absence of ribonucleoside triphosphates (FIG. 41). The pH of the nuclear extract was held at 7.5 in this experiment (nuclear extract activity was not strongly pH-dependent over the range 7.0–7.5). One set of templates was preincubated with oligomer 1 at ambient temperature, while the other was exposed to oligomer 1 only in the presence of nuclear extract. Ribonucleoside triphosphates were added at various times to initiate 30 min transcription reactions. As indicated by the right axis of FIG. 41, it was observed that the overall level of transcription (E4-6 and F1 templates in the absence of oligomer) increased up to 5-fold with increasing template incubation time (up to 80 min) prior to ribonucleoside triphosphate addition. Templates preincubated with oligomer 1 did not become derepressed over this time period. Thus, triple-helix-mediated template repression at the time of nuclear extract addition appears to be stable for at least 80 min at pH 7.5. Furthermore, templates that had not been preincubated with oligomer 1 were not repressed upon subsequent incubation in the presence of nuclear extract. Similar results were obtained with nuclear extract preparations at pH 7.0 (data not shown). Previous studies have shown that oligonucleotide association rate is not strongly pH-dependent, while dissociation rate is increased upon increasing pH (Maher et al. (1990) supra.). Under the present experimental conditions these results suggest that substantial triple-helix formation should occur within 30 min. Thus, activities present in the nuclear extract appear to alter these kinetics, possibly by decreasing either free oligomer concentration and/or double-helical DNA accessibility.

Effects on Sp1-Dependent Transcription Activation

We next tested whether Sp1 would derepress promoters bearing triple-helical complexes. It was therefore necessary to determine the dependence of triple-helix-mediated repression on the number, position, and distribution of triple-helical complexes and Sp1 sites in the test promoter. These results are shown in FIGS. 42 and 43. Transcription from promoters lacking homopurine or Sp1 elements was unaffected by the presence of oligomer or recombinant Sp1 (FIG. 42A, template E4-1; FIG. 43, lanes 1–6). In contrast, promoters bearing one, two, or three copies of the homopurine/Sp1element shown in FIG. 37 were repressed after preincubation in the presence of oligomer 1 and were activated by recombinant Sp1 in the absence of oligomer 1 (FIG. 42A, templates E4-2, E4-3, E4-4, and E4-5). Promoters bearing single triple-helical complexes spaced 26 or 13 bp (in opposite orientations) from the TATA element (templates E4-2 and E4-3) gave similar transcription results. Basal transcription from these templates was inhibited (±SEM) to 0.54±0.03 to 0.64±0.05 of control levels. Addition of Sp1 activated transcription from both promoters by approximately 1.5-fold in the absence of oligomer 1, but gave little activation when triple-helical complexes were present. Templates E4-4 and E4-5 contain two or three copies of the homopurine/Sp1element, and triple-helical complexes at these sites repressed transcription to 0.56±0.01 and 0.46±0.03 of control values. Addition of Sp1 in the absence of oligomer 1 activated transcription to 1.76±0.14 and 2.05±0.27 of control values, respectively, but again failed to substantially derepress transcription in the presence of triple-helical complexes. The response of template E4-6 to oligomers has been described above. Addition of Sp1 in the absence of triple-helical complexes activated transcription from this template by more than 2-fold, but again was not observed to substantially relieve triple-helix-mediated repression (FIG. 43, lanes 7–12).

The results described above suggest that triple-helical complexes repress basal transcription independent of their potential to occlude Sp1 binding. To further explore this observation, we measured transcription from promoters bearing triple-helical complexes that do not overlap Sp1 sites. Single homopurine elements flanked by four copies of high-affinity Sp1 sites from the SV40 early promoter were tested in either orientation 18 bp upstream from the E4 TATA element (FIG. 42A, templates E4-7 and E4-8). Transcription was again found to be relatively insensitive to insert orientation. Oligomer 1 repressed basal transcription from templates E4-7 and E4-8 by approximately 2-fold. Observed template activation by Sp1 (2.47±0.13 and 1.9±0.3 of control values, respectively) in the absence of oligomer 1 was again largely eliminated in the presence of triple-helical complexes. When these inserts were moved further upstream (139 bp from the E4 TATA element), both triple-helix-mediated repression and Sp1 activation were substantially diminished (FIG. 42A, templates E4-9 and E4-10). A similar distance-dependent diminution of repression and activation was observed for three copies of the homopurine/Sp1overlapping element when inserted 145 bp upstream from TATA (FIG. 42A, template E4-11; FIG. 43, lanes 13–18).

We wished to determine if triple-helix-mediated repression by single homopurine elements was somehow dependent on the presence of Sp1 binding sites, regardless of their occupancy by Sp1. Templates F2, F3, and F4 were constructed using the recombinant basal ftz promoter from F1 (FIG. 42B). When transcribed in the presence of internal control template E4-1, F-series templates F2, F3, and F4 were repressed by oligomer 1 to 0.69±0.03, 0.61±0.02, and 0.54±0.03 of controls, respectively. Thus, triple-helix-mediated repression can occur in the context of the ftz basal promoter, is independent of the presence of Sp1 binding sites, and is not strongly dependent on precise triple-helix position in the range 18–30 bp upstream of the TATA element.

Position Dependence of Activating and Repressing Sequence Elements

Taken together, the data presented in FIG. 42 provide evidence for general relationships between the distributions of activating and repressing elements and promoter function observed in these experiments. When analyzed independently, activation by recombinant Sp1 and repression by triple-helical complexes appear to depend upon the number of complexes of each type, inversely weighted by their distance from the TATA element.

Effects on DNA Flexibility

The data presented in FIG. 42 suggest that repression by triple-helical complexes upstream of the TATA element occurs predominantly at the level of basal transcription. An obvious possibility is that repression is due to inhibition of proximal initiation complex assembly. While such inhibition could play a role for triple-helical complexes adjacent to TATA, this mechanism does not readily explain repression at greater distances, nor does it explain increased repression by additional triple-helical complexes positioned further upstream of TATA. We therefore considered alternative mechanisms involving the possibility that oligonucleotide-directed triple-helix formation bends or stiffens the target double helix in a manner that might be antagonistic to promoter function. Discrete alterations in DNA helix axis trajectory are predicted to occur at transitions between DNA helical forms differing in base pair tilt. If such anomalies are phased at odd multiples of half the helical repeat unit, the local bends are predicted to accumulate in a plane, resulting in a uniformly curved structure. Such anomalies in the structure of promoter DNA might inhibit proper assembly of the proximal initiation complex. Comparison of available structural models for double-helical and triple-helical DNA polymers suggests that base pair tilt may differ significantly between these helix families. Upon extrapolation to the case of oligonucleotide-directed triple-helix formation at homopurine target sites, reported values for the base pair tilt of B-form double-helical DNA (ca. −50°; Arnott et al. (1972) *Biochem. Biophys. Res. Commun.* 47:1504–1510) and A' (RNA-like) triple-helical DNA (ca. 8.5°; Arnott et al. (1976) *Nucleic Acids Res.* 3:2459–2470) suggest that conservation of base stacking at junctions between these helix forms could result in a deformation of the helix axis by as much as 13.50. This junctional bending model predicts that, depending on the length and spacing of triple helical complexes in a region of double-helical DNA, the polymer might adopt very different higher order structures ranging from multiply kinked to uniformly curved. Similar extrapolation of polymeric helical repeat parameters (10.5 bp/turn for double-helical DNA and 12 bp/turn for triple helical DNA) to the case of oligonucleotide-directed DNA triple-helix formation suggests that coherent bending should be maximized at certain triple-helical complex distributions, e.g., 18 base triplets separated by 16 or 26 bp (Arnott et al. (1976) supra.; Arnott et al. (1972) supra.).

An alternative stiffening model for the effect of triple-helix formation on double-helical DNA is based upon the reasonable prediction that three-stranded DNA helices may exhibit reduced flexibility and correspondingly increased persistence lengths in solution relative to double helices. This prediction follows from consideration of the increased radial charge density in a triple helix relative to a double helix. In this stiffening model, small changes in triple-helical complex length and spacing in a region of double-helical DNA are not expected to substantially alter the overall trend toward loss of regional flexibility. Regions of increased DNA stiffness within a eukaryotic promoter might repress transcription by interfering with the ability of transcription factors to deform DNA into a functional proximal initiation complex.

An experimental approach for evaluating these models is based on their contrasting predictions concerning the unperturbed root-mean-square end-to-end distance $[((r_0))^{1/2}]$ of DNA fragments bearing such anomalies. In the junctional bending model, the case of triple-helical complexes arrayed to give a coherent bend should lead to a decrease in $((r_0))^{1/2}$. In the stiffening model, all arrangements of triple-helical complexes should act to increase the value of $((r_0))^{1/2}$. An indirect experimental method for measuring effects on $((r_0))^{1/2}$ in solution is provided by assays of permutation-dependent changes in the electrophoretic mobility of DNA fragments in polyacrylamide gels (Wu et al (1984) supra.). Such assays measure changes in the electrophoretic mobility of DNA fragments bearing inherent or ligand-induced structural perturbations as the position of the perturbation is changed within the DNA fragment. In the case of ligand-induced structural perturbations, this approach focuses not on mobility shifts due to ligand binding, but on mobility shifts due to changing the position of the bound ligand. Application of this assay is based on the prevailing view that shape selectivity between molecules of identical mass and electric charge reflects the facility with which molecules proceed through the polyacrylamide matrix in a wormlike manner. For molecules of identical mass and charge, increasing values of $((r_0))^{1/2}$ should increase electrophoretic mobility, while decreasing values of $((r_0))^{1/2}$ should have the opposite effect (Anderson (1986) *Nucleic Acids Res.* 14:8513–8533). Permutation-de pendent mobility assays exploit the expectation that any such mobility anomalies will be maximized when the bent or stiffened region is centrally rather than terminally positioned in a DNA fragment (Wu et al. (1984) supra.).

Relative electrophoretic mobilities of circularly permuted DNA restriction fragments bearing various distributions of triple-helical complexes were determined using the approach diagrammed in FIG. 44A. As a control, insert A contained phased tracts of AT base pairs that cause a well-documented bend in kinetoplast DNA (Id.). Insert B supports a single triple-helical complex involving oligomer I (21 base triplets). Inserts C and E support two and five complexes of this type, respectively, separated by 19 bp segments. Insert D supports four triple-helical complexes involving oligomer 2 (18 base triplets), separated by 16 bp spacer segments. Inserts F(○) and F(Δ) both support six triple-helical complexes. In insert F(○), the complexes involve oligomer 1 (21 base triplets), separated 23 bp segments. In insert F(Δ), the complexes involve oligomer 2 (18 base triplets), separated by 26 bp segments. A key design feature of inserts is the length and phasing of triple-helical complexes. According to the junctional bending model, the helical repeat parameters described above suggest that inserts A, D, and F(~) should be curved upon triple-helix formation, due to the accumulation of coherent junctional bends. Because it is predicted to decrease $((r_0))^{1/2}$, such anomalies are expected to decrease fragment mobility in a permutation-dependent manner, with the most extreme retardation occurring when the anomaly is centrally located. Upon triple-helix formation, this model predicts that junctional bends in inserts B, C, E, and F(°) should not be coherent, leading to mildly kinked, rather than curved, structures. Such anomalies are not expected to product substantial permutation-dependent electrophoretic retardation. In contrast, the stiffening model predicts that all inserts will cause stiffening upon triple-helix formation, with the magnitude of the effect proportional to the number of induced base triplets. As such stiff regions tend to increase the value of $((r_0))^{1/2}$ for fragments bearing them, increased electrophoretic mobility is predicted, with the most extreme enhancement occurring when the anomaly is centrally located.

These predictions were tested by electrophoresis of permuted restriction fragments bearing triple-helical complexes at pH 6.0 where complexes are sufficiently stable to remain intact throughout the course of the experiment. Permuted fragments were then visualized by staining with ethidium bromide. Results of experiments of this type are shown in FIGS. 44B and C. Under these experimental conditions, insert A severely retards fragment mobility in a permutation-dependent manner, as predicted for a curved anomaly (highest mobility fragments in FIG. 44B, lanes 1–5, and FIG. 44C, graph A). As shown in FIGS. 44B and C, in contrast to the predictions of the bending model, all DNA restriction fragments bearing triple-helical DNA complexes exhibited permutation-dependent acceleration rather than retardation. Furthermore, the degree of maximum mobility enhancement for each insert was roughly proportional to the total number of base triplets present upon triple-helix formation, regardless of the precise lengths and spacings of triple-helical complexes nucleotide-directed triple-helix formation changes the physical properties of the target double helix in a manner consistent with DNA stiffening. These results do not support the junctional bending model.

Triple-Helix Effects on Basal Transcription

Site-specific triple-helical DNA complexes upstream of the TATA element are promoter-specific repressors of eukaryotic transcription initiation by RNA polymerase II. It has previously been demonstrated that site-specific DNA triple-helix formation can block Sp1binding (Maher et al. (1989) supra.). We extended this observation to a functional context in which Sp1 acts as an activator of transcription. We find that triple-helical complexes act predominantly as repressors of basal transcription and can do so at a modest distance, regardless of whether such complexes overlap Sp1binding sites. Moreover, it was found that Sp1 is incapable of relieving triple-helix-mediated repression. Repression is strictly dependent on both oligonucleotide sequence and tight linkage of the homopurine target elements to the test promoter. Thus, under no circumstances was nonspecific oligomer 3 observed to affect transcription from any experimental or internal control template. Moreover, specificity of repression was documented through the use of internal control promoters and was observed on supercoiled and linearized templates, as well as in the case of internal control and experimental promoters contained within a single plasmid. Together with the demonstration that promoter-specific repression is not accompanied by increased template degradation, these observations indicate that repression reflects promoter-specific disruption of transcription initiation.

Triple-Helix Preassembly Requirement

Transcriptional repression requires the preassembly of triple-helical complexes before addition of Drosophila nuclear extract. This requirement cannot be overcome by prolonged template incubation in the presence of extract and DNA oligomer at pH 7.0 or 7.5 prior to addition of ribonucleoside triphosphates. Previous experiments conducted in the absence of nuclear extract have examined the rate and extent of triple-helix formation as a function of oligonucleotide concentration between pH 6.8 and 7.2 (Maher et al. (1990) supra.). On the basis of these results, the experimental oligonucleotide concentration (1 $\mu$M) should have been sufficient to permit substantial triple-helix formation on naked DNA within 20 min at pH 7.0. The observed preassembly requirement may therefore reflect one or more activities of the nuclear extract.

The presence of high concentrations of DNA binding proteins in nuclear extract preparations may foster nonspecific interactions with template DNA, resulting in structures that inhibit oligonucleotide-directed triple-helix formation. Such nonspecific interactions may also be responsible for the observation that functional initiation complexes are assembled on only a small fraction of added templates upon incubation in nuclear extracts (Croston et al. (1991) *Science* 251:63–649; Parker et al. (1984) supra.). Thus, the nuclear extract system may erect an unnatural barrier to triple-helix formation that would not exist in the context of nuclear chromatin where DNA:protein stoichiometry is much different. It is also possible that the nuclear extract contains sufficient single-stranded DNA binding or hydrolytic activities to reduce free oligomer concentration below that required to drive complex formation under the kinetic and thermodynamic constraints of this assay.

It is interesting to compare the observed prebinding requirement reported here to repression of in vitro transcription by histone H1 (Croston et al. (1991) supra.). Like triple-helical DNA complexes, H1 acts to repress basal transcription, albeit in a sequence- and promoter-nonspecific manner. It may be noteworthy that H1-mediated repression also requires prebinding of H1 to template DNA. No repression is observed if transcription factors and activating proteins are allowed to bind prior to H1 . It is unknown whether similar mechanisms are responsible for the observed oligonuclectide prebinding requirement reported here.

Position Dependence of Repressing and Activating Sequence Elements

A general result of these experiments is the observation that repression by triple-helical complexes tends to increase with the number and proximity of such complexes to the TATA element. An even stronger relationship of this type is observed for transcriptional activation by bound Sp1-516C molecules. Beyond these general observations, particular distributions and orderings of activating and repressing elements are relatively unimportant. For example, changing the distance of a single triple-helical complex over several helical turns of DNA upstream of TATA had relatively little affect on the degree of repression (e.g., templates E4-2, E4-3, E4-7, E4-8, F2, F3, F4) . Furthermore, order independence was observed when triple-helical complexes were placed adjacent to groups of Sp1 sites. Thus, repression was comparable whether or not triple-helical complexes were positioned to intervene between the group of Sp1-516C monomers and the TATA element (templates E4-7, E4-8, E4-9, E4-10).

Comparison of Sequence-Specific and -Nonspecific Repressors

Our observations support the proposition that preassembled triple helices exert promoter-specific repression that cannot be substantially reversed in the presence of Sp156C. In this regard, the effects of triple-helical complexes may be compared with those observed for nonspecific repressors such as histone HI (Id.). Transcription factors have been shown to enhance transcription in the presence of HI through mechanisms involving either derepression alone or derepression coupled to frank activation (Id.). Interestingly, although it acts in the latter mode relative to repression by H1, Sp1 can neither derepress nor activate transcription in the presence of triple-helical complexes. In fact, triple-helical DNA complexes are sufficient to substantially block Sp1 activation even when the complexes do not overlap Sp1 binding sites (e.g., templates E4-7 and E4-8).

Models

We have considered possible mechanistic explanations for effects of triple-helical complexes on transcription initiation. Five plausible models for promoter-specific repression by triple-helical DNA complexes are shown in FIG. 45.

Model A depicts inhibition of transcriptional activation, reflecting the original experimental design. Elimination of activator binding was expected to reduce transcription to the basal level observed in the absence of activator. As described above, this simple model cannot account for the observed ability of triple-helical complexes to exert substantial effects on the basal level of transcription, although it remains possible that inhibition of Sp1 binding is also occurring.

Model B suggests that promoter-specific repression by triple-helical complexes result from disruption of basal factor interactions at the promoter. Assembly of an RNA polymerase II transcription complex has been shown to protect a region extending from about I.S helical turns upstream of the TATA element to about 1.5 helical turns downstream from the initiation point (Buratowski et al. (1989) *Cell* 56:549–561). A subset of templates tested here contained triple-helical complexes that impinged on the 15 bp region upstream of TATA. However, several experimental results tend to argue against this model as the major mechanism for the observed results. For example, templates E-2 and -3 are spaced 26 and 13 bp, respectively, from the TATA element, but are similarly repressed by triple-helix formation. Templates E4-3, E4-4, E4-5, and E4-6 all possess a homopurine sequence 13 bp upstream of the TATA element, but are subject to increasing repression in the presence on oligomer I. Furthermore, templates in the series F2, F3, and F4 show comparable repression by oligomer I in spite of the increasing separation of the proximal triple-helical complex from the TATA element (18, 24, and 30 bp, respectively). These results suggest that repression is not dictated solely by the most TATA-proximal complex, although direct effects on the promoter may contribute in some cases.

Model C proposes that triple-helical complexes induce changes in the physical properties of promoter DNA that tend to inhibit assembly of the promoter into a productive initiation complex. In particular, bending at duplex-triplex junctions and reduction of DNA flexibility were considered and explicitly tested. It was found that the electrophoretic mobility of DNA restriction fragments bearing triple-helical complexes depended on the position of the complexes within the fragment. We conclude that changes in mobility reflect changes in average molecular shape. Because the electrophoretic anomaly is opposite to that observed for curved DNA fragments, this result supports the proposition that short triple-helical complexes positioned near the center of a larger DNA molecule can act to increase its apparent persistence length. Similar interpretations have been proposed for electrophoretic anomalies of this type arising at certain (A/T)-rich DNA sequences known to resist nucleosome assembly or to be relatively rigid on the basis of other physical studies (Anderson (1986) supra.).

How triple-helix formation substantially upstream of TATA might limit assembly of the basal (Sp1-independent) initiation complex is presently uncertain, but suggests the possibility of propagation or amplification of a primary local effect by other factors. Model D suggests that repression by triple-helical DNA structures may be mediated by an unknown activity in the nuclear extract that recognizes some aspect of the altered DNA structure and acts to repress transcription. The existence of triple-helix-specific binding activities is not implausible in light of evidence favoring a three-stranded structural model for H-DNA elements in vivo (Davis et al. (1989) *Proc. Natl. Acad. Sci. U.S.A.* 86:9682–9686; Lee et al. (1987) *Nucleic Acids Res.* 15:1047–1061; Pasniewski et al. (1990) *Nucleic Acids Res.* 18:605–61). Furthermore, although natural cytosine methylation is notably absent in Drosophila, the presence of DNA binding proteins with preference for 5-methylcytosine could contribute to the formation of a repressive nucleoprotein complex at the triple helix (Boyes et al. (1991) *Cell* 64:1123–1134). The experiments reported here do not support or refute this model, except that we have excluded the specific possibility that the postulated activity acts by nicking or cleaving double-helical DNA at sites of triple-helix formation.

Model E addresses the possibility that triple-helix formation could affect patterns of chromatin assembly on DNA and therefore activate or repress transcription. Evidence that chromatin assembly can act as a general inhibitor of transcription suggests that sequence-specific inhibition of nucleosome assembly could have effects on the accessibility of promoter DNA to basal transcription factors including RNA polymerase II (Croston et al. (1991) supra.; Weintraub (1984) *Cell* 38:17). Although it is uncertain to what extent authentic chromatin assembly occurs in the Drosophila nuclear extract under our experimental conditions, this model suggests mechanisms that may apply to future studies of chromatin assembly after induction of triple-helical structures by oligonucleotide binding or H-DNA strand rearrangement.

Comparison to Triple Helices of the
Purine•Purine•Pyrimidine (Purine Motif) Type It is relevant to compare the results reported here to those described by Hogan and co-workers for triple-helix formation at a purine-rich oligomer (Cooney et al. (1988) *Science* 241:446–459). These workers documented oligonucleotide-specific promoter repression consistent with that reported here, without addressing the issue of promoter specificity. It is also unclear to what extent the observed requirement for triple-helix preassembly reported here differs from this previous report. Purine motif triple-helical complexes have subsequently been shown to involve purine oligonucleotide binding antiparallel to the purine strand of the target double helix (Beal et al. (1991) *Science* 251:1360–1363). Triple-helix formation in the purine motif has the advantage of pH independence. However, perhaps because they are not profoundly G-rich, homopurine target sites chosen for the current study assemble into less stable triple-helical structures in the purine motif than in the pyrimidine motif. Where tested, triple-helical complexes formed using the purine triple-helix motif gave qualitatively similar (although quantitatively diminished) repression relative to that reported here for the pyrimidine triple-helix motif (data not shown).

Extension to Transcription Elongation and
Termination

The experiments reported here specifically address attempts to artificially regulate transcription initiation by oligonucleotide-directed DNA triple-helix formation. It will be important to extent these results to transcriptional elongation and termination by RNA polymerase II. Of interest in this regard are preliminary studies indicating that noncovalent triple-helical DNA complexes do not inhibit transcriptional elongation by bacteriophage RNA polymerases.

Conclusions

We have demonstrated that noncovalent but site-specific oligonucleotide interactions with double-helical DNA can serve to repress transcription initiation in a suitably designed in vitro system. If the observed gene-specific repression by triple-helical complexes extends to nuclei of living cells, our results suggest an unanticipated flexibility in the precise location of triple-helical complexes relative to transcription factor binding sites. Such flexibility would not have been expected on the basis of a simple factor occlusion model. Moreover, unlike the nuclear extract system, enhancement of transcription from great distances is common in cells. In such cases it may be possible to more definitively separate triple-helix effects on upstream activators from effects on basal transcription. Thus, factor occlusion or local DNA stiffening due to triple-helix formation might uncouple enhancer-promoter interactions. Finally, the postulated inhibition of basal promoter activity at modest distance from the site of transcription initiation suggests that naturally occurring potential triple-helix target sites, which do not generally overlap known protein binding sites, might nonetheless have functional significance.

It is to be understood that various other modifications will be apparent to and can readily be made by those skilled in the art, given the disclosure herein, without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A triple-helix comprising a double-helical nucleic acid comprising first and second substantially complementary strands and an oligonucleotide bound to a target sequence within said double-helical nucleic acid, wherein said first strand comprises a first purine-rich sequence and a pyrimidine-rich sequence and said target sequence comprises said first purine-rich target sequence and a second purine-rich target sequence on said second strand based paired with said pyrimidine-rich sequence, and wherein said oligonucleotide has 5' and 3' terminal nucleotides and comprises a first binding domain comprising a pyrimidine-rich portion bound to said first purine-rich target sequence in a parallel orientation and a second binding domain comprising a purine-rich portion bound to said second purine-rich target sequence in an antiparallel orientation and a linking domain between said first and said second binding domains having a length which permits each of the said binding domains to bind to purine-rich target sequences.

2. The triple-helix of claim 1 wherein said pyrimidine-rich sequence is adjacent and 5' to said first purine-rich target sequence and said linking domain comprises two nucleotides.

3. The triple-helix of claim 1 wherein said first binding domain comprises a nucleotide containing a 4-phenylimidazole base when the nucleotide at tie complementary position in said first target sequence comprises T or C.

4. The triple-helix of claim 3 wherein said nucleotide containing a 4-phenylimidazole base comprises a nucleotide containing a 4-phenylimidazole base wherein 3-benzamido is substituted at the C3 position.

5. The triple-helix of claim 3 wherein said first binding domain further comprises a T nucleotide when the nucleotide at the complementary position in said first target sequence is A and a C nucleotide or a nucleotide containing a pyrazolopyrimidine base when the nucleotide at the complementary position in said first target sequences.

6. The triple-helix of claim 1 wherein said first binding domain comprises a nucleotide containing a pyrazolopyrimidine base when said nucleotide at the complementary position in said first target sequence comprises G.

7. The triple-helix of claim 6 wherein said nucleotide containing a pyrazolopyrimidine base comprises a nucleotide containing a pyrazolopyrimidine base linked to ribose at the N1 position.

8. The triple-helix of claim 1 wherein said second target sequence comprises one or more of the pyrimidine nucleotide C and said second binding domain comprises a 2'-deoxynebularine nucleotide when the nucleotide at the complementary position in said second target sequence is C.

9. The triple-helix of claim 8 wherein said second binding domain further comprises a G nucleotide when the nucleotide at the complementary position in said second target sequence is G and an A or a T nucleotide when the nucleotide at the complementary position in said second target sequence is an A.

10. The triple-helix of claim 1 wherein said oligonucleotide bound to said target sequence within said double-helical nucleic acid comprises at least one modified nucleotide.

11. The triple-helix of claim 10 wherein said modified nucleotide is a detectable moiety or a cleaving moiety capable of causing cleavage of said double-helical nucleic acid.

12. An oligonucleotide capable of forming a triple-helix with a double-helical nucleic acid comprising first and second strands wherein said first strand comprises a first purine-rich sequence and a pyrimidine-rich sequence and a target sequence comprises said first purine-rich sequence and a second purine-rich sequence on said second strand based paired with said pyrimidine-rich sequence, said oligonucleotide comprising a first binding domain comprising a pyrimidine-rich portion capable of binding to said first purine-rich target sequence in a parallel orientation and a second binding domain comprising a purine-rich portion capable of binding to said second purine-rich target sequence in an antiparallel orientation and a linking domain between said first and said second binding domains having a length which permits each of the said binding domains to bind to purine-rich target sequences and w herein said first binding domain comprises a nucleotide containing a 4-phenylimidazole base when the nucleotide at the complementary position in said first target sequence is C or T.

13. The oligonucleotide of claim 12 wherein said nucleotide containing a 4-phenylimidazole base comprises a nucleotide containing a 4-phenylimidazole base wherein 3-benzamido is substituted at the C3 position.

14. An oligonucleotide capable of forming a triple-helix with a double-helical nucleic acid comprising first and second strands wherein said first strand comprises a first purine-rich sequence and a pyrimidine-rich sequence and a target sequence comprising said first purine-rich sequence and a second purine-rich sequence on said second strand based paired with said pyrimidine-rich sequence, said oligonucleotide comprising a first binding domain comprising a pyrimidine-rich portion capable of binding to said first purine-rich target sequence in a parallel orientation and a second binding domain comprising a purine-rich portion capable of binding to said second purine-rich target sequence in an antiparallel orientation and a linking domain between said first and said second binding domains having a length which permits each of the said binding domains to bind to purine-rich target sequences and wherein said first binding domain comprises a nucleotide containing a pyrazolopyrimidine base when the nucleotide at the complementary position of said first target sequence comprises G.

15. The oligonucleotide of claim 14 wherein said nucleotide comprises a nucleotide containing a pyrazolopyrimidine base linked to ribose at the N1 position.

16. An oligonucleotide capable of forming a triple-helix with a double-helical nucleic acid comprising first and second strands wherein said first strand comprises a first purine-rich sequence and a pyrimidine-rich sequence and a target sequence comprising said first purine-rich sequence and a second purine-rich sequence on said second strand based paired with said pyrimidine-rich sequence, said oligonucleotide comprising a first binding domain comprising a pyrimidine-rich portion capable of binding to said first purine-rich target sequence in a parallel orientation and a second binding domain comprising a purine-rich portion capable of binding to said second purine-rich target sequence in an antiparallel orientation and a linking domain between said first and said second binding domains having a length which permits each of the said binding domains to bind to purine-rich target sequences and wherein said second purine-rich target sequence comprises one or more of the pyrimidine nucleotide C and said second binding domain comprises a 2'-deoxynebularine nucleotide when the nucleotide at the complementary position in said second target sequence is C.

17. The oligonucleotide of claims 12, 13, 14, 15 or 16 wherein said oligonucleotide comprises at least one modified nucleotide containing a detectable moiety or a cleaving moiety capable of causing cleavage of said double-helical nucleic acid.

18. A method for forming a triple-helix comprising of binding an oligonucleotide to a target sequence within a double-helical nucleic acid wherein said double-helical nucleic acid comprises first and second strands and said first strand comprises a first purine-rich sequence and a pyrimidine-rich sequence and said target sequence comprises said first purine-rich sequence and a second purine-rich sequence on said second strand based paired with said pyrimidine-rich sequence said method comprising oligonucleotide containing said double-helical nucleic acid and comprising a first binding domain comprising a pyrimidine-rich portion capable of binding to said first purine-rich sequence in a parallel orientation and a second binding domain comprising a purine-rich portion bound to said second purine-rich sequence in an antiparallel orientation and a linking domain between said first and said second binding domains having a length which permits each of the said binding domains to bind to purine-rich target sequences.

19. The method of claim 18 wherein said pyrimidine-rich sequence is adjacent and 5 ' to said first purine-rich target sequence and said linking domain comprises two nucleotides.

20. The method of claim 18 wherein said first binding domain comprises a nucleotide containing a 4-phenylimidazole base when the nucleotide at the complementary position in said first target sequence comprises T or C.

21. The method of claim 20 wherein said nucleotide containing a 4-phenylimidazole base comprises a nucleotide containing a 4-phenylimidazole base wherein 3-benzamido is substituted at the C3 position.

22. The method of claim 20 wherein said first binding domain further comprises a T nucleotide when the nucleotide at the complementary position in said target sequence is A and a C nucleotide or a nucleotide containing a pyrazolopyrimidine base when the nucleotide at the complementary position in said first target sequence is G.

23. The method of claim 18 wherein said second binding domain comprises a nucleotide containing a pyrazolopyrimidine base when said nucleotide at the complementary position in said second target sequence comprises G.

24. The method of claim 23 wherein said nucleotide containing a pyrazolopyrimidine base comprises a nucleotide containing a pyrazolopyrimidine base linked to ribose at the N1 position.

25. The method of claim 18 wherein said second target sequence comprises one or more of the pyrimidine nucleotide C and said second binding domain comprises a 2'-deoxynebularine nucleotide when the nucleotide at the complementary position in said second target sequence is C.

26. The method of claim 25 wherein said second binding domain further comprises a G nucleotide when the nucleotide at the complementary position in said second target sequence is G and an A or a T nucleotide when the nucleotide at the complementary position in said second target sequence is an A.

27. The method of claim 18 wherein said oligonucleotide bound to said target sequence within said double-helical nucleic acid comprises at least one modified nucleotide.

28. The method of claim 27 wherein said modified nucleotide contains a detectable moiety or a cleaving moiety capable of causing cleavage of said double-helical nucleic acid.

29. An oligonucleotide capable of forming a triple helix with a double helical nucleic acid comprising first and second strands and a target sequence within said double-helical nucleic acid, said oligonucleotide comprising a binding domain wherein said binding domain comprises a nucleotide containing a 4-phenylimidazole base when the nucleotide at the complementary position in said target sequence is C or T.

30. The oligonucleotide of claim 29 wherein said nucleotide containing a 4-phenylimidazole base comprises a nucleotide containing a 4-phenylimidazole base wherein 3-benzamindo is substituted at the C3 position.

* * * * *